(12) United States Patent
Throsby et al.

(10) Patent No.: US 7,537,764 B2
(45) Date of Patent: *May 26, 2009

(54) BINDING MOLECULES CAPABLE OF NEUTRALIZING WEST NILE VIRUS AND USES THEREOF

(75) Inventors: Mark Throsby, Utrecht (NL); Cornelis Adriaan De Kruif, De Bilt (NL)

(73) Assignee: Crucell Holland B.V., Leiden (NL)

( * ) Notice: Subject to any disclaimer, the term of this patent is extended or adjusted under 35 U.S.C. 154(b) by 147 days.

This patent is subject to a terminal disclaimer.

(21) Appl. No.: 11/511,127

(22) Filed: Aug. 28, 2006

(65) Prior Publication Data

US 2007/0042359 A1 Feb. 22, 2007

Related U.S. Application Data

(63) Continuation-in-part of application No. PCT/EP2005/052160, filed on May 12, 2005, and a continuation-in-part of application No. PCT/EP2004/053609, filed on Dec. 20, 2004, and a continuation-in-part of application No. PCT/EP2005/056926, filed on Dec. 19, 2005, and a continuation-in-part of application No. PCT/EP2005/054002, filed on Aug. 15, 2005, and a continuation-in-part of application No. PCT/EP2005/052946, filed on Jun. 23, 2005, and a continuation-in-part of application No. PCT/EP2005/052648, filed on Jun. 8, 2005.

(51) Int. Cl.
*A61K 39/42* (2006.01)
*A61K 39/12* (2006.01)

(52) U.S. Cl. .................. 424/159.1; 424/218.1
(58) Field of Classification Search ............... None
See application file for complete search history.

(56) References Cited

U.S. PATENT DOCUMENTS

| | | | |
|---|---|---|---|
| 5,494,671 | A | 2/1996 | Lai et al. |
| 5,514,375 | A | 5/1996 | Paoletti et al. |
| 5,744,140 | A | 4/1998 | Paoletti et al. |
| 5,744,141 | A | 4/1998 | Paoletti et al. |
| 6,184,024 | B1 | 2/2001 | Lai et al. |
| 6,258,788 | B1 | 7/2001 | Schmaljohn |
| 6,265,150 | B1 | 7/2001 | Terstappen et al. |
| 6,306,899 | B1 | 10/2001 | Cheng et al. |
| 6,331,415 | B1 | 12/2001 | Cabilly et al. |
| 6,416,763 | B1 | 7/2002 | McDonell et al. |
| 6,432,411 | B1 | 8/2002 | Ivy et al. |
| 6,455,509 | B1 | 9/2002 | Kochel et al. |
| 6,685,948 | B1 | 2/2004 | Zeng et al. |
| 6,875,433 | B2 * | 4/2005 | Hart et al. ............... 424/159.1 |
| 6,946,125 | B2 | 9/2005 | Rahal |
| 7,074,555 | B2 | 7/2006 | Esty et al. |
| 2007/0025992 | A1 | 2/2007 | Takayama et al. |

FOREIGN PATENT DOCUMENTS

| | | |
|---|---|---|
| EP | 0 102 228 A | 3/1984 |
| EP | 0 691 404 A | 1/1996 |
| EP | 0 869 184 A | 10/1998 |
| EP | 0 872 553 A | 10/1998 |
| WO | WO 84/03564 | 9/1984 |
| WO | WO 93/09872 | 5/1993 |
| WO | WO 98/15833 | 4/1998 |
| WO | WO 98/37911 | 9/1998 |
| WO | WO 99/26653 | 6/1999 |
| WO | WO 99/63095 | 12/1999 |
| WO | WO 00/10991 | 3/2000 |
| WO | WO 00/12128 | 3/2000 |
| WO | WO 00/14245 | 3/2000 |
| WO | WO 00/63403 | 10/2000 |
| WO | WO 01/03729 | 1/2001 |
| WO | WO 01/38362 | 5/2001 |
| WO | WO 01/39802 | 6/2001 |
| WO | WO 01/60315 | 8/2001 |
| WO | WO 01/60847 | 8/2001 |
| WO | WO 02/15664 | 2/2002 |
| WO | WO 02/072036 A2 | 9/2002 |
| WO | WO 02/103012 A1 | 12/2002 |
| WO | WO 2005/007800 A2 | 1/2005 |
| WO | WO 2005/106483 A1 | 11/2005 |
| WO | WO 2005/123774 | 12/2005 |
| WO | WO 2006/067122 A2 | 6/2006 |

OTHER PUBLICATIONS

Rudikoff et al. PNAS USA, 1982, 79:1979-1983.*
Bae et al., "Production of Hantaan Virus from Human Immortalized Retina Cell and Its Immunogenicity," J. Microbiol. Biotechnol., Dec. 20, 2002, pp. 882-889, vol. 12, No. 6.
Blitvich et al., Epitope-Blocking Enzyme-Linked Immunosorbent Assays for the Detection of Serum Antibodies to West Nile Virus in Multiple Avian Species, Journal of Clinical Microbiology, Mar. 2003, pp. 1041-47, vol. 41, No. 3.
Bao et al., "Flavivirus Induces MHC Antigen on Human Myoblasts: A Model of Autoimmune Myositis?" Muscle and Nerve, Nov. 1992, pp. 1271-1277, vol. 15, No. 11.

(Continued)

*Primary Examiner*—Stacy B Chen
(74) *Attorney, Agent, or Firm*—TraskBritt

(57) ABSTRACT

The invention provides human binding molecules specifically binding to West Nile virus and having West Nile virus neutralizing activity, nucleic acid molecules encoding the human binding molecules, compositions comprising the human binding molecules and methods of identifying or producing the human binding molecules. The human binding molecules can be used in the diagnosis, post-exposure prophylaxis and/or treatment of a condition resulting from West Nile virus.

15 Claims, 8 Drawing Sheets

OTHER PUBLICATIONS

Boel et al., Functional human monoclonal antibodies of all isotypes constructed from phage display library-derived single-chain Fv antibody fragments, Journal of Immunological Methods, 2000, pp. 153-166, vol. 239.

Chen et al., Preparation of monoclonal antibodies against West Nile virus envelope protein domain, Chinese J. Exp. Clin Virol., Sep. 2006, pp. 213-215, vol. 20, No. 3.

Chung et al., Antibodies against West Nile Virus Nonstructural Protein NS1 Prevent Lethal Infection through Fc gamma Receptor-Dependent and -Independent Mechanisms, Journal of Virology, Feb. 2006, pp. 1340-1351, vol. 80, No. 3.

Fields et al., Virology (Third Ed.), excerpt. pp. 931-932, 1996.

Gallimore et al., Transformation of Human Embryo Retinoblasts with Simian Virus 40, Adenovirus and ras Ocogenes, Anticancer Research, May 3, 1986, pp. 499-508, vol. 6, No. 3.

Goncalvez et al., Chimpanzee Fab Fragments and a Derived Humanized Immunoglobulin G1 Antibody That Efficiently Cross-Neutralize Dengue Type 1 and Type 2 Viruses, Journal of Virology, Dec. 2004, pp. 12910-12918, vol. 78. No. 23.

Gould et al., Protective and Therapeutic Capacity of Human Single-Chain Fv-Fc Fusion Proteins against West Nile Virus, Journal of Virology, Dec. 2005, pp. 14606-14613, vol. 79, No. 23.

Jia et al., "Genetic analysis of West Nile Virus New York 1999 encephalitis virus," The Lancet, Dec. 4, 1999, pp. 1971-1972, vol. 354, No. 9196.

Leibl et al., "Adjuvant/carrier activity of inactivated tick-borne encephalitis virus," Vaccine, 1998, pp. 340-345, vol. 16, No. 4.

Malkinson et al, "Use of Live and Inactivated Vaccines in the Control of West Nile Virus in Domestic Geese," Annals of the New York Academy of Sciences, 2001, pp. 255-261.

Marks et al., By-passing Immunization: Building High Affinity Human Antibodies by Chain Shuffling, Bio/Technology, Jul. 1992, pp. 779-783, vol. 10.

Mehlhop et al., Complement Activation Is Required for Induction of a Protective Antibody Response against West Nile Virus Infection, Journal of Virology, Jun. 2005, pp. 7466-7477, vol. 79, No. 12.

Niedrig et al., Monoclonal Antibodies Directed Against Tick-Borne Encephalitis Virus with Neutralizing Activity In Vivo, Acta virologica, 1994, pp. 141-149, vol. 38.

Nybakken et al., Structural basis of West Nile virus neutralization by a therapeutic antibody, Nature, Sep. 29, 2005, pp. 764-768, vol. 437.

Pau et al., "The human cell line PER.C6 provides a new manufacturing system for the production of influenza vaccines," Vaccine, 2001, pp. 2716-2721, vol. 19.

PCT International Preliminary Examination Report, PCT/EP2003/50806, dated Feb. 17, 2005.

PCT International Preliminary Report on Patentability, PCT/EP2006/063463, dated Sep. 10, 2007, 10 pages.

PCT International Search Report, PCT/EP2003/50806, dated Apr. 26, 2004.

PCT International Search Report, PCT/EP2006/063463, dated Oct. 6, 2006.

Razumov et al., Neutralizing Monoclonal Antibodies Against Russian Strain of the West Nile Virus, Viral Immunolgy, 2005, pp. 558-568, vol. 18, No. 3.

Roehrig et al., Antibody Prophylaxis and Therapy for Flavivirus Encephalitis Infections, Ann. N. Y. Acad. Sci., Dec. 2001, pp. 286-297. vol. 951.

Shen et al., "Early Induction of Interferon-Independent Virus-Specific ICAM-1 (CD54) Expression by Flavivirus in Quiescent but Not Proliferating Fibroblasts—Implications for Virus—Host Interactions," Virology, 1995, pp. 437-449, vol. 208, No. 2.

Shi et al., "Infections cDNA Clone of the Epidemic West Nile Virus from New York City," J. of Virology, Jun. 2002, pp. 5847-5856, vol. 76, No. 12.

Throsby et al., Isolation and Characterization of Human Monoclonal Antibodies from Individuals Infected with West Nile Virus, Journal of Virology, Jul. 2006, pp. 6982-6992, vol. 80, No. 14.

Yamschihikov et al., "An Infectious Clone of the West Nile Flavivirus," Virology, Mar. 15, 2001, pp. 294-304, vol. 281, No. 2.

* cited by examiner

SEQUENCE LISTING

<160> NUMBER OF SEQ ID NOS: 267

<210> SEQ ID NO 1
<211> LENGTH: 13
<212> TYPE: PRT
<213> ORGANISM: Artificial sequence
<220> FEATURE:
<223> OTHER INFORMATION: HCDR3

<400> SEQUENCE: 1

Arg Pro Gly Tyr Asp Tyr Gly Phe Tyr Tyr Phe Asp Tyr
1               5                   10

<210> SEQ ID NO 2
<211> LENGTH: 21
<212> TYPE: PRT
<213> ORGANISM: Artificial sequence
<220> FEATURE:
<223> OTHER INFORMATION: HCDR3

<400> SEQUENCE: 2

Leu Arg Gly Pro Tyr Tyr Asp Phe Trp Asn Gly Tyr Arg Glu Thr His
1               5                   10                  15

Asp Ala Phe Asn Val
            20

<210> SEQ ID NO 3
<211> LENGTH: 21
<212> TYPE: PRT
<213> ORGANISM: Artificial sequence
<220> FEATURE:
<223> OTHER INFORMATION: HCDR3

<400> SEQUENCE: 3

Leu Thr Phe Arg Arg Gly Tyr Ser Gly Ser Asp Ser Phe Leu Pro Pro
1               5                   10                  15

Gly Asp Phe Asp Tyr
            20

<210> SEQ ID NO 4
<211> LENGTH: 16
<212> TYPE: PRT
<213> ORGANISM: Artificial sequence
<220> FEATURE:
<223> OTHER INFORMATION: HCDR3

<400> SEQUENCE: 4

Asp Val Val Gly Val Gly Ala Ser Asp Tyr Tyr Tyr Tyr Met Asp Val
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: HCDR3

<400> SEQUENCE: 5

Glu Ser Gly Gly Pro Ile Trp Tyr Lys Tyr Tyr Gly Val Asp Val
1               5                   10                  15

<210> SEQ ID NO 6
<211> LENGTH: 10
<212> TYPE: PRT

```
<213> ORGANISM: Artificial sequence
<220> FEATURE:
<223> OTHER INFORMATION: HCDR3

<400> SEQUENCE: 6

Gly Tyr Asn Ser Gly His Tyr Phe Asp Tyr
1               5                   10

<210> SEQ ID NO 7
<211> LENGTH: 11
<212> TYPE: PRT
<213> ORGANISM: Artificial sequence
<220> FEATURE:
<223> OTHER INFORMATION: HCDR3

<400> SEQUENCE: 7

Gly Gly Met Ala Thr Thr Pro Gly Leu Asp Tyr
1               5                   10

<210> SEQ ID NO 8
<211> LENGTH: 18
<212> TYPE: PRT
<213> ORGANISM: Artificial sequence
<220> FEATURE:
<223> OTHER INFORMATION: HCDR3

<400> SEQUENCE: 8

Asp Phe Trp Ser Gly Tyr Ser Met Val Asp Ser Tyr Tyr Tyr Tyr Met
1               5                   10                  15

Asp Val

<210> SEQ ID NO 9
<211> LENGTH: 21
<212> TYPE: PRT
<213> ORGANISM: Artificial sequence
<220> FEATURE:
<223> OTHER INFORMATION: HCDR3

<400> SEQUENCE: 9

Leu Arg Gly Pro Tyr Tyr Asp Phe Trp Asn Gly Tyr Arg Glu Thr His
1               5                   10                  15

Asp Ala Phe Asn Val
            20

<210> SEQ ID NO 10
<211> LENGTH: 19
<212> TYPE: PRT
<213> ORGANISM: Artificial sequence
<220> FEATURE:
<223> OTHER INFORMATION: HCDR3

<400> SEQUENCE: 10

His Arg Tyr Tyr Asp Ile Ser Gly Tyr Tyr Arg Leu Phe Ser Asp Ala
1               5                   10                  15

Phe Asp Ile

<210> SEQ ID NO 11
<211> LENGTH: 10
<212> TYPE: PRT
<213> ORGANISM: Artificial sequence
<220> FEATURE:
<223> OTHER INFORMATION: LCDR3

<400> SEQUENCE: 11

Ser Ser Tyr Thr Ser Ser Ser Thr Tyr Val
```

```
                1               5                    10

<210> SEQ ID NO 12
<211> LENGTH: 9
<212> TYPE: PRT
<213> ORGANISM: Artificial sequence
<220> FEATURE:
<223> OTHER INFORMATION: LCDR3

<400> SEQUENCE: 12

Gln Gln Tyr Tyr Ser Thr Pro Pro Thr
1               5

<210> SEQ ID NO 13
<211> LENGTH: 9
<212> TYPE: PRT
<213> ORGANISM: Artificial sequence
<220> FEATURE:
<223> OTHER INFORMATION: LCDR3

<400> SEQUENCE: 13

Gln Gln Tyr Asn Thr Tyr Pro Leu Thr
1               5

<210> SEQ ID NO 14
<211> LENGTH: 10
<212> TYPE: PRT
<213> ORGANISM: Artificial sequence
<220> FEATURE:
<223> OTHER INFORMATION: LCDR3

<400> SEQUENCE: 14

Gln Gln Tyr Asn Asn Trp Pro Pro Ile Thr
1               5                   10

<210> SEQ ID NO 15
<211> LENGTH: 11
<212> TYPE: PRT
<213> ORGANISM: Artificial sequence
<220> FEATURE:
<223> OTHER INFORMATION: LCDR3

<400> SEQUENCE: 15

Ala Ala Trp Asp Asp Thr Leu Ser Ala Trp Val
1               5                   10

<210> SEQ ID NO 16
<211> LENGTH: 11
<212> TYPE: PRT
<213> ORGANISM: Artificial sequence
<220> FEATURE:
<223> OTHER INFORMATION: LCDR3

<400> SEQUENCE: 16

Gly Thr Trp Asp Ser Ser Leu Thr Ala Val Val
1               5                   10

<210> SEQ ID NO 17
<211> LENGTH: 9
<212> TYPE: PRT
<213> ORGANISM: Artificial sequence
<220> FEATURE:
<223> OTHER INFORMATION: LCDR3

<400> SEQUENCE: 17

Gln Gln Tyr Tyr Ser Thr Pro Leu Thr
1               5
```

```
<210> SEQ ID NO 18
<211> LENGTH: 8
<212> TYPE: PRT
<213> ORGANISM: Artificial sequence
<220> FEATURE:
<223> OTHER INFORMATION: LCDR3

<400> SEQUENCE: 18

Gln Gln Tyr Gly Ser Ser Leu Thr
1               5

<210> SEQ ID NO 19
<211> LENGTH: 9
<212> TYPE: PRT
<213> ORGANISM: Artificial sequence
<220> FEATURE:
<223> OTHER INFORMATION: LCDR3

<400> SEQUENCE: 19

Gln Gln Tyr Tyr Asn Thr Pro Ile Thr
1               5

<210> SEQ ID NO 20
<211> LENGTH: 11
<212> TYPE: PRT
<213> ORGANISM: Artificial sequence
<220> FEATURE:
<223> OTHER INFORMATION: LCDR3

<400> SEQUENCE: 20

Gln Ser Tyr Asp Ser Ser Leu Ser Gly Ser Val
1               5                   10

<210> SEQ ID NO 21
<211> LENGTH: 5
<212> TYPE: PRT
<213> ORGANISM: Artificial sequence
<220> FEATURE:
<223> OTHER INFORMATION: HCDR1

<400> SEQUENCE: 21

Asn Tyr Trp Ile Gly
1               5

<210> SEQ ID NO 22
<211> LENGTH: 5
<212> TYPE: PRT
<213> ORGANISM: Artificial sequence
<220> FEATURE:
<223> OTHER INFORMATION: HCDR1

<400> SEQUENCE: 22

Ser Tyr Trp Ile Gly
1               5

<210> SEQ ID NO 23
<211> LENGTH: 5
<212> TYPE: PRT
<213> ORGANISM: Artificial sequence
<220> FEATURE:
<223> OTHER INFORMATION: HCDR1

<400> SEQUENCE: 23

Thr Tyr Trp Ile Gly
1               5
```

```
<210> SEQ ID NO 24
<211> LENGTH: 5
<212> TYPE: PRT
<213> ORGANISM: Artificial sequence
<220> FEATURE:
<223> OTHER INFORMATION: HCDR1

<400> SEQUENCE: 24

Ser Asn Trp Ile Thr
1               5

<210> SEQ ID NO 25
<211> LENGTH: 5
<212> TYPE: PRT
<213> ORGANISM: Artificial sequence
<220> FEATURE:
<223> OTHER INFORMATION: HCDR1

<400> SEQUENCE: 25

Gly Tyr Ala Met His
1               5

<210> SEQ ID NO 26
<211> LENGTH: 5
<212> TYPE: PRT
<213> ORGANISM: Artificial sequence
<220> FEATURE:
<223> OTHER INFORMATION: HCDR1

<400> SEQUENCE: 26

Lys Asp Ala Met His
1               5

<210> SEQ ID NO 27
<211> LENGTH: 5
<212> TYPE: PRT
<213> ORGANISM: Artificial sequence
<220> FEATURE:
<223> OTHER INFORMATION: HCDR1

<400> SEQUENCE: 27

Ser Tyr Ala Ile Ser
1               5

<210> SEQ ID NO 28
<211> LENGTH: 5
<212> TYPE: PRT
<213> ORGANISM: Artificial sequence
<220> FEATURE:
<223> OTHER INFORMATION: HCDR1

<400> SEQUENCE: 28

Asn Tyr Ala Met His
1               5

<210> SEQ ID NO 29
<211> LENGTH: 5
<212> TYPE: PRT
<213> ORGANISM: Artificial sequence
<220> FEATURE:
<223> OTHER INFORMATION: HCDR1

<400> SEQUENCE: 29

Thr Tyr Trp Ile Gly
1               5
```

```
<210> SEQ ID NO 30
<211> LENGTH: 7
<212> TYPE: PRT
<213> ORGANISM: Artificial sequence
<220> FEATURE:
<223> OTHER INFORMATION: HCDR1

<400> SEQUENCE: 30

Thr Ser Gly Val Gly Val Gly
1               5

<210> SEQ ID NO 31
<211> LENGTH: 17
<212> TYPE: PRT
<213> ORGANISM: Artificial sequence
<220> FEATURE:
<223> OTHER INFORMATION: HCDR2

<400> SEQUENCE: 31

Ile Ile Tyr Pro Gly Asp Ser Asp Thr Arg Tyr Ser Pro Ser Val Gln
1               5                   10                  15

Gly

<210> SEQ ID NO 32
<211> LENGTH: 17
<212> TYPE: PRT
<213> ORGANISM: Artificial sequence
<220> FEATURE:
<223> OTHER INFORMATION: HCDR2

<400> SEQUENCE: 32

Ile Ile Tyr Pro Gly Asp Ser Asp Thr Arg Tyr Ser Pro Ser Phe Gln
1               5                   10                  15

Gly

<210> SEQ ID NO 33
<211> LENGTH: 17
<212> TYPE: PRT
<213> ORGANISM: Artificial sequence
<220> FEATURE:
<223> OTHER INFORMATION: HCDR2

<400> SEQUENCE: 33

Ile Ile Tyr Pro Gly Asp Ser Asp Thr Ile Tyr Ser Pro Ser Phe Gln
1               5                   10                  15

Gly

<210> SEQ ID NO 34
<211> LENGTH: 17
<212> TYPE: PRT
<213> ORGANISM: Artificial sequence
<220> FEATURE:
<223> OTHER INFORMATION: HCDR2

<400> SEQUENCE: 34

Arg Ile Asp Pro Ser Asp Ser Tyr Thr Asn Tyr Ser Pro Ser Phe Gln
1               5                   10                  15

Gly

<210> SEQ ID NO 35
<211> LENGTH: 17
<212> TYPE: PRT
<213> ORGANISM: Artificial sequence
<220> FEATURE:
<223> OTHER INFORMATION: HCDR2
```

-continued

```
<400> SEQUENCE: 35

Val Ile Ser Tyr Asp Gly Ser Glu Lys Tyr Ser Ala Asp Ser Val Lys
1               5                   10                  15
Gly

<210> SEQ ID NO 36
<211> LENGTH: 17
<212> TYPE: PRT
<213> ORGANISM: Artificial sequence
<220> FEATURE:
<223> OTHER INFORMATION: HCDR2

<400> SEQUENCE: 36

Val Ile Ser Tyr Asp Gly Ser Asp Lys His Tyr Ala Asp Ser Val Lys
1               5                   10                  15
Gly

<210> SEQ ID NO 37
<211> LENGTH: 14
<212> TYPE: PRT
<213> ORGANISM: Artificial sequence
<220> FEATURE:
<223> OTHER INFORMATION: HCDR2

<400> SEQUENCE: 37

Gly Ile Phe Gly Thr Ala Ser Tyr Ala Gln Lys Phe Gln Gly
1               5                   10

<210> SEQ ID NO 38
<211> LENGTH: 17
<212> TYPE: PRT
<213> ORGANISM: Artificial sequence
<220> FEATURE:
<223> OTHER INFORMATION: HCDR2

<400> SEQUENCE: 38

Val Ile Ser Tyr Asp Gly Gly Asn Lys Tyr Tyr Ala Asp Ser Val Lys
1               5                   10                  15
Gly

<210> SEQ ID NO 39
<211> LENGTH: 17
<212> TYPE: PRT
<213> ORGANISM: Artificial sequence
<220> FEATURE:
<223> OTHER INFORMATION: HCDR2

<400> SEQUENCE: 39

Ile Ile Tyr Pro Ala Asp Ser Asp Thr Arg Tyr Ser Pro Ser Phe Gln
1               5                   10                  15
Gly

<210> SEQ ID NO 40
<211> LENGTH: 16
<212> TYPE: PRT
<213> ORGANISM: Artificial sequence
<220> FEATURE:
<223> OTHER INFORMATION: HCDR2

<400> SEQUENCE: 40

Val Ile Tyr Trp Asn Asp Asp Lys Leu Tyr Arg Pro Ser Leu Lys Ser
1               5                   10                  15
```

```
<210> SEQ ID NO 41
<211> LENGTH: 14
<212> TYPE: PRT
<213> ORGANISM: Artificial sequence
<220> FEATURE:
<223> OTHER INFORMATION: LCDR1

<400> SEQUENCE: 41

Thr Gly Thr Ser Ser Asp Val Gly Gly Tyr Asn Tyr Val Ser
1               5                   10

<210> SEQ ID NO 42
<211> LENGTH: 17
<212> TYPE: PRT
<213> ORGANISM: Artificial sequence
<220> FEATURE:
<223> OTHER INFORMATION: LCDR1

<400> SEQUENCE: 42

Lys Ser Ser Gln Ser Val Leu Tyr Ser Ser Asn Asn Lys Asn Tyr Leu
1               5                   10                  15

Ala

<210> SEQ ID NO 43
<211> LENGTH: 11
<212> TYPE: PRT
<213> ORGANISM: Artificial sequence
<220> FEATURE:
<223> OTHER INFORMATION: LCDR1

<400> SEQUENCE: 43

Arg Ala Ser Gln Ser Ile Ser Ser Trp Leu Ala
1               5                   10

<210> SEQ ID NO 44
<211> LENGTH: 12
<212> TYPE: PRT
<213> ORGANISM: Artificial sequence
<220> FEATURE:
<223> OTHER INFORMATION: LCDR1

<400> SEQUENCE: 44

Arg Thr Ser Gln Ser Val Ser Ser Ser Tyr Leu Gly
1               5                   10

<210> SEQ ID NO 45
<211> LENGTH: 13
<212> TYPE: PRT
<213> ORGANISM: Artificial sequence
<220> FEATURE:
<223> OTHER INFORMATION: LCDR1

<400> SEQUENCE: 45

Ser Gly Ser Ser Ser Asn Ile Gly Asn Tyr Gly Val Asn
1               5                   10

<210> SEQ ID NO 46
<211> LENGTH: 13
<212> TYPE: PRT
<213> ORGANISM: Artificial sequence
<220> FEATURE:
<223> OTHER INFORMATION: LCDR1

<400> SEQUENCE: 46

Ser Gly Thr Ser Ser Asn Ile Gly Asp Asn Tyr Val Ser
1               5                   10
```

```
<210> SEQ ID NO 47
<211> LENGTH: 17
<212> TYPE: PRT
<213> ORGANISM: Artificial sequence
<220> FEATURE:
<223> OTHER INFORMATION: LCDR1

<400> SEQUENCE: 47

Lys Ser Ser Gln Ser Val Leu Tyr Ser Asn Asn Lys Asn Tyr Leu
1               5                   10                  15
Ala

<210> SEQ ID NO 48
<211> LENGTH: 12
<212> TYPE: PRT
<213> ORGANISM: Artificial sequence
<220> FEATURE:
<223> OTHER INFORMATION: LCDR1

<400> SEQUENCE: 48

Arg Ala Ser Gln Ser Val Ser Asn Thr Phe Leu Ala
1               5                   10

<210> SEQ ID NO 49
<211> LENGTH: 17
<212> TYPE: PRT
<213> ORGANISM: Artificial sequence
<220> FEATURE:
<223> OTHER INFORMATION: LCDR1

<400> SEQUENCE: 49

Lys Ser Ser Gln Asn Ile Leu Asp Asn Ser Asp Asn Lys Asn Phe Leu
1               5                   10                  15
Ala

<210> SEQ ID NO 50
<211> LENGTH: 14
<212> TYPE: PRT
<213> ORGANISM: Artificial sequence
<220> FEATURE:
<223> OTHER INFORMATION: LCDR1

<400> SEQUENCE: 50

Thr Gly Ser Ser Ser Asn Ile Gly Ala Gly Tyr Asp Val His
1               5                   10

<210> SEQ ID NO 51
<211> LENGTH: 7
<212> TYPE: PRT
<213> ORGANISM: Artificial sequence
<220> FEATURE:
<223> OTHER INFORMATION: LCDR2

<400> SEQUENCE: 51

Asp Val Ser Asn Arg Pro Leu
1               5

<210> SEQ ID NO 52
<211> LENGTH: 7
<212> TYPE: PRT
<213> ORGANISM: Artificial sequence
<220> FEATURE:
<223> OTHER INFORMATION: LCDR2

<400> SEQUENCE: 52
```

```
Trp Ala Ser Thr Arg Glu Ser
1               5

<210> SEQ ID NO 53
<211> LENGTH: 7
<212> TYPE: PRT
<213> ORGANISM: Artificial sequence
<220> FEATURE:
<223> OTHER INFORMATION: LCDR2

<400> SEQUENCE: 53

Ala Ala Ser Ser Leu Gln Ser
1               5

<210> SEQ ID NO 54
<211> LENGTH: 7
<212> TYPE: PRT
<213> ORGANISM: Artificial sequence
<220> FEATURE:
<223> OTHER INFORMATION: LCDR2

<400> SEQUENCE: 54

Gly Ala Ser Ile Arg Ala Thr
1               5

<210> SEQ ID NO 55
<211> LENGTH: 7
<212> TYPE: PRT
<213> ORGANISM: Artificial sequence
<220> FEATURE:
<223> OTHER INFORMATION: LCDR2

<400> SEQUENCE: 55

Tyr Asp Asp Leu Leu Pro Ser
1               5

<210> SEQ ID NO 56
<211> LENGTH: 7
<212> TYPE: PRT
<213> ORGANISM: Artificial sequence
<220> FEATURE:
<223> OTHER INFORMATION: LCDR2

<400> SEQUENCE: 56

Asp Asn Asn Lys Arg Pro Ser
1               5

<210> SEQ ID NO 57
<211> LENGTH: 7
<212> TYPE: PRT
<213> ORGANISM: Artificial sequence
<220> FEATURE:
<223> OTHER INFORMATION: LCDR2

<400> SEQUENCE: 57

Trp Ala Ser Thr Arg Glu Ser
1               5

<210> SEQ ID NO 58
<211> LENGTH: 7
<212> TYPE: PRT
<213> ORGANISM: Artificial sequence
<220> FEATURE:
<223> OTHER INFORMATION: LCDR2

<400> SEQUENCE: 58
```

```
Gly Ala Ser Ser Arg Ala Thr
1               5

<210> SEQ ID NO 59
<211> LENGTH: 7
<212> TYPE: PRT
<213> ORGANISM: Artificial sequence
<220> FEATURE:
<223> OTHER INFORMATION: LCDR2

<400> SEQUENCE: 59

Trp Ala Ser Ala Arg Glu Ser
1               5

<210> SEQ ID NO 60
<211> LENGTH: 7
<212> TYPE: PRT
<213> ORGANISM: Artificial sequence
<220> FEATURE:
<223> OTHER INFORMATION: LCDR2

<400> SEQUENCE: 60

Gly Asn Ser Asn Arg Pro Ser
1               5

<210> SEQ ID NO 61
<211> LENGTH: 747
<212> TYPE: DNA
<213> ORGANISM: Artificial sequence
<220> FEATURE:
<223> OTHER INFORMATION: SC04-271
<220> FEATURE:
<221> NAME/KEY: CDS
<222> LOCATION: (1)..(747)

<400> SEQUENCE: 61 gag gtg cag ctg gtg gag act gga gca gag gtg aaa aag ccc ggg gag      48
Glu Val Gln Leu Val Glu Thr Gly Ala Glu Val Lys Lys Pro Gly Glu
1               5                   10                  15 tct ctg agg att tcc tgt aag ggt tct gga tac acc ttt aac aat tat      96
Ser Leu Arg Ile Ser Cys Lys Gly Ser Gly Tyr Thr Phe Asn Asn Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc gtc     192
Gly Ile Ile Tyr Pro Gly Asp Ser Asp Thr Arg Tyr Ser Pro Ser Val
    50                  55                  60 caa ggc cac gtc acc atc tca gcc gac aag tcc atc aac acc gcc tac     240
Gln Gly His Val Thr Ile Ser Ala Asp Lys Ser Ile Asn Thr Ala Tyr
65                  70                  75                  80 ctg cag tgg agc agc ctg aag gcc tcg gac acc gcc gtg tat tac tgt     288
Leu Gln Trp Ser Ser Leu Lys Ala Ser Asp Thr Ala Val Tyr Tyr Cys
                85                  90                  95 gcg aga cgg cct gga tac gac tat gga ttt tac tac ttt gac tac tgg     336
Ala Arg Arg Pro Gly Tyr Asp Tyr Gly Phe Tyr Tyr Phe Asp Tyr Trp
            100                 105                 110 ggc cag gga acc ctg gtc acc gtc tcg agc ggt acg ggc ggt tca ggc     384
Gly Gln Gly Thr Leu Val Thr Val Ser Ser Gly Thr Gly Gly Ser Gly
        115                 120                 125 gga acc ggc agc ggc act ggg gga tcg acg cag tct gcc ctg act cag     432
Gly Thr Gly Ser Gly Thr Gly Gly Ser Thr Gln Ser Ala Leu Thr Gln
    130                 135                 140 cct cgc tca gtg tcc ggg tct cct gga cag tca gtc acc atc tcc tgc     480
```

```
Pro Arg Ser Val Ser Gly Ser Pro Gly Gln Ser Val Thr Ile Ser Cys
145                 150                 155                 160 act gga acc agc agt gat gtt ggt ggt tat aac tat gtc tcc tgg tac     528
Thr Gly Thr Ser Ser Asp Val Gly Gly Tyr Asn Tyr Val Ser Trp Tyr
                165                 170                 175 caa cat cac cca ggc aaa gcc ccc aaa ctc atg att tat gat gtc agt     576
Gln His His Pro Gly Lys Ala Pro Lys Leu Met Ile Tyr Asp Val Ser
                180                 185                 190 aat cgg ccc tta ggg gtt tct aat cgc ttc tct ggc tcc aag tct ggc     624
Asn Arg Pro Leu Gly Val Ser Asn Arg Phe Ser Gly Ser Lys Ser Gly
            195                 200                 205 aac acg gcc tcc ctg acc atc tct ggg ctc cag gct gag gac gag gct     672
Asn Thr Ala Ser Leu Thr Ile Ser Gly Leu Gln Ala Glu Asp Glu Ala
    210                 215                 220 gat tat tac tgc agc tca tat aca agc agc agc act tat gtc ttc gga     720
Asp Tyr Tyr Cys Ser Ser Tyr Thr Ser Ser Ser Thr Tyr Val Phe Gly
225                 230                 235                 240 act ggg acc cat ctc acc gtt tta agt                                 747
Thr Gly Thr His Leu Thr Val Leu Ser
                245
```

<210> SEQ ID NO 62
<211> LENGTH: 249
<212> TYPE: PRT
<213> ORGANISM: Artificial sequence
<220> FEATURE:
<223> OTHER INFORMATION: SC04-271

<400> SEQUENCE: 62

```
Glu Val Gln Leu Val Glu Thr Gly Ala Glu Val Lys Lys Pro Gly Glu
1               5                   10                  15

Ser Leu Arg Ile Ser Cys Lys Gly Ser Gly Tyr Thr Phe Asn Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Val
        50                  55                  60

Gln Gly His Val Thr Ile Ser Ala Asp Lys Ser Ile Asn Thr Ala Tyr
65                  70                  75                  80

Leu Gln Trp Ser Ser Leu Lys Ala Ser Asp Thr Ala Val Tyr Tyr Cys
                85                  90                  95

Ala Arg Arg Pro Gly Tyr Asp Tyr Gly Phe Tyr Tyr Phe Asp Tyr Trp
            100                 105                 110

Gly Gln Gly Thr Leu Val Thr Val Ser Ser Gly Thr Gly Gly Ser Gly
        115                 120                 125

Gly Thr Gly Ser Gly Thr Gly Gly Ser Thr Gln Ser Ala Leu Thr Gln
    130                 135                 140

Pro Arg Ser Val Ser Gly Ser Pro Gly Gln Ser Val Thr Ile Ser Cys
145                 150                 155                 160

Thr Gly Thr Ser Ser Asp Val Gly Gly Tyr Asn Tyr Val Ser Trp Tyr
                165                 170                 175

Gln His His Pro Gly Lys Ala Pro Lys Leu Met Ile Tyr Asp Val Ser
            180                 185                 190

Asn Arg Pro Leu Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220
```

```
Asp Tyr Tyr Cys Ser Ser Tyr Thr Ser Ser Thr Tyr Val Phe Gly
225                 230                 235                 240

Thr Gly Thr His Leu Thr Val Leu Ser
                245
```

<210> SEQ ID NO 63
<211> LENGTH: 780
<212> TYPE: DNA
<213> ORGANISM: Artificial sequence
<220> FEATURE:
<223> OTHER INFORMATION: SC04-274
<220> FEATURE:
<221> NAME/KEY: CDS
<222> LOCATION: (1)..(780)

<400> SEQUENCE: 63

```
cag gtc cag ctg gtg cag tct gga gca gag gtg aaa aag ccc ggg gag      48
Gln Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac      96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggc atc atc tat cct ggt gac tct gat acc aga tac agc ccg tcc ttc     192
Gly Ile Ile Tyr Pro Gly Asp Ser Asp Thr Arg Tyr Ser Pro Ser Phe
    50                  55                  60 caa ggc cag gtc acc atc tca gcc gac agg tcc atc agc acc gcc tac     240
Gln Gly Gln Val Thr Ile Ser Ala Asp Arg Ser Ile Ser Thr Ala Tyr
65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga ctc cga ggc ccc tat tac gat ttt tgg aat ggc tat cgg gag     336
Ala Arg Leu Arg Gly Pro Tyr Tyr Asp Phe Trp Asn Gly Tyr Arg Glu
            100                 105                 110 aca cat gat gct ttt aat gtg tgg ggc caa ggg acc acg gtc acc gtc     384
Thr His Asp Ala Phe Asn Val Trp Gly Gln Gly Thr Thr Val Thr Val
        115                 120                 125 tcg agc ggt acg ggc ggt tca ggc gga acc ggc agc ggc act ggc ggg     432
Ser Ser Gly Thr Gly Gly Ser Gly Gly Thr Gly Ser Gly Thr Gly Gly
    130                 135                 140 tcg acg gac atc cag atg acc cag tct cca gac tcc ctg gct gtg tct     480
Ser Thr Asp Ile Gln Met Thr Gln Ser Pro Asp Ser Leu Ala Val Ser
145                 150                 155                 160 ctg ggc gag agg gcc acc atc aac tgc aag tcc agc cag agt gtt tta     528
Leu Gly Glu Arg Ala Thr Ile Asn Cys Lys Ser Ser Gln Ser Val Leu
                165                 170                 175 tac agc tcc aac aat aag aac tac tta gct tgg tac cag cag aaa cca     576
Tyr Ser Ser Asn Asn Lys Asn Tyr Leu Ala Trp Tyr Gln Gln Lys Pro
            180                 185                 190 gga cag cct cct aag ctg ctc att tac tgg gca tct acc cgg gaa tcc     624
Gly Gln Pro Pro Lys Leu Leu Ile Tyr Trp Ala Ser Thr Arg Glu Ser
        195                 200                 205 ggg gtc cct gac cga ttc agt ggc agc ggg tct ggg aca gat ttc act     672
Gly Val Pro Asp Arg Phe Ser Gly Ser Gly Ser Gly Thr Asp Phe Thr
    210                 215                 220 ctc acc atc agc agc ctg cag gct gaa gat gtg gca gtt tat tat tgt     720
Leu Thr Ile Ser Ser Leu Gln Ala Glu Asp Val Ala Val Tyr Tyr Cys
225                 230                 235                 240
```

```
cag caa tat tat agt act cct ccg act ttc ggc gga ggg acc aag gtg      768
Gln Gln Tyr Tyr Ser Thr Pro Pro Thr Phe Gly Gly Gly Thr Lys Val
                245                 250                 255 gag atc aaa cgt                                                      780
Glu Ile Lys Arg
            260
```

<210> SEQ ID NO 64
<211> LENGTH: 260
<212> TYPE: PRT
<213> ORGANISM: Artificial sequence
<220> FEATURE:
<223> OTHER INFORMATION: SC04-274

<400> SEQUENCE: 64

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Arg Gly Pro Tyr Tyr Asp Phe Trp Asn Gly Tyr Arg Glu
            100                 105                 110

Thr His Asp Ala Phe Asn Val Trp Gly Gln Gly Thr Thr Val Thr Val
        115                 120                 125

Ser Ser Gly Thr Gly Gly Ser Gly Gly Thr Gly Ser Gly Thr Gly Gly
    130                 135                 140

Ser Thr Asp Ile Gln Met Thr Gln Ser Pro Asp Ser Leu Ala Val Ser
145                 150                 155                 160

Leu Gly Glu Arg Ala Thr Ile Asn Cys Lys Ser Ser Gln Ser Val Leu
                165                 170                 175

Tyr Ser Ser Asn Asn Lys Asn Tyr Leu Ala Trp Tyr Gln Gln Lys Pro
            180                 185                 190

Gly Gln Pro Pro Lys Leu Leu Ile Tyr Trp Ala Ser Thr Arg Glu Ser
        195                 200                 205

Gly Val Pro Asp Arg Phe Ser Gly Ser Gly Ser Gly Thr Asp Phe Thr
    210                 215                 220

Leu Thr Ile Ser Ser Leu Gln Ala Glu Asp Val Ala Val Tyr Tyr Cys
225                 230                 235                 240

Gln Gln Tyr Tyr Ser Thr Pro Pro Thr Phe Gly Gly Gly Thr Lys Val
                245                 250                 255

Glu Ile Lys Arg
            260
```

<210> SEQ ID NO 65
<211> LENGTH: 762
<212> TYPE: DNA
<213> ORGANISM: Artificial sequence
<220> FEATURE:
<223> OTHER INFORMATION: SC04-283
<220> FEATURE:
<221> NAME/KEY: CDS
<222> LOCATION: (1)..(762)

<400> SEQUENCE: 65

```
gaa gtg cag ctg gtg cag tct gga gca gag gtg aaa aag tcc ggg gag      48
Glu Val Gln Leu Val Gln Ser Gly Ala Glu Val Lys Lys Ser Gly Glu
1               5                   10                  15 tct ctg aag atc tcc tgt aag ggt tct gga tac acc ttt aat acc tac      96
Ser Leu Lys Ile Ser Cys Lys Gly Ser Gly Tyr Thr Phe Asn Thr Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc att tat cct ggt gac tct gat acc ata tac agc ccg tcc ttc     192
Gly Ile Ile Tyr Pro Gly Asp Ser Asp Thr Ile Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg aag gcc tcg gac agc gcc atg tat tac tgt     288
Leu Gln Trp Ser Ser Leu Lys Ala Ser Asp Ser Ala Met Tyr Tyr Cys
                85                  90                  95 gcg aga ctt acc ttt cga cgt gga tat agt ggc tcc gat tcg ttt ctc     336
Ala Arg Leu Thr Phe Arg Arg Gly Tyr Ser Gly Ser Asp Ser Phe Leu
            100                 105                 110 cct ccg ggg gac ttt gac tac tgg ggc cag gga acc ctg gtc acc gtc     384
Pro Pro Gly Asp Phe Asp Tyr Trp Gly Gln Gly Thr Leu Val Thr Val
        115                 120                 125 tcg agc ggt acg ggc ggt tca ggc gga acc ggc agc ggc act ggc ggg     432
Ser Ser Gly Thr Gly Gly Ser Gly Gly Thr Gly Ser Gly Thr Gly Gly
    130                 135                 140 tcg acg gac atc cag atg acc cag tct cct tcc acc ctg tct gca tct     480
Ser Thr Asp Ile Gln Met Thr Gln Ser Pro Ser Thr Leu Ser Ala Ser
145                 150                 155                 160 gta gga gac aga gtc acc atc act tgc cgg gcc agt cag agt att agt     528
Val Gly Asp Arg Val Thr Ile Thr Cys Arg Ala Ser Gln Ser Ile Ser
                165                 170                 175 agc tgg ttg gcc tgg tat cag cag aaa cca ggg aaa gcc cct aat ctc     576
Ser Trp Leu Ala Trp Tyr Gln Gln Lys Pro Gly Lys Ala Pro Asn Leu
            180                 185                 190 ctg atc tat gct gca tcc agt ttg caa agt ggg gtc cca tca agg ttc     624
Leu Ile Tyr Ala Ala Ser Ser Leu Gln Ser Gly Val Pro Ser Arg Phe
        195                 200                 205 agc ggc agt gga tct ggg aca gat ttc act ctc acc atc agc agc ctg     672
Ser Gly Ser Gly Ser Gly Thr Asp Phe Thr Leu Thr Ile Ser Ser Leu
    210                 215                 220 cag cct gat gac tct gca act tat tac tgc caa cag tat aat act tat     720
Gln Pro Asp Asp Ser Ala Thr Tyr Tyr Cys Gln Gln Tyr Asn Thr Tyr
225                 230                 235                 240 ccc ctc act ttc ggc gga ggg acc aag gtg gaa atc aaa cgt             762
Pro Leu Thr Phe Gly Gly Gly Thr Lys Val Glu Ile Lys Arg
                245                 250

<210> SEQ ID NO 66
<211> LENGTH: 254
<212> TYPE: PRT
<213> ORGANISM: Artificial sequence
<220> FEATURE:
<223> OTHER INFORMATION: SC04-283

<400> SEQUENCE: 66

Glu Val Gln Leu Val Gln Ser Gly Ala Glu Val Lys Lys Ser Gly Glu
1               5                   10                  15
```

-continued

```
Ser Leu Lys Ile Ser Cys Lys Gly Ser Gly Tyr Thr Phe Asn Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Ser Ala Met Tyr Tyr Cys
                85                  90                  95

Ala Arg Leu Thr Phe Arg Arg Gly Tyr Ser Gly Ser Asp Ser Phe Leu
            100                 105                 110

Pro Pro Gly Asp Phe Asp Tyr Trp Gly Gln Gly Thr Leu Val Thr Val
        115                 120                 125

Ser Ser Gly Thr Gly Gly Ser Gly Gly Thr Gly Ser Gly Thr Gly Gly
    130                 135                 140

Ser Thr Asp Ile Gln Met Thr Gln Ser Pro Ser Thr Leu Ser Ala Ser
145                 150                 155                 160

Val Gly Asp Arg Val Thr Ile Thr Cys Arg Ala Ser Gln Ser Ile Ser
                165                 170                 175

Ser Trp Leu Ala Trp Tyr Gln Gln Lys Pro Gly Lys Ala Pro Asn Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Asp Asp Ser Ala Thr Tyr Tyr Cys Gln Gln Tyr Asn Thr Tyr
225                 230                 235                 240

Pro Leu Thr Phe Gly Gly Gly Thr Lys Val Glu Ile Lys Arg
                245                 250
```

<210> SEQ ID NO 67
<211> LENGTH: 753
<212> TYPE: DNA
<213> ORGANISM: Artificial sequence
<220> FEATURE:
<223> OTHER INFORMATION: SC04-289
<220> FEATURE:
<221> NAME/KEY: CDS
<222> LOCATION: (1)..(753)

<400> SEQUENCE: 67

```
cag atg cag ctg gtg caa tct gga gca gag gtg aaa aag ccc ggg gag     48
Gln Met Gln Leu Val Gln Ser Gly Ala Glu Val Lys Lys Pro Gly Glu
1               5                   10                  15 tct ctg agg atc tcc tgt aag ggt tct gga tac agc ttt acc agt aac     96
Ser Leu Arg Ile Ser Cys Lys Gly Ser Gly Tyr Ser Phe Thr Ser Asn
            20                  25                  30 tgg atc acc tgg gtg cgc cag atg ccc ggg aaa ggc ctg gag tgg atg    144
Trp Ile Thr Trp Val Arg Gln Met Pro Gly Lys Gly Leu Glu Trp Met
        35                  40                  45 ggg agg att gat cct agt gac tct tat acc aac tac agc ccg tcc ttc    192
Gly Arg Ile Asp Pro Ser Asp Ser Tyr Thr Asn Tyr Ser Pro Ser Phe
    50                  55                  60 caa ggc cac gtc acc atc tca gct gac aag tcc atc agc act gcc tac    240
Gln Gly His Val Thr Ile Ser Ala Asp Lys Ser Ile Ser Thr Ala Tyr
65                  70                  75                  80
```

-continued

```
ctg cag tgg agc agc ctg aag gcc tcg gac acc gcc atg tat tac tgt      288
Leu Gln Trp Ser Ser Leu Lys Ala Ser Asp Thr Ala Met Tyr Tyr Cys
                85                  90                  95 gcg aga gac gta gtt ggg gtg gga gct tcc gac tac tat tac atg          336
Ala Arg Asp Val Val Gly Val Gly Ala Ser Asp Tyr Tyr Tyr Met
                100                 105                 110 gac gtc tgg ggc aaa ggg acc acg gtc acc gtc tcg agc ggt acg ggc      384
Asp Val Trp Gly Lys Gly Thr Thr Val Thr Val Ser Ser Gly Thr Gly
            115                 120                 125 ggt tca ggc gga acc ggc agc ggc act ggg tcg acg gaa att gtg          432
Gly Ser Gly Gly Thr Gly Ser Gly Thr Gly Gly Ser Thr Glu Ile Val
130                 135                 140 ttg acg cag tct cca ggc acc ctg tct ttg tct cca ggg gaa aca gcc      480
Leu Thr Gln Ser Pro Gly Thr Leu Ser Leu Ser Pro Gly Glu Thr Ala
145                 150                 155                 160 acc ctc tcc tgc agg acc agt cag agt gtt agt agc agc tac tta ggc      528
Thr Leu Ser Cys Arg Thr Ser Gln Ser Val Ser Ser Ser Tyr Leu Gly
                165                 170                 175 tgg tac cag cag aaa cct ggc cag gct ccc agg ctc ctc atc tat ggt      576
Trp Tyr Gln Gln Lys Pro Gly Gln Ala Pro Arg Leu Leu Ile Tyr Gly
                180                 185                 190 gca tcc atc agg gcc act ggc atc cca gcc agg ttc agt ggc agt ggg      624
Ala Ser Ile Arg Ala Thr Gly Ile Pro Ala Arg Phe Ser Gly Ser Gly
                195                 200                 205 tct ggg aca gag ttc act ctc acc atc gac agc cta cag tct gaa gat      672
Ser Gly Thr Glu Phe Thr Leu Thr Ile Asp Ser Leu Gln Ser Glu Asp
            210                 215                 220 ttt gca gtt tat tac tgt cag cag tat aat aac tgg cct ccg atc acc      720
Phe Ala Val Tyr Tyr Cys Gln Gln Tyr Asn Asn Trp Pro Pro Ile Thr
225                 230                 235                 240 ttc ggc caa ggg aca cga ctg gag att aaa cgt                          753
Phe Gly Gln Gly Thr Arg Leu Glu Ile Lys Arg
                245                 250
```

<210> SEQ ID NO 68
<211> LENGTH: 251
<212> TYPE: PRT
<213> ORGANISM: Artificial sequence
<220> FEATURE:
<223> OTHER INFORMATION: SC04-289

<400> SEQUENCE: 68

```
Gln Met Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Asn
                20                  25                  30

Trp Ile Thr Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Val Val Gly Val Gly Ala Ser Asp Tyr Tyr Tyr Met
                100                 105                 110

Asp Val Trp Gly Lys Gly Thr Thr Val Thr Val Ser Ser Gly Thr Gly
            115                 120                 125

Gly Ser Gly Gly Thr Gly Ser Gly Thr Gly Gly Ser Thr Glu Ile Val
```

```
              130                 135                 140
Leu Thr Gln Ser Pro Gly Thr Leu Ser Leu Ser Pro Gly Glu Thr Ala
145                 150                 155                 160

Thr Leu Ser Cys Arg Thr Ser Gln Ser Val Ser Ser Ser Tyr Leu Gly
                165                 170                 175

Trp Tyr Gln Gln Lys Pro Gly Gln Ala Pro Arg Leu Leu Ile Tyr Gly
            180                 185                 190

Ala Ser Ile Arg Ala Thr Gly Ile Pro Ala Arg Phe Ser Gly Ser Gly
            195                 200                 205

Ser Gly Thr Glu Phe Thr Leu Thr Ile Asp Ser Leu Gln Ser Glu Asp
        210                 215                 220

Phe Ala Val Tyr Tyr Cys Gln Gln Tyr Asn Asn Trp Pro Pro Ile Thr
225                 230                 235                 240

Phe Gly Gln Gly Thr Arg Leu Glu Ile Lys Arg
                245                 250

<210> SEQ ID NO 69
<211> LENGTH: 753
<212> TYPE: DNA
<213> ORGANISM: Artificial sequence
<220> FEATURE:
<223> OTHER INFORMATION: SC04-299
<220> FEATURE:
<221> NAME/KEY: CDS
<222> LOCATION: (1)..(753)

<400> SEQUENCE: 69 gag gtg cag ctg gtg gag act ggg gga ggc gtg gtc cag cct ggg agg       48
Glu Val Gln Leu Val Glu Thr Gly Gly Gly Val Val Gln Pro Gly Arg
1               5                  10                  15 tcc ctg aga ctc tcc tgt gca gcc tct gga ttc acc ttc agt ggc tat       96
Ser Leu Arg Leu Ser Cys Ala Ala Ser Gly Phe Thr Phe Ser Gly Tyr
            20                  25                  30 gct atg cac tgg gtc cgc cag gct cca ggc aag ggg cta gac tgg gtg      144
Ala Met His Trp Val Arg Gln Ala Pro Gly Lys Gly Leu Asp Trp Val
        35                  40                  45 gca gtt ata tca tat gat gga agt gaa aaa tat tcc gcc gac tct gtg      192
Ala Val Ile Ser Tyr Asp Gly Ser Glu Lys Tyr Ser Ala Asp Ser Val
    50                  55                  60 aag ggc cgg ttc acc atc tcc aga gac aat tcc aag aac acg ctc tat      240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tat tgt      288
Leu Gln Met Asn Ser Leu Arg Ala Glu Asp Thr Ala Val Tyr Tyr Cys
                85                  90                  95 gcg aaa gag tcc ggg gga cct ata tgg tac aag tac tac ggc gtg gac      336
Ala Lys Glu Ser Gly Gly Pro Ile Trp Tyr Lys Tyr Tyr Gly Val Asp
            100                 105                 110 gtc tgg ggc caa ggg acc acg gtc acc gtc tcg agc ggt acg ggc ggt      384
Val Trp Gly Gln Gly Thr Thr Val Thr Val Ser Ser Gly Thr Gly Gly
        115                 120                 125 tca ggc gga acc ggc agc ggc act ggg tcg acg tcc tat gtg ctg          432
Ser Gly Gly Thr Gly Ser Gly Thr Gly Ser Thr Ser Tyr Val Leu
    130                 135                 140 act cag cca ccc tcg ctg tct gca gcc ccc agg cag agg gtc acc atc      480
Thr Gln Pro Pro Ser Leu Ser Ala Ala Pro Arg Gln Arg Val Thr Ile
145                 150                 155                 160 tcc tgt tct gga agc agc tcc aat atc gga aat tat ggt gtg aac tgg      528
Ser Cys Ser Gly Ser Ser Ser Asn Ile Gly Asn Tyr Gly Val Asn Trp
                165                 170                 175
```

```
tac cag cag ctc cca gga aag gct ccc aaa ctc ctc atc tat tat gat      576
Tyr Gln Gln Leu Pro Gly Lys Ala Pro Lys Leu Leu Ile Tyr Tyr Asp
            180                 185                 190 gat ctg ctg ccc tca ggg gtc tct gac cga ttc tct ggc tcc aag tct      624
Asp Leu Leu Pro Ser Gly Val Ser Asp Arg Phe Ser Gly Ser Lys Ser
            195                 200                 205 ggc acc tca gcc tcc ctg gcc atc agt ggg ctc cag tct gag gat gaa      672
Gly Thr Ser Ala Ser Leu Ala Ile Ser Gly Leu Gln Ser Glu Asp Glu
210                 215                 220 ggt gat tat tac tgt gca gcg tgg gat gac acc cta agt gct tgg gtg      720
Gly Asp Tyr Tyr Cys Ala Ala Trp Asp Asp Thr Leu Ser Ala Trp Val
225                 230                 235                 240 ttc ggc gga ggg acc aag ctg acc gtc cta ggt                          753
Phe Gly Gly Gly Thr Lys Leu Thr Val Leu Gly
                245                 250

<210> SEQ ID NO 70
<211> LENGTH: 251
<212> TYPE: PRT
<213> ORGANISM: Artificial sequence
<220> FEATURE:
<223> OTHER INFORMATION: SC04-299

<400> SEQUENCE: 70

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Asp Trp Val
        35                  40                  45

Ala Val Ile Ser Tyr Asp Gly Ser Glu Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Gly Gly Pro Ile Trp Tyr Lys Tyr Gly Val Asp
            100                 105                 110

Val Trp Gly Gln Gly Thr Thr Val Thr Val Ser Ser Gly Thr Gly Gly
        115                 120                 125

Ser Gly Gly Thr Gly Ser Gly Thr Gly Ser Thr Ser Tyr Val Leu
    130                 135                 140

Thr Gln Pro Pro Ser Leu Ser Ala Ala Pro Arg Gln Arg Val Thr Ile
145                 150                 155                 160

Ser Cys Ser Gly Ser Ser Ser Asn Ile Gly Asn Tyr Gly Val Asn Trp
                165                 170                 175

Tyr Gln Gln Leu Pro Gly Lys Ala Pro Lys Leu Leu Ile Tyr Tyr Asp
            180                 185                 190

Asp Leu Leu Pro Ser Gly Val Ser Asp Arg Phe Ser Gly Ser Lys Ser
        195                 200                 205

Gly Thr Ser Ala Ser Leu Ala Ile Ser Gly Leu Gln Ser Glu Asp Glu
    210                 215                 220

Gly Asp Tyr Tyr Cys Ala Ala Trp Asp Asp Thr Leu Ser Ala Trp Val
225                 230                 235                 240

Phe Gly Gly Gly Thr Lys Leu Thr Val Leu Gly
                245                 250
```

<210> SEQ ID NO 71
<211> LENGTH: 738
<212> TYPE: DNA
<213> ORGANISM: Artificial sequence
<220> FEATURE:
<223> OTHER INFORMATION: SC04-311
<220> FEATURE:
<221> NAME/KEY: CDS
<222> LOCATION: (1)..(738)

<400> SEQUENCE: 71

```
gaa gtg cag ctg gtg cag tct ggg gga ggc gtg gtc cag cct ggc agg      48
Glu Val Gln Leu Val Gln Ser Gly Gly Gly Val Val Gln Pro Gly Arg
1               5                   10                  15 tcc ctg aga ctc tcc tgt gta gcc tct gga ttc acc ttc agt aag gac      96
Ser Leu Arg Leu Ser Cys Val Ala Ser Gly Phe Thr Phe Ser Lys Asp
            20                  25                  30 gct atg cac tgg gtc cgc cag gct cca ggc aag ggg cta gag tgg gtg     144
Ala Met His Trp Val Arg Gln Ala Pro Gly Lys Gly Leu Glu Trp Val
        35                  40                  45 gca gtt ata tca tat gat gga agt gat aaa cac tac gca gac tcc gtg     192
Ala Val Ile Ser Tyr Asp Gly Ser Asp Lys His Tyr Ala Asp Ser Val
    50                  55                  60 aag ggc cga gtc acc atc tcc aga gac aat tcc agg aaa acg ctg tat     240
Lys Gly Arg Val Thr Ile Ser Arg Asp Asn Ser Arg Lys Thr Leu Tyr
65                  70                  75                  80 ctg cga atg gac agc ctg aga gct gag gac acg gct cta tat tac tgt     288
Leu Arg Met Asp Ser Leu Arg Ala Glu Asp Thr Ala Leu Tyr Tyr Cys
                85                  90                  95 gcg aga gga tac aac tct ggt cat tac ttt gac tac tgg ggc cag gga     336
Ala Arg Gly Tyr Asn Ser Gly His Tyr Phe Asp Tyr Trp Gly Gln Gly
            100                 105                 110 acc ctg atc acc gtc tcg agc ggt acg ggc ggt tca ggc gga acc ggc     384
Thr Leu Ile Thr Val Ser Ser Gly Thr Gly Gly Ser Gly Gly Thr Gly
        115                 120                 125 agc ggc act ggc ggg tcg acg cag tct gtg ctg acg cag ccg ccc tca     432
Ser Gly Thr Gly Gly Ser Thr Gln Ser Val Leu Thr Gln Pro Pro Ser
    130                 135                 140 gtg tct gcg gcc cca gga cag aag gtc acc atc tcc tgc tct gga acc     480
Val Ser Ala Ala Pro Gly Gln Lys Val Thr Ile Ser Cys Ser Gly Thr
145                 150                 155                 160 agc tcc aat att ggg gat aat tat gta tcc tgg tac cag cac ctc cca     528
Ser Ser Asn Ile Gly Asp Asn Tyr Val Ser Trp Tyr Gln His Leu Pro
                165                 170                 175 gga aca gcc ccc aaa ctc ctc att tat gac aat aat aag cga ccc tca     576
Gly Thr Ala Pro Lys Leu Leu Ile Tyr Asp Asn Asn Lys Arg Pro Ser
            180                 185                 190 ggg att cct gac cga ttc tct ggc tcc aag tct ggc acg tca gcc acc     624
Gly Ile Pro Asp Arg Phe Ser Gly Ser Lys Ser Gly Thr Ser Ala Thr
        195                 200                 205 ctg ggc gtc acc gga ctc cag act ggg gac gag gcc gat tat tac tgc     672
Leu Gly Val Thr Gly Leu Gln Thr Gly Asp Glu Ala Asp Tyr Tyr Cys
    210                 215                 220 gga aca tgg gat agc agc ctg act gct gtg gtc ttc ggc gga ggg acc     720
Gly Thr Trp Asp Ser Ser Leu Thr Ala Val Val Phe Gly Gly Gly Thr
225                 230                 235                 240 aag ctg acc gtc cta ggt                                             738
Lys Leu Thr Val Leu Gly
                245
```

<210> SEQ ID NO 72

```
<211> LENGTH: 246
<212> TYPE: PRT
<213> ORGANISM: Artificial sequence
<220> FEATURE:
<223> OTHER INFORMATION: SC04-311

<400> SEQUENCE: 72

Glu Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Lys Asp
            20                  25                  30

Ala Met His Trp Val Arg Gln Ala Pro Gly Lys Gly Leu Glu Trp Val
        35                  40                  45

Ala Val Ile Ser Tyr Asp Gly Ser Asp Lys His Tyr Ala Asp Ser Val
    50                  55                  60

Lys Gly Arg Val Thr Ile Ser Arg Asp Asn Ser Arg Lys Thr Leu Tyr
65                  70                  75                  80

Leu Arg Met Asp Ser Leu Arg Ala Glu Asp Thr Ala Leu Tyr Tyr Cys
                85                  90                  95

Ala Arg Gly Tyr Asn Ser Gly His Tyr Phe Asp Tyr Trp Gly Gln Gly
            100                 105                 110

Thr Leu Ile Thr Val Ser Ser Gly Thr Gly Gly Ser Gly Gly Thr Gly
        115                 120                 125

Ser Gly Thr Gly Gly Ser Thr Gln Ser Val Leu Thr Gln Pro Pro Ser
    130                 135                 140

Val Ser Ala Ala Pro Gly Gln Lys Val Thr Ile Ser Cys Ser Gly Thr
145                 150                 155                 160

Ser Ser Asn Ile Gly Asp Asn Tyr Val Ser Trp Tyr Gln His Leu Pro
                165                 170                 175

Gly Thr Ala Pro Lys Leu Leu Ile Tyr Asp Asn Asn Lys Arg Pro Ser
            180                 185                 190

Gly Ile Pro Asp Arg Phe Ser Gly Ser Lys Ser Gly Thr Ser Ala Thr
        195                 200                 205

Leu Gly Val Thr Gly Leu Gln Thr Gly Asp Glu Ala Asp Tyr Tyr Cys
    210                 215                 220

Gly Thr Trp Asp Ser Ser Leu Thr Ala Val Val Phe Gly Gly Gly Thr
225                 230                 235                 240

Lys Leu Thr Val Leu Gly
                245

<210> SEQ ID NO 73
<211> LENGTH: 741
<212> TYPE: DNA
<213> ORGANISM: Artificial sequence
<220> FEATURE:
<223> OTHER INFORMATION: SC04-325
<220> FEATURE:
<221> NAME/KEY: CDS
<222> LOCATION: (1)..(741)

<400> SEQUENCE: 73 cag atg cag ctg gtg cag tct ggg gct gag gtg aag aag cct ggg tcc      48
Gln Met Gln Leu Val Gln Ser Gly Ala Glu Val Lys Lys Pro Gly Ser
1               5                   10                  15 tcg gtg aag gtc tcc tgc aag gct tct gga gac acc ttc agc agt tat      96
Ser Val Lys Val Ser Cys Lys Ala Ser Gly Asp Thr Phe Ser Ser Tyr
            20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
```

```
                35                  40                  45
ggg ggg atc ttt ggt aca gca agc tac gca cag aag ttc cag ggc aga      192
Gly Gly Ile Phe Gly Thr Ala Ser Tyr Ala Gln Lys Phe Gln Gly Arg
     50                  55                  60 gtc acg att acc gcg gac gaa tcc acg agc aca gcc tac atg gag ctg      240
Val Thr Ile Thr Ala Asp Glu Ser Thr Ser Thr Ala Tyr Met Glu Leu
 65                  70                  75                  80 agc agc ctg aga tct gag gac acg gcc gtg tat tac tgt gcg aga gga      288
Ser Ser Leu Arg Ser Glu Asp Thr Ala Val Tyr Tyr Cys Ala Arg Gly
                 85                  90                  95 ggg atg gct aca aca ccg gga ctt gac tac tgg ggc cag gga acc ctg      336
Gly Met Ala Thr Thr Pro Gly Leu Asp Tyr Trp Gly Gln Gly Thr Leu
            100                 105                 110 gtc acc gtc tcg agc ggt acg ggc ggt tca ggc gga acc ggc agc ggc      384
Val Thr Val Ser Ser Gly Thr Gly Gly Ser Gly Gly Thr Gly Ser Gly
        115                 120                 125 act ggg ggg tcg acg gac atc cag ttg acc cag tct cca gac tcc ctg      432
Thr Gly Gly Ser Thr Asp Ile Gln Leu Thr Gln Ser Pro Asp Ser Leu
    130                 135                 140 gct gtg tct ctg ggc gag agg gcc acc atc aac tgc aag tcc agc cag      480
Ala Val Ser Leu Gly Glu Arg Ala Thr Ile Asn Cys Lys Ser Ser Gln
145                 150                 155                 160 agt gtt tta tac agc tcc aac aat aag aac tac tta gct tgg tac cag      528
Ser Val Leu Tyr Ser Ser Asn Asn Lys Asn Tyr Leu Ala Trp Tyr Gln
                165                 170                 175 cag aaa cca gga cag cct cct aag ctg ctc att tac tgg gca tct acc      576
Gln Lys Pro Gly Gln Pro Pro Lys Leu Leu Ile Tyr Trp Ala Ser Thr
            180                 185                 190 cgg gaa tcc ggg gtc cct gac cga ttc agt ggc agc ggg tct ggg aca      624
Arg Glu Ser Gly Val Pro Asp Arg Phe Ser Gly Ser Gly Ser Gly Thr
        195                 200                 205 gat ttc act ctc acc atc agc agc ctg cag gct gaa gat gtg gca gtt      672
Asp Phe Thr Leu Thr Ile Ser Ser Leu Gln Ala Glu Asp Val Ala Val
    210                 215                 220 tat tac tgt cag caa tat tat agt acc ccg ttg acg ttc ggc caa ggg      720
Tyr Tyr Cys Gln Gln Tyr Tyr Ser Thr Pro Leu Thr Phe Gly Gln Gly
225                 230                 235                 240 acc aag gtg gag atc aaa cgt                                          741
Thr Lys Val Glu Ile Lys Arg
                245

<210> SEQ ID NO 74
<211> LENGTH: 247
<212> TYPE: PRT
<213> ORGANISM: Artificial sequence
<220> FEATURE:
<223> OTHER INFORMATION: SC04-325

<400> SEQUENCE: 74

Gln Met Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Phe Gly Thr Ala Ser Tyr Ala Gln Lys Phe Gln Gly Arg
    50                  55                  60

Val Thr Ile Thr Ala Asp Glu Ser Thr Ser Thr Ala Tyr Met Glu Leu
65                  70                  75                  80
```

```
Ser Ser Leu Arg Ser Glu Asp Thr Ala Val Tyr Tyr Cys Ala Arg Gly
                85                  90                  95

Gly Met Ala Thr Thr Pro Gly Leu Asp Tyr Trp Gly Gln Gly Thr Leu
            100                 105                 110

Val Thr Val Ser Ser Gly Thr Gly Gly Ser Gly Gly Thr Gly Ser Gly
        115                 120                 125

Thr Gly Gly Ser Thr Asp Ile Gln Leu Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Val Leu Tyr Ser Ser Asn Asn Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Gln Tyr Tyr Ser Thr Pro Leu Thr Phe Gly Gln Gly
225                 230                 235                 240

Thr Lys Val Glu Ile Lys Arg
                245

<210> SEQ ID NO 75
<211> LENGTH: 753
<212> TYPE: DNA
<213> ORGANISM: Artificial sequence
<220> FEATURE:
<223> OTHER INFORMATION: SC04-353
<220> FEATURE:
<221> NAME/KEY: CDS
<222> LOCATION: (1)..(753)

<400> SEQUENCE: 75 gaa gtg cag ctg gtg cag tct ggg gga ggc gtg gtc cag cct ggg agg      48
Glu Val Gln Leu Val Gln Ser Gly Gly Gly Val Val Gln Pro Gly Arg
1               5                   10                  15 tcc ctg aga ctc tcc tgt gca gcc tct gga ttc acc ttc agt aat tat      96
Ser Leu Arg Leu Ser Cys Ala Ala Ser Gly Phe Thr Phe Ser Asn Tyr
            20                  25                  30 gct atg cac tgg gtc cgc cag gct cca ggc aag ggg cta gag tgg gtg     144
Ala Met His Trp Val Arg Gln Ala Pro Gly Lys Gly Leu Glu Trp Val
        35                  40                  45 gca gtt ata tca tat gat gga ggt aat aaa tac tac gca gac tcc gtg     192
Ala Val Ile Ser Tyr Asp Gly Gly Asn Lys Tyr Tyr Ala Asp Ser Val
    50                  55                  60 aag ggc cga ttc acc atg tcc aga gac aat tcc aag aac acg ctg tat     240
Lys Gly Arg Phe Thr Met Ser Arg Asp Asn Ser Lys Asn Thr Leu Tyr
65                  70                  75                  80 ctg caa atg aac agc ctg aga gct gag gac acg gct gtg tat tat tgt     288
Leu Gln Met Asn Ser Leu Arg Ala Glu Asp Thr Ala Val Tyr Tyr Cys
                85                  90                  95 gcg aga gat ttt tgg agt ggt tac tca atg gta gac tcc tac tac tac     336
Ala Arg Asp Phe Trp Ser Gly Tyr Ser Met Val Asp Ser Tyr Tyr Tyr
            100                 105                 110 tac atg gac gtg tgg ggc aag ggg acc acg gtc acc gtc tcg agc ggt     384
Tyr Met Asp Val Trp Gly Lys Gly Thr Thr Val Thr Val Ser Ser Gly
        115                 120                 125 acg ggc ggt tca ggc gga acc ggc agc ggc act ggc ggg tcg acg gaa     432
```

-continued

```
            Thr Gly Gly Ser Gly Gly Thr Gly Ser Gly Thr Gly Gly Ser Thr Glu
                130                 135                 140 acg aca ctc acg cag tcc cca ggc acc ctg tct ttg tct ccc ggg gaa       480
Thr Thr Leu Thr Gln Ser Pro Gly Thr Leu Ser Leu Ser Pro Gly Glu
145                 150                 155                 160 aga gcc acc ctc tcc tgc aga gcc agt cag agt gtt agc aac acc ttc       528
Arg Ala Thr Leu Ser Cys Arg Ala Ser Gln Ser Val Ser Asn Thr Phe
                165                 170                 175 tta gcc tgg tac cag cag aaa cct ggc cag gct ccc agg ctc ctc atc       576
Leu Ala Trp Tyr Gln Gln Lys Pro Gly Gln Ala Pro Arg Leu Leu Ile
            180                 185                 190 tat ggt gca tcc agc agg gcc act ggc atc cca gac agg ttc agt ggc       624
Tyr Gly Ala Ser Ser Arg Ala Thr Gly Ile Pro Asp Arg Phe Ser Gly
        195                 200                 205 agt ggg tct ggg aca gac ttc act ctc acc atc agc aga ctg gag cct       672
Ser Gly Ser Gly Thr Asp Phe Thr Leu Thr Ile Ser Arg Leu Glu Pro
    210                 215                 220 gaa gat ttt gca gcg tat tac tgt cag cag tat ggt agc tcg ctc act       720
Glu Asp Phe Ala Ala Tyr Tyr Cys Gln Gln Tyr Gly Ser Ser Leu Thr
225                 230                 235                 240 ttc ggc cct ggg acc aaa gtg gat atc aaa cgt                           753
Phe Gly Pro Gly Thr Lys Val Asp Ile Lys Arg
                245                 250

<210> SEQ ID NO 76
<211> LENGTH: 251
<212> TYPE: PRT
<213> ORGANISM: Artificial sequence
<220> FEATURE:
<223> OTHER INFORMATION: SC04-353

<400> SEQUENCE: 76

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Trp Ser Gly Tyr Ser Met Val Asp Ser Tyr Tyr Tyr
            100                 105                 110

Tyr Met Asp Val Trp Gly Lys Gly Thr Thr Val Thr Val Ser Ser Gly
        115                 120                 125

Thr Gly Gly Ser Gly Gly Thr Gly Ser Gly Thr Gly Gly Ser Thr Glu
    130                 135                 140

Thr Thr Leu Thr Gln Ser Pro Gly Thr Leu Ser Leu Ser Pro Gly Glu
145                 150                 155                 160

Arg Ala Thr Leu Ser Cys Arg Ala Ser Gln Ser Val Ser Asn Thr Phe
                165                 170                 175

Leu Ala Trp Tyr Gln Gln Lys Pro Gly Gln Ala Pro Arg Leu Leu Ile
            180                 185                 190

Tyr Gly Ala Ser Ser Arg Ala Thr Gly Ile Pro Asp Arg Phe Ser Gly
        195                 200                 205
```

```
Ser Gly Ser Gly Thr Asp Phe Thr Leu Thr Ile Ser Arg Leu Glu Pro
    210                 215                 220

Glu Asp Phe Ala Ala Tyr Tyr Cys Gln Gln Tyr Gly Ser Ser Leu Thr
225                 230                 235                 240

Phe Gly Pro Gly Thr Lys Val Asp Ile Lys Arg
                245                 250

<210> SEQ ID NO 77
<211> LENGTH: 780
<212> TYPE: DNA
<213> ORGANISM: Artificial sequence
<220> FEATURE:
<223> OTHER INFORMATION: SC04-361
<220> FEATURE:
<221> NAME/KEY: CDS
<222> LOCATION: (1)..(780)

<400> SEQUENCE: 77 gag gtc cag ctg gta cag tct gga gca gaa gtg aaa aag ccc ggg gag     48
Glu Val Gln Leu Val Gln Ser Gly Ala Glu Val Lys Lys Pro Gly Glu
1               5                   10                  15 tct ctg aag atc tcc tgt aag gcc tct gga ttc agc ttt agc acc tat    96
Ser Leu Lys Ile Ser Cys Lys Ala Ser Gly Phe Ser Phe Ser Thr Tyr
            20                  25                  30 tgg atc ggc tgg gta cgc cag atg ccc ggg aaa ggc ctg gag tgg atg   144
Trp Ile Gly Trp Val Arg Gln Met Pro Gly Lys Gly Leu Glu Trp Met
        35                  40                  45 ggg atc atc tat cct gct gac tct gat acc aga tac agc ccg tcc ttc   192
Gly Ile Ile Tyr Pro Ala Asp Ser Asp Thr Arg Tyr Ser Pro Ser Phe
    50                  55                  60 caa ggc cag gtc acc atc tca gcc gac aag tcc atc agc acc gcc tac   240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt   288
Leu Gln Trp Ser Ser Leu Lys Ala Ser Asp Thr Ala Met Tyr Tyr Cys
                85                  90                  95 gcg aga ctc cga ggc ccc tat tac gat ttt tgg aat ggc tat cgg gag   336
Ala Arg Leu Arg Gly Pro Tyr Tyr Asp Phe Trp Asn Gly Tyr Arg Glu
            100                 105                 110 aca cat gat gct ttt aat gtg tgg ggc caa ggg aca atg gtc acc gtc   384
Thr His Asp Ala Phe Asn Val Trp Gly Gln Gly Thr Met Val Thr Val
        115                 120                 125 tcg agc ggt acg ggc ggt tca ggc gga acc ggc agc ggc act ggc ggg   432
Ser Ser Gly Thr Gly Gly Ser Gly Gly Thr Gly Ser Gly Thr Gly Gly
    130                 135                 140 tcg acg gat gtt gtg atg act cag tct cca gac tcc ctg gct gtg tct   480
Ser Thr Asp Val Val Met Thr Gln Ser Pro Asp Ser Leu Ala Val Ser
145                 150                 155                 160 ctg ggc gag agg gcc acc atc aac tgc aag tcc agc cag aat att tta   528
Leu Gly Glu Arg Ala Thr Ile Asn Cys Lys Ser Ser Gln Asn Ile Leu
                165                 170                 175 gac aac tcc gac aat aag aac ttc tta gct tgg tac cag cag aaa cca   576
Asp Asn Ser Asp Asn Lys Asn Phe Leu Ala Trp Tyr Gln Gln Lys Pro
            180                 185                 190 gga cag cct cct aaa ttg ctc att tac tgg gca tct gcc cgg gag tcc   624
Gly Gln Pro Pro Lys Leu Leu Ile Tyr Trp Ala Ser Ala Arg Glu Ser
        195                 200                 205 ggg gtc cct gac cga ttc agt ggc agc ggg tct ggg aca gat ttc act   672
Gly Val Pro Asp Arg Phe Ser Gly Ser Gly Ser Gly Thr Asp Phe Thr
    210                 215                 220
```

```
ctc acc atc agc agc ctg cag gct gaa gat gtg gca ctt tat tac tgt    720
Leu Thr Ile Ser Ser Leu Gln Ala Glu Asp Val Ala Leu Tyr Tyr Cys
225                 230                 235                 240 cag caa tat tat aat act ccc atc acc ttc ggt caa ggg aca cga ctg    768
Gln Gln Tyr Tyr Asn Thr Pro Ile Thr Phe Gly Gln Gly Thr Arg Leu
                245                 250                 255 gag att aaa cgt                                                    780
Glu Ile Lys Arg
            260
```

<210> SEQ ID NO 78
<211> LENGTH: 260
<212> TYPE: PRT
<213> ORGANISM: Artificial sequence
<220> FEATURE:
<223> OTHER INFORMATION: SC04-361

<400> SEQUENCE: 78

Glu Val Gln Leu Val Gln Ser Gly Ala Glu Val Lys Lys Pro Gly Glu
1               5                   10                  15

Ser Leu Lys Ile Ser Cys Lys Ala Ser Gly Phe Ser Phe Ser Thr Tyr
            20                  25                  30

Trp Ile Gly Trp Val Arg Gln Met Pro Gly Lys Gly Leu Glu Trp Met
        35                  40                  45

Gly Ile Ile Tyr Pro Ala Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Arg Gly Pro Tyr Tyr Asp Phe Trp Asn Gly Tyr Arg Glu
            100                 105                 110

Thr His Asp Ala Phe Asn Val Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Asp Val Val Met Thr Gln Ser Pro Asp Ser Leu Ala Val Ser
145                 150                 155                 160

Leu Gly Glu Arg Ala Thr Ile Asn Cys Lys Ser Ser Gln Asn Ile Leu
                165                 170                 175

Asp Asn Ser Asp Asn Lys Asn Phe Leu Ala Trp Tyr Gln Gln Lys Pro
            180                 185                 190

Gly Gln Pro Pro Lys Leu Leu Ile Tyr Trp Ala Ser Ala Arg Glu Ser
        195                 200                 205

Gly Val Pro Asp Arg Phe Ser Gly Ser Gly Ser Gly Thr Asp Phe Thr
    210                 215                 220

Leu Thr Ile Ser Ser Leu Gln Ala Glu Asp Val Ala Leu Tyr Tyr Cys
225                 230                 235                 240

Gln Gln Tyr Tyr Asn Thr Pro Ile Thr Phe Gly Gln Gly Thr Arg Leu
                245                 250                 255

Glu Ile Lys Arg
            260

<210> SEQ ID NO 79
<211> LENGTH: 774
<212> TYPE: DNA
<213> ORGANISM: Artificial sequence
<220> FEATURE:

<223> OTHER INFORMATION: SC04-374
<220> FEATURE:
<221> NAME/KEY: CDS
<222> LOCATION: (1)..(774)

<400> SEQUENCE: 79

| | | | | | | | | | | | | | | | | |
|---|---|---|---|---|---|---|---|---|---|---|---|---|---|---|---|---|
| cag | gtc | acc | ttg | aag | gag | tct | ggt | cct | acg | ctg | gtg | aaa | ccc | aca | cag | 48 |
| Gln | Val | Thr | Leu | Lys | Glu | Ser | Gly | Pro | Thr | Leu | Val | Lys | Pro | Thr | Gln | |
| 1 | | | | 5 | | | | | 10 | | | | | 15 | | |
| acc | ctc | acg | ttg | acc | tgc | acc | ttc | tct | ggg | ttc | tca | ctc | agc | act | agt | 96 |
| Thr | Leu | Thr | Leu | Thr | Cys | Thr | Phe | Ser | Gly | Phe | Ser | Leu | Ser | Thr | Ser | |
| | | | 20 | | | | | 25 | | | | | 30 | | | |
| gga | gtg | ggt | gtg | ggc | tgg | atc | cgt | cag | ccc | cca | gga | aag | gcc | ctg | gag | 144 |
| Gly | Val | Gly | Val | Gly | Trp | Ile | Arg | Gln | Pro | Pro | Gly | Lys | Ala | Leu | Glu | |
| | | 35 | | | | | 40 | | | | | 45 | | | | |
| tgg | ctt | gca | gtc | att | tat | tgg | aat | gat | gat | aag | ctc | tac | agg | cca | tct | 192 |
| Trp | Leu | Ala | Val | Ile | Tyr | Trp | Asn | Asp | Asp | Lys | Leu | Tyr | Arg | Pro | Ser | |
| | 50 | | | | | 55 | | | | | 60 | | | | | |
| ctg | aag | agc | agg | ctc | acc | atc | acc | aag | gac | acc | tcc | aaa | aac | cag | gtg | 240 |
| Leu | Lys | Ser | Arg | Leu | Thr | Ile | Thr | Lys | Asp | Thr | Ser | Lys | Asn | Gln | Val | |
| 65 | | | | | 70 | | | | | 75 | | | | | 80 | |
| gtc | ctt | aca | atg | acc | aag | atg | gac | cct | gtg | gac | aca | gcc | aca | tat | tac | 288 |
| Val | Leu | Thr | Met | Thr | Lys | Met | Asp | Pro | Val | Asp | Thr | Ala | Thr | Tyr | Tyr | |
| | | | | 85 | | | | | 90 | | | | | 95 | | |
| tgt | gca | cac | aga | cac | cgt | tac | tat | gat | att | agt | ggt | tat | tac | cgt | ctc | 336 |
| Cys | Ala | His | Arg | His | Arg | Tyr | Tyr | Asp | Ile | Ser | Gly | Tyr | Tyr | Arg | Leu | |
| | | | 100 | | | | | 105 | | | | | 110 | | | |
| ttc | tct | gat | gct | ttt | gat | atc | tgg | ggc | caa | ggg | aca | atg | gtc | acc | gtc | 384 |
| Phe | Ser | Asp | Ala | Phe | Asp | Ile | Trp | Gly | Gln | Gly | Thr | Met | Val | Thr | Val | |
| | | 115 | | | | | 120 | | | | | 125 | | | | |
| tcg | agc | ggt | acg | ggc | ggt | tca | ggc | gga | acc | ggc | agc | ggc | act | ggc | ggg | 432 |
| Ser | Ser | Gly | Thr | Gly | Gly | Ser | Gly | Gly | Thr | Gly | Ser | Gly | Thr | Gly | Gly | |
| | 130 | | | | | 135 | | | | | 140 | | | | | |
| tcg | acg | cag | tct | gtc | gtg | acg | cag | ccg | ccc | tca | gtg | tct | ggg | gcc | cca | 480 |
| Ser | Thr | Gln | Ser | Val | Val | Thr | Gln | Pro | Pro | Ser | Val | Ser | Gly | Ala | Pro | |
| 145 | | | | | 150 | | | | | 155 | | | | | 160 | |
| ggg | cag | agg | gtc | acc | atc | tcc | tgc | act | ggg | agc | agc | tcc | aac | atc | ggg | 528 |
| Gly | Gln | Arg | Val | Thr | Ile | Ser | Cys | Thr | Gly | Ser | Ser | Ser | Asn | Ile | Gly | |
| | | | | 165 | | | | | 170 | | | | | 175 | | |
| gca | ggt | tat | gat | gta | cac | tgg | tac | cag | cag | ctt | cca | gga | aca | gcc | ccc | 576 |
| Ala | Gly | Tyr | Asp | Val | His | Trp | Tyr | Gln | Gln | Leu | Pro | Gly | Thr | Ala | Pro | |
| | | | 180 | | | | | 185 | | | | | 190 | | | |
| aaa | ctc | ctc | atc | tat | ggt | aac | agc | aat | cgg | ccc | tca | ggg | gtc | cct | gac | 624 |
| Lys | Leu | Leu | Ile | Tyr | Gly | Asn | Ser | Asn | Arg | Pro | Ser | Gly | Val | Pro | Asp | |
| | | 195 | | | | | 200 | | | | | 205 | | | | |
| cga | ttc | tct | ggc | tcc | aag | tct | ggc | acc | tca | gcc | tcc | ctg | gcc | atc | act | 672 |
| Arg | Phe | Ser | Gly | Ser | Lys | Ser | Gly | Thr | Ser | Ala | Ser | Leu | Ala | Ile | Thr | |
| | 210 | | | | | 215 | | | | | 220 | | | | | |
| ggg | ctc | cag | gct | gag | gat | gag | gct | gat | tat | tac | tgc | cag | tcc | tat | gac | 720 |
| Gly | Leu | Gln | Ala | Glu | Asp | Glu | Ala | Asp | Tyr | Tyr | Cys | Gln | Ser | Tyr | Asp | |
| 225 | | | | | 230 | | | | | 235 | | | | | 240 | |
| agc | agc | ttg | agt | ggt | tcg | gtg | ttc | ggc | gga | ggg | acc | aag | ctg | acc | gtc | 768 |
| Ser | Ser | Leu | Ser | Gly | Ser | Val | Phe | Gly | Gly | Gly | Thr | Lys | Leu | Thr | Val | |
| | | | | 245 | | | | | 250 | | | | | 255 | | |
| cta | ggt | | | | | | | | | | | | | | | 774 |
| Leu | Gly | | | | | | | | | | | | | | | |

<210> SEQ ID NO 80
<211> LENGTH: 258
<212> TYPE: PRT
<213> ORGANISM: Artificial sequence

```
<220> FEATURE:
<223> OTHER INFORMATION: SC04-374

<400> SEQUENCE: 80
```

| | | | | | | | | | | | | | | |
|---|---|---|---|---|---|---|---|---|---|---|---|---|---|---|
| Gln | Val | Thr | Leu | Lys | Glu | Ser | Gly | Pro | Thr | Leu | Val | Lys | Pro | Thr | Gln |
| 1 | | | | 5 | | | | | 10 | | | | | 15 |
| Thr | Leu | Thr | Leu | Thr | Cys | Thr | Phe | Ser | Gly | Phe | Ser | Leu | Ser | Thr | Ser |
| | | | 20 | | | | | 25 | | | | | 30 | | |
| Gly | Val | Gly | Val | Gly | Trp | Ile | Arg | Gln | Pro | Pro | Gly | Lys | Ala | Leu | Glu |
| | | 35 | | | | | 40 | | | | | 45 | | | |
| Trp | Leu | Ala | Val | Ile | Tyr | Trp | Asn | Asp | Asp | Lys | Leu | Tyr | Arg | Pro | Ser |
| 50 | | | | | 55 | | | | | 60 | | | | | |
| Leu | Lys | Ser | Arg | Leu | Thr | Ile | Thr | Lys | Asp | Thr | Ser | Lys | Asn | Gln | Val |
| 65 | | | | | 70 | | | | | 75 | | | | | 80 |
| Val | Leu | Thr | Met | Thr | Lys | Met | Asp | Pro | Val | Asp | Thr | Ala | Thr | Tyr | Tyr |
| | | | | 85 | | | | | 90 | | | | | 95 | |
| Cys | Ala | His | Arg | His | Arg | Tyr | Tyr | Asp | Ile | Ser | Gly | Tyr | Tyr | Arg | Leu |
| | | | 100 | | | | | 105 | | | | | 110 | | |
| Phe | Ser | Asp | Ala | Phe | Asp | Ile | Trp | Gly | Gln | Gly | Thr | Met | Val | Thr | Val |
| | | 115 | | | | | 120 | | | | | 125 | | | |
| Ser | Ser | Gly | Thr | Gly | Gly | Ser | Gly | Gly | Thr | Gly | Ser | Gly | Thr | Gly | Gly |
| | 130 | | | | | 135 | | | | | 140 | | | | |
| Ser | Thr | Gln | Ser | Val | Val | Thr | Gln | Pro | Pro | Ser | Val | Ser | Gly | Ala | Pro |
| 145 | | | | | 150 | | | | | 155 | | | | | 160 |
| Gly | Gln | Arg | Val | Thr | Ile | Ser | Cys | Thr | Gly | Ser | Ser | Ser | Asn | Ile | Gly |
| | | | | 165 | | | | | 170 | | | | | 175 | |
| Ala | Gly | Tyr | Asp | Val | His | Trp | Tyr | Gln | Gln | Leu | Pro | Gly | Thr | Ala | Pro |
| | | | 180 | | | | | 185 | | | | | 190 | | |
| Lys | Leu | Leu | Ile | Tyr | Gly | Asn | Ser | Asn | Arg | Pro | Ser | Gly | Val | Pro | Asp |
| | | | 195 | | | | | 200 | | | | | 205 | | |
| Arg | Phe | Ser | Gly | Ser | Lys | Ser | Gly | Thr | Ser | Ala | Ser | Leu | Ala | Ile | Thr |
| | 210 | | | | | 215 | | | | | 220 | | | | |
| Gly | Leu | Gln | Ala | Glu | Asp | Glu | Ala | Asp | Tyr | Tyr | Cys | Gln | Ser | Tyr | Asp |
| 225 | | | | | 230 | | | | | 235 | | | | | 240 |
| Ser | Ser | Leu | Ser | Gly | Ser | Val | Phe | Gly | Gly | Gly | Thr | Lys | Leu | Thr | Val |
| | | | | 245 | | | | | 250 | | | | | 255 | |

Leu Gly

```
<210> SEQ ID NO 81
<211> LENGTH: 24
<212> TYPE: DNA
<213> ORGANISM: Artificial sequence
<220> FEATURE:
<223> OTHER INFORMATION: Primer HuCkappa

<400> SEQUENCE: 81
acactctccc ctgttgaagc tctt                                              24

<210> SEQ ID NO 82
<211> LENGTH: 23
<212> TYPE: DNA
<213> ORGANISM: Artificial sequence
<220> FEATURE:
<223> OTHER INFORMATION: Primer HuClambda2

<400> SEQUENCE: 82
tgaacattct gtaggggcca ctg                                               23
```

<210> SEQ ID NO 83
<211> LENGTH: 23
<212> TYPE: DNA
<213> ORGANISM: Artificial sequence
<220> FEATURE:
<223> OTHER INFORMATION: Primer HuClambda7

<400> SEQUENCE: 83
agagcattct gcaggggcca ctg						23

<210> SEQ ID NO 84
<211> LENGTH: 4941
<212> TYPE: DNA
<213> ORGANISM: Artificial sequence
<220> FEATURE:
<223> OTHER INFORMATION: Vector PDV-C06

<400> SEQUENCE: 84

```
aagcttgcat gcaaattcta tttcaaggag acagtcataa tgaaatacct attgcctacg      60
gcagccgctg gattgttatt actcgcggcc cagccggcca tggccgaggt gtttgactaa     120
tggggcgcgc ctcagggaac cctggtcacc gtctcgagcg gtacgggcgg ttcaggcgga     180
accggcagcg gcactggcgg gtcgacggaa attgtgctca cacagtctcc agccaccctg     240
tctttgtctc caggggaaag agccaccctc tcctgcaggg ccagtcagag tgttagcagc     300
tacttagcct ggtaccaaca gaaacctggc caggctccca ggctcctcat ctatgatgca     360
tccaacaggg ccactggcat cccagccagg ttcagtggca gtgggtctgg gacagacttc     420
actctcacca tcagcagcct agagcctgaa gattttgcag tttattactg tcagcagcgt     480
agcaactggc ctccggcttt cggcggaggg accaaggtgg agatcaaacg tgcggccgca     540
catcatcatc accatcacgg ggccgcatat accgatattg aaatgaaccg cctgggcaaa     600
ggggccgcat agactgttga agttgtttta gcaaaacctc atacagaaaa ttcatttact     660
aacgtctgga aagacgacaa acttttagat cgttacgcta actatgaggg ctgtctgtgg     720
aatgctacag gcgttgtggt ttgtactggt gacgaaactc agtgttacgg tacatgggtt     780
cctattgggc ttgctatccc tgaaaatgag ggtggtggct ctgagggtgg cggttctgag     840
ggtggcggtt ctgagggtgg cggtactaaa cctcctgagt acggtgatac acctattccg     900
ggctatactt atatcaaccc tctcgacggc acttatccgc tggtactgag caaaaccccg     960
ctaatcctca tccttctct tgaggagtct cagcctctta atactttcat gtttcagaat    1020
aataggttcc gaaataggca gggtgcatta actgtttata cgggcactgt tactcaaggc    1080
actgaccccg ttaaaactta ttaccagtac actcctgtat catcaaaagc catgtatgac    1140
gcttactgga acggtaaatt cagagactgc gctttccatt ctggctttaa tgaggatcca    1200
ttcgtttgtg aatatcaagg ccaatcgtct gacctgcctc aacctcctgt caatgctggc    1260
ggcggctctg gtggtggttc tggtggcggc tctgagggtg cggctctga gggtggcggt    1320
tctgagggtg cggctctga gggtggcggt tccggtggcg ctccggttc cggtgatttt    1380
gattatgaaa aaatggcaaa cgctaataag ggggctatga ccgaaaatgc cgatgaaaac    1440
gcgctacagt ctgacgctaa aggcaaactt gattctgtcg ctactgatta cggtgctgct    1500
atcgatggtt tcattggtga cgtttccggc cttgctaatg gtaatggtgc tactggtgat    1560
tttgctggct ctaattccca aatggctcaa gtcggtgacg gtgataattc acctttaatg    1620
aataatttcc gtcaatattt accttctttg cctcagtcgg ttgaatgtcg cccttatgtc    1680
tttggcgctg gtaaaccata tgaattttct attgattgtg acaaaataaa cttattccgt    1740
```

```
ggtgtctttg cgtttctttt atatgttgcc acctttatgt atgtattttc gacgtttgct    1800
aacatactgc gtaataagga gtcttaataa gaattcactg gccgtcgttt tacaacgtcg    1860
tgactgggaa aaccctggcg ttacccaact taatcgcctt gcagcacatc cccctttcgc    1920
cagctggcgt aatagcgaag aggcccgcac cgatcgccct tcccaacagt tgcgcagcct    1980
gaatggcgaa tggcgcctga tgcggtattt tctccttacg catctgtgcg gtatttcaca    2040
ccgcatacgt caaagcaacc atagtacgcg ccctgtagcg cgcattaag cgcggcgggt     2100
gtggtggtta cgcgcagcgt gaccgctaca cttgccagcg ccctagcgcc cgctcctttc    2160
gctttcttcc cttcctttct cgccacgttc gccggctttc cccgtcaagc tctaaatcgg    2220
gggctccctt tagggttccg atttagtgct ttacggcacc tcgaccccaa aaaacttgat    2280
ttgggtgatg gttcacgtag tgggccatcg ccctgataga cggtttttcg ccctttgacg    2340
ttggagtcca cgttctttaa tagtggactc ttgttccaaa ctggaacaac actcaaccct    2400
atctcgggct attcttttga tttataaggg attttgccga tttcggccta ttggttaaaa    2460
aatgagctga tttaacaaaa atttaacgcg aattttaaca aaatattaac gtttacaatt    2520
ttatggtgca ctctcagtac aatctgctct gatgccgcat agttaagcca gccccgacac    2580
ccgccaacac ccgctgacgc gccctgacgg gcttgtctgc tcccggcatc cgcttacaga    2640
caagctgtga ccgtctccgg gagctgcatg tgtcagaggt tttcaccgtc atcaccgaaa    2700
cgcgcgagac gaaagggcct cgtgatacgc ctatttttat aggttaatgt catgataata    2760
atggtttctt agacgtcagg tggcactttt cggggaaatg tgcgcggaac ccctatttgt    2820
ttattttct aaatacattc aaatatgtat ccgctcatga caataaccc ctgataaatg     2880
cttcaataat attgaaaaag gaagagtatg agtattcaac atttccgtgt cgcccttatt    2940
ccctttttg cggcattttg ccttcctgtt tttgctcacc cagaaacgct ggtgaaagta     3000
aaagatgctg aagatcagtt gggtgcacga gtgggttaca tcgaactgga tctcaacagc    3060
ggtaagatcc ttgagagttt tcgccccgaa gaacgttttc caatgatgag cacttttaaa    3120
gttctgctat gtggcgcggt attatcccgt attgacgccg ggcaagagca actcggtcgc    3180
cgcatacact attctcagaa tgacttggtt gagtactcac cagtcacaga aaagcatctt    3240
acggatggca tgacagtaag agaattatgc agtgctgcca taaccatgag tgataacact    3300
gcggccaact tacttctgac aacgatcgga ggaccgaagg agctaaccgc ttttttgcac    3360
aacatggggg atcatgtaac tcgccttgat cgttgggaac cggagctgaa tgaagccata    3420
ccaaacgacg agcgtgacac cacgatgcct gtagcaatgg caacaacgtt gcgcaaacta    3480
ttaactggcg aactacttac tctagcttcc cggcaacaat taatagactg gatggaggcg    3540
gataaagttg caggaccact tctgcgctcg gcccttccgg ctggctggtt tattgctgat    3600
aaatctggag ccggtgagcg tgggtctcgc ggtatcattg cagcactggg gccagatggt    3660
aagccctccc gtatcgtagt tatctacacg acggggagtc aggcaactat ggatgaacga    3720
aatagacaga tcgctgagat aggtgcctca ctgattaagc attggtaact gtcagaccaa    3780
gtttactcat atatacttta gattgattta aaacttcatt tttaatttaa aaggatctag    3840
gtgaagatcc tttttgataa tctcatgacc aaaatccctt aacgtgagtt ttcgttccac    3900
tgagcgtcag accccgtaga aaagatcaaa ggatcttctt gagatccttt ttttctgcgc    3960
gtaatctgct gcttgcaaac aaaaaaacca ccgctaccag cggtggtttg tttgccggat    4020
caagagctac caactctttt tccgaaggta actggcttca gcagagcgca gataccaaat    4080
```

```
actgtccttc tagtgtagcc gtagttaggc caccacttca agaactctgt agcaccgcct    4140
acatacctcg ctctgctaat cctgttacca gtggctgctg ccagtggcga taagtcgtgt    4200
cttaccgggt tggactcaag acgatagtta ccggataagg cgcagcggtc gggctgaacg    4260
gggggttcgt gcacacagcc cagcttggag cgaacgacct acaccgaact gagataccta    4320
cagcgtgagc tatgagaaag cgccacgctt cccgaaggga gaaaggcgga caggtatccg    4380
gtaagcggca gggtcggaac aggagagcgc acgagggagc ttccaggggg aaacgcctgg    4440
tatctttata gtcctgtcgg gtttcgccac ctctgacttg agcgtcgatt tttgtgatgc    4500
tcgtcagggg ggcggagcct atggaaaaac gccagcaacg cggccttttt acggttcctg    4560
gccttttgct ggccttttgc tcacatgttc tttcctgcgt tatcccctga ttctgtggat    4620
aaccgtatta ccgcctttga gtgagctgat accgctcgcc gcagccgaac gaccgagcgc    4680
agcgagtcag tgagcgagga gcggaagag cgcccaatac gcaaaccgcc tctccccgcg    4740
cgttggccga ttcattaatg cagctggcac gacaggtttc ccgactggaa agcgggcagt    4800
gagcgcaacg caattaatgt gagttagctc actcattagg caccccaggc tttacacttt    4860
atgcttccgg ctcgtatgtt gtgtggaatt gtgagcggat aacaatttca cacaggaaac    4920
agctatgacc atgattacgc c                                              4941
```

<210> SEQ ID NO 85
<211> LENGTH: 24
<212> TYPE: DNA
<213> ORGANISM: Artificial sequence
<220> FEATURE:
<223> OTHER INFORMATION: Primer HuCIgG

<400> SEQUENCE: 85

```
gtccaccttg gtgttgctgg gctt                                           24
```

<210> SEQ ID NO 86
<211> LENGTH: 669
<212> TYPE: PRT
<213> ORGANISM: West Nile virus

<400> SEQUENCE: 86

```
Met Val Thr Leu Ser Asn Phe Gln Gly Lys Val Met Met Thr Val Asn
1               5                   10                  15

Ala Thr Asp Val Thr Asp Val Ile Thr Ile Pro Thr Ala Ala Gly Lys
            20                  25                  30

Asn Leu Cys Ile Val Arg Ala Met Asp Val Gly Tyr Met Cys Asp Asp
        35                  40                  45

Thr Ile Thr Tyr Glu Cys Pro Val Leu Ser Ala Gly Asn Asp Pro Glu
    50                  55                  60

Asp Ile Asp Cys Trp Cys Thr Lys Ser Ala Val Tyr Val Arg Tyr Gly
65                  70                  75                  80

Arg Cys Thr Lys Thr Arg His Ser Arg Arg Ser Arg Arg Ser Leu Thr
                85                  90                  95

Val Gln Thr His Gly Glu Ser Thr Leu Ala Asn Lys Lys Gly Ala Trp
            100                 105                 110

Met Asp Ser Thr Lys Ala Thr Arg Tyr Leu Val Lys Thr Glu Ser Trp
        115                 120                 125

Ile Leu Arg Asn Pro Gly Tyr Ala Leu Val Ala Ala Val Ile Gly Trp
    130                 135                 140

Met Leu Gly Ser Asn Thr Met Gln Arg Val Val Phe Val Val Leu Leu
145                 150                 155                 160
```

-continued

```
Leu Leu Val Ala Pro Ala Tyr Ser Phe Asn Cys Leu Gly Met Ser Asn
                165                 170                 175
Arg Asp Phe Leu Glu Gly Val Ser Gly Ala Thr Trp Val Asp Leu Val
            180                 185                 190
Leu Glu Gly Asp Ser Cys Val Thr Ile Met Ser Lys Asp Lys Pro Thr
        195                 200                 205
Ile Asp Val Lys Met Met Asn Met Glu Ala Ala Asn Leu Ala Glu Val
    210                 215                 220
Arg Ser Tyr Cys Tyr Leu Ala Thr Val Ser Asp Leu Ser Thr Lys Ala
225                 230                 235                 240
Ala Cys Pro Thr Met Gly Glu Ala His Asn Asp Lys Arg Ala Asp Pro
                245                 250                 255
Ala Phe Val Cys Arg Gln Gly Val Val Asp Arg Gly Trp Gly Asn Gly
            260                 265                 270
Cys Gly Leu Phe Gly Lys Gly Ser Ile Asp Thr Cys Ala Lys Phe Ala
        275                 280                 285
Cys Ser Thr Lys Ala Ile Gly Arg Thr Ile Leu Lys Glu Asn Ile Lys
    290                 295                 300
Tyr Glu Val Ala Ile Phe Val His Gly Pro Thr Thr Val Glu Ser His
305                 310                 315                 320
Gly Asn Tyr Ser Thr Gln Val Gly Ala Thr Gln Ala Gly Arg Phe Ser
                325                 330                 335
Ile Thr Pro Ala Ala Pro Ser Tyr Thr Leu Lys Leu Gly Glu Tyr Gly
            340                 345                 350
Glu Val Thr Val Asp Cys Glu Pro Arg Ser Gly Ile Asp Thr Asn Ala
        355                 360                 365
Tyr Tyr Val Met Thr Val Gly Thr Lys Thr Phe Leu Val His Arg Glu
    370                 375                 380
Trp Phe Met Asp Leu Asn Leu Pro Trp Ser Ser Ala Gly Ser Thr Val
385                 390                 395                 400
Trp Arg Asn Arg Glu Thr Leu Met Glu Phe Glu Glu Pro His Ala Thr
                405                 410                 415
Lys Gln Ser Val Ile Ala Leu Gly Ser Gln Glu Gly Ala Leu His Gln
            420                 425                 430
Ala Leu Ala Gly Ala Ile Pro Val Glu Phe Ser Ser Asn Thr Val Lys
        435                 440                 445
Leu Thr Ser Gly His Leu Lys Cys Arg Val Lys Met Glu Lys Leu Gln
    450                 455                 460
Leu Lys Gly Thr Thr Tyr Gly Val Cys Ser Lys Ala Phe Lys Phe Leu
465                 470                 475                 480
Gly Thr Pro Ala Asp Thr Gly His Gly Thr Val Val Leu Glu Leu Gln
                485                 490                 495
Tyr Thr Gly Thr Asp Gly Pro Cys Lys Val Pro Ile Ser Ser Val Ala
            500                 505                 510
Ser Leu Asn Asp Leu Thr Pro Val Gly Arg Leu Val Thr Val Asn Pro
        515                 520                 525
Phe Val Ser Val Ala Thr Ala Asn Ala Lys Val Leu Ile Glu Leu Glu
    530                 535                 540
Pro Pro Phe Gly Asp Ser Tyr Ile Val Val Gly Arg Gly Glu Gln Gln
545                 550                 555                 560
Ile Asn His His Trp His Lys Ser Gly Ser Ser Ile Gly Lys Ala Phe
                565                 570                 575
```

-continued

```
Thr Thr Thr Leu Lys Gly Ala Gln Arg Leu Ala Ala Leu Gly Asp Thr
            580                 585                 590

Ala Trp Asp Phe Gly Ser Val Gly Gly Val Phe Thr Ser Val Gly Lys
        595                 600                 605

Ala Val His Gln Val Phe Gly Gly Ala Phe Arg Ser Leu Phe Gly Gly
    610                 615                 620

Met Ser Trp Ile Thr Gln Gly Leu Leu Gly Ala Leu Leu Leu Trp Met
625                 630                 635                 640

Gly Ile Asn Ala Arg Asp Arg Ser Ile Ala Leu Thr Phe Leu Ala Val
                645                 650                 655

Gly Gly Val Leu Leu Phe Leu Ser Val Asn Val His Ala
            660                 665

<210> SEQ ID NO 87
<211> LENGTH: 23
<212> TYPE: DNA
<213> ORGANISM: Artificial sequence
<220> FEATURE:
<223> OTHER INFORMATION: Primer CMV-Spe

<400> SEQUENCE: 87
ccatgttgac attgattatt gac                                             23

<210> SEQ ID NO 88
<211> LENGTH: 26
<212> TYPE: DNA
<213> ORGANISM: Artificial sequence
<220> FEATURE:
<223> OTHER INFORMATION: Primer WNV-E-95 REV

<400> SEQUENCE: 88
gctctagact tgccgatgct gctgcc                                          26

<210> SEQ ID NO 89
<211> LENGTH: 40
<212> TYPE: DNA
<213> ORGANISM: Artificial sequence
<220> FEATURE:
<223> OTHER INFORMATION: Primer clefsmaquwnv

<400> SEQUENCE: 89
ggaattcagc atggcccagg tgaccctgag caacttccag                           40

<210> SEQ ID NO 90
<211> LENGTH: 26
<212> TYPE: DNA
<213> ORGANISM: Artificial sequence
<220> FEATURE:
<223> OTHER INFORMATION: Primer reverse WNVmychis

<400> SEQUENCE: 90
gactagtcaa ctcaatggtg atggtg                                          26

<210> SEQ ID NO 91
<211> LENGTH: 6760
<212> TYPE: DNA
<213> ORGANISM: Artificial sequence
<220> FEATURE:
<223> OTHER INFORMATION: Vector pSyn-C18-HCgamma1

<400> SEQUENCE: 91
ctagcaccaa gggccccagc gtgttccccc tggcccccag cagcaagagc accagcggcg     60
gcacagccgc cctgggctgc ctggtgaagg actacttccc cgagcccgtg accgtgagct    120
```

```
ggaacagcgg cgccttgacc agcggcgtgc acaccttccc cgccgtgctg cagagcagcg    180
gcctgtacag cctgagcagc gtggtgaccg tgcccagcag cagcctgggc acccagacct    240
acatctgcaa cgtgaaccac aagcccagca acaccaaggt ggacaaacgc gtggagccca    300
agagctgcga caagacccac acctgccccc cctgccctgc ccccgagctg ctgggcggac    360
cctccgtgtt cctgttcccc cccaagccca aggacaccct catgatcagc cggacccccg    420
aggtgacctg cgtggtggtg gacgtgagcc acgaggaccc cgaggtgaag ttcaactggt    480
acgtggacgg cgtggaggtg cacaacgcca agaccaagcc cgggaggag cagtacaaca    540
gcacctaccg ggtggtgagc gtgctcaccg tgctgcacca ggactggctg aacggcaagg    600
agtacaagtg caaggtgagc aacaaggccc tgcctgcccc catcgagaag accatcagca    660
aggccaaggg ccagccccgg gagcccagg tgtacaccct gcccccagc cgggaggaga    720
tgaccaagaa ccaggtgtcc ctcacctgtc tggtgaaggg cttctacccc agcgacatcg    780
ccgtggagtg ggagagcaac ggccagcccg agaacaacta caagaccacc cccctgtgc    840
tggacagcga cggcagcttc ttcctgtaca gcaagctcac cgtggacaag agccggtggc    900
agcagggcaa cgtgttcagc tgcagcgtga tgcacgaggc cctgcacaac cactacaccc    960
agaagagcct gagcctgagc cccggcaagt gataatctag agggcccgtt taaacccgct   1020
gatcagcctc gactgtgcct tctagttgcc agccatctgt tgtttgcccc tccccgtgc    1080
cttccttgac cctggaaggt gccactccca ctgtcctttc ctaataaaat gaggaaattg   1140
catcgcattg tctgagtagg tgtcattcta ttctgggggg tggggtgggg caggacagca   1200
agggggagga ttgggaagac aatagcaggc atgctgggga tgcggtgggc tctatggctt   1260
ctgaggcgga aagaaccagc tggggctcta ggggtatcc ccacgcgccc tgtagcggcg   1320
cattaagcgc ggcgggtgtg gtggttacgc gcagcgtgac cgctacactt gccagcgccc   1380
tagcgcccgc tcctttcgct ttcttccctt cctttctcgc cacgttcgcc ggctttcccc   1440
gtcaagctct aaatcggggg ctcccttag ggttccgatt tagtgcttta cggcacctcg   1500
accccaaaaa acttgattag ggtgatggtt cacgtagtgg gccatcgccc tgatagacgg   1560
ttttcgccc tttgacgttg gagtccacgt tctttaatag tggactcttg ttccaaactg   1620
gaacaacact caaccctatc tcggtctatt cttttgattt ataagggatt ttgccgattt   1680
cggcctattg gttaaaaaat gagctgattt aacaaaaatt taacgcgaat taattctgtg   1740
gaatgtgtgt cagttagggt gtggaaagtc cccaggctcc ccagcaggca gaagtatgca   1800
aagcatgcat ctcaattagt cagcaaccag gtgtggaaag tccccaggct ccccagcagg   1860
cagaagtatg caaagcatgc atctcaatta gtcagcaacc atagtcccgc ccctaactcc   1920
gcccatcccg cccctaactc cgcccagttc cgcccattct ccgccccatg gctgactaat   1980
ttttttatt tatgcagagg ccgaggccgc ctctgcctct gagctattcc agaagtagtg   2040
aggaggcttt tttggaggcc taggcttttg caaaaagctc ccgggagctt gtatatccat   2100
tttcggatct gatcaagaga caggatgagg atcgtttcgc atgattgaac aagatggatt   2160
gcacgcaggt tctccggccg cttgggtgga gaggctattc ggctatgact gggcacaaca   2220
gacaatcggc tgctctgatg ccgccgtgtt ccggctgtca gcgcaggggc gcccggttct   2280
ttttgtcaag accgacctgt ccggtgccct gaatgaactg caggacgagg cagcgcggct   2340
atcgtggctg gccacgacgg gcgttccttg cgcagctgtg ctcgacgttg tcactgaagc   2400
gggaagggac tggctgctat tgggcgaagt gccggggcag gatctcctgt catctcacct   2460
```

```
tgctcctgcc gagaaagtat ccatcatggc tgatgcaatg cggcggctgc atacgcttga    2520
tccggctacc tgcccattcg accaccaagc gaaacatcgc atcgagcgag cacgtactcg    2580
gatggaagcc ggtcttgtcg atcaggatga tctggacgaa gagcatcagg ggctcgcgcc    2640
agccgaactg ttcgccaggc tcaaggcgcg catgcccgac ggcgaggatc tcgtcgtgac    2700
ccatggcgat gcctgcttgc cgaatatcat ggtggaaaat ggccgctttt ctggattcat    2760
cgactgtggc cggctgggtg tggcggaccg ctatcaggac atagcgttgg ctacccgtga    2820
tattgctgaa gagcttggcg gcgaatgggc tgaccgcttc ctcgtgcttt acggtatcgc    2880
cgctcccgat tcgcagcgca tcgccttcta tcgccttctt gacgagttct tctgagcggg    2940
actctggggt tcgaaatgac cgaccaagcg acgcccaacc tgccatcacg agatttcgat    3000
tccaccgccg ccttctatga aaggttgggc ttcggaatcg ttttccggga cgccggctgg    3060
atgatcctcc agcgcgggga tctcatgctg gagttcttcg cccaccccaa cttgtttatt    3120
gcagcttata atggttacaa ataaagcaat agcatcacaa atttcacaaa taaagcattt    3180
ttttcactgc attctagttg tggtttgtcc aaactcatca atgtatctta tcatgtctgt    3240
ataccgtcga cctctagcta gagcttggcg taatcatggt catagctgtt tcctgtgtga    3300
aattgttatc cgctcacaat tccacacaac atacgagccg aagcataaa gtgtaaagcc    3360 tggggtgcct aatgagtgag ctaactcaca ttaattgcgt tgcgctcact gcccgctttc    3420
cagtcgggaa acctgtcgtg ccagctgcat taatgaatcg gccaacgcgc ggggagaggc    3480
ggtttgcgta ttgggcgctc ttccgcttcc tcgctcactg actcgctgcg ctcggtcgtt    3540
cggctgcggc gagcggtatc agctcactca aaggcggtaa tacggttatc cacagaatca    3600
ggggataacg caggaaagaa catgtgagca aaaggccagc aaaaggccag gaaccgtaaa    3660
aaggccgcgt tgctggcgtt tttccatagg ctccgccccc ctgacgagca tcacaaaaat    3720
cgacgctcaa gtcagaggtg gcgaaacccg acaggactat aaagatacca ggcgtttccc    3780
cctggaagct ccctcgtgcg ctctcctgtt ccgaccctgc cgcttaccgg atacctgtcc    3840
gcctttctcc cttcgggaag cgtggcgctt tctcatagct cacgctgtag gtatctcagt    3900
tcggtgtagg tcgttcgctc caagctgggc tgtgtgcacg aaccccccgt tcagcccgac    3960
cgctgcgcct tatccggtaa ctatcgtctt gagtccaacc cggtaagaca cgacttatcg    4020
ccactggcag cagccactgg taacaggatt agcagagcga ggtatgtagg cggtgctaca    4080
gagttcttga agtggtggcc taactacggc tacactagaa gaacagtatt tggtatctgc    4140
gctctgctga agccagttac cttcggaaaa agagttggta gctcttgatc cggcaaacaa    4200
accaccgctg gtagcggttt ttttgtttgc aagcagcaga ttacgcgcag aaaaaaagga    4260
tctcaagaag atcctttgat cttttctacg gggtctgacg ctcagtggaa cgaaaactca    4320
cgttaaggga ttttggtcat gagattatca aaaaggatct tcacctagat ccttttaaat    4380
taaaaatgaa gttttaaatc aatctaaagt atatatgagt aaacttggtc tgacagttac    4440
caatgcttaa tcagtgaggc acctatctca gcgatctgtc tatttcgttc atccatagtt    4500
gcctgactcc ccgtcgtgta gataactacg atacgggagg gcttaccatc tggccccagt    4560
gctgcaatga taccgcgaga cccacgctca ccggctccag atttatcagc aataaaccag    4620
ccagccggaa gggccgagcg cagaagtggt cctgcaactt tatccgcctc catccagtct    4680
attaattgtt gccgggaagc tagagtaagt agttcgccag ttaatagttt gcgcaacgtt    4740
gttgccattg ctacaggcat cgtggtgtca cgctcgtcgt ttggtatggc ttcattcagc    4800
tccggttccc aacgatcaag gcgagttaca tgatccccca tgttgtgcaa aaaagcggtt    4860
```

```
agctccttcg gtcctccgat cgttgtcaga agtaagttgg ccgcagtgtt atcactcatg    4920
gttatggcag cactgcataa ttctcttact gtcatgccat ccgtaagatg cttttctgtg    4980
actggtgagt actcaaccaa gtcattctga aatagtgta tgcggcgacc gagttgctct    5040
tgcccggcgt caatacggga ataccgcg ccacatagca aactttaaa agtgctcatc    5100 attggaaaac gttcttcggg gcgaaaactc tcaaggatct taccgctgtt gagatccagt    5160
tcgatgtaac ccactcgtgc acccaactga tcttcagcat cttttacttt caccagcgtt    5220
tctgggtgag caaaaacagg aaggcaaaat gccgcaaaaa agggaataag ggcgacacgg    5280
aaatgttgaa tactcatact cttcctttt caatattatt gaagcattta tcagggttat    5340
tgtctcatga gcggatacat atttgaatgt atttagaaaa ataaacaaat aggggttccg    5400
cgcacatttc cccgaaaagt gccacctgac gtcgacggat cgggagatct cccgatcccc    5460
tatggtgcac tctcagtaca atctgctctg atgccgcata gttaagccag tatctgctcc    5520
ctgcttgtgt gttggaggtc gctgagtagt gcgcgagcaa aatttaagct acaacaaggc    5580
aaggcttgac cgacaattgc atgaagaatc tgcttagggt taggcgtttt gcgctgcttc    5640
gctaggtggt caatattggc cattagccat attattcatt ggttatatag cataaatcaa    5700
tattggctat tggccattgc atacgttgta tccatatcat aatatgtaca tttatattgg    5760
ctcatgtcca acattaccgc catgttgaca ttgattattg actagttatt aatagtaatc    5820
aattacgggg tcattagttc atagcccata tatggagttc cgcgttacat aacttacggt    5880
aaatggcccg cctggctgac cgcccaacga ccccgccca ttgacgtcaa taatgacgta    5940
tgttcccata gtaacgccaa tagggacttt ccattgacgt caatgggtgg agtatttacg    6000
gtaaactgcc cacttggcag tacatcaagt gtatcatatg ccaagtacgc ccctattga    6060 cgtcaatgac ggtaaatggc ccgcctggca ttatgcccag tacatgacct tatgggactt    6120
tcctacttgg cagtacatct acgtattagt catcgctatt accatggtga tgcggttttg    6180
gcagtacatc aatgggcgtg atagcggtt tgactcacgg ggatttccaa gtctccaccc    6240
cattgacgtc aatgggagtt tgttttggca ccaaaatcaa cgggactttc caaaatgtcg    6300
taacaactcc gccccattga cgcaaatggg cggtaggcgt gtacggtggg aggtctatat    6360
aagcagagct cgtttagtga accgtcagat cgcctggaga cgccatccac gctgttttga    6420
cctccataga agacaccggg accgatccag cctccgcggc cgggaacggt gcattggaag    6480
ctggcctgga tggcctgact ctcttaggta gccttgcaga agttggtcgt gaggcactgg    6540
gcaggtaagt atcaaggtta caagacaggt ttaaggagat caatagaaac tgggcttgtc    6600
gagacagaga agactcttgc gtttctgata ggcacctatt ggtcttactg acatccactt    6660
tgcctttctc tccacaggtg tccactccca gttcaattac agctcgccac catggcctgc    6720
cccggcttcc tgtgggccct ggtgatcagc acctgcctgg                           6760
```

<210> SEQ ID NO 92
<211> LENGTH: 6267
<212> TYPE: DNA
<213> ORGANISM: Artificial sequence
<220> FEATURE:
<223> OTHER INFORMATION: Vector pSyn-C05-Ckappa

<400> SEQUENCE: 92

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
```

```
cgagcaaaat ttaagctaca acaaggcaag gcttgaccga caattgttaa ttaacatgaa        180
gaatctgctt agggttaggc gttttgcgct gcttcgctag gtggtcaata ttggccatta        240
gccatattat tcattggtta tatagcataa atcaatattg gctattggcc attgcatacg        300
ttgtatccat atcataatat gtacatttat attggctcat gtccaacatt accgccatgt        360
tgacattgat tattgactag ttattaatag taatcaatta cggggtcatt agttcatagc        420
ccatatatgg agttccgcgt tacataactt acggtaaatg gcccgcctgg ctgaccgccc        480
aacgaccccc gcccattgac gtcaataatg acgtatgttc ccatagtaac gccaatalggg        540 actttccatt gacgtcaatg ggtggagtat ttacggtaaa ctgcccactt ggcagtacat        600
caagtgtatc atatgccaag tacgccccct attgacgtca atgacggtaa atggcccgcc        660
tggcattatg cccagtacat gaccttatgg gactttccta cttggcagta catctacgta        720
ttagtcatcg ctattaccat ggtgatgcgg ttttggcagt acatcaatgg gcgtggatag        780
cggtttgact cacggggatt tccaagtctc cacccccattg acgtcaatgg gagtttgttt        840
tggcaccaaa atcaacggga ctttccaaaa tgtcgtaaca actccgcccc attgacgcaa        900
atgggcggta ggcgtgtacg gtgggaggtc tatataagca gagctcgttt agtgaaccgt        960
cagatcgcct ggagacgcca tccacgctgt tttgacctcc atagaagaca ccgggaccga       1020
tccagcctcc gcggccggga acggtgcatt ggaatcgatg actctcttag gtagccttgc       1080
agaagttggt cgtgaggcac tgggcaggta agtatcaagg ttacaagaca ggtttaagga       1140
gatcaataga aactgggctt gtcgagacag agaagactct tgcgtttctg ataggcacct       1200
attggtctta ctgacatcca ctttgccttt ctctccacag gtgtccactc ccagttcaat       1260
tacagctcgc caccatggcc tgccccggct tcctgtgggc cctggtgatc agcacctgcc       1320
tcgagttcag cggccctaag cggaccgtgg ccgctcccag cgtgttcatc ttccccccct       1380
ccgacgagca gctgaagagc ggcaccgcca gcgtggtgtg cctgctgaac aacttctacc       1440
cccgggaggc caaggtgcag tggaaggtgg acaacgccct gcagagcggc aacagccagg       1500
agagcgtgac cgagcaggac agcaaggact ccacctacag cctgagcagc accctcaccc       1560
tgagcaaggc cgactacgag aagcacaagg tgtacgcctg cgaggtgacc caccagggcc       1620
tgagcagccc cgtgaccaag agcttcaacc ggggcgagtg ttaatagact taagtttaaa       1680
ccgctgatca gcctcgactg tgccttctag ttgccagcca tctgttgttt gcccctcccc       1740
cgtgccttcc ttgacccctgg aaggtgccac tcccactgtc ctttcctaat aaaatgagga       1800
aattgcatcg cattgtctga gtaggtgtca ttctattctg ggggtgggg tgggcagga       1860 cagcaagggg gaggattggg aagacaatag caggcatgct ggggatgcgg tgggctctat       1920
ggcttctgag gcggaaagaa ccagctgggg ctctagggga tatccccacg cgccctgtag       1980
cggcgcatta gcgcggcgg gtgtggtggt tacgcgcagc gtgaccgcta cacttgccag       2040
cgccctagcg cccgctcctt tcgctttctt cccttccttt ctcgccacgt tcgccggctt       2100
tccccgtcaa gctctaaatc gggggctccc tttagggttc cgatttagtg ctttacggca       2160
cctcgacccc aaaaaacttg attagggtga tggttcacgt agtgggccat cgccctgata       2220
gacggttttt cgccctttga cgttggagtc cacgttcttt aatagtggac tcttgttcca       2280
aactggaaca cactcaacc ctatctcggt ctattctttt gatttataag gattttggc       2340 catttcggcc tattggttaa aaaatgagct gatttaacaa aaatttaacg cgaattaatt       2400
ctgtggaatg tgtgtcagtt agggtgtgga aagtccccag gctccccagc aggcagaagt       2460
atgcaaagca tgcatctcaa ttagtcagca accaggtgtg gaaagtcccc aggctcccca       2520
```

```
gcaggcagaa gtatgcaaag catgcatctc aattagtcag caaccatagt cccgcccta    2580 actccgccca tcccgcccct aactccgccc agttccgccc attctccgcc ccatggctga    2640
ctaatttttt ttatttatgc agaggccgag gccgcctctg cctctgagct attccagaag    2700
tagtgaggag gcttttttgg aggcctaggc ttttgcaaaa agctcccggg agcttgtata    2760
tccattttcg gatctgatca gcacgtgatg aaaaagcctg aactcaccgc gacgtctgtc    2820
gagaagtttc tgatcgaaaa gttcgacagc gtctccgacc tgatgcagct ctcggagggc    2880
gaagaatctc gtgcttcag cttcgatgta ggagggcgtg gatatgtcct gcgggtaaat    2940
agctgcgccg atggttcta caaagatcgt tatgtttatc ggcactttgc atcggccgcg    3000
ctcccgattc cggaagtgct tgacattggg gaattcagcg agagcctgac ctattgcatc    3060
tcccgccgtg cacagggtgt cacgttgcaa gacctgcctg aaaccgaact gcccgctgtt    3120
ctgcagccgg tcgcggaggc catggatgcg atcgctgcgg ccgatcttag ccagacgagc    3180
gggttcggcc cattcggacc acaaggaatc ggtcaataca ctacatggcg tgatttcata    3240
tgcgcgattg ctgatcccca tgtgtatcac tggcaaactg tgatggacga caccgtcagt    3300
gcgtccgtcg cgcaggctct cgatgagctg atgctttggg ccgaggactg ccccgaagtc    3360
cggcacctcg tgcacgcgga tttcggctcc aacaatgtcc tgacgacaa tggccgcata    3420 acagcggtca ttgactggag cgaggcgatg ttcggggatt cccaatacga ggtcgccaac    3480
atcttcttct ggaggccgtg gttggcttgt atggagcagc agacgcgcta cttcgagcgg    3540
aggcatccgg agcttgcagg atcgccgcg ctccgggcgt atatgctccg cattggtctt    3600
gaccaactct atcagagctt ggttgacggc aatttcgatg atgcagcttg ggcgcagggt    3660
cgatgcgacg caatcgtccg atccggagcc gggactgtcg ggcgtacaca aatcgcccgc    3720
agaagcgcgg ccgtctggac cgatggctgt gtagaagtac tcgccgatag tggaaaccga    3780
cgccccagca ctcgtccgag ggcaaaggaa tagcacgtgc tacgagattt cgattccacc    3840
gccgccttct atgaaaggtt gggcttcgga atcgttttcc gggacgccgg ctggatgatc    3900
ctccagcgcg gggatctcat gctggagttc ttcgcccacc ccaacttgtt tattgcagct    3960
tataatggtt acaaataaag caatagcatc acaaatttca caaataaagc atttttttca    4020
ctgcattcta gttgtggttt gtccaaactc atcaatgtat cttatcatgt ctgtataccg    4080
tcgacctcta gctagagctt ggcgtaatca tggtcatagc tgtttcctgt gtgaaattgt    4140
tatccgctca caattccaca caacatacga gccggaagca taagtgtaa agcctggggt    4200 gcctaatgag tgagctaact cacattaatt gcgttgcgct cactgcccgc tttccagtcg    4260
ggaaacctgt cgtgccagct gcattaatga atcggccaac gcgcggggag aggcggtttg    4320
cgtattgggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgttttcca taggctccgc cccctgacg agcatcacaa aaatcgacgc    4560
tcaagtcaga ggtggcgaaa cccgacagga ctataaagat accaggcgtt tccccctgga    4620
agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
```

```
gcagcagcca ctggtaacag gattagcaga gcgaggtatg taggcggtgc tacagagttc   4920
ttgaagtggt ggcctaacta cggctacact agaagaacag tatttggtat ctgcgctctg   4980
ctgaagccag ttccttcgg aaaaagagtt ggtagctctt gatccggcaa acaaaccacc   5040
gctggtagcg gttttttgt ttgcaagcag cagattacgc gcagaaaaaa aggatctcaa   5100
gaagatcctt tgatctttc tacggggtct gacgctcagt ggaacgaaaa ctcacgttaa   5160
gggattttgg tcatgagatt atcaaaaagg atcttcacct agatcctttt aaattaaaaa   5220
tgaagtttta aatcaatcta agtatatat gagtaaactt ggtctgacag ttaccaatgc   5280
ttaatcagtg aggcacctat ctcagcgatc tgtctatttc gttcatccat agttgcctga   5340
ctccccgtcg tgtagataac tacgatacgg gagggcttac catctggccc cagtgctgca   5400
atgataccgc gagacccacg ctcaccggct ccagatttat cagcaataaa ccagccagcc   5460
ggaagggccg agcgcagaag tggtcctgca actttatccg cctccatcca gtctattaat   5520
tgttgccggg aagctagagt aagtagttcg ccagttaata gtttgcgcaa cgttgttgcc   5580
attgctacag gcatcgtggt gtcacgctcg tcgtttggta tggcttcatt cagctccggt   5640
tcccaacgat caaggcgagt tacatgatcc cccatgttgt gcaaaaaagc ggttagctcc   5700
ttcggtcctc cgatcgttgt cagaagtaag ttggccgcag tgttatcact catggttatg   5760
gcagcactgc ataattctct tactgtcatg ccatccgtaa gatgcttttc tgtgactggt   5820
gagtactcaa ccaagtcatt ctgagaatag tgtatgcggc gaccgagttg ctcttgcccg   5880
gcgtcaatac gggataatac cgcgccacat agcagaactt taaaagtgct catcattgga   5940
aaacgttctt cggggcgaaa actctcaagg atcttaccgc tgttgagatc cagttcgatg   6000
taacccactc gtgcacccaa ctgatcttca gcatctttta ctttcaccag cgtttctggg   6060
tgagcaaaaa caggaaggca aaatgccgca aaaagggaa taagggcgac acggaaatgt   6120
tgaatactca tactcttcct ttttcaatat tattgaagca tttatcaggg ttattgtctc   6180
atgagcggat acatatttga atgtatttag aaaaataaac aaataggggt tccgcgcaca   6240
tttccccgaa aagtgccacc tgacgtc                                      6267
```

<210> SEQ ID NO 93
<211> LENGTH: 6283
<212> TYPE: DNA
<213> ORGANISM: Artificial sequence
<220> FEATURE:
<223> OTHER INFORMATION: Vector pSyn-C04-Clambda

<400> SEQUENCE: 93

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgttaa ttaacatgaa    180
gaatctgctt agggttaggc gttttgcgct gcttcgctag gtggtcaata ttggccatta    240
gccatattat tcattggtta tatagcataa atcaatattg ctattggcc attgcatacg    300 ttgtatccat atcataatat gtacattat attggctcat gtccaacatt accgccatgt    360
tgacattgat tattgactag ttattaatag taatcaatta cggggtcatt agttcatagc    420
ccatatatgg agttccgcgt tacataactt acggtaaatg gcccgcctgg ctgaccgccc    480
aacgaccccc gcccattgac gtcaataatg acgtatgttc ccatagtaac gccaataggg    540
actttccatt gacgtcaatg ggtggagtat ttacggtaaa ctgcccactt ggcagtacat    600
caagtgtatc atatgccaag tacgccccct attgacgtca atgacggtaa atggcccgcc    660
```

```
tggcattatg cccagtacat gaccttatgg gactttccta cttggcagta catctacgta    720
ttagtcatcg ctattaccat ggtgatgcgg ttttggcagt acatcaatgg gcgtggatag    780
cggtttgact cacggggatt ccaagtctc cacccattg acgtcaatgg gagtttgttt     840
tggcaccaaa atcaacggga cttTccaaaa tgtcgtaaca actccgcccc attgacgcaa    900
atgggcggta ggcgtgtacg gtgggaggtc tatataagca gagctcgttt agtgaaccgt    960
cagatcgcct ggagacgcca tccacgctgt tttgacctcc atagaagaca ccgggaccga   1020
tccagcctcc gcggcgggaa acggtgcatt ggaatcgatg actctcttag gtagccttgc   1080
agaagttggt cgtgaggcac tgggcaggta agtatcaagg ttacaagaca ggtttaagga   1140
gatcaataga aactgggctt gtcgagacag agaagactct tgcgtttctg ataggcacct   1200
attggtctta ctgacatcca cttTgccttt ctctccacag gtgtccactc ccagttcaat   1260
tacagctcgc caccatggcc tgccccggct cctgtgggc cctggtgatc agcacctgcc    1320
tcgagatccc cggaccgcgg ccgcaagctt accgtgctgg gccagcccaa ggccgctccc   1380
agcgtgaccc tgttcccccc ctcctccgag gagctgcagg ccaacaaggc caccctggtg   1440
tgcctcatca gcgacttcta ccctggcgcc gtgaccgtgg cctggaaggc cgacagcagc   1500
cccgtgaagg ccggcgtgga gaccaccacc cccagcaagc agagcaacaa caagtacgcc   1560
gccagcagct acctgagcct cacccccgag cagtggaaga gccaccggag ctacagctgc   1620
caggtgaccc acgagggcag caccgtggag aagaccgtgg cccccaccga gtgcagctaa   1680
tagacttaag tttaaaccgc tgatcagcct cgactgtgcc ttctagttgc cagccatctg   1740
ttgtttgccc ctcccccgtg ccttccttga ccctggaagg tgccactccc actgtccttt   1800
cctaataaaa tgaggaaatt gcatcgcatt gtctgagtag gtgtcattct attctggggg   1860
gtggggtggg gcaggacagc aaggggagg attgggaaga caatagcagg catgctgggg   1920
atgcggtggg ctctatggct tctgaggcgg aaagaaccag ctggggctct aggggggtatc   1980 cccacgcgcc ctgtagcggc gcattaagcg cggcgggtgt ggtggttacg cgcagcgtga   2040
ccgctacact tgccagcgcc ctagcgcccg ctcctttcgc tttcttccct tcctttctcg   2100
ccacgttcgc cggctttccc cgtcaagctc taaatcgggg gctcccttta gggttccgat   2160
ttagtgcttt acggcacctc gaccccaaaa aacttgatta gggtgatggt tcacgtagtg   2220
ggccatcgcc ctgatagacg ttttttcgcc ctttgacgtt ggagtccacg ttctttaata   2280
gtggactctt gttccaaact ggaacaacac tcaaccctat ctcggtctat tcttttgatt   2340
tataagggat tttggccatt tcggcctatt ggttaaaaaa tgagctgatt taacaaaaat   2400
ttaacgcgaa ttaattctgt ggaatgtgtg tcagttaggg tgtggaaagt ccccaggctc   2460
cccagcaggc agaagtatgc aaagcatgca tctcaattag tcagcaacca ggtgtggaaa   2520
gtccccaggc tccccagcag gcagaagtat gcaaagcatg catctcaatt agtcagcaac   2580
catagtcccg cccctaactc cgcccatccc gcccctaact ccgcccagtt ccgcccattc   2640
tccgccccat ggctgactaa ttttttttat ttatgcagag gccgaggccg cctctgcctc   2700
tgagctattc cagaagtagt gaggaggctt ttttggaggc ctaggctttt gcaaaaagct   2760
cccgggagct gtatatcca ttttcggatc tgatcagcac gtgatgaaaa agcctgaact    2820
caccgcgacg tctgtcgaga gtttctgat cgaaaagttc gacagcgtct ccgacctgat    2880
gcagctctcg agggcgaag aatctcgtgc tttcagcttc gatgtaggag ggcgtggata    2940
tgtcctgcgg gtaaatagct gcgccgatgg tttctacaaa gatcgttatg tttatcggca   3000
```

```
ctttgcatcg gccgcgctcc cgattccgga agtgcttgac attggggaat tcagcgagag    3060
cctgacctat tgcatctccc gccgtgcaca gggtgtcacg ttgcaagacc tgcctgaaac    3120
cgaactgccc gctgttctgc agccggtcgc ggaggccatg gatgcgatcg ctgcggccga    3180
tcttagccag acgagcgggt tcggcccatt cggaccgcaa ggaatcggtc aatacactac    3240
atggcgtgat ttcatatgcg cgattgctga tccccatgtg tatcactggc aaactgtgat    3300
ggacgacacc gtcagtgcgt ccgtcgcgca ggctctcgat gagctgatgc tttgggccga    3360
ggactgcccc gaagtccggc acctcgtgca cgcggatttc ggctccaaca atgtcctgac    3420
ggacaatggc cgcataacag cggtcattga ctggagcgag gcgatgttcg gggattccca    3480
atacgaggtc gccaacatct tcttctggag gccgtggttg gcttgtatgg agcagcagac    3540
gcgctacttc gagcggaggc atccggagct tgcaggatcg ccgcggctcc gggcgtatat    3600
gctccgcatt ggtcttgacc aactctatca gagcttggtt gacggcaatt cgatgatgc    3660
agcttgggcg cagggtcgat gcgacgcaat cgtccgatcc ggagccggga ctgtcgggcg    3720
tacacaaatc gcccgcagaa gcgcggccgt ctggaccgat ggctgtgtag aagtactcgc    3780
cgatagtgga aaccgacgcc ccagcactcg tccgagggca aaggaatagc acgtgctacg    3840
agatttcgat tccaccgccg ccttctatga aggttgggc ttcggaatcg ttttccggga    3900
cgccggctgg atgatcctcc agcgcgggga tctcatgctg gagttcttcg cccacccccaa    3960
cttgtttatt gcagcttata atggttacaa ataaagcaat agcatcacaa atttcacaaa    4020
taaagcattt ttttcactgc attctagttg tggtttgtcc aaactcatca atgtatctta    4080
tcatgtctgt ataccgtcga cctctagcta gagcttggcg taatcatggt catagctgtt    4140
tcctgtgtga aattgttatc cgctcacaat tccacacaac atacgagccg gaagcataaa    4200
gtgtaaagcc tggggtgcct aatgagtgag ctaactcaca ttaattgcgt tgcgctcact    4260
gcccgctttc cagtcgggaa acctgtcgtg ccagctgcat taatgaatcg ccaacgcgc    4320
ggggagaggc ggtttgcgta ttgggcgctc ttccgcttcc tcgctcactg actcgctgcg    4380
ctcggtcgtt cggctgcggc gagcggtatc agctcactca aaggcggtaa tacggttatc    4440
cacagaatca ggggataacg caggaaagaa catgtgagca aaaggccagc aaaaggccag    4500
gaaccgtaaa aaggccgcgt tgctggcgtt tttccatagg ctccgccccc ctgacgagca    4560
tcacaaaaat cgacgctcaa gtcagaggtg gcgaaacccg acaggactat aaagatacca    4620
ggcgtttccc cctggaagct ccctcgtgcg ctctcctgtt ccgaccctgc cgcttaccgg    4680
atacctgtcc gcctttctcc cttcgggaag cgtggcgctt tctcatagct cacgctgtag    4740
gtatctcagt tcggtgtagg tcgttcgctc caagctgggc tgtgtgcacg aaccccccgt    4800
tcagcccgac cgctgcgcct tatccggtaa ctatcgtctt gagtccaacc cggtaagaca    4860
cgacttatcg ccactggcag cagccactgg taacaggatt agcagagcga ggtatgtagg    4920
cggtgctaca gagttcttga agtggtggcc taactacggc tacactagaa gaacagtatt    4980
tggtatctgc gctctgctga agccagttac cttcggaaaa agagttggta gctcttgatc    5040
cggcaaacaa accaccgctg gtagcggttt ttttgtttgc aagcagcaga ttacgcgcag    5100
aaaaaaagga tctcaagaag atcctttgat cttttctacg gggtctgacg ctcagtggaa    5160
cgaaaactca cgttaaggga ttttggtcat gagattatca aaaaggatct tcacctagat    5220
ccttttaaat taaaaatgaa gttttaaatc aatctaaagt atatatgagt aaacttggtc    5280
tgacagttac caatgcttaa tcagtgaggc acctatctca gcgatctgtc tatttcgttc    5340
atccatagtt gcctgactcc ccgtcgtgta gataactacg atacgggagg gcttaccatc    5400
```

```
tggccccagt gctgcaatga taccgcgaga cccacgctca ccggctccag atttatcagc    5460
aataaaccag ccagccggaa gggccgagcg cagaagtggt cctgcaactt tatccgcctc    5520
catccagtct attaattgtt gccgggaagc tagagtaagt agttcgccag ttaatagttt    5580
gcgcaacgtt gttgccattg ctacaggcat cgtggtgtca cgctcgtcgt ttggtatggc    5640
ttcattcagc tccggttccc aacgatcaag gcgagttaca tgatccccca tgttgtgcaa    5700
aaaagcggtt agctccttcg gtcctccgat cgttgtcaga agtaagttgg ccgcagtgtt    5760
atcactcatg gttatggcag cactgcataa ttctcttact gtcatgccat ccgtaagatg    5820
cttttctgtg actggtgagt actcaaccaa gtcattctga aatagtgta tgcggcgacc     5880 gagttgctct gcccggcgt caatacggga taataccgcg ccacatagca gaactttaaa     5940
agtgctcatc attggaaaac gttcttcggg gcgaaaactc tcaaggatct taccgctgtt    6000
gagatccagt tcgatgtaac ccactcgtgc acccaactga tcttcagcat cttttacttt    6060
caccagcgtt tctgggtgag caaaaacagg aaggcaaaat gccgcaaaaa agggaataag    6120
ggcgacacgg aaatgttgaa tactcatact cttccttttt caatattatt gaagcattta    6180
tcagggttat tgtctcatga gcggatacat atttgaatgt atttagaaaa ataaacaaat    6240
aggggttccg cgcacatttc cccgaaaagt gccacctgac gtc                     6283
```

<210> SEQ ID NO 94
<211> LENGTH: 47
<212> TYPE: DNA
<213> ORGANISM: Artificial sequence
<220> FEATURE:
<223> OTHER INFORMATION: Oligonucleotide 5K-G

<400> SEQUENCE: 94

```
acctgtctcg agttttccat ggctgacatc gtgatgaccc agtctcc              47
```

<210> SEQ ID NO 95
<211> LENGTH: 42
<212> TYPE: DNA
<213> ORGANISM: Artificial sequence
<220> FEATURE:
<223> OTHER INFORMATION: Oligonucleotide sy3K-F

<400> SEQUENCE: 95

```
gctgggggcg gccacggtcc gcttgatctc caccttggtc cc                   42
```

<210> SEQ ID NO 96
<211> LENGTH: 44
<212> TYPE: DNA
<213> ORGANISM: Artificial sequence
<220> FEATURE:
<223> OTHER INFORMATION: Oligonucleotide 5K-B

<400> SEQUENCE: 96

```
acctgtctcg agttttccat ggctgacatc cagatgaccc agtc                 44
```

<210> SEQ ID NO 97
<211> LENGTH: 49
<212> TYPE: DNA
<213> ORGANISM: Artificial sequence
<220> FEATURE:
<223> OTHER INFORMATION: Oligonucleotide 5K-J

<400> SEQUENCE: 97

```
acctgtctcg agttttccat ggctgacatc gtgatgaccc agtctccag            49
```

<210> SEQ ID NO 98
<211> LENGTH: 52
<212> TYPE: DNA
<213> ORGANISM: Artificial sequence
<220> FEATURE:
<223> OTHER INFORMATION: Oligonucleotide 5L-B

<400> SEQUENCE: 98
acctgtctcg agttttccat ggctcagtcc gccctgaccc agccccgctc ag             52

<210> SEQ ID NO 99
<211> LENGTH: 28
<212> TYPE: DNA
<213> ORGANISM: Artificial sequence
<220> FEATURE:
<223> OTHER INFORMATION: Oligonucleotide sy3L-E

<400> SEQUENCE: 99
ccagcacggt aagcttggtc ccagttcc                                         28

<210> SEQ ID NO 100
<211> LENGTH: 44
<212> TYPE: DNA
<213> ORGANISM: Artificial sequence
<220> FEATURE:
<223> OTHER INFORMATION: Oligonucleotide 5L-G

<400> SEQUENCE: 100
acctgtctcg agttttccat ggcttcctac gtgctgactc agcc                       44

<210> SEQ ID NO 101
<211> LENGTH: 28
<212> TYPE: DNA
<213> ORGANISM: Artificial sequence
<220> FEATURE:
<223> OTHER INFORMATION: Oligonucleotide sy3L-Cmod

<400> SEQUENCE: 101
ccagcacggt aagcttggtg cctccgcc                                         28

<210> SEQ ID NO 102
<211> LENGTH: 52
<212> TYPE: DNA
<213> ORGANISM: Artificial sequence
<220> FEATURE:
<223> OTHER INFORMATION: Oligonucleotide 5L-C

<400> SEQUENCE: 102
acctgtctcg agttttccat ggctcagtcc gtgctgaccc agcctccctc ag              52

<210> SEQ ID NO 103
<211> LENGTH: 47
<212> TYPE: DNA
<213> ORGANISM: Artificial sequence
<220> FEATURE:
<223> OTHER INFORMATION: Oligonucleotide 5H-H

<400> SEQUENCE: 103
acctgtcttg aattctccat ggccgaggtg cagctggtgc agtctgg                    47

<210> SEQ ID NO 104
<211> LENGTH: 47
<212> TYPE: DNA
<213> ORGANISM: Artificial sequence
<220> FEATURE:
<223> OTHER INFORMATION: Oligonucleotide sy3H-A -continued

<400> SEQUENCE: 104
gcccttggtg ctagcgctgg agacggtcac cagggtgccc tggcccc    47

<210> SEQ ID NO 105
<211> LENGTH: 47
<212> TYPE: DNA
<213> ORGANISM: Artificial sequence
<220> FEATURE:
<223> OTHER INFORMATION: Oligonucleotide sy3H-C

<400> SEQUENCE: 105
gcccttggtg ctagcgctgg agacggtcac ggtggtgccc tggcccc    47

<210> SEQ ID NO 106
<211> LENGTH: 47
<212> TYPE: DNA
<213> ORGANISM: Artificial sequence
<220> FEATURE:
<223> OTHER INFORMATION: Oligonucleotide 5H-C

<400> SEQUENCE: 106
acctgtcttg aattctccat ggcccaggtg cagctggtgg agtctgg    47

<210> SEQ ID NO 107
<211> LENGTH: 47
<212> TYPE: DNA
<213> ORGANISM: Artificial sequence
<220> FEATURE:
<223> OTHER INFORMATION: Oligonucleotide 5H-A

<400> SEQUENCE: 107
acctgtcttg aattctccat ggcccaggtg cagctggtgc agtctgg    47

<210> SEQ ID NO 108
<211> LENGTH: 47
<212> TYPE: DNA
<213> ORGANISM: Artificial sequence
<220> FEATURE:
<223> OTHER INFORMATION: Oligonucleotide 5H-N

<400> SEQUENCE: 108
acctgtcttg aattctccat ggcccagatc accttgaagg agtctgg    47

<210> SEQ ID NO 109
<211> LENGTH: 47
<212> TYPE: DNA
<213> ORGANISM: Artificial sequence
<220> FEATURE:
<223> OTHER INFORMATION: Oligonucleotide sy3H-D

<400> SEQUENCE: 109
gcccttggtg ctagcgctgg acacggtcac catggtgccc tggcccc    47

<210> SEQ ID NO 110
<211> LENGTH: 10515
<212> TYPE: DNA
<213> ORGANISM: Artificial sequence
<220> FEATURE:
<223> OTHER INFORMATION: pIg-C911-HCgamma1
<220> FEATURE:
<221> NAME/KEY: misc_feature
<222> LOCATION: (1326)..(5076)
<223> OTHER INFORMATION: Stuffer

<400> SEQUENCE: 110

```
tcgacggatc gggagatctc ccgatcccct atggtgcact ctcagtacaa tctgctctga    60
tgccgcatag ttaagccagt atctgctccc tgcttgtgtg ttggaggtcg ctgagtagtg   120
cgcgagcaaa atttaagcta caacaaggca aggcttgacc gacaattgca tgaagaatct   180
gcttagggtt aggcgttttg cgctgcttcg ctaggtggtc aatattggcc attagccata   240
ttattcattg gttatatagc ataaatcaat attggctatt ggccattgca tacgttgtat   300
ccatatcata atatgtacat ttatattggc tcatgtccaa cattaccgcc atgttgacat   360
tgattattga ctagttatta atagtaatca attacggggt cattagttca tagcccatat   420
atggagttcc gcgttacata acttacggta aatggcccgc ctggctgacc gcccaacgac   480
ccccgcccat tgacgtcaat aatgacgtat gttcccatag taacgccaat agggactttc   540
cattgacgtc aatgggtgga gtatttacgg taaactgccc acttggcagt acatcaagtg   600
tatcatatgc caagtacgcc ccctattgac gtcaatgacg gtaaatggcc cgcctggcat   660
tatgcccagt acatgacctt atgggacttt cctacttggc agtacatcta cgtattagtc   720
atcgctatta ccatggtgat gcggttttgg cagtacatca atgggcgtgg atagcggttt   780
gactcacggg gatttccaag tctccacccc attgacgtca atgggagttt gttttggcac   840
caaaatcaac gggactttcc aaaatgtcgt aacaactccg ccccattgac gcaaatgggc   900
ggtaggcgtg tacggtggga ggtctatata agcagagctc gtttagtgaa ccgtcagatc   960
gcctggagac gccatccacg ctgttttgac ctccatagaa gacaccggga ccgatccagc  1020
ctccgcggcc gggaacggtg cattggaagc tgcctggat atcctgactc tcttaggtag  1080
ccttgcagaa gttggtcgtg aggcactggg caggtaagta tcaaggttac aagacaggtt  1140
taaggagatc aatagaaact gggcttgtcg agacagagaa gactcttgcg tttctgatag  1200
gcacctattg gtcttactga catccacttt gcctttctct ccacaggtgt ccactcccag  1260
ttcaattaca gctcgccacc atgggatgga gctgtatcat cctcttcttg gtactgctgc  1320
tggcccagcc ggccagtgac cttgaccggt gcaccacttt tgatgatgtt caagctccta  1380
attacactca acatacttca tctatgaggg gggtttacta tcctgatgaa attttttagat  1440
cggacactct ttatttaact caggatttat ttcttccatt ttattctaat gttacagggt  1500
ttcatactat taatcatacg tttggcaacc ctgtcatacc ttttaaggat ggtatttatt  1560
ttgctgccac agagaaatca aatgttgtcc gtggttgggt ttttggttct accatgaaca  1620
acaagtcaca gtcggtgatt attattaaca attctactaa tgttgttata cgagcatgta  1680
actttgaatt gtgtgacaac cctttctttg ctgtttctaa acccatgggt acacagacac  1740
atactatgat attcgataat gcatttaatt gcactttcga gtacatatct gatgcctttt  1800
cgcttgatgt ttcagaaaag tcaggtaatt ttaaacactt acgagagttt gtgtttaaaa  1860
ataaagatgg gtttctctat gtttataagg gctatcaacc tatagatgta gttcgtgatc  1920
taccttctgg ttttaacact ttgaaaccta ttttaagtt gcctcttggt attaacatta  1980
caaattttag agccattctt acagccttt cacctgctca agacatttgg ggcacgtcag  2040
ctgcagccta ttttgttggc tatttaaagc caactacatt tatgctcaag tatgatgaaa  2100
atggtacaat cacagatgct gttgattgtt ctcaaaatcc acttgctgaa ctcaaatgct  2160
ctgttaagag ctttgagatt gacaaaggaa tttaccagt ctctaatttc agggttgttc  2220
cctcaggaga tgttgtgaga ttccctaata ttacaaactt gtgtccttt ggagaggttt  2280
ttaatgctac taaattccct tctgtctatg catgggagag aaaaaaatt tctaattgtg  2340
ttgctgatta ctctgtgctc tacaactcaa cattttttc aacctttaag tgctatggcg  2400
```

```
tttctgccac taagttgaat gatctttgct tctccaatgt ctatgcagat tcttttgtag    2460
tcaagggaga tgatgtaaga caaatagcgc caggacaaac tggtgttatt gctgattata    2520
attataaatt gccagatgat ttcatgggtt gtgtccttgc ttggaatact aggaacattg    2580
atgctacttc aactggtaat tataattata aatataggta tcttagacat ggcaagctta    2640 ggcccttttga gagagacata tctaatgtgc ctttctcccc tgatggcaaa ccttgcaccc    2700
cacctgctct taattgttat tggccattaa atgattatgg ttttttacacc actactggca    2760 ttggctacca accttacaga gttgtagtac tttcttttga acttttaaat gcaccggcca    2820
cggtttgtgg accaaaatta tccactgacc ttattaagaa ccagtgtgtc aattttaatt    2880
ttaatggact cactggtact ggtgtgttaa ctccttcttc aaagagattt caaccatttc    2940
aacaatttgg ccgtgatgtt tctgatttca ctgattccgt tcgagatcct aaaacatctg    3000
aaatattaga catttcacct tgctcttttg ggggtgtaag tgtaattaca cctggaacaa    3060
atgcttcatc tgaagttgct gttctatatc aagatgttaa ctgcactgat gtttctacag    3120
caattcatgc agatcaactc acaccagctt ggcgcatata ttctactgga acaatgtat    3180 tccagactca ggcaggctgt cttataggag ctgagcatgt cgacacttct tatgagtgcg    3240
acattcctat tggagctggc atttgtgcta gttaccatac agtttcttta ttacgtagta    3300
ctagccaaaa atctattgtg gcttatacta tgtctttagg tgctgatagt tcaattgctt    3360
actctaataa caccattgct atacctacta acttttcaat tagcattact acagaagtaa    3420
tgcctgtttc tatggctaaa acctccgtag attgtaatat gtacatctgc ggagattcta    3480
ctgaatgtgc taatttgctt ctccaatatg gtagcttttg cacacaacta aatcgtgcac    3540
tctcaggtat tgctgctgaa caggatcgca acacacgtga agtgttcgct caagtcaaac    3600
aaatgtacaa acccccaact ttgaaatatt ttggtggttt taattttttca caaatattac    3660 ctgaccctct aaagccaact aagaggtctt ttattgagga cttgctcttt aataaggtga    3720
cactcgctga tgctggcttc atgaagcaat atggcgaatg cctaggtgat attaatgcta    3780
gagatctcat ttgtgcgcag aagttcaatg gacttacagt gttgccacct ctgctcactg    3840
atgatatgat tgctgcctac actgctgctc tagttagtgg tactgccact gctggatgga    3900
catttggtgc tggcgctgct cttcaaatac cttttgctat gcaaatggca tataggttca    3960
atggcattgg agttacccaa atgttctctc tatgagaacca aaaacaaatc gccaaccaat    4020
ttaacaaggc gattagtcaa attcaagaat cacttacaac aacatcaact gcattgggca    4080
agctgcaaga cgttgttaac cagaatgctc aagcattaaa cacacttgtt aaacaactta    4140
gctctaattt tggtgcaatt tcaagtgtgc taaatgatat cctttcgcga cttgataaag    4200
tcgaggcgga ggtacaaatt gacaggttaa ttacaggcag acttcaaagc cttcaaacct    4260
atgtaacaca acaactaatc agggctgctg aaatcagggc ttctgctaat cttgctgcta    4320
ctaaaatgtc tgagtgtgtt cttggacaat caaaaagagt tgacttttgt ggaaagggct    4380
accaccttat gtccttccca caagcagccc cgcatggtgt tgtcttccta catgtcacgt    4440
atgtgccatc ccaggagagg aacttcacca cagcgccagc aatttgtcat gaaggcaaag    4500
catacttccc tcgtgaaggt gttttttgtgt taatggcac ttcttggttt attcacaga    4560 ggaacttctt ttctccacaa ataattacta cagacaatac atttgtctca ggaaattgtg    4620
atgtcgttat tggcatcatt aacaacacag tttatgatcc tctgcaacct gagcttgact    4680
cattcaaaga agagctggac aagtacttca aaaatcatac atcaccagat gttgattttg    4740
```

```
gcgacatttc aggcattaac gcttctgtcg tcaacattca aaaagaaatt gaccgcctca   4800
atgaggtcgc taaaaattta aatgaatcac tcattgacct tcaagaactg ggaaaatatg   4860
agcaatatat taaatggcct ctcgacgaac aaaaactcat ctcagaagag gatctgaatg   4920
ctgtgggcca ggacacgcag gaggtcatcg tggtgccaca ctccttgccc tttaaggtgg   4980
tggtgatctc agccatcctg gccctggtgg tgctcaccat catctccctt atcatcctca   5040
tcatgctttg gcagaagaag ccacgttagg cggccgctcg agtgctagca ccaagggccc   5100
cagcgtgttc cccctggccc ccagcagcaa gagcaccagc ggcggcacag ccgccctggg   5160
ctgcctggtg aaggactact tccccgagcc cgtgaccgtg agctggaaca gcggcgcctt   5220
gaccagcggc gtgcacacct tccccgccgt gctgcagagc agcggcctgt acagcctgag   5280
cagcgtggtg accgtgccca gcagcagcct gggcacccag acctacatct gcaacgtgaa   5340
ccacaagccc agcaacacca aggtggacaa gcgcgtggag cccaagagct gcgacaagac   5400
ccacacctgc cccccctgcc ctgccccccga gctgctgggc ggaccctccg tgttcctgtt   5460
cccccccaag cccaaggaca ccctcatgat cagccggacc cccgaggtga cctgcgtggt   5520
ggtggacgtg agccacgagg accccgaggt gaagttcaac tggtacgtgg acggcgtgga   5580
ggtgcacaac gccaagacca gccccgggga ggagcagtac aacagcacct accgggtggt   5640
gagcgtgctc accgtgctgc accaggactg gctgaacggc aaggagtaca agtgcaaggt   5700
gagcaacaag gccctgcctg cccccatcga gaagaccatc agcaaggcca agggccagcc   5760
ccgggagccc caggtgtaca ccctgccccc cagccgggag gagatgacca gaaccaggt   5820 gtccctcacc tgtctggtga agggcttcta ccccagcgac atcgccgtgg agtgggagag   5880
caacggccag cccgagaaca actacaagac cacccccct gtgctggaca gcgacggcag   5940
cttcttcctg tacagcaagc tcaccgtgga caagagccgg tggcagcagg gcaacgtgtt   6000
cagctgcagc gtgatgcacg aggccctgca caaccactac acccagaaga gcctgagcct   6060
gagcccccgg caagtgataat ctagagggcc cgtttaaacc cgctgatcag cctcgactgt   6120
gccttctagt tgccagccat ctgttgtttg cccctccccc gtgccttcct tgaccctgga   6180
aggtgccact cccactgtcc tttcctaata aaatgaggaa attgcatcgc attgtctgag   6240
taggtgtcat tctattctgg ggggtgggt ggggcaggac agcaagggggg aggattggga   6300 agacaatagc aggcatgctg gggatgcggt gggctctatg gcttctgagg cggaaagaac   6360
cagctggggc tctagggggt atccccacgc gccctgtagc ggcgcattaa gcgcggcggg   6420
tgtggtggtt acgcgcagcg tgaccgctac acttgccagc gccctagcgc ccgctccttt   6480
cgctttcttc ccttcctttc tcgccacgtt cgccggcttt cccgtcaag ctctaaatcg   6540 ggggctccct ttagggttcc gatttagtgc tttacggcac ctcgacccca aaaaacttga   6600
ttagggtgat ggttcacgta gtgggccatc gccctgatag acggtttttc gccctttgac   6660
gttggagtcc acgttcttta atagtggact cttgttccaa actggaacaa cactcaaccc   6720
tatctcggtc tattcttttg atttataagg gattttgccg atttcggcct attggttaaa   6780
aaatgagctg atttaacaaa aatttaacgc gaattaattc tgtggaatgt gtgtcagtta   6840
gggtgtggaa agtccccagg ctccccagca ggcagaagta tgcaaagcat gcatctcaat   6900
tagtcagcaa ccaggtgtgg aaagtcccca ggctccccag caggcagaag tatgcaaagc   6960
atgcatctca attagtcagc aaccatagtc ccgcccctaa ctccgcccat cccgccccta   7020
actccgccca gttccgccca ttctccgccc catggctgac taatttttt tatttatgca   7080 gaggccgagg ccgcctctgc ctctgagcta ttccagaagt agtgaggagg cttttttgga   7140
```

```
ggcctaggct tttgcaaaaa gctcccggga gcttgtatat ccattttcgg atctgatcaa   7200
gagacaggat gaggatcgtt tcgcatgatt gaacaagatg gattgcacgc aggttctccg   7260
gccgcttggg tggagaggct attcggctat gactgggcac aacagacaat cggctgctct   7320
gatgccgccg tgttccggct gtcagcgcag gggcgcccgg ttcttttgt caagaccgac    7380
ctgtccggtg ccctgaatga actgcaggac gaggcagcgc ggctatcgtg gctggccacg   7440
acgggcgttc cttgcgcagc tgtgctcgac gttgtcactg aagcgggaag ggactggctg   7500
ctattgggcg aagtgccggg gcaggatctc ctgtcatctc accttgctcc tgccgagaaa   7560
gtatccatca tggctgatgc aatgcggcgg ctgcatacgc ttgatccggc tacctgccca   7620
ttcgaccacc aagcgaaaca tcgcatcgag cgagcacgta ctcggatgga agccggtctt   7680
gtcgatcagg atgatctgga cgaagagcat caggggctcg cgccagccga actgttcgcc   7740
aggctcaagg cgcgcatgcc cgacggcgag gatctcgtcg tgacccatgg cgatgcctgc   7800
ttgccgaata tcatggtgga aaatggccgc ttttctggat tcatcgactg tggccggctg   7860
ggtgtggcgg accgctatca ggacatagcg ttggctaccc gtgatattgc tgaagagctt   7920
ggcggcgaat gggctgaccg cttcctcgtg ctttacggta tcgccgctcc cgattcgcag   7980
cgcatcgcct tctatcgcct tcttgacgag ttcttctgag cgggactctg gggttcgaaa   8040
tgaccgacca agcgacgccc aacctgccat cacgagattt cgattccacc gccgccttct   8100
atgaaaggtt gggcttcgga atcgttttcc gggacgccgg ctggatgatc ctccagcgcg   8160
gggatctcat gctggagttc ttcgcccacc ccaacttgtt tattgcagct tataatggtt   8220
acaaataaag caatagcatc acaaatttca caaataaagc atttttttca ctgcattcta   8280
gttgtggttt gtccaaactc atcaatgtat cttatcatgt ctgtataccg tcgacctcta   8340
gctagagctt ggcgtaatca tggtcatagc tgtttcctgt gtgaaattgt tatccgctca   8400
caattccaca acatacga gccggaagca taaagtgtaa agcctggggt gcctaatgag    8460
tgagctaact cacattaatt gcgttgcgct cactgcccgc tttccagtcg ggaaacctgt   8520
cgtgccagct gcattaatga atcggccaac gcgcggggag aggcggtttg cgtattgggc   8580
gctcttccgc ttcctcgctc actgactcgc tgcgctcggt cgttcggctg cggcgagcgg   8640
tatcagctca ctcaaaggcg gtaatacggt tatccacaga atcaggggat aacgcaggaa   8700
agaacatgtg agcaaaaggc cagcaaaagg ccaggaaccg taaaaaggcc gcgttgctgg   8760
cgttttccca taggctccgc cccctgacg agcatcacaa aaatcgacgc tcaagtcaga    8820
ggtggcgaaa cccgacagga ctataaagat accaggcgtt tccccctgga agctccctcg   8880
tgcgctctcc tgttccgacc ctgccgctta ccggatacct gtccgccttt ctcccttcgg   8940
gaagcgtggc gctttctcat agctcacgct gtaggtatct cagttcggtg taggtcgttc   9000
gctccaagct gggctgtgtg cacgaacccc cgttcagcc cgaccgctgc gccttatccg    9060
gtaactatcg tcttgagtcc aacccggtaa gacacgactt atcgccactg gcagcagcca   9120
ctggtaacag gattagcaga gcgaggtatg taggcggtgc tacagagttc ttgaagtggt   9180
ggcctaacta cggctacact agaagaacag tatttggtat ctgcgctctg ctgaagccag   9240
ttaccttcgg aaaaagagtt ggtagctctt gatccggcaa acaaaccacc gctggtagcg   9300
gttttttttgt ttgcaagcag cagattacgc gcagaaaaaa aggatctcaa gaagatcctt   9360
tgatcttttc tacggggtct gacgctcagt ggaacgaaaa ctcacgttaa gggattttgg   9420
tcatgagatt atcaaaaagg atcttcacct agatcctttt aaattaaaaa tgaagtttta   9480
```

```
aatcaatcta aagtatatat gagtaaactt ggtctgacag ttaccaatgc ttaatcagtg    9540
aggcacctat ctcagcgatc tgtctatttc gttcatccat agttgcctga ctccccgtcg    9600
tgtagataac tacgatacgg gagggcttac catctggccc cagtgctgca atgataccgc    9660
gagacccacg ctcaccggct ccagatttat cagcaataaa ccagccagcc ggaagggcca    9720
agcgcagaag tggtcctgca actttatccg cctccatcca gtctattaat tgttgccggg    9780
aagctagagt aagtagttcg ccagttaata gtttgcgcaa cgttgttgcc attgctacag    9840
gcatcgtggt gtcacgctcg tcgtttggta tggcttcatt cagctccggt tcccaacgat    9900
caaggcgagt tacatgatcc cccatgttgt gcaaaaaagc ggttagctcc ttcggtcctc    9960
cgatcgttgt cagaagtaag ttggccgcag tgttatcact catggttatg gcagcactgc   10020
ataattctct tactgtcatg ccatccgtaa gatgcttttc tgtgactggt gagtactcaa   10080
ccaagtcatt ctgagaatag tgtatgcggc gaccgagttg ctcttgcccg gcgtcaatac   10140
gggataatac cgcgccacat agcagaactt taaaagtgct catcattgga aaacgttctt   10200
cggggcgaaa actctcaagg atcttaccgc tgttgagatc cagttcgatg taacccactc   10260
gtgcacccaa ctgatcttca gcatctttta ctttcaccag cgtttctggg tgagcaaaaa   10320
caggaaggca aaatgccgca aaaaagggaa taagggcgac acggaaatgt tgaatactca   10380
tactcttcct ttttcaatat tattgaagca tttatcaggg ttattgtctc atgagcggat   10440
acatatttga atgtatttag aaaaataaac aaatagcggt tccgcgcaca tttccccgaa   10500
aagtgccacc tgacg                                                   10515

<210> SEQ ID NO 111
<211> LENGTH: 8777
<212> TYPE: DNA
<213> ORGANISM: Artificial sequence
<220> FEATURE:
<223> OTHER INFORMATION: pIg-C909-Ckappa
<220> FEATURE:
<221> NAME/KEY: misc_feature
<222> LOCATION: (1328)..(3860)

<400> SEQUENCE: 111
tcgacggatc gggagatctc ccgatcccct atggtgcact ctcagtacaa tctgctctga     60
tgccgcatag ttaagccagt atctgctccc tgcttgtgtg ttggaggtcg ctgagtagtg    120
cgcgagcaaa atttaagcta caacaaggca aggcttgacc gacaattgtt aattaacatg    180
aagaatctgc ttagggttag gcgttttgcg ctgcttcgct aggtggtcaa tattggccat    240
tagccatatt attcattggt tatatagcat aaatcaatat tggctattgg ccattgcata    300
cgttgtatcc atatcataat atgtacattt atattggctc atgtccaaca ttaccgccat    360
gttgacattg attattgact agttattaat agtaatcaat tacgggtca ttagttcata    420 gcccatatat ggagttccgc gttacataac ttacggtaaa tggcccgcct ggctgaccgc    480
ccaacgaccc ccgcccattg acgtcaataa tgacgtatgt tcccatagta acgccaatag    540
ggactttcca ttgacgtcaa tgggtggagt atttacggta aactgcccac ttggcagtac    600
atcaagtgta tcatatgcca agtacgcccc ctattgacgt caatgacggt aaatggcccg    660
cctggcatta tgcccagtac atgaccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
```

```
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggctgcccgc ccagctgctg ggccttctca tgctgtgggt   1320
gcccgcctcg agatctatcg atgcatgcca tggtaccaag cttgccacca tgagcagcag   1380
ctcttggctg ctgctgagcc tggtggccgt gacagccgcc cagagcacca tcgaggagca   1440
ggccaagacc ttcctggaca gttcaacca cgaggccgag gacctgttct accagagcag   1500
cctggccagc tggaactaca caccaacat accgaggag aacgtgcaga acatgaacaa   1560
cgccggcgac aagtggagcg ccttcctgaa ggagcagagc acactggccc agatgtaccc   1620
cctgcaggag atccagaacc tgaccgtgaa gctgcagctg caggccctgc agcagaacgg   1680
cagcagcgtg ctgagcgagg acaagagcaa gcggctgaac accatcctga acaccatgtc   1740
caccatctac agcaccggca aagtgtgcaa ccccgacaac ccccaggagt gcctgctgct   1800
ggagcccggc ctgaacgaga tcatggccaa cagcctggac tacaacgagc ggctgtgggc   1860
ctgggagagc tggcggagcg aagtgggcaa gcagctgcgg cccctgtacg aggagtacgt   1920
ggtgctgaag aacgagatgg ccagggccaa ccactacgag gactacggcg actactggag   1980
aggcgactac gaagtgaacg gcgtggacgg ctacgactac agcagaggcc agctgatcga   2040
ggacgtggag cacccttcg aggagatcaa gcctctgtac gagcacctgc acgcctacgt   2100
gcgggccaag ctgatgaacg cctacccag ctacatcagc cccatcggct gcctgcccgc   2160
ccacctgctg ggcgacatgt ggggccggtt ctggaccaac ctgtacagcc tgaccgtgcc   2220
cttcggccag aagcccaaca tcgacgtgac cgacgccatg gtggaccagg cctgggacgc   2280
ccagcggatc ttcaaggagg ccgagaagtt cttcgtgagc gtgggcctgc caacatgac   2340
ccagggcttt tgggagaaca gcatgctgac cgaccccggc aatgtgcaga aggccgtgtg   2400
ccacccacc gcctgggacc tgggcaaggg cgacttccgg atcctgatgt gcaccaaagt   2460
gaccatggac gacttcctga ccgccccacca cgagatgggc cacatccagt acgacatggc   2520
ctacgccgcc cagcccttcc tgctgcggaa cggcgccaac gagggctttc acgaggccgt   2580
gggcgagatc atgagcctga cgccgccac ccccaagcac ctgaagagca tcggcctgct   2640
gagccccgac ttccaggagg acaacgagac cgagatcaac ttcctgctga agcaggccct   2700
gaccatcgtg ggcaccctgc ccttcaccta catgctggag aagtggcggt ggatggtgtt   2760
taagggcgag atccccaagg accagtggat gaagaagtgg tgggagatga gcgggagat   2820
cgtgggcgtg gtggagcccg tgccccacga cgagacctac tgcgacccg ccagcctgtt   2880
ccacgtgagc aacgactact ccttcatccg gtactacacc cggaccctgt accagttcca   2940
gttccaggag gccctgtgcc aggccgccaa gcacgagggc cccctgcaca gtgcgacat   3000
cagcaacagc accgaggccg acagaaact gttcaacatg ctgcggctgg caagagcga   3060
gccctggacc ctggccctgg agaatgtggt gggcgccaag aacatgaatg tgcgcccct   3120
gctgaactac ttcgagcccc tgttcacctg gctgaaggac cagaacaaga cagcttcgt   3180
gggctggagc accgactgga gccccctacgc cgaccagagc atcaaagtgc ggatcagcct   3240
gaagagcgcc ctgggcgaca aggcctacga gtggaacgac aacgagatgt acctgttccg   3300
```

```
gagcagcgtg gcctatgcca tgcggcagta cttcctgaaa gtgaagaacc agatgatcct   3360
gttcggcgag gaggacgtga gagtggccaa cctgaagccc cggatcagct tcaacttctt   3420
cgtgaccgcc cccaagaacg tgagcgacat catcccccgg accgaagtgg agaaggccat   3480
ccggatgagc cggagccgga tcaacgacgc cttccggctg aacgacaact ccctggagtt   3540
cctgggcatc cagcccaccc tgggccctcc caaccagccc cccgtgagca tctggctgat   3600
cgtgtttggc gtggtgatgg gcgtgatcgt ggtgggaatc gtgatcctga tcttcaccgg   3660
catccgggac cggaagaaga gaacaaggc ccggagcggc gagaaccct acgccagcat    3720
cgatatcagc aagggcgaga caaccccgg cttccagaac accgacgacg tgcagaccag    3780
cttctgataa tctagaacga gctcgaattc gaagcttctg cagacgcgtc gacgtcatat   3840
ggatccgata tcgccgtggc ggccgcaccc agcgtgttca tcttcccccc ctccgacgag   3900
cagctgaaga gcggcaccgc cagcgtggtg tgcctgctga caacttcta cccccgggag    3960
gccaaggtgc agtggaaggt ggacaacgcc ctgcagagcg gcaacagcca ggagagcgtg   4020
accgagcagg acagcaagga ctccacctac agcctgagca gccctcac cctgagcaag     4080
gccgactacg agaagcacaa ggtgtacgcc tgcgaggtga cccaccaggg cctgagcagc   4140
cccgtgacca gagcttcaa ccggggcgag tgttaataga cttaagttta aaccgctgat    4200
cagcctcgac tgtgccttct agttgccagc catctgttgt ttgcccctcc ccgtgcctt    4260
ccttgaccct ggaaggtgcc actcccactg tcctttccta ataaaatgag gaaattgcat   4320
cgcattgtct gagtaggtgt cattctattc tggggggtgg ggtggggcag gacagcaagg   4380
gggaggattg ggaagacaat agcaggcatg ctggggatgc ggtgggctct atggcttctg   4440
aggcggaaag aaccagctgg ggctctaggg ggtatcccca cgcgcccgt agcggcgcat     4500
taagcgcggc gggtgtggtg gttacgcgca gcgtgaccgc tacacttgcc agcgccctag   4560
cgcccgctcc tttcgctttc ttcccttcct ttctcgccac gttcgccggc tttccccgtc   4620
aagctctaaa tcggggggctc cctttagggt tccgatttag tgctttacgg cacctcgacc   4680
ccaaaaaact tgattagggt gatggttcac gtagtgggcc atcgccctga tagacggttt   4740
ttcgcccttt gacgttggag tccacgttct ttaatagtgg actcttgttc caaactggaa   4800
caacactcaa ccctatctcg gtctattctt ttgatttata agggattttg gccatttcgg   4860
cctattggtt aaaaaatgag ctgatttaac aaaaatttaa cgcgaattaa ttctgtggaa   4920
tgtgtgtcag ttagggtgtg gaaagtcccc aggctcccca gcaggcagaa gtatgcaaag   4980
catgcatctc aattagtcag caaccaggtg tggaaagtcc ccaggctccc cagcaggcag   5040
aagtatgcaa agcatgcatc tcaattagtc agcaaccata gtcccgcccc taactccgcc   5100
catcccgccc ctaactccgc ccagttccgc ccattctccg ccccatggct gactaatttt   5160
ttttatttat gcagaggccg aggccgcctc tgcctctgag ctattccaga agtagtgagg   5220
aggcttttt ggaggcctag gcttttgcaa aaagctcccg ggagcttgta tatccatttt    5280
cggatctgat cagcacgtga tgaaaaagcc tgaactcacc gcgacgtctg tcgagaagtt   5340
tctgatcgaa aagttcgaca gcgtctccga cctgatgcag ctctcggagg gcgaagaatc   5400
tcgtgctttc agcttcgatg taggagggcg tggatatgtc ctgcgggtaa atagctgcgc   5460
cgatggtttc tacaaagatc gttatgttta tcggcacttt gcatcggccg cgctcccgat   5520
tccggaagtg cttgacattg gggaattcag cgagagcctg acctattgca tctcccgccg   5580
tgcacagggt gtcacgttgc aagacctgcc tgaaaccgaa ctgcccgctg ttctgcagcc   5640
```

```
ggtcgcggag gccatggatg cgatcgctgc ggccgatctt agccagacga gcgggttcgg    5700
cccattcgga ccacaaggaa tcggtcaata cactacatgg cgtgatttca tatgcgcgat    5760
tgctgatccc catgtgtatc actggcaaac tgtgatggac gacaccgtca gtgcgtccgt    5820
cgcgcaggct ctcgatgagc tgatgctttg gccgaggac tgccccgaag tccggcacct     5880
cgtgcacgcg gatttcggct ccaacaatgt cctgacggac aatggccgca taacagcggt    5940
cattgactgg agcgaggcga tgttcgggga ttcccaatac gaggtcgcca acatcttctt    6000
ctggaggccg tggttggctt gtatggagca gcagacgcgc tacttcgagc ggaggcatcc    6060
ggagcttgca ggatcgccgc ggctccgggc gtatatgctc cgcattggtc ttgaccaact    6120
ctatcagagc ttggttgacg gcaatttcga tgatgcagct gggcgcagg gtcgatgcga     6180
cgcaatcgtc cgatccggag ccgggactgt cgggcgtaca caaatcgccc gcagaagcgc    6240
ggccgtctgg accgatggct gtgtagaagt actcgccgat agtggaaacc gacgcccag    6300
cactcgtccg agggcaaagg aatagcacgt gctacgagat ttcgattcca ccgccgcctt    6360
ctatgaaagg ttgggcttcg gaatcgtttt ccgggacgcc ggctggatga tcctccagcg    6420
cggggatctc atgctggagt tcttcgccca ccccaacttg tttattgcag cttataatgg    6480
ttacaaataa agcaatagca tcacaaattt cacaaataaa gcattttttt cactgcattc    6540
tagttgtggt ttgtccaaac tcatcaatgt atcttatcat gtctgtatac cgtcgacctc    6600
tagctagagc ttggcgtaat catggtcata gctgtttcct gtgtgaaatt gttatccgct    6660
cacaattcca cacaacatac gagccggaag cataaagtgt aaagcctggg gtgcctaatg    6720
agtgagctaa ctcacattaa ttgcgttgcg ctcactgccc gctttccagt cgggaaacct    6780
gtcgtgccag ctgcattaat gaatcggcca acgcgcgggg agaggcggtt tgcgtattgg    6840
gcgctcttcc gcttcctcgc tcactgactc gctgcgctcg gtcgttcggc tgcggcgagc    6900
ggtatcagct cactcaaagg cggtaatacg gttatccaca gaatcagggg ataacgcagg    6960
aaagaacatg tgagcaaaag gccagcaaaa ggccaggaac cgtaaaaagg ccgcgttgct    7020
ggcgtttttc cataggctcc gcccccctga cgagcatcac aaaaatcgac gctcaagtca    7080
gaggtggcga aacccgacag gactataaag ataccaggcg tttccccctg gaagctccct    7140
cgtgcgctct cctgttccga ccctgccgct taccggatac ctgtccgcct ttctcccttc    7200
gggaagcgtg gcgctttctc atagctcacg ctgtaggtat ctcagttcgg tgtaggtcgt    7260
tcgctccaag ctgggctgtg tgcacgaacc ccccgttcag cccgaccgct gcgccttatc    7320
cggtaactat cgtcttgagt ccaacccggt aagacacgac ttatcgccac tggcagcagc    7380
cactggtaac aggattagca gagcgaggta tgtaggcggt gctacagagt tcttgaagtg    7440
gtggcctaac tacggctaca ctagaagaac agtatttggt atctgcgctc tgctgaagcc    7500
agttaccttc ggaaaaagag ttggtagctc ttgatccggc aaacaaacca ccgctggtag    7560
cggtttttttt gtttgcaagc agcagattac gcgcagaaaa aaggatctc aagaagatcc     7620
tttgatcttt tctacggggt ctgacgctca gtggaacgaa aactcacgtt aagggatttt    7680
ggtcatgaga ttatcaaaaa ggatcttcac ctagatcctt ttaaattaaa aatgaagttt    7740
taaatcaatc taaagtatat atgagtaaac ttggtctgac agttaccaat gcttaatcag    7800
tgaggcacct atctcagcga tctgtctatt tcgttcatcc atagttgcct gactccccgt    7860
cgtgtagata actacgatac gggagggctt accatctggc cccagtgctg caatgatacc    7920
gcgagaccca cgctcaccgg ctccagattt atcagcaata aaccagccag ccggaagggc    7980
cgagcgcaga agtggtcctg caactttatc cgcctccatc cagtctatta attgttgccg    8040
```

-continued

```
ggaagctaga gtaagtagtt cgccagttaa tagtttgcgc aacgttgttg ccattgctac    8100
aggcatcgtg gtgtcacgct cgtcgtttgg tatggcttca ttcagctccg gttcccaacg    8160
atcaaggcga gttacatgat cccccatgtt gtgcaaaaaa gcggttagct ccttcggtcc    8220
tccgatcgtt gtcagaagta agttggccgc agtgttatca ctcatggtta tggcagcact    8280
gcataattct cttactgtca tgccatccgt aagatgcttt tctgtgactg gtgagtactc    8340
aaccaagtca ttctgagaat agtgtatgcg gcgaccgagt tgctcttgcc cggcgtcaat    8400
acgggataat accgcgccac atagcagaac tttaaaagtg ctcatcattg gaaaacgttc    8460
ttcggggcga aaactctcaa ggatcttacc gctgttgaga tccagttcga tgtaacccac    8520
tcgtgcaccc aactgatctt cagcatcttt tactttcacc agcgtttctg ggtgagcaaa    8580
aacaggaagg caaaatgccg caaaaaaggg aataagggcg acacggaaat gttgaatact    8640
catactcttc ctttttcaat attattgaag catttatcag ggttattgtc tcatgagcgg    8700
atacatattt gaatgtattt agaaaaataa acaaataggg gttccgcgca catttccccg    8760
aaaagtgcca cctgacg                                                  8777
```

<210> SEQ ID NO 112
<211> LENGTH: 1356
<212> TYPE: DNA
<213> ORGANISM: Artificial sequence
<220> FEATURE:
<223> OTHER INFORMATION: Heavy chain CR4271
<220> FEATURE:
<221> NAME/KEY: CDS
<222> LOCATION: (1)..(1356)

<400> SEQUENCE: 112

```
gag gtg cag ctg gtg cag tct gga gca gag gtg aaa aag ccc ggg gag     48
Glu Val Gln Leu Val Gln Ser Gly Ala Glu Val Lys Lys Pro Gly Glu
1               5                   10                  15 tct ctg agg att tcc tgt aag ggt tct gga tac acc ttt aac aat tat     96
Ser Leu Arg Ile Ser Cys Lys Gly Ser Gly Tyr Thr Phe Asn Asn Tyr
            20                  25                  30 tgg atc ggc tgg gtg cgc cag atg ccc ggg aaa ggc ctg gag tgg atg    144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc gtc    192
Gly Ile Ile Tyr Pro Gly Asp Ser Asp Thr Arg Tyr Ser Pro Ser Val
    50                  55                  60 caa ggc cac gtc acc atc tca gcc gac aag tcc atc aac acc gcc tac    240
Gln Gly His Val Thr Ile Ser Ala Asp Lys Ser Ile Asn Thr Ala Tyr
65                  70                  75                  80 ctg cag tgg agc agc ctg aag gcc tcg gac acc gcc gtg tat tac tgt    288
Leu Gln Trp Ser Ser Leu Lys Ala Ser Asp Thr Ala Val Tyr Tyr Cys
                85                  90                  95 gcg aga cgg cct gga tac gac tat gga ttt tac tac ttt gac tac tgg    336
Ala Arg Arg Pro Gly Tyr Asp Tyr Gly Phe Tyr Tyr Phe Asp Tyr Trp
            100                 105                 110 ggc cag ggc acc ctg gtg acc gtc tcc agc gct agc acc aag ggc ccc    384
Gly Gln Gly Thr Leu Val Thr Val Ser Ser Ala Ser Thr Lys Gly Pro
        115                 120                 125 agc gtg ttc ccc ctg gcc ccc agc agc aag agc acc agc ggc ggc aca    432
Ser Val Phe Pro Leu Ala Pro Ser Ser Lys Ser Thr Ser Gly Gly Thr
    130                 135                 140 gcc gcc ctg ggc tgc ctg gtg aag gac tac ttc ccc gag ccc gtg acc    480
Ala Ala Leu Gly Cys Leu Val Lys Asp Tyr Phe Pro Glu Pro Val Thr
145                 150                 155                 160
```

```
gtg agc tgg aac agc ggc gcc ttg acc agc ggc gtg cac acc ttc ccc    528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc    576
Ala Val Leu Gln Ser Ser Gly Leu Tyr Ser Leu Ser Ser Val Val Thr
            180                 185                 190 gtg ccc agc agc agc ctg ggc acc cag acc tac atc tgc aac gtg aac    624
Val Pro Ser Ser Ser Leu Gly Thr Gln Thr Tyr Ile Cys Asn Val Asn
        195                 200                 205 cac aag ccc agc aac acc aag gtg gac aaa cgc gtg gag ccc aag agc    672
His Lys Pro Ser Asn Thr Lys Val Asp Lys Arg Val Glu Pro Lys Ser
    210                 215                 220 tgc gac aag acc cac acc tgc ccc ccc tgc cct gcc ccc gag ctg ctg    720
Cys Asp Lys Thr His Thr Cys Pro Pro Cys Pro Ala Pro Glu Leu Leu
225                 230                 235                 240 ggc gga ccc tcc gtg ttc ctg ttc ccc ccc aag ccc aag gac acc ctc    768
Gly Gly Pro Ser Val Phe Leu Phe Pro Pro Lys Pro Lys Asp Thr Leu
                245                 250                 255 atg atc agc cgg acc ccc gag gtg acc tgc gtg gtg gtg gac gtg agc    816
Met Ile Ser Arg Thr Pro Glu Val Thr Cys Val Val Val Asp Val Ser
            260                 265                 270 cac gag gac ccc gag gtg aag ttc aac tgg tac gtg gac ggc gtg gag    864
His Glu Asp Pro Glu Val Lys Phe Asn Trp Tyr Val Asp Gly Val Glu
        275                 280                 285 gtg cac aac gcc aag acc aag ccc cgg gag gag cag tac aac agc acc    912
Val His Asn Ala Lys Thr Lys Pro Arg Glu Glu Gln Tyr Asn Ser Thr
    290                 295                 300 tac cgg gtg gtg agc gtg ctc acc gtg ctg cac cag gac tgg ctg aac    960
Tyr Arg Val Val Ser Val Leu Thr Val Leu His Gln Asp Trp Leu Asn
305                 310                 315                 320 ggc aag gag tac aag tgc aag gtg agc aac aag gcc ctg cct gcc ccc   1008
Gly Lys Glu Tyr Lys Cys Lys Val Ser Asn Lys Ala Leu Pro Ala Pro
                325                 330                 335 atc gag aag acc atc agc aag gcc aag ggc cag ccc cgg gag ccc cag   1056
Ile Glu Lys Thr Ile Ser Lys Ala Lys Gly Gln Pro Arg Glu Pro Gln
            340                 345                 350 gtg tac acc ctg ccc ccc agc cgg gag gag atg acc aag aac cag gtg   1104
Val Tyr Thr Leu Pro Pro Ser Arg Glu Glu Met Thr Lys Asn Gln Val
        355                 360                 365 tcc ctc acc tgt ctg gtg aag ggc ttc tac ccc agc gac atc gcc gtg   1152
Ser Leu Thr Cys Leu Val Lys Gly Phe Tyr Pro Ser Asp Ile Ala Val
    370                 375                 380 gag tgg gag agc aac ggc cag ccc gag aac aac tac aag acc acc ccc   1200
Glu Trp Glu Ser Asn Gly Gln Pro Glu Asn Asn Tyr Lys Thr Thr Pro
385                 390                 395                 400 cct gtg ctg gac agc gac ggc agc ttc ttc ctg tac agc aag ctc acc   1248
Pro Val Leu Asp Ser Asp Gly Ser Phe Phe Leu Tyr Ser Lys Leu Thr
                405                 410                 415 gtg gac aag agc cgg tgg cag cag ggc aac gtg ttc agc tgc agc gtg   1296
Val Asp Lys Ser Arg Trp Gln Gln Gly Asn Val Phe Ser Cys Ser Val
            420                 425                 430 atg cac gag gcc ctg cac aac cac tac acc cag aag agc ctg agc ctg   1344
Met His Glu Ala Leu His Asn His Tyr Thr Gln Lys Ser Leu Ser Leu
        435                 440                 445 agc ccc ggc aag                                                   1356
Ser Pro Gly Lys
    450
```

<210> SEQ ID NO 113

```
<211> LENGTH: 452
<212> TYPE: PRT
<213> ORGANISM: Artificial sequence
<220> FEATURE:
<223> OTHER INFORMATION: Heavy chain CR4271

<400> SEQUENCE: 113
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Pro | Gly | Glu |
| 1 | | | | 5 | | | | | 10 | | | | | 15 |
| Ser | Leu | Arg | Ile | Ser | Cys | Lys | Gly | Ser | Gly | Tyr | Thr | Phe | Asn | Asn | Tyr |
| | | | 20 | | | | | 25 | | | | | 30 | |
| Trp | Ile | Gly | Trp | Val | Arg | Gln | Met | Pro | Gly | Lys | Gly | Leu | Glu | Trp | Met |
| | | 35 | | | | | 40 | | | | | 45 | | |
| Gly | Ile | Ile | Tyr | Pro | Gly | Asp | Ser | Asp | Thr | Arg | Tyr | Ser | Pro | Ser | Val |
| 50 | | | | | 55 | | | | | 60 | | | | |
| Gln | Gly | His | Val | Thr | Ile | Ser | Ala | Asp | Lys | Ser | Ile | Asn | Thr | Ala | Tyr |
| 65 | | | | 70 | | | | | 75 | | | | | 80 |
| Leu | Gln | Trp | Ser | Ser | Leu | Lys | Ala | Ser | Asp | Thr | Ala | Val | Tyr | Tyr | Cys |
| | | | | 85 | | | | | 90 | | | | | 95 |
| Ala | Arg | Arg | Pro | Gly | Tyr | Asp | Tyr | Gly | Phe | Tyr | Tyr | Phe | Asp | Tyr | Trp |
| | | | 100 | | | | | 105 | | | | | 110 | |
| Gly | Gln | Gly | Thr | Leu | Val | Thr | Val | Ser | Ser | Ala | Ser | Thr | Lys | Gly | Pro |
| | | 115 | | | | | 120 | | | | | 125 | | |
| Ser | Val | Phe | Pro | Leu | Ala | Pro | Ser | Ser | Lys | Ser | Thr | Ser | Gly | Gly | Thr |
| 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | |
| His | Lys | Pro | Ser | Asn | Thr | Lys | Val | Asp | Lys | Arg | Val | Glu | Pro | Lys | Ser |
| 210 | | | | | 215 | | | | | 220 | | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 |
| Met | Ile | Ser | Arg | Thr | Pro | Glu | Val | Thr | Cys | Val | Val | Val | Asp | Val | Ser |
| | | | 260 | | | | | 265 | | | | | 270 | |
| His | Glu | Asp | Pro | Glu | Val | Lys | Phe | Asn | Trp | Tyr | Val | Asp | Gly | Val | Glu |
| | | 275 | | | | | 280 | | | | | 285 | | |
| Val | His | Asn | Ala | Lys | Thr | Lys | Pro | Arg | Glu | Glu | Gln | Tyr | Asn | Ser | Thr |
| 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | |
| Val | Tyr | Thr | Leu | Pro | Pro | Ser | Arg | Glu | Glu | Met | Thr | Lys | Asn | Gln | Val |
| | | 355 | | | | | 360 | | | | | 365 | | |
| Ser | Leu | Thr | Cys | Leu | Val | Lys | Gly | Phe | Tyr | Pro | Ser | Asp | Ile | Ala | Val |
| 370 | | | | | 375 | | | | | 380 | | | | |

-continued

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 114
<211> LENGTH: 1380
<212> TYPE: DNA
<213> ORGANISM: Artificial sequence
<220> FEATURE:
<223> OTHER INFORMATION: Heavy chain CR4274
<220> FEATURE:
<221> NAME/KEY: CDS
<222> LOCATION: (1)..(1380)

<400> SEQUENCE: 114 gag gtg cag ctg gtg cag tct gga gca gag gtg aaa aag ccc ggg gag      48
Glu Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac      96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggc atc atc tat cct ggt gac tct gat acc aga tac agc ccg tcc ttc     192
Gly Ile Ile Tyr Pro Gly Asp Ser Asp Thr Arg Tyr Ser Pro Ser Phe
    50                  55                  60 caa ggc cag gtc acc atc tca gcc gac agg tcc atc agc acc gcc tac     240
Gln Gly Gln Val Thr Ile Ser Ala Asp Arg Ser Ile Ser Thr Ala Tyr
65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga ctc cga ggc ccc tat tac gat ttt tgg aat ggc tat cgg gag     336
Ala Arg Leu Arg Gly Pro Tyr Tyr Asp Phe Trp Asn Gly Tyr Arg Glu
            100                 105                 110 aca cat gat gct ttt aat gtg tgg ggc cag ggc acc acc gtg acc gtc     384
Thr His Asp Ala Phe Asn Val Trp Gly Gln Gly Thr Thr Val Thr Val
        115                 120                 125 tcc agc gct agc acc aag ggc ccc agc gtg ttc ccc ctg gcc ccc agc     432
Ser Ser Ala Ser Thr Lys Gly Pro Ser Val Phe Pro Leu Ala Pro Ser
    130                 135                 140 agc aag agc acc agc ggc ggc aca gcc gcc ctg ggc tgc ctg gtg aag     480
Ser Lys Ser Thr Ser Gly Gly Thr Ala Ala Leu Gly Cys Leu Val Lys
145                 150                 155                 160 gac tac ttc ccc gag ccc gtg acc gtg agc tgg aac agc ggc gcc ttg     528
Asp Tyr Phe Pro Glu Pro Val Thr Val Ser Trp Asn Ser Gly Ala Leu
                165                 170                 175 acc agc ggc gtg cac acc ttc ccc gcc gtg ctg cag agc agc ggc ctg     576
Thr Ser Gly Val His Thr Phe Pro Ala Val Leu Gln Ser Ser Gly Leu
            180                 185                 190 tac agc ctg agc agc gtg gtg acc gtg ccc agc agc agc ctg ggc acc     624
Tyr Ser Leu Ser Ser Val Val Thr Val Pro Ser Ser Ser Leu Gly Thr
```

-continued

```
              195                 200                 205
cag acc tac atc tgc aac gtg aac cac aag ccc agc aac acc aag gtg      672
Gln Thr Tyr Ile Cys Asn Val Asn His Lys Pro Ser Asn Thr Lys Val
210                 215                 220 gac aaa cgc gtg gag ccc aag agc tgc gac aag acc cac acc tgc ccc      720
Asp Lys Arg Val Glu Pro Lys Ser Cys Asp Lys Thr His Thr Cys Pro
225                 230                 235                 240 ccc tgc cct gcc ccc gag ctg ctg ggc gga ccc tcc gtg ttc ctg ttc      768
Pro Cys Pro Ala Pro Glu Leu Leu Gly Gly Pro Ser Val Phe Leu Phe
                245                 250                 255 ccc ccc aag ccc aag gac acc ctc atg atc agc cgg acc ccc gag gtg      816
Pro Pro Lys Pro Lys Asp Thr Leu Met Ile Ser Arg Thr Pro Glu Val
            260                 265                 270 acc tgc gtg gtg gtg gac gtg agc cac gag gac ccc gag gtg aag ttc      864
Thr Cys Val Val Val Asp Val Ser His Glu Asp Pro Glu Val Lys Phe
        275                 280                 285 aac tgg tac gtg gac ggc gtg gag gtg cac aac gcc aag acc aag ccc      912
Asn Trp Tyr Val Asp Gly Val Glu Val His Asn Ala Lys Thr Lys Pro
    290                 295                 300 cgg gag gag cag tac aac agc acc tac cgg gtg gtg agc gtg ctc acc      960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg     1008
Val Leu His Gln Asp Trp Leu Asn Gly Lys Glu Tyr Lys Cys Lys Val
                325                 330                 335 agc aac aag gcc ctg cct gcc ccc atc gag aag acc atc agc aag gcc     1056
Ser Asn Lys Ala Leu Pro Ala Pro Ile Glu Lys Thr Ile Ser Lys Ala
            340                 345                 350 aag ggc cag ccc cgg gag ccc cag gtg tac acc ctg ccc ccc agc cgg     1104
Lys Gly Gln Pro Arg Glu Pro Gln Val Tyr Thr Leu Pro Pro Ser Arg
        355                 360                 365 gag gag atg acc aag aac cag gtg tcc ctc acc tgt ctg gtg aag ggc     1152
Glu Glu Met Thr Lys Asn Gln Val Ser Leu Thr Cys Leu Val Lys Gly
    370                 375                 380 ttc tac ccc agc gac atc gcc gtg gag tgg gag agc aac ggc cag ccc     1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc     1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag     1296
Phe Phe Leu Tyr Ser Lys Leu Thr Val Asp Lys Ser Arg Trp Gln Gln
            420                 425                 430 ggc aac gtg ttc agc tgc agc gtg atg cac gag gcc ctg cac aac cac     1344
Gly Asn Val Phe Ser Cys Ser Val Met His Glu Ala Leu His Asn His
        435                 440                 445 tac acc cag aag agc ctg agc ctg agc ccc ggc aag                     1380
Tyr Thr Gln Lys Ser Leu Ser Leu Ser Pro Gly Lys
    450                 455                 460
```

<210> SEQ ID NO 115
<211> LENGTH: 460
<212> TYPE: PRT
<213> ORGANISM: Artificial sequence
<220> FEATURE:
<223> OTHER INFORMATION: Heavy chain CR4274

<400> SEQUENCE: 115

```
Glu Val Gln Leu Val Gln Ser Gly Ala Glu Val Lys Lys Pro Gly Glu
1               5                   10                  15
```

-continued

```
Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Arg Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Leu Arg Gly Pro Tyr Tyr Asp Phe Trp Asn Gly Tyr Arg Glu
            100                 105                 110

Thr His Asp Ala Phe Asn Val Trp Gly Gln Gly Thr Thr Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Leu
        180                 185                 190

Tyr Ser Leu Ser Ser Val Val Thr Val Pro Ser Ser Ser Leu Gly Thr
    195                 200                 205

Gln Thr Tyr Ile Cys Asn Val Asn His Lys Pro Ser Asn Thr Lys Val
210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
            245                 250                 255

Pro Pro Lys Pro Lys Asp Thr Leu Met Ile Ser Arg Thr Pro Glu Val
        260                 265                 270

Thr Cys Val Val Val Asp Val Ser His Glu Asp Pro Glu Val Lys Phe
    275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Ala Leu Pro Ala Pro Ile Glu Lys Thr Ile Ser Lys Ala
        340                 345                 350

Lys Gly Gln Pro Arg Glu Pro Gln Val Tyr Thr Leu Pro Pro Ser Arg
    355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Lys Leu Thr Val Asp Lys Ser Arg Trp Gln Gln
        420                 425                 430

Gly Asn Val Phe Ser Cys Ser Val Met His Glu Ala Leu His Asn His
```

| | | 435 | | | 440 | | | 445 | |
|---|---|---|---|---|---|---|---|---|---|
| Tyr | Thr | Gln | Lys | Ser | Leu | Ser | Leu | Ser | Pro | Gly | Lys |
| | | 450 | | | | 455 | | | 460 |

<210> SEQ ID NO 116
<211> LENGTH: 1380
<212> TYPE: DNA
<213> ORGANISM: Artificial sequence
<220> FEATURE:
<223> OTHER INFORMATION: Heavy chain CR4283
<220> FEATURE:
<221> NAME/KEY: CDS
<222> LOCATION: (1)..(1380)

<400> SEQUENCE: 116

```
gag gtg cag ctg gtg cag tct gga gca gag gtg aaa aag tcc ggg gag      48
Glu Val Gln Leu Val Gln Ser Gly Ala Glu Val Lys Lys Ser Gly Glu
1               5                   10                  15 tct ctg aag atc tcc tgt aag ggt tct gga tac acc ttt aat acc tac      96
Ser Leu Lys Ile Ser Cys Lys Gly Ser Gly Tyr Thr Phe Asn Thr Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc att tat cct ggt gac tct gat acc ata tac agc ccg tcc ttc     192
Gly Ile Ile Tyr Pro Gly Asp Ser Asp Thr Ile Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg aag gcc tcg gac agc gcc atg tat tac tgt     288
Leu Gln Trp Ser Ser Leu Lys Ala Ser Asp Ser Ala Met Tyr Tyr Cys
                85                  90                  95 gcg aga ctt acc ttt cga cgt gga tat agt ggc tcc gat tcg ttt ctc     336
Ala Arg Leu Thr Phe Arg Arg Gly Tyr Ser Gly Ser Asp Ser Phe Leu
            100                 105                 110 cct ccg ggg gac ttt gac tac tgg ggc cag ggc acc ctg gtg acc gtc     384
Pro Pro Gly Asp Phe Asp Tyr Trp Gly Gln Gly Thr Leu Val Thr Val
        115                 120                 125 tcc agc gct agc acc aag ggc ccc agc gtg ttc ccc ctg gcc ccc agc     432
Ser Ser Ala Ser Thr Lys Gly Pro Ser Val Phe Pro Leu Ala Pro Ser
    130                 135                 140 agc aag agc acc agc ggc ggc aca gcc gcc ctg ggc tgc ctg gtg aag     480
Ser Lys Ser Thr Ser Gly Gly Thr Ala Ala Leu Gly Cys Leu Val Lys
145                 150                 155                 160 gac tac ttc ccc gag ccc gtg acc gtg agc tgg aac agc ggc gcc ttg     528
Asp Tyr Phe Pro Glu Pro Val Thr Val Ser Trp Asn Ser Gly Ala Leu
                165                 170                 175 acc agc ggc gtg cac acc ttc ccc gcc gtg ctg cag agc agc ggc ctg     576
Thr Ser Gly Val His Thr Phe Pro Ala Val Leu Gln Ser Ser Gly Leu
            180                 185                 190 tac agc ctg agc agc gtg gtg acc gtg ccc agc agc agc ctg ggc acc     624
Tyr Ser Leu Ser Ser Val Val Thr Val Pro Ser Ser Ser Leu Gly Thr
        195                 200                 205 cag acc tac atc tgc aac gtg aac cac aag ccc agc aac acc aag gtg     672
Gln Thr Tyr Ile Cys Asn Val Asn His Lys Pro Ser Asn Thr Lys Val
    210                 215                 220 gac aaa cgc gtg gag ccc aag agc tgc gac aag acc cac acc tgc ccc     720
Asp Lys Arg Val Glu Pro Lys Ser Cys Asp Lys Thr His Thr Cys Pro
225                 230                 235                 240 ccc tgc cct gcc ccc gag ctg ctg ggc gga ccc tcc gtg ttc ctg ttc     768
```

```
Pro Cys Pro Ala Pro Glu Leu Leu Gly Gly Pro Ser Val Phe Leu Phe
                245                 250                 255 ccc ccc aag ccc aag gac acc ctc atg atc agc cgg acc ccc gag gtg      816
Pro Pro Lys Pro Lys Asp Thr Leu Met Ile Ser Arg Thr Pro Glu Val
            260                 265                 270 acc tgc gtg gtg gtg gac gtg agc cac gag gac ccc gag gtg aag ttc      864
Thr Cys Val Val Val Asp Val Ser His Glu Asp Pro Glu Val Lys Phe
        275                 280                 285 aac tgg tac gtg gac ggc gtg gag gtg cac aac gcc aag acc aag ccc      912
Asn Trp Tyr Val Asp Gly Val Glu Val His Asn Ala Lys Thr Lys Pro
    290                 295                 300 cgg gag gag cag tac aac agc acc tac cgg gtg gtg agc gtg ctc acc      960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg     1008
Val Leu His Gln Asp Trp Leu Asn Gly Lys Glu Tyr Lys Cys Lys Val
                325                 330                 335 agc aac aag gcc ctg cct gcc ccc atc gag aag acc atc agc aag gcc     1056
Ser Asn Lys Ala Leu Pro Ala Pro Ile Glu Lys Thr Ile Ser Lys Ala
            340                 345                 350 aag ggc cag ccc cgg gag ccc cag gtg tac acc ctg ccc ccc agc cgg     1104
Lys Gly Gln Pro Arg Glu Pro Gln Val Tyr Thr Leu Pro Pro Ser Arg
        355                 360                 365 gag gag atg acc aag aac cag gtg tcc ctc acc tgt ctg gtg aag ggc     1152
Glu Glu Met Thr Lys Asn Gln Val Ser Leu Thr Cys Leu Val Lys Gly
    370                 375                 380 ttc tac ccc agc gac atc gcc gtg gag tgg gag agc aac ggc cag ccc     1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc     1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag     1296
Phe Phe Leu Tyr Ser Lys Leu Thr Val Asp Lys Ser Arg Trp Gln Gln
            420                 425                 430 ggc aac gtg ttc agc tgc agc gtg atg cac gag gcc ctg cac aac cac     1344
Gly Asn Val Phe Ser Cys Ser Val Met His Glu Ala Leu His Asn His
        435                 440                 445 tac acc cag aag agc ctg agc ctg agc ccc ggc aag                     1380
Tyr Thr Gln Lys Ser Leu Ser Leu Ser Pro Gly Lys
    450                 455                 460

<210> SEQ ID NO 117
<211> LENGTH: 460
<212> TYPE: PRT
<213> ORGANISM: Artificial sequence
<220> FEATURE:
<223> OTHER INFORMATION: Heavy chain CR4283

<400> SEQUENCE: 117

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Thr Phe Asn Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Ser Ala Met Tyr Tyr Cys
                85                  90                  95

Ala Arg Leu Thr Phe Arg Arg Gly Tyr Ser Gly Ser Asp Ser Phe Leu
            100                 105                 110

Pro Pro Gly Asp Phe Asp Tyr Trp Gly Gln Gly Thr Leu Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 118
<211> LENGTH: 1365
<212> TYPE: DNA
<213> ORGANISM: Artificial sequence
<220> FEATURE:
```

<223> OTHER INFORMATION: Heavy chain CR4289
<220> FEATURE:
<221> NAME/KEY: CDS
<222> LOCATION: (1)..(1365)

<400> SEQUENCE: 118

| | | | | | | | | | | | | | | | | |
|---|---|---|---|---|---|---|---|---|---|---|---|---|---|---|---|---|
| gag | gtg | cag | ctg | gtg | cag | tct | gga | gca | gag | gtg | aaa | aag | ccc | ggg | gag | 48 |
| Glu | Val | Gln | Leu | Val | Gln | Ser | Gly | Ala | Glu | Val | Lys | Lys | Pro | Gly | Glu | |
| 1 | | | | 5 | | | | | 10 | | | | | 15 | | |
| tct | ctg | agg | atc | tcc | tgt | aag | ggt | tct | gga | tac | agc | ttt | acc | agt | aac | 96 |
| Ser | Leu | Arg | Ile | Ser | Cys | Lys | Gly | Ser | Gly | Tyr | Ser | Phe | Thr | Ser | Asn | |
| | | | 20 | | | | | 25 | | | | | 30 | | | |
| tgg | atc | acc | tgg | gtg | cgc | cag | atg | ccc | ggg | aaa | ggc | ctg | gag | tgg | atg | 144 |
| Trp | Ile | Thr | Trp | Val | Arg | Gln | Met | Pro | Gly | Lys | Gly | Leu | Glu | Trp | Met | |
| | | 35 | | | | | 40 | | | | | 45 | | | | |
| ggg | agg | att | gat | cct | agt | gac | tct | tat | acc | aac | tac | agc | ccg | tcc | ttc | 192 |
| Gly | Arg | Ile | Asp | Pro | Ser | Asp | Ser | Tyr | Thr | Asn | Tyr | Ser | Pro | Ser | Phe | |
| | 50 | | | | | 55 | | | | | 60 | | | | | |
| caa | ggc | cac | gtc | acc | atc | tca | gct | gac | aag | tcc | atc | agc | act | gcc | tac | 240 |
| Gln | Gly | His | Val | Thr | Ile | Ser | Ala | Asp | Lys | Ser | Ile | Ser | Thr | Ala | Tyr | |
| 65 | | | | | 70 | | | | | 75 | | | | | 80 | |
| ctg | cag | tgg | agc | agc | ctg | aag | gcc | tcg | gac | acc | gcc | atg | tat | tac | tgt | 288 |
| Leu | Gln | Trp | Ser | Ser | Leu | Lys | Ala | Ser | Asp | Thr | Ala | Met | Tyr | Tyr | Cys | |
| | | | | 85 | | | | | 90 | | | | | 95 | | |
| gcg | aga | gac | gta | gtt | ggg | gtg | gga | gct | tcc | gac | tac | tat | tat | tac | atg | 336 |
| Ala | Arg | Asp | Val | Val | Gly | Val | Gly | Ala | Ser | Asp | Tyr | Tyr | Tyr | Tyr | Met | |
| | | | 100 | | | | | 105 | | | | | 110 | | | |
| gac | gtc | tgg | ggc | cag | ggc | acc | acc | gtg | acc | gtc | tcc | agc | gct | agc | acc | 384 |
| Asp | Val | Trp | Gly | Gln | Gly | Thr | Thr | Val | Thr | Val | Ser | Ser | Ala | Ser | Thr | |
| | | 115 | | | | | 120 | | | | | 125 | | | | |
| aag | ggc | ccc | agc | gtg | ttc | ccc | ctg | gcc | ccc | agc | agc | aag | agc | acc | agc | 432 |
| Lys | Gly | Pro | Ser | Val | Phe | Pro | Leu | Ala | Pro | Ser | Ser | Lys | Ser | Thr | Ser | |
| | 130 | | | | | 135 | | | | | 140 | | | | | |
| ggc | ggc | aca | gcc | gcc | ctg | ggc | tgc | ctg | gtg | aag | gac | tac | ttc | ccc | gag | 480 |
| Gly | Gly | Thr | Ala | Ala | Leu | Gly | Cys | Leu | Val | Lys | Asp | Tyr | Phe | Pro | Glu | |
| 145 | | | | | 150 | | | | | 155 | | | | | 160 | |
| ccc | gtg | acc | gtg | agc | tgg | aac | agc | ggc | gcc | ttg | acc | agc | ggc | gtg | cac | 528 |
| Pro | Val | Thr | Val | Ser | Trp | Asn | Ser | Gly | Ala | Leu | Thr | Ser | Gly | Val | His | |
| | | | | 165 | | | | | 170 | | | | | 175 | | |
| acc | ttc | ccc | gcc | gtg | ctg | cag | agc | agc | ggc | ctg | tac | agc | ctg | agc | agc | 576 |
| Thr | Phe | Pro | Ala | Val | Leu | Gln | Ser | Ser | Gly | Leu | Tyr | Ser | Leu | Ser | Ser | |
| | | | 180 | | | | | 185 | | | | | 190 | | | |
| gtg | gtg | acc | gtg | ccc | agc | agc | agc | ctg | ggc | acc | cag | acc | tac | atc | tgc | 624 |
| Val | Val | Thr | Val | Pro | Ser | Ser | Ser | Leu | Gly | Thr | Gln | Thr | Tyr | Ile | Cys | |
| | | 195 | | | | | 200 | | | | | 205 | | | | |
| aac | gtg | aac | cac | aag | ccc | agc | aac | acc | aag | gtg | gac | aaa | cgc | gtg | gag | 672 |
| Asn | Val | Asn | His | Lys | Pro | Ser | Asn | Thr | Lys | Val | Asp | Lys | Arg | Val | Glu | |
| | 210 | | | | | 215 | | | | | 220 | | | | | |
| ccc | aag | agc | tgc | gac | aag | acc | cac | acc | tgc | ccc | ccc | tgc | cct | gcc | ccc | 720 |
| Pro | Lys | Ser | Cys | Asp | Lys | Thr | His | Thr | Cys | Pro | Pro | Cys | Pro | Ala | Pro | |
| 225 | | | | | 230 | | | | | 235 | | | | | 240 | |
| gag | ctg | ctg | ggc | gga | ccc | tcc | gtg | ttc | ctg | ttc | ccc | ccc | aag | ccc | aag | 768 |
| Glu | Leu | Leu | Gly | Gly | Pro | Ser | Val | Phe | Leu | Phe | Pro | Pro | Lys | Pro | Lys | |
| | | | | 245 | | | | | 250 | | | | | 255 | | |
| gac | acc | ctc | atg | atc | agc | cgg | acc | ccc | gag | gtg | acc | tgc | gtg | gtg | gtg | 816 |
| Asp | Thr | Leu | Met | Ile | Ser | Arg | Thr | Pro | Glu | Val | Thr | Cys | Val | Val | Val | |
| | | | 260 | | | | | 265 | | | | | 270 | | | |
| gac | gtg | agc | cac | gag | gac | ccc | gag | gtg | aag | ttc | aac | tgg | tac | gtg | gac | 864 |
| Asp | Val | Ser | His | Glu | Asp | Pro | Glu | Val | Lys | Phe | Asn | Trp | Tyr | Val | Asp | |
| | | 275 | | | | | 280 | | | | | 285 | | | | |

```
ggc gtg gag gtg cac aac gcc aag acc aag ccc cgg gag gag cag tac     912
Gly Val Glu Val His Asn Ala Lys Thr Lys Pro Arg Glu Glu Gln Tyr
    290                 295                 300 aac agc acc tac cgg gtg gtc agc gtc ctc acc gtg ctg cac cag gac     960
Asn Ser Thr Tyr Arg Val Val Ser Val Leu Thr Val Leu His Gln Asp
305                 310                 315                 320 tgg ctg aac ggc aag gag tac aag tgc aag gtg agc aac aag gcc ctg    1008
Trp Leu Asn Gly Lys Glu Tyr Lys Cys Lys Val Ser Asn Lys Ala Leu
                325                 330                 335 cct gcc ccc atc gag aag acc atc agc aag gcc aag ggc cag ccc cgg    1056
Pro Ala Pro Ile Glu Lys Thr Ile Ser Lys Ala Lys Gly Gln Pro Arg
            340                 345                 350 gag ccc cag gtg tac acc ctg ccc ccc agc cgg gag gag atg acc aag    1104
Glu Pro Gln Val Tyr Thr Leu Pro Pro Ser Arg Glu Glu Met Thr Lys
        355                 360                 365 aac cag gtg tcc ctc acc tgt ctg gtg aag ggc ttc tac ccc agc gac    1152
Asn Gln Val Ser Leu Thr Cys Leu Val Lys Gly Phe Tyr Pro Ser Asp
    370                 375                 380 atc gcc gtg gag tgg gag agc aac ggc cag ccc gag aac aac tac aag    1200
Ile Ala Val Glu Trp Glu Ser Asn Gly Gln Pro Glu Asn Asn Tyr Lys
385                 390                 395                 400 acc acc ccc cct gtg ctg gac agc gac ggc agc ttc ttc ctg tac agc    1248
Thr Thr Pro Pro Val Leu Asp Ser Asp Gly Ser Phe Phe Leu Tyr Ser
                405                 410                 415 aag ctc acc gtg gac aag agc cgg tgg cag cag ggc aac gtg ttc agc    1296
Lys Leu Thr Val Asp Lys Ser Arg Trp Gln Gln Gly Asn Val Phe Ser
            420                 425                 430 tgc agc gtg atg cac gag gcc ctg cac aac cac tac acc cag aag agc    1344
Cys Ser Val Met His Glu Ala Leu His Asn His Tyr Thr Gln Lys Ser
        435                 440                 445 ctg agc ctg agc ccc ggc aag                                        1365
Leu Ser Leu Ser Pro Gly Lys
    450                 455

<210> SEQ ID NO 119
<211> LENGTH: 455
<212> TYPE: PRT
<213> ORGANISM: Artificial sequence
<220> FEATURE:
<223> OTHER INFORMATION: Heavy chain CR4289

<400> SEQUENCE: 119

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Asn
            20                  25                  30

Trp Ile Thr Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Val Val Gly Val Gly Ala Ser Asp Tyr Tyr Tyr Tyr Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
```

```
                130              135              140
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 120
<211> LENGTH: 1362
<212> TYPE: DNA
<213> ORGANISM: Artificial sequence
<220> FEATURE:
<223> OTHER INFORMATION: Heavy chain CR4299
<220> FEATURE:
<221> NAME/KEY: CDS
<222> LOCATION: (1)..(1362)

<400> SEQUENCE: 120 cag gtg cag ctg gtg gag tct ggg gga ggc gtg gtc cag cct ggg agg        48
Gln Val Gln Leu Val Glu Ser Gly Gly Gly Val Val Gln Pro Gly Arg
1               5                   10                  15
```

-continued

| | | |
|---|---|---|
| tcc ctg aga ctc tcc tgt gca gcc tct gga ttc acc ttc agt ggc tat<br>Ser Leu Arg Leu Ser Cys Ala Ala Ser Gly Phe Thr Phe Ser Gly Tyr<br>          20                     25                    30 | | 96 |
| gct atg cac tgg gtc cgc cag gct cca ggc aag ggg cta gac tgg gtg<br>Ala Met His Trp Val Arg Gln Ala Pro Gly Lys Gly Leu Asp Trp Val<br>      35                     40                     45 | | 144 |
| gca gtt ata tca tat gat gga agt gaa aaa tat tcc gcc gac tct gtg<br>Ala Val Ile Ser Tyr Asp Gly Ser Glu Lys Tyr Ser Ala Asp Ser Val<br>50                     55                     60 | | 192 |
| aag ggc cgg ttc acc atc tcc aga gac aat tcc aag aac acg ctc tat<br>Lys Gly Arg Phe Thr Ile Ser Arg Asp Asn Ser Lys Asn Thr Leu Tyr<br>65                     70                     75                     80 | | 240 |
| ctg caa atg aac agc ctg aga gct gag gac acg gct gtg tat tat tgt<br>Leu Gln Met Asn Ser Leu Arg Ala Glu Asp Thr Ala Val Tyr Tyr Cys<br>          85                     90                     95 | | 288 |
| gcg aaa gag tcc ggg gga cct ata tgg tac aag tac tac ggc gtg gac<br>Ala Lys Glu Ser Gly Gly Pro Ile Trp Tyr Lys Tyr Tyr Gly Val Asp<br>               100                   105                   110 | | 336 |
| gtc tgg ggc cag ggc acc acc gtg acc gtc tcc agc gct agc acc aag<br>Val Trp Gly Gln Gly Thr Thr Val Thr Val Ser Ser Ala Ser Thr Lys<br>             115                   120                   125 | | 384 |
| ggc ccc agc gtg ttc ccc ctg gcc ccc agc agc aag agc acc agc ggc<br>Gly Pro Ser Val Phe Pro Leu Ala Pro Ser Ser Lys Ser Thr Ser Gly<br>130                     135                   140 | | 432 |
| ggc aca gcc gcc ctg ggc tgc ctg gtg aag gac tac ttc ccc gag ccc<br>Gly Thr Ala Ala Leu Gly Cys Leu Val Lys Asp Tyr Phe Pro Glu Pro<br>145                     150                   155                   160 | | 480 |
| gtg acc gtg agc tgg aac agc ggc gcc ttg acc agc ggc gtg cac acc<br>Val Thr Val Ser Trp Asn Ser Gly Ala Leu Thr Ser Gly Val His Thr<br>                    165                   170                   175 | | 528 |
| ttc ccc gcc gtg ctg cag agc agc ggc ctg tac agc ctg agc agc gtg<br>Phe Pro Ala Val Leu Gln Ser Ser Gly Leu Tyr Ser Leu Ser Ser Val<br>             180                   185                   190 | | 576 |
| gtg acc gtg ccc agc agc agc ctg ggc acc cag acc tac atc tgc aac<br>Val Thr Val Pro Ser Ser Ser Leu Gly Thr Gln Thr Tyr Ile Cys Asn<br>          195                     200                   205 | | 624 |
| gtg aac cac aag ccc agc aac acc aag gtg gac aaa cgc gtg gag ccc<br>Val Asn His Lys Pro Ser Asn Thr Lys Val Asp Lys Arg Val Glu Pro<br>210                     215                   220 | | 672 |
| aag agc tgc gac aag acc cac acc tgc ccc ccc tgc cct gcc ccc gag<br>Lys Ser Cys Asp Lys Thr His Thr Cys Pro Pro Cys Pro Ala Pro Glu<br>225                     230                   235                   240 | | 720 |
| ctg ctg ggc gga ccc tcc gtg ttc ctg ttc ccc ccc aag ccc aag gac<br>Leu Leu Gly Gly Pro Ser Val Phe Leu Phe Pro Pro Lys Pro Lys Asp<br>             245                   250                   255 | | 768 |
| acc ctc atg atc agc cgg acc ccc gag gtg acc tgc gtg gtg gtg gac<br>Thr Leu Met Ile Ser Arg Thr Pro Glu Val Thr Cys Val Val Val Asp<br>             260                   265                   270 | | 816 |
| gtg agc cac gag gac ccc gag gtg aag ttc aac tgg tac gtg gac ggc<br>Val Ser His Glu Asp Pro Glu Val Lys Phe Asn Trp Tyr Val Asp Gly<br>          275                     280                   285 | | 864 |
| gtg gag gtg cac aac gcc aag acc aag ccc cgg gag gag cag tac aac<br>Val Glu Val His Asn Ala Lys Thr Lys Pro Arg Glu Glu Gln Tyr Asn<br>290                     295                   300 | | 912 |
| agc acc tac cgg gtg gtg agc gtg ctc acc gtg ctg cac cag gac tgg<br>Ser Thr Tyr Arg Val Val Ser Val Leu Thr Val Leu His Gln Asp Trp<br>305                     310                   315                   320 | | 960 |
| ctg aac ggc aag gag tac aag tgc aag gtg agc aac aag gcc ctg cct<br>Leu Asn Gly Lys Glu Tyr Lys Cys Lys Val Ser Asn Lys Ala Leu Pro<br>             325                   330                   335 | | 1008 |

```
gcc ccc atc gag aag acc atc agc aag gcc aag ggc cag ccc cgg gag     1056
Ala Pro Ile Glu Lys Thr Ile Ser Lys Ala Lys Gly Gln Pro Arg Glu
        340                 345                 350 ccc cag gtg tac acc ctg ccc ccc agc cgg gag gag atg acc aag aac     1104
Pro Gln Val Tyr Thr Leu Pro Pro Ser Arg Glu Glu Met Thr Lys Asn
            355                 360                 365 cag gtg tcc ctc acc tgt ctg gtg aag ggc ttc tac ccc agc gac atc     1152
Gln Val Ser Leu Thr Cys Leu Val Lys Gly Phe Tyr Pro Ser Asp Ile
    370                 375                 380 gcc gtg gag tgg gag agc aac ggc cag ccc gag aac aac tac aag acc     1200
Ala Val Glu Trp Glu Ser Asn Gly Gln Pro Glu Asn Asn Tyr Lys Thr
385                 390                 395                 400 acc ccc cct gtg ctg gac agc gac ggc agc ttc ttc ctg tac agc aag     1248
Thr Pro Pro Val Leu Asp Ser Asp Gly Ser Phe Phe Leu Tyr Ser Lys
                405                 410                 415 ctc acc gtg gac aag agc cgg tgg cag cag ggc aac gtg ttc agc tgc     1296
Leu Thr Val Asp Lys Ser Arg Trp Gln Gln Gly Asn Val Phe Ser Cys
            420                 425                 430 agc gtg atg cac gag gcc ctg cac aac cac tac acc cag aag agc ctg     1344
Ser Val Met His Glu Ala Leu His Asn His Tyr Thr Gln Lys Ser Leu
        435                 440                 445 agc ctg agc ccc ggc aag                                             1362
Ser Leu Ser Pro Gly Lys
    450

<210> SEQ ID NO 121
<211> LENGTH: 454
<212> TYPE: PRT
<213> ORGANISM: Artificial sequence
<220> FEATURE:
<223> OTHER INFORMATION: Heavy chain CR4299

<400> SEQUENCE: 121

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Asp Trp Val
        35                  40                  45

Ala Val Ile Ser Tyr Asp Gly Ser Glu Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Gly Gly Pro Ile Trp Tyr Lys Tyr Tyr Gly Val Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
        450

<210> SEQ ID NO 122
<211> LENGTH: 1347
<212> TYPE: DNA
<213> ORGANISM: Artificial sequence
<220> FEATURE:
<223> OTHER INFORMATION: Heavy chain CR4311
<220> FEATURE:
<221> NAME/KEY: CDS
<222> LOCATION: (1)..(1347)

<400> SEQUENCE: 122 cag gtg cag ctg gtg gag tct ggg gga ggc gtg gtc cag cct ggc agg         48
Gln Val Gln Leu Val Glu Ser Gly Gly Gly Val Val Gln Pro Gly Arg
1               5                   10                  15 tcc ctg aga ctc tcc tgt gta gcc tct gga ttc acc ttc agt aag gac         96
Ser Leu Arg Leu Ser Cys Val Ala Ser Gly Phe Thr Phe Ser Lys Asp
            20                  25                  30 gct atg cac tgg gtc cgc cag gct cca ggc aag ggg cta gag tgg gtg        144
Ala Met His Trp Val Arg Gln Ala Pro Gly Lys Gly Leu Glu Trp Val
        35                  40                  45 gca gtt ata tca tat gat gga agt gat aaa cac tac gca gac tcc gtg        192
Ala Val Ile Ser Tyr Asp Gly Ser Asp Lys His Tyr Ala Asp Ser Val
    50                  55                  60
```

```
aag ggc cga gtc acc atc tcc aga gac aat tcc agg aaa acg ctg tat      240
Lys Gly Arg Val Thr Ile Ser Arg Asp Asn Ser Arg Lys Thr Leu Tyr
 65                  70                  75                  80 ctg cga atg gac agc ctg aga gct gag gac acg gct cta tat tac tgt      288
Leu Arg Met Asp Ser Leu Arg Ala Glu Asp Thr Ala Leu Tyr Tyr Cys
                 85                  90                  95 gcg aga gga tac aac tct ggt cat tac ttt gac tac tgg ggc cag ggc      336
Ala Arg Gly Tyr Asn Ser Gly His Tyr Phe Asp Tyr Trp Gly Gln Gly
            100                 105                 110 acc ctg gtg acc gtc tcc agc gct agc acc aag ggc ccc agc gtg ttc      384
Thr Leu Val Thr Val Ser Ser Ala Ser Thr Lys Gly Pro Ser Val Phe
        115                 120                 125 ccc ctg gcc ccc agc agc aag agc acc agc ggc ggc aca gcc gcc ctg      432
Pro Leu Ala Pro Ser Ser Lys Ser Thr Ser Gly Gly Thr Ala Ala Leu
    130                 135                 140 ggc tgc ctg gtg aag gac tac ttc ccc gag ccc gtg acc gtg agc tgg      480
Gly Cys Leu Val Lys Asp Tyr Phe Pro Glu Pro Val Thr Val Ser Trp
145                 150                 155                 160 aac agc ggc gcc ttg acc agc ggc gtg cac acc ttc ccc gcc gtg ctg      528
Asn Ser Gly Ala Leu Thr Ser Gly Val His Thr Phe Pro Ala Val Leu
                165                 170                 175 cag agc agc ggc ctg tac agc ctg agc agc gtg gtg acc gtg ccc agc      576
Gln Ser Ser Gly Leu Tyr Ser Leu Ser Ser Val Val Thr Val Pro Ser
            180                 185                 190 agc agc ctg ggc acc cag acc tac atc tgc aac gtg aac cac aag ccc      624
Ser Ser Leu Gly Thr Gln Thr Tyr Ile Cys Asn Val Asn His Lys Pro
        195                 200                 205 agc aac acc aag gtg gac aaa cgc gtg gag ccc aag agc tgc gac aag      672
Ser Asn Thr Lys Val Asp Lys Arg Val Glu Pro Lys Ser Cys Asp Lys
    210                 215                 220 acc cac acc tgc ccc ccc tgc cct gcc ccc gag ctg ctg ggc gga ccc      720
Thr His Thr Cys Pro Pro Cys Pro Ala Pro Glu Leu Leu Gly Gly Pro
225                 230                 235                 240 tcc gtg ttc ctg ttc ccc ccc aag ccc aag gac acc ctc atg atc agc      768
Ser Val Phe Leu Phe Pro Pro Lys Pro Lys Asp Thr Leu Met Ile Ser
                245                 250                 255 cgg acc ccc gag gtg acc tgc gtg gtg gtg gac gtg agc cac gag gac      816
Arg Thr Pro Glu Val Thr Cys Val Val Val Asp Val Ser His Glu Asp
            260                 265                 270 ccc gag gtg aag ttc aac tgg tac gtg gac ggc gtg gag gtg cac aac      864
Pro Glu Val Lys Phe Asn Trp Tyr Val Asp Gly Val Glu Val His Asn
        275                 280                 285 gcc aag acc aag ccc cgg gag gag cag tac aac agc acc tac cgg gtg      912
Ala Lys Thr Lys Pro Arg Glu Glu Gln Tyr Asn Ser Thr Tyr Arg Val
    290                 295                 300 gtg agc gtg ctc acc gtg ctg cac cag gac tgg ctg aac ggc aag gag      960
Val Ser Val Leu Thr Val Leu His Gln Asp Trp Leu Asn Gly Lys Glu
305                 310                 315                 320 tac aag tgc aag gtg agc aac aag gcc ctg cct gcc ccc atc gag aag      1008
Tyr Lys Cys Lys Val Ser Asn Lys Ala Leu Pro Ala Pro Ile Glu Lys
                325                 330                 335 acc atc agc aag gcc aag ggc cag ccc cgg gag ccc cag gtg tac acc      1056
Thr Ile Ser Lys Ala Lys Gly Gln Pro Arg Glu Pro Gln Val Tyr Thr
            340                 345                 350 ctg ccc ccc agc cgg gag gag atg acc aag aac cag gtg tcc ctg acc      1104
Leu Pro Pro Ser Arg Glu Glu Met Thr Lys Asn Gln Val Ser Leu Thr
        355                 360                 365 tgt ctg gtg aag ggc ttc tac ccc agc gac atc gcc gtg gag tgg gag      1152
Cys Leu Val Lys Gly Phe Tyr Pro Ser Asp Ile Ala Val Glu Trp Glu
```

```
                370             375             380
agc aac ggc cag ccc gag aac aac tac aag acc acc ccc cct gtg ctg    1200
Ser Asn Gly Gln Pro Glu Asn Asn Tyr Lys Thr Thr Pro Pro Val Leu
385                 390                 395                 400 gac agc gac ggc agc ttc ttc ctg tac agc aag ctc acc gtg gac aag    1248
Asp Ser Asp Gly Ser Phe Phe Leu Tyr Ser Lys Leu Thr Val Asp Lys
                405                 410                 415 agc cgg tgg cag cag ggc aac gtg ttc agc tgc agc gtg atg cac gag    1296
Ser Arg Trp Gln Gln Gly Asn Val Phe Ser Cys Ser Val Met His Glu
            420                 425                 430 gcc ctg cac aac cac tac acc cag aag agc ctg agc ctg agc ccc ggc    1344
Ala Leu His Asn His Tyr Thr Gln Lys Ser Leu Ser Leu Ser Pro Gly
        435                 440                 445 aag                                                                 1347
Lys

<210> SEQ ID NO 123
<211> LENGTH: 449
<212> TYPE: PRT
<213> ORGANISM: Artificial sequence
<220> FEATURE:
<223> OTHER INFORMATION: Heavy chain CR4311

<400> SEQUENCE: 123

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Lys Asp
                20                  25                  30

Ala Met His Trp Val Arg Gln Ala Pro Gly Lys Gly Leu Glu Trp Val
            35                  40                  45

Ala Val Ile Ser Tyr Asp Gly Ser Asp Lys His Tyr Ala Asp Ser Val
        50                  55                  60

Lys Gly Arg Val Thr Ile Ser Arg Asp Asn Ser Arg Lys Thr Leu Tyr
65                  70                  75                  80

Leu Arg Met Asp Ser Leu Arg Ala Glu Asp Thr Ala Leu Tyr Tyr Cys
                85                  90                  95

Ala Arg Gly Tyr Asn Ser Gly His Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys
```

```
<210> SEQ ID NO 124
<211> LENGTH: 1341
<212> TYPE: DNA
<213> ORGANISM: Artificial sequence
<220> FEATURE:
<223> OTHER INFORMATION: Heavy chain CR4325
<220> FEATURE:
<221> NAME/KEY: CDS
<222> LOCATION: (1)..(1341)

<400> SEQUENCE: 124
```

```
cag gtg cag ctg gtg cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gct tct gga gac acc ttc agc agt tat      96
Ser Val Lys Val Ser Cys Lys Ala Ser Gly Asp Thr Phe Ser Ser Tyr
            20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
        35                  40                  45 gga ggg atc ttt ggt aca gca agc tac gca cag aag ttc cag ggc aga     192
Gly Gly Ile Phe Gly Thr Ala Ser Tyr Ala Gln Lys Phe Gln Gly Arg
    50                  55                  60 gtc acg att acc gcg gac gaa tcc acg agc aca gcc tac atg gag ctg     240
Val Thr Ile Thr Ala Asp Glu Ser Thr Ser Thr Ala Tyr Met Glu Leu
65                  70                  75                  80 agc agc ctg aga tct gag gac acg gcc gtg tat tac tgt gcg aga gga     288
Ser Ser Leu Arg Ser Glu Asp Thr Ala Val Tyr Tyr Cys Ala Arg Gly
                85                  90                  95 ggg atg gct aca aca ccg gga ctt gac tac tgg ggc cag ggc acc ctg     336
Gly Met Ala Thr Thr Pro Gly Leu Asp Tyr Trp Gly Gln Gly Thr Leu
            100                 105                 110
```

-continued

| | | |
|---|---|---|
| gtg acc gtc tcc agc gct agc acc aag ggc ccc agc gtg ttc ccc ctg<br>Val Thr Val Ser Ser Ala Ser Thr Lys Gly Pro Ser Val Phe Pro Leu<br>115 120 125 | 384 | |
| gcc ccc agc agc aag agc acc agc ggc ggc aca gcc gcc ctg ggc tgc<br>Ala Pro Ser Ser Lys Ser Thr Ser Gly Gly Thr Ala Ala Leu Gly Cys<br>130 135 140 | 432 | |
| ctg gtg aag gac tac ttc ccc gag ccc gtg acc gtg agc tgg aac agc<br>Leu Val Lys Asp Tyr Phe Pro Glu Pro Val Thr Val Ser Trp Asn Ser<br>145 150 155 160 | 480 | |
| ggc gcc ttg acc agc ggc gtg cac acc ttc ccc gcc gtg ctg cag agc<br>Gly Ala Leu Thr Ser Gly Val His Thr Phe Pro Ala Val Leu Gln Ser<br>165 170 175 | 528 | |
| agc ggc ctg tac agc ctg agc agc gtg gtg acc gtg ccc agc agc agc<br>Ser Gly Leu Tyr Ser Leu Ser Ser Val Val Thr Val Pro Ser Ser Ser<br>180 185 190 | 576 | |
| ctg ggc acc cag acc tac atc tgc aac gtg aac cac aag ccc agc aac<br>Leu Gly Thr Gln Thr Tyr Ile Cys Asn Val Asn His Lys Pro Ser Asn<br>195 200 205 | 624 | |
| acc aag gtg gac aaa cgc gtg gag ccc aag agc tgc gac aag acc cac<br>Thr Lys Val Asp Lys Arg Val Glu Pro Lys Ser Cys Asp Lys Thr His<br>210 215 220 | 672 | |
| acc tgc ccc ccc tgc cct gcc ccc gag ctg ctg ggc gga ccc tcc gtg<br>Thr Cys Pro Pro Cys Pro Ala Pro Glu Leu Leu Gly Gly Pro Ser Val<br>225 230 235 240 | 720 | |
| ttc ctg ttc ccc ccc aag ccc aag gac acc ctc atg atc agc cgg acc<br>Phe Leu Phe Pro Pro Lys Pro Lys Asp Thr Leu Met Ile Ser Arg Thr<br>245 250 255 | 768 | |
| ccc gag gtg acc tgc gtg gtg gtg gac gtg agc cac gag gac ccc gag<br>Pro Glu Val Thr Cys Val Val Val Asp Val Ser His Glu Asp Pro Glu<br>260 265 270 | 816 | |
| gtg aag ttc aac tgg tac gtg gac ggc gtg gag gtg cac aac gcc aag<br>Val Lys Phe Asn Trp Tyr Val Asp Gly Val Glu Val His Asn Ala Lys<br>275 280 285 | 864 | |
| acc aag ccc cgg gag gag cag tac aac agc acc tac cgg gtg gtg agc<br>Thr Lys Pro Arg Glu Glu Gln Tyr Asn Ser Thr Tyr Arg Val Val Ser<br>290 295 300 | 912 | |
| gtg ctc acc gtg ctg cac cag gac tgg ctg aac ggc aag gag tac aag<br>Val Leu Thr Val Leu His Gln Asp Trp Leu Asn Gly Lys Glu Tyr Lys<br>305 310 315 320 | 960 | |
| tgc aag gtg agc aac aag gcc ctg cct gcc ccc atc gag aag acc atc<br>Cys Lys Val Ser Asn Lys Ala Leu Pro Ala Pro Ile Glu Lys Thr Ile<br>325 330 335 | 1008 | |
| agc aag gcc aag ggc cag ccc cgg gag ccc cag gtg tac acc ctg ccc<br>Ser Lys Ala Lys Gly Gln Pro Arg Glu Pro Gln Val Tyr Thr Leu Pro<br>340 345 350 | 1056 | |
| ccc agc cgg gag gag atg acc aag aac cag gtg tcc ctc acc tgt ctg<br>Pro Ser Arg Glu Glu Met Thr Lys Asn Gln Val Ser Leu Thr Cys Leu<br>355 360 365 | 1104 | |
| gtg aag ggc ttc tac ccc agc gac atc gcc gtg gag tgg gag agc aac<br>Val Lys Gly Phe Tyr Pro Ser Asp Ile Ala Val Glu Trp Glu Ser Asn<br>370 375 380 | 1152 | |
| ggc cag ccc gag aac aac tac aag acc acc ccc cct gtg ctg gac agc<br>Gly Gln Pro Glu Asn Asn Tyr Lys Thr Thr Pro Pro Val Leu Asp Ser<br>385 390 395 400 | 1200 | |
| gac ggc agc ttc ttc ctg tac agc aag ctc acc gtg gac aag agc cgg<br>Asp Gly Ser Phe Phe Leu Tyr Ser Lys Leu Thr Val Asp Lys Ser Arg<br>405 410 415 | 1248 | |
| tgg cag cag ggc aac gtg ttc agc tgc agc gtg atg cac gag gcc ctg<br>Trp Gln Gln Gly Asn Val Phe Ser Cys Ser Val Met His Glu Ala Leu<br>420 425 430 | 1296 | |

```
cac aac cac tac acc cag aag agc ctg agc ctg agc ccc ggc aag          1341
His Asn His Tyr Thr Gln Lys Ser Leu Ser Leu Ser Pro Gly Lys
        435                 440                 445
```

<210> SEQ ID NO 125
<211> LENGTH: 447
<212> TYPE: PRT
<213> ORGANISM: Artificial sequence
<220> FEATURE:
<223> OTHER INFORMATION: Heavy chain CR4325

<400> SEQUENCE: 125

```
Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Phe Gly Thr Ala Ser Tyr Ala Gln Lys Phe Gln Gly Arg
    50                  55                  60

Val Thr Ile Thr Ala Asp Glu Ser Thr Ser Thr Ala Tyr Met Glu Leu
65                  70                  75                  80

Ser Ser Leu Arg Ser Glu Asp Thr Ala Val Tyr Tyr Cys Ala Arg Gly
                85                  90                  95

Gly Met Ala Thr Thr Pro Gly Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
                    340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 126
<211> LENGTH: 1371
<212> TYPE: DNA
<213> ORGANISM: Artificial sequence
<220> FEATURE:
<223> OTHER INFORMATION: Heavy chain CR4353
<220> FEATURE:
<221> NAME/KEY: CDS
<222> LOCATION: (1)..(1371)

<400> SEQUENCE: 126 cag gtg cag ctg gtg gag tct ggg gga ggc gtg gtc cag cct ggg agg       48
Gln Val Gln Leu Val Glu Ser Gly Gly Gly Val Val Gln Pro Gly Arg
1               5                   10                  15 tcc ctg aga ctc tcc tgt gca gcc tct gga ttc acc ttc agt aat tat       96
Ser Leu Arg Leu Ser Cys Ala Ala Ser Gly Phe Thr Phe Ser Asn Tyr
                20                  25                  30 gct atg cac tgg gtc cgc cag gct cca ggc aag ggg cta gag tgg gtg      144
Ala Met His Trp Val Arg Gln Ala Pro Gly Lys Gly Leu Glu Trp Val
            35                  40                  45 gca gtt ata tca tat gat gga ggt aat aaa tac tac gca gac tcc gtg      192
Ala Val Ile Ser Tyr Asp Gly Gly Asn Lys Tyr Tyr Ala Asp Ser Val
        50                  55                  60 aag ggc cga ttc acc atg tcc aga gac aat tcc aag aac acg ctg tat      240
Lys Gly Arg Phe Thr Met Ser Arg Asp Asn Ser Lys Asn Thr Leu Tyr
65                  70                  75                  80 ctg caa atg aac agc ctg aga gct gag gac acg gct gtg tat tat tgt      288
Leu Gln Met Asn Ser Leu Arg Ala Glu Asp Thr Ala Val Tyr Tyr Cys
                85                  90                  95 gcg aga gat ttt tgg agt ggt tac tca atg gta gac tcc tac tac tac      336
Ala Arg Asp Phe Trp Ser Gly Tyr Ser Met Val Asp Ser Tyr Tyr Tyr
                100                 105                 110 tac atg gac gtg tgg ggc cag ggc acc acc gtg acc gtc tcc agc gct      384
Tyr Met Asp Val Trp Gly Gln Gly Thr Thr Val Thr Val Ser Ser Ala
            115                 120                 125 agc acc aag ggc ccc agc gtg ttc ccc ctg gcc ccc agc agc aag agc      432
Ser Thr Lys Gly Pro Ser Val Phe Pro Leu Ala Pro Ser Ser Lys Ser
        130                 135                 140 acc agc ggc ggc aca gcc gcc ctg ggc tgc ctg gtg aag gac tac ttc      480
Thr Ser Gly Gly Thr Ala Ala Leu Gly Cys Leu Val Lys Asp Tyr Phe
145                 150                 155                 160 ccc gag ccc gtg acc gtg agc tgg aac agc ggc gcc ttg acc agc ggc      528
Pro Glu Pro Val Thr Val Ser Trp Asn Ser Gly Ala Leu Thr Ser Gly
                165                 170                 175 gtg cac acc ttc ccc gcc gtg ctg cag agc agc ggc ctg tac agc ctg      576
Val His Thr Phe Pro Ala Val Leu Gln Ser Ser Gly Leu Tyr Ser Leu
```

|  |  |  |  |  |  |  |  |  |  |  |  |  |  |  |  |  |
|---|---|---|---|---|---|---|---|---|---|---|---|---|---|---|---|---|
|  |  |  | 180 |  |  |  |  | 185 |  |  |  |  | 190 |  |  |  |

```
agc agc gtg gtg acc gtg ccc agc agc agc ctg ggc acc cag acc tac    624
Ser Ser Val Val Thr Val Pro Ser Ser Ser Leu Gly Thr Gln Thr Tyr
        195                 200                 205 atc tgc aac gtg aac cac aag ccc agc aac acc aag gtg gac aaa cgc    672
Ile Cys Asn Val Asn His Lys Pro Ser Asn Thr Lys Val Asp Lys Arg
210                 215                 220 gtg gag ccc aag agc tgc gac aag acc cac acc tgc ccc ccc tgc cct    720
Val Glu Pro Lys Ser Cys Asp Lys Thr His Thr Cys Pro Pro Cys Pro
225                 230                 235                 240 gcc ccc gag ctg ctg ggc gga ccc tcc gtg ttc ctg ttc ccc ccc aag    768
Ala Pro Glu Leu Leu Gly Gly Pro Ser Val Phe Leu Phe Pro Pro Lys
                245                 250                 255 ccc aag gac acc ctc atg atc agc cgg acc ccc gag gtg acc tgc gtg    816
Pro Lys Asp Thr Leu Met Ile Ser Arg Thr Pro Glu Val Thr Cys Val
            260                 265                 270 gtg gtg gac gtg agc cac gag gac ccc gag gtg aag ttc aac tgg tac    864
Val Val Asp Val Ser His Glu Asp Pro Glu Val Lys Phe Asn Trp Tyr
        275                 280                 285 gtg gac ggc gtg gag gtg cac aac gcc aag acc aag ccc cgg gag gag    912
Val Asp Gly Val Glu Val His Asn Ala Lys Thr Lys Pro Arg Glu Glu
290                 295                 300 cag tac aac agc acc tac cgg gtg gtg agc gtg ctc acc gtg ctg cac    960
Gln Tyr Asn Ser Thr Tyr Arg Val Val Ser Val Leu Thr Val Leu His
305                 310                 315                 320 cag gac tgg ctg aac ggc aag gag tac aag tgc aag gtg agc aac aag   1008
Gln Asp Trp Leu Asn Gly Lys Glu Tyr Lys Cys Lys Val Ser Asn Lys
                325                 330                 335 gcc ctg cct gcc ccc atc gag aag acc atc agc aag gcc aag ggc cag   1056
Ala Leu Pro Ala Pro Ile Glu Lys Thr Ile Ser Lys Ala Lys Gly Gln
            340                 345                 350 ccc cgg gag ccc cag gtg tac acc ctg ccc ccc agc cgg gag gag atg   1104
Pro Arg Glu Pro Gln Val Tyr Thr Leu Pro Pro Ser Arg Glu Glu Met
        355                 360                 365 acc aag aac cag gtg tcc ctc acc tgt ctg gtg aag ggc ttc tac ccc   1152
Thr Lys Asn Gln Val Ser Leu Thr Cys Leu Val Lys Gly Phe Tyr Pro
370                 375                 380 agc gac atc gcc gtg gag tgg gag agc aac ggc cag ccc gag aac aac   1200
Ser Asp Ile Ala Val Glu Trp Glu Ser Asn Gly Gln Pro Glu Asn Asn
385                 390                 395                 400 tac aag acc acc ccc cct gtg ctg gac agc gac ggc agc ttc ttc ctg   1248
Tyr Lys Thr Thr Pro Pro Val Leu Asp Ser Asp Gly Ser Phe Phe Leu
                405                 410                 415 tac agc aag ctc acc gtg gac aag agc cgg tgg cag cag ggc aac gtg   1296
Tyr Ser Lys Leu Thr Val Asp Lys Ser Arg Trp Gln Gln Gly Asn Val
            420                 425                 430 ttc agc tgc agc gtg atg cac gag gcc ctg cac aac cac tac acc cag   1344
Phe Ser Cys Ser Val Met His Glu Ala Leu His Asn His Tyr Thr Gln
        435                 440                 445 aag agc ctg agc ctg agc ccc ggc aag                                1371
Lys Ser Leu Ser Leu Ser Pro Gly Lys
    450                 455
```

<210> SEQ ID NO 127
<211> LENGTH: 457
<212> TYPE: PRT
<213> ORGANISM: Artificial sequence
<220> FEATURE:
<223> OTHER INFORMATION: Heavy chain CR4353

<400> SEQUENCE: 127

```
Gln Val Gln Leu Val Glu Ser Gly Gly Val Gln Pro Gly Arg
1               5                   10              15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
            35                  40                  45

Ala Val Ile Ser Tyr Asp Gly Asn Lys Tyr Tyr Ala Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Trp Ser Gly Tyr Ser Met Val Asp Ser Tyr Tyr Tyr
            100                 105                 110

Tyr Met Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
    195                 200                 205

Ile Cys Asn Val Asn His Lys Pro Ser Asn Thr Lys Val Asp Lys Arg
            210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415
```

```
Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 128
<211> LENGTH: 1380
<212> TYPE: DNA
<213> ORGANISM: Artificial sequence
<220> FEATURE:
<223> OTHER INFORMATION: Heavy chain CR4361
<220> FEATURE:
<221> NAME/KEY: CDS
<222> LOCATION: (1)..(1380)

<400> SEQUENCE: 128 gag gtg cag ctg gtg cag tct gga gca gaa gtg aaa aag ccc ggg gag      48
Glu Val Gln Leu Val Gln Ser Gly Ala Glu Val Lys Lys Pro Gly Glu
1               5                   10                  15 tct ctg aag atc tcc tgt aag gcc tct gga ttc agc ttt agc acc tat      96
Ser Leu Lys Ile Ser Cys Lys Ala Ser Gly Phe Ser Phe Ser Thr Tyr
            20                  25                  30 tgg atc ggc tgg gta cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc atc tat cct gct gac tct gat acc aga tac agc ccg tcc ttc     192
Gly Ile Ile Tyr Pro Ala Asp Ser Asp Thr Arg Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga ctc cga ggc ccc tat tac gat ttt tgg aat ggc tat cgg gag     336
Ala Arg Leu Arg Gly Pro Tyr Tyr Asp Phe Trp Asn Gly Tyr Arg Glu
            100                 105                 110 aca cat gat gct ttt aat gtg tgg ggc cag ggc acc atg gtg acc gtg     384
Thr His Asp Ala Phe Asn Val Trp Gly Gln Gly Thr Met Val Thr Val
        115                 120                 125 tcc agc gct agc acc aag ggc ccc agc gtg ttc ccc ctg gcc ccc agc     432
Ser Ser Ala Ser Thr Lys Gly Pro Ser Val Phe Pro Leu Ala Pro Ser
    130                 135                 140 agc aag agc acc agc ggc ggc aca gcc gcc ctg ggc tgc ctg gtg aag     480
Ser Lys Ser Thr Ser Gly Gly Thr Ala Ala Leu Gly Cys Leu Val Lys
145                 150                 155                 160 gac tac ttc ccc gag ccc gtg acc gtg agc tgg aac agc ggc gcc ttg     528
Asp Tyr Phe Pro Glu Pro Val Thr Val Ser Trp Asn Ser Gly Ala Leu
                165                 170                 175 acc agc ggc gtg cac acc ttc ccc gcc gtg ctg cag agc agc ggc ctg     576
Thr Ser Gly Val His Thr Phe Pro Ala Val Leu Gln Ser Ser Gly Leu
            180                 185                 190 tac agc ctg agc agc gtg gtg acc gtg ccc agc agc agc ctg ggc acc     624
Tyr Ser Leu Ser Ser Val Val Thr Val Pro Ser Ser Ser Leu Gly Thr
        195                 200                 205 cag acc tac atc tgc aac gtg aac cac aag ccc agc aac acc aag gtg     672
Gln Thr Tyr Ile Cys Asn Val Asn His Lys Pro Ser Asn Thr Lys Val
    210                 215                 220 gac aaa cgc gtg gag ccc aag agc tgc gac aag acc cac acc tgc ccc     720
```

-continued

```
Asp Lys Arg Val Glu Pro Lys Ser Cys Asp Lys Thr His Thr Cys Pro
225                 230                 235                 240 ccc tgc cct gcc ccc gag ctg ctg ggc gga ccc tcc gtg ttc ctg ttc      768
Pro Cys Pro Ala Pro Glu Leu Leu Gly Gly Pro Ser Val Phe Leu Phe
                    245                 250                 255 ccc ccc aag ccc aag gac acc ctc atg atc agc cgg acc ccc gag gtg      816
Pro Pro Lys Pro Lys Asp Thr Leu Met Ile Ser Arg Thr Pro Glu Val
                260                 265                 270 acc tgc gtg gtg gtg gac gtg agc cac gag gac ccc gag gtg aag ttc      864
Thr Cys Val Val Val Asp Val Ser His Glu Asp Pro Glu Val Lys Phe
            275                 280                 285 aac tgg tac gtg gac ggc gtg gag gtg cac aac gcc aag acc aag ccc      912
Asn Trp Tyr Val Asp Gly Val Glu Val His Asn Ala Lys Thr Lys Pro
        290                 295                 300 cgg gag gag cag tac aac agc acc tac cgg gtg gtg agc gtg ctc acc      960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg      1008
Val Leu His Gln Asp Trp Leu Asn Gly Lys Glu Tyr Lys Cys Lys Val
                    325                 330                 335 agc aac aag gcc ctg cct gcc ccc atc gag aag acc atc agc aag gcc      1056
Ser Asn Lys Ala Leu Pro Ala Pro Ile Glu Lys Thr Ile Ser Lys Ala
                340                 345                 350 aag ggc cag ccc cgg gag ccc cag gtg tac acc ctg ccc ccc agc cgg      1104
Lys Gly Gln Pro Arg Glu Pro Gln Val Tyr Thr Leu Pro Pro Ser Arg
            355                 360                 365 gag gag atg acc aag aac cag gtg tcc ctc acc tgt ctg gtg aag ggc      1152
Glu Glu Met Thr Lys Asn Gln Val Ser Leu Thr Cys Leu Val Lys Gly
        370                 375                 380 ttc tac ccc agc gac atc gcc gtg gag tgg gag agc aac ggc cag ccc      1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc      1248
Glu Asn Asn Tyr Lys Thr Thr Pro Pro Val Leu Asp Ser Asp Gly Ser
                    405                 410                 415 ttc ttc ctg tac agc aag ctc acc gtg gac aag agc cgg tgg cag cag      1296
Phe Phe Leu Tyr Ser Lys Leu Thr Val Asp Lys Ser Arg Trp Gln Gln
                420                 425                 430 ggc aac gtg ttc agc tgc agc gtg atg cac gag gcc ctg cac aac cac      1344
Gly Asn Val Phe Ser Cys Ser Val Met His Glu Ala Leu His Asn His
            435                 440                 445 tac acc cag aag agc ctg agc ctg agc ccc ggc aag                      1380
Tyr Thr Gln Lys Ser Leu Ser Leu Ser Pro Gly Lys
450                 455                 460
```

<210> SEQ ID NO 129
<211> LENGTH: 460
<212> TYPE: PRT
<213> ORGANISM: Artificial sequence
<220> FEATURE:
<223> OTHER INFORMATION: Heavy chain CR4361

<400> SEQUENCE: 129

```
Glu Val Gln Leu Val Gln Ser Gly Ala Glu Val Lys Lys Pro Gly Glu
1               5                   10                  15

Ser Leu Lys Ile Ser Cys Lys Ala Ser Gly Phe Ser Phe Ser Thr Tyr
            20                  25                  30

Trp Ile Gly Trp Val Arg Gln Met Pro Gly Lys Gly Leu Glu Trp Met
        35                  40                  45

Gly Ile Ile Tyr Pro Ala Asp Ser Asp Thr Arg Tyr Ser Pro Ser Phe
```

-continued

```
                50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                     85                  90                  95
Ala Arg Leu Arg Gly Pro Tyr Tyr Asp Phe Trp Asn Gly Tyr Arg Glu
                100                 105                 110
Thr His Asp Ala Phe Asn Val Trp Gly Gln Gly Thr Met Val Thr Val
                115                 120                 125
Ser Ser Ala Ser Thr Lys Gly Pro Ser Val Phe Pro Leu Ala Pro Ser
                130                 135                 140
Ser Lys Ser Thr Ser Gly Gly Thr Ala Ala Leu Gly Cys Leu Val Lys
145                 150                 155                 160
Asp Tyr Phe Pro Glu Pro Val Thr Val Ser Trp Asn Ser Gly Ala Leu
                165                 170                 175
Thr Ser Gly Val His Thr Phe Pro Ala Val Leu Gln Ser Ser Gly Leu
                180                 185                 190
Tyr Ser Leu Ser Ser Val Val Thr Val Pro Ser Ser Ser Leu Gly Thr
                195                 200                 205
Gln Thr Tyr Ile Cys Asn Val Asn His Lys Pro Ser Asn Thr Lys Val
                210                 215                 220
Asp Lys Arg Val Glu Pro Lys Ser Cys Asp Lys Thr His Thr Cys Pro
225                 230                 235                 240
Pro Cys Pro Ala Pro Glu Leu Leu Gly Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Lys Phe
                275                 280                 285
Asn Trp Tyr Val Asp Gly Val Glu Val His Asn Ala Lys Thr Lys Pro
                290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Ala Leu Pro Ala Pro Ile Glu Lys Thr Ile Ser Lys Ala
                340                 345                 350
Lys Gly Gln Pro Arg Glu Pro Gln Val Tyr Thr Leu Pro Pro Ser Arg
                355                 360                 365
Glu Glu Met Thr Lys Asn Gln Val Ser Leu Thr Cys Leu Val Lys Gly
                370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
                420                 425                 430
Gly Asn Val Phe Ser Cys Ser Val Met His Glu Ala Leu His Asn His
                435                 440                 445
Tyr Thr Gln Lys Ser Leu Ser Leu Ser Pro Gly Lys
                450                 455                 460

<210> SEQ ID NO 130
```

<211> LENGTH: 1380
<212> TYPE: DNA
<213> ORGANISM: Artificial sequence
<220> FEATURE:
<223> OTHER INFORMATION: Heavy chain CR4374
<220> FEATURE:
<221> NAME/KEY: CDS
<222> LOCATION: (1)..(1380)

<400> SEQUENCE: 130

| | | | | | | | | | | | | | | | | |
|---|---|---|---|---|---|---|---|---|---|---|---|---|---|---|---|---|
| cag | atc | acc | ttg | aag | gag | tct | ggt | cct | acg | ctg | gtg | aaa | ccc | aca | cag | 48 |
| Gln | Ile | Thr | Leu | Lys | Glu | Ser | Gly | Pro | Thr | Leu | Val | Lys | Pro | Thr | Gln | |
| 1 | | | | 5 | | | | | 10 | | | | | 15 | | |
| acc | ctc | acg | ttg | acc | tgc | acc | ttc | tct | ggg | ttc | tca | ctc | agc | act | agt | 96 |
| Thr | Leu | Thr | Leu | Thr | Cys | Thr | Phe | Ser | Gly | Phe | Ser | Leu | Ser | Thr | Ser | |
| | | | 20 | | | | | 25 | | | | | 30 | | | |
| gga | gtg | ggt | gtg | ggc | tgg | atc | cgt | cag | ccc | cca | gga | aag | gcc | ctg | gag | 144 |
| Gly | Val | Gly | Val | Gly | Trp | Ile | Arg | Gln | Pro | Pro | Gly | Lys | Ala | Leu | Glu | |
| | | 35 | | | | | 40 | | | | | 45 | | | | |
| tgg | ctt | gca | gtc | att | tat | tgg | aat | gat | gat | aag | ctc | tac | agg | cca | tct | 192 |
| Trp | Leu | Ala | Val | Ile | Tyr | Trp | Asn | Asp | Asp | Lys | Leu | Tyr | Arg | Pro | Ser | |
| | 50 | | | | | 55 | | | | | 60 | | | | | |
| ctg | aag | agc | agg | ctc | acc | atc | acc | aag | gac | acc | tcc | aaa | aac | cag | gtg | 240 |
| Leu | Lys | Ser | Arg | Leu | Thr | Ile | Thr | Lys | Asp | Thr | Ser | Lys | Asn | Gln | Val | |
| 65 | | | | | 70 | | | | | 75 | | | | | 80 | |
| gtc | ctt | aca | atg | acc | aag | atg | gac | cct | gtg | gac | aca | gcc | aca | tat | tac | 288 |
| Val | Leu | Thr | Met | Thr | Lys | Met | Asp | Pro | Val | Asp | Thr | Ala | Thr | Tyr | Tyr | |
| | | | | 85 | | | | | 90 | | | | | 95 | | |
| tgt | gca | cac | aga | cac | cgt | tac | tat | gat | att | agt | ggt | tat | tac | cgt | ctc | 336 |
| Cys | Ala | His | Arg | His | Arg | Tyr | Tyr | Asp | Ile | Ser | Gly | Tyr | Tyr | Arg | Leu | |
| | | | 100 | | | | | 105 | | | | | 110 | | | |
| ttc | tct | gat | gct | ttt | gat | atc | tgg | ggc | cag | ggc | acc | atg | gtg | acc | gtg | 384 |
| Phe | Ser | Asp | Ala | Phe | Asp | Ile | Trp | Gly | Gln | Gly | Thr | Met | Val | Thr | Val | |
| | | 115 | | | | | 120 | | | | | 125 | | | | |
| tcc | agc | gct | agc | acc | aag | ggc | ccc | agc | gtg | ttc | ccc | ctg | gcc | ccc | agc | 432 |
| Ser | Ser | Ala | Ser | Thr | Lys | Gly | Pro | Ser | Val | Phe | Pro | Leu | Ala | Pro | Ser | |
| | 130 | | | | | 135 | | | | | 140 | | | | | |
| agc | aag | agc | acc | agc | ggc | ggc | aca | gcc | gcc | ctg | ggc | tgc | ctg | gtg | aag | 480 |
| Ser | Lys | Ser | Thr | Ser | Gly | Gly | Thr | Ala | Ala | Leu | Gly | Cys | Leu | Val | Lys | |
| 145 | | | | | 150 | | | | | 155 | | | | | 160 | |
| gac | tac | ttc | ccc | gag | ccc | gtg | acc | gtg | agc | tgg | aac | agc | ggc | gcc | ttg | 528 |
| Asp | Tyr | Phe | Pro | Glu | Pro | Val | Thr | Val | Ser | Trp | Asn | Ser | Gly | Ala | Leu | |
| | | | | 165 | | | | | 170 | | | | | 175 | | |
| acc | agc | ggc | gtg | cac | acc | ttc | ccc | gcc | gtg | ctg | cag | agc | agc | ggc | ctg | 576 |
| Thr | Ser | Gly | Val | His | Thr | Phe | Pro | Ala | Val | Leu | Gln | Ser | Ser | Gly | Leu | |
| | | | 180 | | | | | 185 | | | | | 190 | | | |
| tac | agc | ctg | agc | agc | gtg | gtg | acc | gtg | ccc | agc | agc | agc | ctg | ggc | acc | 624 |
| Tyr | Ser | Leu | Ser | Ser | Val | Val | Thr | Val | Pro | Ser | Ser | Ser | Leu | Gly | Thr | |
| | | 195 | | | | | 200 | | | | | 205 | | | | |
| cag | acc | tac | atc | tgc | aac | gtg | aac | cac | aag | ccc | agc | aac | acc | aag | gtg | 672 |
| Gln | Thr | Tyr | Ile | Cys | Asn | Val | Asn | His | Lys | Pro | Ser | Asn | Thr | Lys | Val | |
| | 210 | | | | | 215 | | | | | 220 | | | | | |
| gac | aaa | cgc | gtg | gag | ccc | aag | agc | tgc | gac | aag | acc | cac | acc | tgc | ccc | 720 |
| Asp | Lys | Arg | Val | Glu | Pro | Lys | Ser | Cys | Asp | Lys | Thr | His | Thr | Cys | Pro | |
| 225 | | | | | 230 | | | | | 235 | | | | | 240 | |
| ccc | tgc | cct | gcc | ccc | gag | ctg | ctg | ggc | gga | ccc | tcc | gtg | ttc | ctg | ttc | 768 |
| Pro | Cys | Pro | Ala | Pro | Glu | Leu | Leu | Gly | Gly | Pro | Ser | Val | Phe | Leu | Phe | |
| | | | | 245 | | | | | 250 | | | | | 255 | | |
| ccc | ccc | aag | ccc | aag | gac | acc | ctc | atg | atc | agc | cgg | acc | ccc | gag | gtg | 816 |
| Pro | Pro | Lys | Pro | Lys | Asp | Thr | Leu | Met | Ile | Ser | Arg | Thr | Pro | Glu | Val | |
| | | | 260 | | | | | 265 | | | | | 270 | | | |

```
acc tgc gtg gtg gtg gac gtg agc cac gag gac ccc gag gtg aag ttc        864
Thr Cys Val Val Val Asp Val Ser His Glu Asp Pro Glu Val Lys Phe
        275                 280                 285 aac tgg tac gtg gac ggc gtg gag gtg cac aac gcc aag acc aag ccc        912
Asn Trp Tyr Val Asp Gly Val Glu Val His Asn Ala Lys Thr Lys Pro
    290                 295                 300 cgg gag gag cag tac aac agc acc tac cgg gtg gtg agc gtc ctc acc        960
Arg Glu Glu Gln Tyr Asn Ser Thr Tyr Arg Val Val Ser Val Leu Thr
305                 310                 315                 320 gtg ctg cac cag gac tgg ctg aac ggc aag gag tac aag tgc aag gtg       1008
Val Leu His Gln Asp Trp Leu Asn Gly Lys Glu Tyr Lys Cys Lys Val
                325                 330                 335 agc aac aag gcc ctg cct gcc ccc atc gag aag acc atc agc aag gcc       1056
Ser Asn Lys Ala Leu Pro Ala Pro Ile Glu Lys Thr Ile Ser Lys Ala
        340                 345                 350 aag ggc cag ccc cgg gag ccc cag gtg tac acc ctg ccc ccc agc cgg       1104
Lys Gly Gln Pro Arg Glu Pro Gln Val Tyr Thr Leu Pro Pro Ser Arg
    355                 360                 365 gag gag atg acc aag aac cag gtg tcc ctc acc tgt ctg gtg aag ggc       1152
Glu Glu Met Thr Lys Asn Gln Val Ser Leu Thr Cys Leu Val Lys Gly
370                 375                 380 ttc tac ccc agc gac atc gcc gtg gag tgg gag agc aac ggc cag ccc       1200
Phe Tyr Pro Ser Asp Ile Ala Val Glu Trp Glu Ser Asn Gly Gln Pro
385                 390                 395                 400 gag aac aac tac aag acc acc ccc cct gtg ctg gac agc gac ggc agc       1248
Glu Asn Asn Tyr Lys Thr Thr Pro Pro Val Leu Asp Ser Asp Gly Ser
                405                 410                 415 ttc ttc ctg tac agc aag ctc acc gtg gac aag agc cgg tgg cag cag       1296
Phe Phe Leu Tyr Ser Lys Leu Thr Val Asp Lys Ser Arg Trp Gln Gln
        420                 425                 430 ggc aac gtg ttc agc tgc agc gtg atg cac gag gcc ctg cac aac cac       1344
Gly Asn Val Phe Ser Cys Ser Val Met His Glu Ala Leu His Asn His
    435                 440                 445 tac acc cag aag agc ctg agc ctg agc ccc ggc aag                       1380
Tyr Thr Gln Lys Ser Leu Ser Leu Ser Pro Gly Lys
450                 455                 460

<210> SEQ ID NO 131
<211> LENGTH: 460
<212> TYPE: PRT
<213> ORGANISM: Artificial sequence
<220> FEATURE:
<223> OTHER INFORMATION: Heavy chain CR4374

<400> SEQUENCE: 131

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
            100                 105                 110
```

Phe Ser Asp Ala Phe Asp Ile Trp Gly Gln Gly Thr Met Val Thr Val
            115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 132
<211> LENGTH: 648
<212> TYPE: DNA
<213> ORGANISM: Artificial sequence
<220> FEATURE:
<223> OTHER INFORMATION: Light chain CR4271
<220> FEATURE:
<221> NAME/KEY: CDS
<222> LOCATION: (1)..(648)

<400> SEQUENCE: 132

| | | |
|---|---|---|
| cag tcc gcc ctg acc cag ccc cgc tca gtg tcc ggg tct cct gga cag<br>Gln Ser Ala Leu Thr Gln Pro Arg Ser Val Ser Gly Ser Pro Gly Gln<br>1               5                   10                  15 | | 48 |
| tca gtc acc atc tcc tgc act gga acc agc agt gat gtt ggt ggt tat<br>Ser Val Thr Ile Ser Cys Thr Gly Thr Ser Ser Asp Val Gly Gly Tyr<br>            20                  25                  30 | | 96 |
| aac tat gtc tcc tgg tac caa cat cac cca ggc aaa gcc ccc aaa ctc<br>Asn Tyr Val Ser Trp Tyr Gln His His Pro Gly Lys Ala Pro Lys Leu<br>        35                  40                  45 | | 144 |
| atg att tat gat gtc agt aat cgg ccc tta ggg gtt tct aat cgc ttc<br>Met Ile Tyr Asp Val Ser Asn Arg Pro Leu Gly Val Ser Asn Arg Phe<br>    50                  55                  60 | | 192 |
| tct ggc tcc aag tct ggc aac acg gcc tcc ctg acc atc tct ggg ctc<br>Ser Gly Ser Lys Ser Gly Asn Thr Ala Ser Leu Thr Ile Ser Gly Leu<br>65                  70                  75                  80 | | 240 |
| cag gct gag gac gag gct gat tat tac tgc agc tca tat aca agc agc<br>Gln Ala Glu Asp Glu Ala Asp Tyr Tyr Cys Ser Ser Tyr Thr Ser Ser<br>                85                  90                  95 | | 288 |
| agc act tat gtc ttc gga act ggg acc aag ctt acc gtc ctg ggc cag<br>Ser Thr Tyr Val Phe Gly Thr Gly Thr Lys Leu Thr Val Leu Gly Gln<br>            100                 105                 110 | | 336 |
| ccc aag gcc gct ccc agc gtg acc ctg ttc ccc ccc tcc tcc gag gag<br>Pro Lys Ala Ala Pro Ser Val Thr Leu Phe Pro Pro Ser Ser Glu Glu<br>        115                 120                 125 | | 384 |
| ctg cag gcc aac aag gcc acc ctg gtg tgc ctc atc agc gac ttc tac<br>Leu Gln Ala Asn Lys Ala Thr Leu Val Cys Leu Ile Ser Asp Phe Tyr<br>    130                 135                 140 | | 432 |
| cct ggc gcc gtg acc gtg gcc tgg aag gcc gac agc agc ccc gtg aag<br>Pro Gly Ala Val Thr Val Ala Trp Lys Ala Asp Ser Ser Pro Val Lys<br>145                 150                 155                 160 | | 480 |
| gcc ggc gtg gag acc acc acc ccc agc aag cag agc aac aac aag tac<br>Ala Gly Val Glu Thr Thr Thr Pro Ser Lys Gln Ser Asn Asn Lys Tyr<br>                165                 170                 175 | | 528 |
| gcc gcc agc agc tac ctg agc ctc acc ccc gag cag tgg aag agc cac<br>Ala Ala Ser Ser Tyr Leu Ser Leu Thr Pro Glu Gln Trp Lys Ser His<br>            180                 185                 190 | | 576 |
| cgg agc tac agc tgc cag gtg acc cac gag ggc agc acc gtg gag aag<br>Arg Ser Tyr Ser Cys Gln Val Thr His Glu Gly Ser Thr Val Glu Lys<br>        195                 200                 205 | | 624 |
| acc gtg gcc ccc acc gag tgc agc<br>Thr Val Ala Pro Thr Glu Cys Ser<br>    210                 215 | | 648 |

<210> SEQ ID NO 133
<211> LENGTH: 216
<212> TYPE: PRT
<213> ORGANISM: Artificial sequence
<220> FEATURE:
<223> OTHER INFORMATION: Light chain CR4271

<400> SEQUENCE: 133

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Met Ile Tyr Asp Val Ser Asn Arg Pro Leu Gly Val Ser Asn Arg Phe
    50                  55                  60

Ser Gly Ser Lys Ser Gly Asn Thr Ala Ser Leu Thr Ile Ser Gly Leu

```
                  65                  70                  75                  80
Gln Ala Glu Asp Glu Ala Asp Tyr Tyr Cys Ser Ser Tyr Thr Ser Ser
                        85                  90                  95

Ser Thr Tyr Val Phe Gly Thr Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
    195                 200                 205

Thr Val Ala Pro Thr Glu Cys Ser
    210                 215

<210> SEQ ID NO 134
<211> LENGTH: 660
<212> TYPE: DNA
<213> ORGANISM: Artificial sequence
<220> FEATURE:
<223> OTHER INFORMATION: Light chain CR4274
<220> FEATURE:
<221> NAME/KEY: CDS
<222> LOCATION: (1)..(660)

<400> SEQUENCE: 134 gac atc gtg atg acc cag tct cca gac tcc ctg gct gtg tct ctg ggc      48
Asp Ile Val Met Thr Gln Ser Pro Asp Ser Leu Ala Val Ser Leu Gly
1               5                   10                  15 gag agg gcc acc atc aac tgc aag tcc agc cag agt gtt tta tac agc      96
Glu Arg Ala Thr Ile Asn Cys Lys Ser Ser Gln Ser Val Leu Tyr Ser
            20                  25                  30 tcc aac aat aag aac tac tta gct tgg tac cag cag aaa cca gga cag     144
Ser Asn Asn Lys Asn Tyr Leu Ala Trp Tyr Gln Gln Lys Pro Gly Gln
        35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tat tgt cag caa     288
Ile Ser Ser Leu Gln Ala Glu Asp Val Ala Val Tyr Tyr Cys Gln Gln
                85                  90                  95 tat tat agt act cct ccg act ttc ggc gga ggg acc aag gtg gag atc     336
Tyr Tyr Ser Thr Pro Pro Thr Phe Gly Gly Gly Thr Lys Val Glu Ile
            100                 105                 110 aag cgg acc gtg gcc gct ccc agc gtg ttc atc ttc ccc ccc tcc gac     384
Lys Arg Thr Val Ala Ala Pro Ser Val Phe Ile Phe Pro Pro Ser Asp
        115                 120                 125 gag cag ctg aag agc ggc acc gcc agc gtg gtg tgc ctg ctg aac aac     432
Glu Gln Leu Lys Ser Gly Thr Ala Ser Val Val Cys Leu Leu Asn Asn
    130                 135                 140 ttc tac ccc cgg gag gcc aag gtg cag tgg aag gtg gac aac gcc ctg     480
```

```
Phe Tyr Pro Arg Glu Ala Lys Val Gln Trp Lys Val Asp Asn Ala Leu
145                 150                 155                 160 cag agc ggc aac agc cag gag agc gtg acc gag cag gac agc aag gac        528
Gln Ser Gly Asn Ser Gln Glu Ser Val Thr Glu Gln Asp Ser Lys Asp
                165                 170                 175 tcc acc tac agc ctg agc agc acc ctc acc ctg agc aag gcc gac tac        576
Ser Thr Tyr Ser Leu Ser Ser Thr Leu Thr Leu Ser Lys Ala Asp Tyr
            180                 185                 190 gag aag cac aag gtg tac gcc tgc gag gtg acc cac cag ggc ctg agc        624
Glu Lys His Lys Val Tyr Ala Cys Glu Val Thr His Gln Gly Leu Ser
        195                 200                 205 agc ccc gtg acc aag agc ttc aac cgg ggc gag tgt                        660
Ser Pro Val Thr Lys Ser Phe Asn Arg Gly Glu Cys
    210                 215                 220

<210> SEQ ID NO 135
<211> LENGTH: 220
<212> TYPE: PRT
<213> ORGANISM: Artificial sequence
<220> FEATURE:
<223> OTHER INFORMATION: Light chain CR4274

<400> SEQUENCE: 135

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 136
<211> LENGTH: 636
<212> TYPE: DNA
<213> ORGANISM: Artificial sequence
<220> FEATURE:
<223> OTHER INFORMATION: Light chain CR4283
<220> FEATURE:
```

```
<221> NAME/KEY: CDS
<222> LOCATION: (1)..(636)

<400> SEQUENCE: 136 gac atc cag atg acc cag tct cct tcc acc ctg tct gca tct gta gga        48
Asp Ile Gln Met Thr Gln Ser Pro Ser Thr Leu Ser Ala Ser Val Gly
1               5                   10                  15 gac aga gtc acc atc act tgc cgg gcc agt cag agt att agt agc tgg        96
Asp Arg Val Thr Ile Thr Cys Arg Ala Ser Gln Ser Ile Ser Ser Trp
            20                  25                  30 ttg gcc tgg tat cag cag aaa cca ggg aaa gcc cct aat ctc ctg atc       144
Leu Ala Trp Tyr Gln Gln Lys Pro Gly Lys Ala Pro Asn Leu Leu Ile
        35                  40                  45 tat gct gca tcc agt ttg caa agt ggg gtc cca tca agg ttc agc ggc       192
Tyr Ala Ala Ser Ser Leu Gln Ser Gly Val Pro Ser Arg Phe Ser Gly
    50                  55                  60 agt gga tct ggg aca gat ttc act ctc acc atc agc agc ctg cag cct       240
Ser Gly Ser Gly Thr Asp Phe Thr Leu Thr Ile Ser Ser Leu Gln Pro
65                  70                  75                  80 gat gac tct gca act tat tac tgc caa cag tat aat act tat ccc ctc       288
Asp Asp Ser Ala Thr Tyr Tyr Cys Gln Gln Tyr Asn Thr Tyr Pro Leu
                85                  90                  95 act ttc ggg acc aag gtg gag atc aag cgg acc gtg gct gct ccc agc       336
Thr Phe Gly Thr Lys Val Glu Ile Lys Arg Thr Val Ala Ala Pro Ser
            100                 105                 110 gtg ttc atc ttc ccc ccc tcc gac gag cag ctg aag agc ggc acc gcc       384
Val Phe Ile Phe Pro Pro Ser Asp Glu Gln Leu Lys Ser Gly Thr Ala
        115                 120                 125 agc gtg gtg tgc ctg ctg aac aac ttc tac ccc cgg gag gcc aag gtg       432
Ser Val Val Cys Leu Leu Asn Asn Phe Tyr Pro Arg Glu Ala Lys Val
    130                 135                 140 cag tgg aag gtg gac aac gcc ctg cag agc ggc aac agc cag gag agc       480
Gln Trp Lys Val Asp Asn Ala Leu Gln Ser Gly Asn Ser Gln Glu Ser
145                 150                 155                 160 gtg acc gag cag gac agc aag gac tcc acc tac agc ctg agc agc acc       528
Val Thr Glu Gln Asp Ser Lys Asp Ser Thr Tyr Ser Leu Ser Ser Thr
                165                 170                 175 ctc acc ctg agc aag gcc gac tac gag aag cac aag gtg tac gcc tgc       576
Leu Thr Leu Ser Lys Ala Asp Tyr Glu Lys His Lys Val Tyr Ala Cys
            180                 185                 190 gag gtg acc cac cag ggc ctg agc agc ccc gtg acc aag agc ttc aac       624
Glu Val Thr His Gln Gly Leu Ser Ser Pro Val Thr Lys Ser Phe Asn
        195                 200                 205 cgg ggc gag tgt                                                       636
Arg Gly Glu Cys
    210

<210> SEQ ID NO 137
<211> LENGTH: 212
<212> TYPE: PRT
<213> ORGANISM: Artificial sequence
<220> FEATURE:
<223> OTHER INFORMATION: Light chain CR4283

<400> SEQUENCE: 137

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Asp Asp Ser Ala Thr Tyr Tyr Cys Gln Gln Tyr Asn Thr Tyr Pro Leu
                85                  90                  95

Thr Phe Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 138
<211> LENGTH: 651
<212> TYPE: DNA
<213> ORGANISM: Artificial sequence
<220> FEATURE:
<223> OTHER INFORMATION: Light chain CR4289
<220> FEATURE:
<221> NAME/KEY: CDS
<222> LOCATION: (1)..(651)

<400> SEQUENCE: 138 tcg acg gaa att gtg ttg acg cag tct cca ggc acc ctg tct ttg tct        48
Ser Thr Glu Ile Val Leu Thr Gln Ser Pro Gly Thr Leu Ser Leu Ser
1               5                   10                  15 cca ggg gaa aca gcc acc ctc tcc tgc agg acc agt cag agt gtt agt        96
Pro Gly Glu Thr Ala Thr Leu Ser Cys Arg Thr Ser Gln Ser Val Ser
            20                  25                  30 agc agc tac tta ggc tgg tac cag cag aaa cct ggc cag gct ccc agg       144
Ser Ser Tyr Leu Gly Trp Tyr Gln Gln Lys Pro Gly Gln Ala Pro Arg
        35                  40                  45 ctc ctc atc tat ggt gca tcc atc agg gcc act ggc atc cca gcc agg       192
Leu Leu Ile Tyr Gly Ala Ser Ile Arg Ala Thr Gly Ile Pro Ala Arg
    50                  55                  60 ttc agt ggc agt ggg tct ggg aca gag ttc act ctc acc atc gac agc       240
Phe Ser Gly Ser Gly Ser Gly Thr Glu Phe Thr Leu Thr Ile Asp Ser
65                  70                  75                  80 cta cag tct gaa gat ttt gca gtt tat tac tgt cag cag tat aat aac       288
Leu Gln Ser Glu Asp Phe Ala Val Tyr Tyr Cys Gln Gln Tyr Asn Asn
                85                  90                  95 tgg cct ccg atc acc ttc ggc caa ggg aca cga ctg gag att aaa cgt       336
Trp Pro Pro Ile Thr Phe Gly Gln Gly Thr Arg Leu Glu Ile Lys Arg
            100                 105                 110 gcg gcc gca ccc agc gtg ttc atc ttc ccc ccc tcc gac gag cag ctg       384
Ala Ala Ala Pro Ser Val Phe Ile Phe Pro Pro Ser Asp Glu Gln Leu
        115                 120                 125
```

```
aag agc ggc acc gcc agc gtg gtg tgc ctg ctg aac aac ttc tac ccc      432
Lys Ser Gly Thr Ala Ser Val Val Cys Leu Leu Asn Asn Phe Tyr Pro
    130                 135                 140 cgg gag gcc aag gtg cag tgg aag gtg gac aac gcc ctg cag agc ggc      480
Arg Glu Ala Lys Val Gln Trp Lys Val Asp Asn Ala Leu Gln Ser Gly
145                 150                 155                 160 aac agc cag gag agc gtg acc gag cag gac agc aag gac tcc acc tac      528
Asn Ser Gln Glu Ser Val Thr Glu Gln Asp Ser Lys Asp Ser Thr Tyr
                165                 170                 175 agc ctg agc agc acc ctc acc ctg agc aag gcc gac tac gag aag cac      576
Ser Leu Ser Ser Thr Leu Thr Leu Ser Lys Ala Asp Tyr Glu Lys His
            180                 185                 190 aag gtg tac gcc tgc gag gtg acc cac cag ggc ctg agc agc ccc gtg      624
Lys Val Tyr Ala Cys Glu Val Thr His Gln Gly Leu Ser Ser Pro Val
        195                 200                 205 acc aag agc ttc aac cgg ggc gag tgt                                  651
Thr Lys Ser Phe Asn Arg Gly Glu Cys
    210                 215

<210> SEQ ID NO 139
<211> LENGTH: 217
<212> TYPE: PRT
<213> ORGANISM: Artificial sequence
<220> FEATURE:
<223> OTHER INFORMATION: Light chain CR4289

<400> SEQUENCE: 139

Ser Thr Glu Ile Val Leu Thr Gln Ser Pro Gly Thr Leu Ser Leu Ser
1               5                   10                  15

Pro Gly Glu Thr Ala Thr Leu Ser Cys Arg Thr Ser Gln Ser Val Ser
            20                  25                  30

Ser Ser Tyr Leu Gly Trp Tyr Gln Gln Lys Pro Gly Gln Ala Pro Arg
        35                  40                  45

Leu Leu Ile Tyr Gly Ala Ser Ile Arg Ala Thr Gly Ile Pro Ala Arg
    50                  55                  60

Phe Ser Gly Ser Gly Ser Gly Thr Glu Phe Thr Leu Thr Ile Asp Ser
65                  70                  75                  80

Leu Gln Ser Glu Asp Phe Ala Val Tyr Tyr Cys Gln Gln Tyr Asn Asn
                85                  90                  95

Trp Pro Pro Ile Thr Phe Gly Gln Gly Thr Arg Leu Glu Ile Lys Arg
            100                 105                 110

Ala Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 140
<211> LENGTH: 648
```

```
<212> TYPE: DNA
<213> ORGANISM: Artificial sequence
<220> FEATURE:
<223> OTHER INFORMATION: Light chain CR4299
<220> FEATURE:
<221> NAME/KEY: CDS
<222> LOCATION: (1)..(648)

<400> SEQUENCE: 140 tcc tac gtg ctg act cag cca ccc tcg ctg tct gca gcc ccc agg cag       48
Ser Tyr Val Leu Thr Gln Pro Pro Ser Leu Ser Ala Ala Pro Arg Gln
 1               5                  10                  15 agg gtc acc atc tcc tgt tct gga agc agc tcc aat atc gga aat tat       96
Arg Val Thr Ile Ser Cys Ser Gly Ser Ser Ser Asn Ile Gly Asn Tyr
             20                  25                  30 ggt gtg aac tgg tac cag cag ctc cca gga aag gct ccc aaa ctc ctc      144
Gly Val Asn Trp Tyr Gln Gln Leu Pro Gly Lys Ala Pro Lys Leu Leu
         35                  40                  45 atc tat tat gat gat ctg ctg ccc tca ggg gtc tct gac cga ttc tct      192
Ile Tyr Tyr Asp Asp Leu Leu Pro Ser Gly Val Ser Asp Arg Phe Ser
     50                  55                  60 ggc tcc aag tct ggc acc tca gcc tcc ctg gcc atc agt ggg ctc cag      240
Gly Ser Lys Ser Gly Thr Ser Ala Ser Leu Ala Ile Ser Gly Leu Gln
 65                  70                  75                  80 tct gag gat gaa ggt gat tat tac tgt gca gcg tgg gat gac acc cta      288
Ser Glu Asp Glu Gly Asp Tyr Tyr Cys Ala Ala Trp Asp Asp Thr Leu
                 85                  90                  95 agt gct tgg gtg ttc ggc gga ggc acc aag ctt acc gtc ctg ggc cag      336
Ser Ala Trp Val Phe Gly Gly Gly Thr Lys Leu Thr Val Leu Gly Gln
            100                 105                 110 ccc aag gcc gct ccc agc gtg acc ctg ttc ccc ccc tcc tcc gag gag      384
Pro Lys Ala Ala Pro Ser Val Thr Leu Phe Pro Pro Ser Ser Glu Glu
        115                 120                 125 ctg cag gcc aac aag gcc acc ctg gtg tgc ctc atc agc gac ttc tac      432
Leu Gln Ala Asn Lys Ala Thr Leu Val Cys Leu Ile Ser Asp Phe Tyr
    130                 135                 140 cct ggc gcc gtg acc gtg gcc tgg aag gcc gac agc agc ccc gtg aag      480
Pro Gly Ala Val Thr Val Ala Trp Lys Ala Asp Ser Ser Pro Val Lys
145                 150                 155                 160 gcc ggc gtg gag acc acc acc ccc agc aag cag agc aac aac aag tac      528
Ala Gly Val Glu Thr Thr Thr Pro Ser Lys Gln Ser Asn Asn Lys Tyr
                165                 170                 175 gcc gcc agc agc tac ctg agc ctc acc ccc gag cag tgg aag agc cac      576
Ala Ala Ser Ser Tyr Leu Ser Leu Thr Pro Glu Gln Trp Lys Ser His
            180                 185                 190 cgg agc tac agc tgc cag gtg acc cac gag ggc agc acc gtg gag aag      624
Arg Ser Tyr Ser Cys Gln Val Thr His Glu Gly Ser Thr Val Glu Lys
        195                 200                 205 acc gtg gcc ccc acc gag tgc agc                                      648
Thr Val Ala Pro Thr Glu Cys Ser
    210                 215

<210> SEQ ID NO 141
<211> LENGTH: 216
<212> TYPE: PRT
<213> ORGANISM: Artificial sequence
<220> FEATURE:
<223> OTHER INFORMATION: Light chain CR4299

<400> SEQUENCE: 141

Ser Tyr Val Leu Thr Gln Pro Pro Ser Leu Ser Ala Ala Pro Arg Gln
 1               5                  10                  15
```

```
Arg Val Thr Ile Ser Cys Ser Gly Ser Ser Asn Ile Gly Asn Tyr
             20                  25                  30

Gly Val Asn Trp Tyr Gln Gln Leu Pro Gly Lys Ala Pro Lys Leu Leu
         35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Gly Asp Tyr Tyr Cys Ala Ala Trp Asp Asp Thr Leu
                 85                  90                  95

Ser Ala Trp Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 142
<211> LENGTH: 648
<212> TYPE: DNA
<213> ORGANISM: Artificial sequence
<220> FEATURE:
<223> OTHER INFORMATION: Light chain CR4311
<220> FEATURE:
<221> NAME/KEY: CDS
<222> LOCATION: (1)..(648)

<400> SEQUENCE: 142 cag tcc gtg ctg acc cag cct ccc tca gtg tct gcg gcc cca gga cag     48
Gln Ser Val Leu Thr Gln Pro Pro Ser Val Ser Ala Ala Pro Gly Gln
 1               5                  10                  15 aag gtc acc atc tcc tgc tct gga acc agc tcc aat att ggg gat aat     96
Lys Val Thr Ile Ser Cys Ser Gly Thr Ser Ser Asn Ile Gly Asp Asn
             20                  25                  30 tat gta tcc tgg tac cag cac ctc cca gga aca gcc ccc aaa ctc ctc    144
Tyr Val Ser Trp Tyr Gln His Leu Pro Gly Thr Ala Pro Lys Leu Leu
         35                  40                  45 att tat gac aat aat aag cga ccc tca ggg att cct gac cga ttc tct    192
Ile Tyr Asp Asn Asn Lys Arg Pro Ser Gly Ile Pro Asp Arg Phe Ser
 50                  55                  60 ggc tcc aag tct ggc acg tca gcc acc ctg ggc gtc acc gga ctc cag    240
Gly Ser Lys Ser Gly Thr Ser Ala Thr Leu Gly Val Thr Gly Leu Gln
 65                  70                  75                  80 act ggg gac gag gcc gat tat tac tgc gga aca tgg gat agc agc ctg    288
Thr Gly Asp Glu Ala Asp Tyr Tyr Cys Gly Thr Trp Asp Ser Ser Leu
                 85                  90                  95 act gct gtg gtc ttc ggc gga ggc acc aag ctt acc gtg ctg ggc cag    336
Thr Ala Val Val Phe Gly Gly Gly Thr Lys Leu Thr Val Leu Gly Gln
            100                 105                 110
```

```
ccc aag gcc gct ccc agc gtg acc ctg ttc ccc ccc tcc tcc gag gag      384
Pro Lys Ala Ala Pro Ser Val Thr Leu Phe Pro Pro Ser Ser Glu Glu
        115                 120                 125 ctg cag gcc aac aag gcc acc ctg gtg tgc ctc atc agc gac ttc tac      432
Leu Gln Ala Asn Lys Ala Thr Leu Val Cys Leu Ile Ser Asp Phe Tyr
130                 135                 140 cct ggc gcc gtg acc gtg gcc tgg aag gcc gac agc agc ccc gtg aag      480
Pro Gly Ala Val Thr Val Ala Trp Lys Ala Asp Ser Ser Pro Val Lys
145                 150                 155                 160 gcc ggc gtg gag acc acc acc ccc agc aag cag agc aac aac aag tac      528
Ala Gly Val Glu Thr Thr Thr Pro Ser Lys Gln Ser Asn Asn Lys Tyr
                165                 170                 175 gcc gcc agc agc tac ctg agc ctc acc ccc gag cag tgg aag agc cac      576
Ala Ala Ser Ser Tyr Leu Ser Leu Thr Pro Glu Gln Trp Lys Ser His
        180                 185                 190 cgg agc tac agc tgc cag gtg acc cac gag ggc agc acc gtg gag aag      624
Arg Ser Tyr Ser Cys Gln Val Thr His Glu Gly Ser Thr Val Glu Lys
        195                 200                 205 acc gtg gcc ccc acc gag tgc agc                                      648
Thr Val Ala Pro Thr Glu Cys Ser
        210                 215

<210> SEQ ID NO 143
<211> LENGTH: 216
<212> TYPE: PRT
<213> ORGANISM: Artificial sequence
<220> FEATURE:
<223> OTHER INFORMATION: Light chain CR4311

<400> SEQUENCE: 143

Gln Ser Val Leu Thr Gln Pro Pro Ser Val Ser Ala Ala Pro Gly Gln
1               5                   10                  15

Lys Val Thr Ile Ser Cys Ser Gly Thr Ser Ser Asn Ile Gly Asp Asn
            20                  25                  30

Tyr Val Ser Trp Tyr Gln His Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Val Thr Gly Leu Gln
65                  70                  75                  80

Thr Gly Asp Glu Ala Asp Tyr Tyr Cys Gly Thr Trp Asp Ser Ser Leu
                85                  90                  95

Thr Ala Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
        180                 185                 190

Arg Ser Tyr Ser Cys Gln Val Thr His Glu Gly Ser Thr Val Glu Lys
        195                 200                 205

Thr Val Ala Pro Thr Glu Cys Ser
```

<210> SEQ ID NO 144
<211> LENGTH: 654
<212> TYPE: DNA
<213> ORGANISM: Artificial sequence
<220> FEATURE:
<223> OTHER INFORMATION: Light chain CR4325
<220> FEATURE:
<221> NAME/KEY: CDS
<222> LOCATION: (1)..(654)

<400> SEQUENCE: 144

```
gac atc gtg atg acc cag tct cca gac tcc ctg gct gtg tct ctg ggc        48
Asp Ile Val Met Thr Gln Ser Pro Asp Ser Leu Ala Val Ser Leu Gly
  1               5                  10                  15 gag agg gcc acc atc aac tgc aag tcc agc cag agt gtt tta tac agc        96
Glu Arg Ala Thr Ile Asn Cys Lys Ser Ser Gln Ser Val Leu Tyr Ser
             20                  25                  30 tcc aac aat aag aac tac tta gct tgg tac cag cag aaa cca gga cag       144
Ser Asn Asn Lys Asn Tyr Leu Ala Trp Tyr Gln Gln Lys Pro Gly Gln
         35                  40                  45 cct cct aag ctg ctc att tac tgg gca tct acc cgg gaa tcc ggg gtc       192
Pro Pro Lys Leu Leu Ile Tyr Trp Ala Ser Thr Arg Glu Ser Gly Val
     50                  55                  60 cct gac cga ttc agt ggc agc ggg tct ggg aca gat ttc act ctc acc       240
Pro Asp Arg Phe Ser Gly Ser Gly Ser Gly Thr Asp Phe Thr Leu Thr
 65                  70                  75                  80 atc agc agc ctg cag gct gaa gat gtg gca gtt tat tac tgt cag caa       288
Ile Ser Ser Leu Gln Ala Glu Asp Val Ala Val Tyr Tyr Cys Gln Gln
                 85                  90                  95 tat tat agt acc ccg ttg acg ttc ggg acc aag gtg gag atc aag cgg       336
Tyr Tyr Ser Thr Pro Leu Thr Phe Gly Thr Lys Val Glu Ile Lys Arg
            100                 105                 110 acc gtg gcc gct ccc agc gtg ttc atc ttc ccc ccc tcc gac gag cag       384
Thr Val Ala Ala Pro Ser Val Phe Ile Phe Pro Pro Ser Asp Glu Gln
        115                 120                 125 ctg aag agc ggc acc gcc agc gtg gtg tgc ctg ctg aac aac ttc tac       432
Leu Lys Ser Gly Thr Ala Ser Val Val Cys Leu Leu Asn Asn Phe Tyr
    130                 135                 140 ccc cgg gag gcc aag gtg cag tgg aag gtg gac aac gcc ctg cag agc       480
Pro Arg Glu Ala Lys Val Gln Trp Lys Val Asp Asn Ala Leu Gln Ser
145                 150                 155                 160 ggc aac agc cag gag agc gtg acc gag cag gac agc aag gac tcc acc       528
Gly Asn Ser Gln Glu Ser Val Thr Glu Gln Asp Ser Lys Asp Ser Thr
                165                 170                 175 tac agc ctg agc agc acc ctc acc ctg agc aag gcc gac tac gag aag       576
Tyr Ser Leu Ser Ser Thr Leu Thr Leu Ser Lys Ala Asp Tyr Glu Lys
            180                 185                 190 cac aag gtg tac gcc tgc gag gtg acc cac cag ggc ctg agc agc ccc       624
His Lys Val Tyr Ala Cys Glu Val Thr His Gln Gly Leu Ser Ser Pro
        195                 200                 205 gtg acc aag agc ttc aac cgg ggc gag tgt                               654
Val Thr Lys Ser Phe Asn Arg Gly Glu Cys
    210                 215
```

<210> SEQ ID NO 145
<211> LENGTH: 218
<212> TYPE: PRT
<213> ORGANISM: Artificial sequence
<220> FEATURE:
<223> OTHER INFORMATION: Light chain CR4325

-continued

```
<400> SEQUENCE: 145

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 146
<211> LENGTH: 645
<212> TYPE: DNA
<213> ORGANISM: Artificial sequence
<220> FEATURE:
<223> OTHER INFORMATION: Light chain CR4353
<220> FEATURE:
<221> NAME/KEY: CDS
<222> LOCATION: (1)..(645)

<400> SEQUENCE: 146 tcg acg gaa acg aca ctc acg cag tcc cca ggc acc ctg tct ttg tct        48
Ser Thr Glu Thr Thr Leu Thr Gln Ser Pro Gly Thr Leu Ser Leu Ser
1               5                   10                  15 ccc ggg gaa aga gcc acc ctc tcc tgc aga gcc agt cag agt gtt agc        96
Pro Gly Glu Arg Ala Thr Leu Ser Cys Arg Ala Ser Gln Ser Val Ser
            20                  25                  30 aac acc ttc tta gcc tgg tac cag cag aaa cct ggc cag gct ccc agg       144
Asn Thr Phe Leu Ala Trp Tyr Gln Gln Lys Pro Gly Gln Ala Pro Arg
        35                  40                  45 ctc ctc atc tat ggt gca tcc agc agg gcc act ggc atc cca gac agg       192
Leu Leu Ile Tyr Gly Ala Ser Ser Arg Ala Thr Gly Ile Pro Asp Arg
    50                  55                  60 ttc agt ggc agt ggg tct ggg aca gac ttc act ctc acc atc agc aga       240
Phe Ser Gly Ser Gly Ser Gly Thr Asp Phe Thr Leu Thr Ile Ser Arg
65                  70                  75                  80 ctg gag cct gaa gat ttt gca gcg tat tac tgt cag cag tat ggt agc       288
Leu Glu Pro Glu Asp Phe Ala Ala Tyr Tyr Cys Gln Gln Tyr Gly Ser
```

```
                85                   90                   95
tcg ctc act ttc ggc cct ggg acc aaa gtg gat atc aaa cgt gcg gcc    336
Ser Leu Thr Phe Gly Pro Gly Thr Lys Val Asp Ile Lys Arg Ala Ala
            100                 105                 110 gca ccc agc gtg ttc atc ttc ccc ccc tcc gac gag cag ctg aag agc    384
Ala Pro Ser Val Phe Ile Phe Pro Pro Ser Asp Glu Gln Leu Lys Ser
        115                 120                 125 ggc acc gcc agc gtg gtg tgc ctg ctg aac aac ttc tac ccc cgg gag    432
Gly Thr Ala Ser Val Val Cys Leu Leu Asn Asn Phe Tyr Pro Arg Glu
    130                 135                 140 gcc aag gtg cag tgg aag gtg gac aac gcc ctg cag agc ggc aac agc    480
Ala Lys Val Gln Trp Lys Val Asp Asn Ala Leu Gln Ser Gly Asn Ser
145                 150                 155                 160 cag gag agc gtg acc gag cag gac agc aag gac tcc acc tac agc ctg    528
Gln Glu Ser Val Thr Glu Gln Asp Ser Lys Asp Ser Thr Tyr Ser Leu
                165                 170                 175 agc agc acc ctc acc ctg agc aag gcc gac tac gag aag cac aag gtg    576
Ser Ser Thr Leu Thr Leu Ser Lys Ala Asp Tyr Glu Lys His Lys Val
            180                 185                 190 tac gcc tgc gag gtg acc cac cag ggc ctg agc agc ccc gtg acc aag    624
Tyr Ala Cys Glu Val Thr His Gln Gly Leu Ser Ser Pro Val Thr Lys
        195                 200                 205 agc ttc aac cgg ggc gag tgt                                        645
Ser Phe Asn Arg Gly Glu Cys
    210                 215

<210> SEQ ID NO 147
<211> LENGTH: 215
<212> TYPE: PRT
<213> ORGANISM: Artificial sequence
<220> FEATURE:
<223> OTHER INFORMATION: Light chain CR4353

<400> SEQUENCE: 147

Ser Thr Glu Thr Thr Leu Thr Gln Ser Pro Gly Thr Leu Ser Leu Ser
1               5                   10                  15

Pro Gly Glu Arg Ala Thr Leu Ser Cys Arg Ala Ser Gln Ser Val Ser
            20                  25                  30

Asn Thr Phe Leu Ala Trp Tyr Gln Gln Lys Pro Gly Gln Ala Pro Arg
        35                  40                  45

Leu Leu Ile Tyr Gly Ala Ser Ser Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Ala Tyr Tyr Cys Gln Gln Tyr Gly Ser
                85                  90                  95

Ser Leu Thr Phe Gly Pro Gly Thr Lys Val Asp Ile Lys Arg Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 148
<211> LENGTH: 663
<212> TYPE: DNA
<213> ORGANISM: Artificial sequence
<220> FEATURE:
<223> OTHER INFORMATION: Light chain CR4361
<220> FEATURE:
<221> NAME/KEY: CDS
<222> LOCATION: (1)..(663)

<400> SEQUENCE: 148 tcg acg gat gtt gtg atg act cag tct cca gac tcc ctg gct gtg tct      48
Ser Thr Asp Val Val Met Thr Gln Ser Pro Asp Ser Leu Ala Val Ser
1               5                  10                  15 ctg ggc gag agg gcc acc atc aac tgc aag tcc agc cag aat att tta      96
Leu Gly Glu Arg Ala Thr Ile Asn Cys Lys Ser Ser Gln Asn Ile Leu
            20                  25                  30 gac aac tcc gac aat aag aac ttc tta gct tgg tac cag cag aaa cca     144
Asp Asn Ser Asp Asn Lys Asn Phe Leu Ala Trp Tyr Gln Gln Lys Pro
        35                  40                  45 gga cag cct cct aaa ttg ctc att tac tgg gca tct gcc cgg gag tcc     192
Gly Gln Pro Pro Lys Leu Leu Ile Tyr Trp Ala Ser Ala Arg Glu Ser
    50                  55                  60 ggg gtc cct gac cga ttc agt ggc agc ggg tct ggg aca gat ttc act     240
Gly Val Pro Asp Arg Phe Ser Gly Ser Gly Ser Gly Thr Asp Phe Thr
65                  70                  75                  80 ctc acc atc agc agc ctg cag gct gaa gat gtg gca ctt tat tac tgt     288
Leu Thr Ile Ser Ser Leu Gln Ala Glu Asp Val Ala Leu Tyr Tyr Cys
                85                  90                  95 cag caa tat tat aat act ccc atc acc ttc ggt caa ggg aca cga ctg     336
Gln Gln Tyr Tyr Asn Thr Pro Ile Thr Phe Gly Gln Gly Thr Arg Leu
            100                 105                 110 gag att aaa cgt gcg gcc gca ccc agc gtg ttc atc ttc ccc ccc tcc     384
Glu Ile Lys Arg Ala Ala Ala Pro Ser Val Phe Ile Phe Pro Pro Ser
        115                 120                 125 gac gag cag ctg aag agc ggc acc gcc agc gtg gtg tgc ctg ctg aac     432
Asp Glu Gln Leu Lys Ser Gly Thr Ala Ser Val Val Cys Leu Leu Asn
    130                 135                 140 aac ttc tac ccc cgg gag gcc aag gtg cag tgg aag gtg gac aac gcc     480
Asn Phe Tyr Pro Arg Glu Ala Lys Val Gln Trp Lys Val Asp Asn Ala
145                 150                 155                 160 ctg cag agc ggc aac agc cag gag agc gtg acc gag cag gac agc aag     528
Leu Gln Ser Gly Asn Ser Gln Glu Ser Val Thr Glu Gln Asp Ser Lys
                165                 170                 175 gac tcc acc tac agc ctg agc agc acc ctc acc ctg agc aag gcc gac     576
Asp Ser Thr Tyr Ser Leu Ser Ser Thr Leu Thr Leu Ser Lys Ala Asp
            180                 185                 190 tac gag aag cac aag gtg tac gcc tgc gag gtg acc cac cag ggc ctg     624
Tyr Glu Lys His Lys Val Tyr Ala Cys Glu Val Thr His Gln Gly Leu
        195                 200                 205 agc agc ccc gtg acc aag agc ttc aac cgg ggc gag tgt                 663
Ser Ser Pro Val Thr Lys Ser Phe Asn Arg Gly Glu Cys
    210                 215                 220

<210> SEQ ID NO 149
<211> LENGTH: 221
```

<210> SEQ ID NO 149
<211> LENGTH: 220
<212> TYPE: PRT
<213> ORGANISM: Artificial sequence
<220> FEATURE:
<223> OTHER INFORMATION: Light chain CR4361

<400> SEQUENCE: 149

```
Ser Thr Asp Val Val Met Thr Gln Ser Pro Asp Ser Leu Ala Val Ser
1               5                   10                  15

Leu Gly Glu Arg Ala Thr Ile Asn Cys Lys Ser Gln Asn Ile Leu
            20                  25                  30

Asp Asn Ser Asp Asn Lys Asn Phe Leu Ala Trp Tyr Gln Gln Lys Pro
        35                  40                  45

Gly Gln Pro Pro Lys Leu Leu Ile Tyr Trp Ala Ser Ala Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Leu Tyr Tyr Cys
                85                  90                  95

Gln Gln Tyr Tyr Asn Thr Pro Ile Thr Phe Gly Gln Gly Thr Arg Leu
            100                 105                 110

Glu Ile Lys Arg Ala Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220
```

<210> SEQ ID NO 150
<211> LENGTH: 651
<212> TYPE: DNA
<213> ORGANISM: Artificial sequence
<220> FEATURE:
<223> OTHER INFORMATION: Light chain CR4374
<220> FEATURE:
<221> NAME/KEY: CDS
<222> LOCATION: (1)..(651)

<400> SEQUENCE: 150

```
cag tcc gtg ctg acc cag cct ccc tca gtg tct ggg gcc cca ggg cag        48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg gca ggt        96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc       144
Tyr Asp Val His Trp Tyr Gln Gln Leu Pro Gly Thr Ala Pro Lys Leu
        35                  40                  45 ctc atc tat ggt aac agc aat cgg ccc tca ggg gtc cct gac cga ttc       192
Leu Ile Tyr Gly Asn Ser Asn Arg Pro Ser Gly Val Pro Asp Arg Phe
    50                  55                  60 tct ggc tcc aag tct ggc acc tca gcc tcc ctg gcc atc act ggg ctc       240
```

-continued

```
Ser Gly Ser Lys Ser Gly Thr Ser Ala Ser Leu Ala Ile Thr Gly Leu
 65                  70                  75                  80 cag gct gag gat gag gct gat tat tac tgc cag tcc tat gac agc agc        288
Gln Ala Glu Asp Glu Ala Asp Tyr Tyr Cys Gln Ser Tyr Asp Ser Ser
                 85                  90                  95 ttg agt ggt tcg gtg ttc ggc gga ggc acc aag ctt acc gtg ctg ggc        336
Leu Ser Gly Ser Val Phe Gly Gly Gly Thr Lys Leu Thr Val Leu Gly
            100                 105                 110 cag ccc aag gcc gct ccc agc gtg acc ctg ttc ccc ccc tcc tcc gag        384
Gln Pro Lys Ala Ala Pro Ser Val Thr Leu Phe Pro Pro Ser Ser Glu
        115                 120                 125 gag ctg cag gcc aac aag gcc acc ctg gtg tgc ctc atc agc gac ttc        432
Glu Leu Gln Ala Asn Lys Ala Thr Leu Val Cys Leu Ile Ser Asp Phe
    130                 135                 140 tac cct ggc gcc gtg acc gtg gcc tgg aag gcc gac agc agc ccc gtg        480
Tyr Pro Gly Ala Val Thr Val Ala Trp Lys Ala Asp Ser Ser Pro Val
145                 150                 155                 160 aag gcc ggc gtg gag acc acc acc ccc agc aag cag agc aac aac aag        528
Lys Ala Gly Val Glu Thr Thr Thr Pro Ser Lys Gln Ser Asn Asn Lys
                165                 170                 175 tac gcc gcc agc agc tac ctg agc ctc acc ccc gag cag tgg aag agc        576
Tyr Ala Ala Ser Ser Tyr Leu Ser Leu Thr Pro Glu Gln Trp Lys Ser
            180                 185                 190 cac cgg agc tac agc tgc cag gtg acc cac gag ggc agc acc gtg gag        624
His Arg Ser Tyr Ser Cys Gln Val Thr His Glu Gly Ser Thr Val Glu
        195                 200                 205 aag acc gtg gcc ccc acc gag tgc agc                                    651
Lys Thr Val Ala Pro Thr Glu Cys Ser
    210                 215

<210> SEQ ID NO 151
<211> LENGTH: 217
<212> TYPE: PRT
<213> ORGANISM: Artificial sequence
<220> FEATURE:
<223> OTHER INFORMATION: Light chain CR4374

<400> SEQUENCE: 151

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160
```

```
Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 152
<211> LENGTH: 23
<212> TYPE: DNA
<213> ORGANISM: Artificial sequence
<220> FEATURE:
<223> OTHER INFORMATION: HuVlambda1A

<400> SEQUENCE: 152
cagtctgtgc tgactcagcc acc                                              23

<210> SEQ ID NO 153
<211> LENGTH: 23
<212> TYPE: DNA
<213> ORGANISM: Artificial sequence
<220> FEATURE:
<223> OTHER INFORMATION: HuVlambda1B

<400> SEQUENCE: 153
cagtctgtgy tgacgcagcc gcc                                              23

<210> SEQ ID NO 154
<211> LENGTH: 23
<212> TYPE: DNA
<213> ORGANISM: Artificial sequence
<220> FEATURE:
<223> OTHER INFORMATION: HuVlambda1C

<400> SEQUENCE: 154
cagtctgtcg tgacgcagcc gcc                                              23

<210> SEQ ID NO 155
<211> LENGTH: 21
<212> TYPE: DNA
<213> ORGANISM: Artificial sequence
<220> FEATURE:
<223> OTHER INFORMATION: HuVlambda2

<400> SEQUENCE: 155
cartctgccc tgactcagcc t                                                21

<210> SEQ ID NO 156
<211> LENGTH: 23
<212> TYPE: DNA
<213> ORGANISM: Artificial sequence
<220> FEATURE:
<223> OTHER INFORMATION: HuVlambda3A

<400> SEQUENCE: 156
tcctatgwgc tgactcagcc acc                                              23

<210> SEQ ID NO 157
<211> LENGTH: 23
<212> TYPE: DNA
<213> ORGANISM: Artificial sequence
<220> FEATURE:
<223> OTHER INFORMATION: HuVlambda3B
```

<400> SEQUENCE: 157
tcttctgagc tgactcagga ccc                              23

<210> SEQ ID NO 158
<211> LENGTH: 23
<212> TYPE: DNA
<213> ORGANISM: Artificial sequence
<220> FEATURE:
<223> OTHER INFORMATION: HuVlambda4

<400> SEQUENCE: 158
cacgttatac tgactcaacc gcc                              23

<210> SEQ ID NO 159
<211> LENGTH: 23
<212> TYPE: DNA
<213> ORGANISM: Artificial sequence
<220> FEATURE:
<223> OTHER INFORMATION: HuVlambda5

<400> SEQUENCE: 159
caggctgtgc tgactcagcc gtc                              23

<210> SEQ ID NO 160
<211> LENGTH: 23
<212> TYPE: DNA
<213> ORGANISM: Artificial sequence
<220> FEATURE:
<223> OTHER INFORMATION: HuVlambda6

<400> SEQUENCE: 160
aattttatgc tgactcagcc cca                              23

<210> SEQ ID NO 161
<211> LENGTH: 23
<212> TYPE: DNA
<213> ORGANISM: Artificial sequence
<220> FEATURE:
<223> OTHER INFORMATION: HuVlambda7/8

<400> SEQUENCE: 161
cagrctgtgg tgacycagga gcc                              23

<210> SEQ ID NO 162
<211> LENGTH: 23
<212> TYPE: DNA
<213> ORGANISM: Artificial sequence
<220> FEATURE:
<223> OTHER INFORMATION: HuVlambda9

<400> SEQUENCE: 162
cwgcctgtgc tgactcagcc mcc                              23

<210> SEQ ID NO 163
<211> LENGTH: 23
<212> TYPE: DNA
<213> ORGANISM: Artificial sequence
<220> FEATURE:
<223> OTHER INFORMATION: HuVkappa1B

<400> SEQUENCE: 163
gacatccagw tgacccagtc tcc                              23

<210> SEQ ID NO 164

```
<211> LENGTH: 23
<212> TYPE: DNA
<213> ORGANISM: Artificial sequence
<220> FEATURE:
<223> OTHER INFORMATION: HuVkappa2

<400> SEQUENCE: 164
gatgttgtga tgactcagtc tcc                                              23

<210> SEQ ID NO 165
<211> LENGTH: 23
<212> TYPE: DNA
<213> ORGANISM: Artificial sequence
<220> FEATURE:
<223> OTHER INFORMATION: HuVkappa3

<400> SEQUENCE: 165
gaaattgtgw tgacrcagtc tcc                                              23

<210> SEQ ID NO 166
<211> LENGTH: 23
<212> TYPE: DNA
<213> ORGANISM: Artificial sequence
<220> FEATURE:
<223> OTHER INFORMATION: HuVkappa4

<400> SEQUENCE: 166
gatattgtga tgacccacac tcc                                              23

<210> SEQ ID NO 167
<211> LENGTH: 23
<212> TYPE: DNA
<213> ORGANISM: Artificial sequence
<220> FEATURE:
<223> OTHER INFORMATION: HuVkappa5

<400> SEQUENCE: 167
gaaacgacac tcacgcagtc tcc                                              23

<210> SEQ ID NO 168
<211> LENGTH: 23
<212> TYPE: DNA
<213> ORGANISM: Artificial sequence
<220> FEATURE:
<223> OTHER INFORMATION: HuVkappa6

<400> SEQUENCE: 168
gaaattgtgc tgactcagtc tcc                                              23

<210> SEQ ID NO 169
<211> LENGTH: 41
<212> TYPE: DNA
<213> ORGANISM: Artificial sequence
<220> FEATURE:
<223> OTHER INFORMATION: HuVkappa1B-SalI

<400> SEQUENCE: 169
tgagcacaca ggtcgacgga catccagwtg acccagtctc c                          41

<210> SEQ ID NO 170
<211> LENGTH: 41
<212> TYPE: DNA
<213> ORGANISM: Artificial sequence
<220> FEATURE:
<223> OTHER INFORMATION: HuVkappa2-SalI

<400> SEQUENCE: 170
```

```
tgagcacaca ggtcgacgga tgttgtgatg actcagtctc c                          41

<210> SEQ ID NO 171
<211> LENGTH: 41
<212> TYPE: DNA
<213> ORGANISM: Artificial sequence
<220> FEATURE:
<223> OTHER INFORMATION: HuVkappa3B-SalI

<400> SEQUENCE: 171
tgagcacaca ggtcgacgga aattgtgwtg acrcagtctc c                          41

<210> SEQ ID NO 172
<211> LENGTH: 41
<212> TYPE: DNA
<213> ORGANISM: Artificial sequence
<220> FEATURE:
<223> OTHER INFORMATION: HuVkappa4B-SalI

<400> SEQUENCE: 172
tgagcacaca ggtcgacgga tattgtgatg acccacactc c                          41

<210> SEQ ID NO 173
<211> LENGTH: 41
<212> TYPE: DNA
<213> ORGANISM: Artificial sequence
<220> FEATURE:
<223> OTHER INFORMATION: HuVkappa5-SalI

<400> SEQUENCE: 173
tgagcacaca ggtcgacgga aacgacactc acgcagtctc c                          41

<210> SEQ ID NO 174
<211> LENGTH: 41
<212> TYPE: DNA
<213> ORGANISM: Artificial sequence
<220> FEATURE:
<223> OTHER INFORMATION: HuVkappa6-SalI

<400> SEQUENCE: 174
tgagcacaca ggtcgacgga aattgtgctg actcagtctc c                          41

<210> SEQ ID NO 175
<211> LENGTH: 48
<212> TYPE: DNA
<213> ORGANISM: Artificial sequence
<220> FEATURE:
<223> OTHER INFORMATION: HuJkappa1-NotI

<400> SEQUENCE: 175
gagtcattct cgacttgcgg ccgcacgttt gatttccacc ttggtccc                   48

<210> SEQ ID NO 176
<211> LENGTH: 48
<212> TYPE: DNA
<213> ORGANISM: Artificial sequence
<220> FEATURE:
<223> OTHER INFORMATION: HuJkappa2-NotI

<400> SEQUENCE: 176
gagtcattct cgacttgcgg ccgcacgttt gatctccagc ttggtccc                   48

<210> SEQ ID NO 177
<211> LENGTH: 48
<212> TYPE: DNA
```

<213> ORGANISM: Artificial sequence
<220> FEATURE:
<223> OTHER INFORMATION: HuJkappa3-NotI

<400> SEQUENCE: 177
gagtcattct cgacttgcgg ccgcacgttt gatatccact ttggtccc         48

<210> SEQ ID NO 178
<211> LENGTH: 48
<212> TYPE: DNA
<213> ORGANISM: Artificial sequence
<220> FEATURE:
<223> OTHER INFORMATION: HuJkappa4-NotI

<400> SEQUENCE: 178
gagtcattct cgacttgcgg ccgcacgttt gatctccacc ttggtccc         48

<210> SEQ ID NO 179
<211> LENGTH: 48
<212> TYPE: DNA
<213> ORGANISM: Artificial sequence
<220> FEATURE:
<223> OTHER INFORMATION: HuJkappa5-NotI

<400> SEQUENCE: 179
gagtcattct cgacttgcgg ccgcacgttt aatctccagt cgtgtccc         48

<210> SEQ ID NO 180
<211> LENGTH: 41
<212> TYPE: DNA
<213> ORGANISM: Artificial sequence
<220> FEATURE:
<223> OTHER INFORMATION: HuVlambda1A-SalI

<400> SEQUENCE: 180
tgagcacaca ggtcgacgca gtctgtgctg actcagccac c              41

<210> SEQ ID NO 181
<211> LENGTH: 41
<212> TYPE: DNA
<213> ORGANISM: Artificial sequence
<220> FEATURE:
<223> OTHER INFORMATION: HuVlambda1B-SalI

<400> SEQUENCE: 181
tgagcacaca ggtcgacgca gtctgtgytg acgcagccgc c              41

<210> SEQ ID NO 182
<211> LENGTH: 41
<212> TYPE: DNA
<213> ORGANISM: Artificial sequence
<220> FEATURE:
<223> OTHER INFORMATION: HuVlambda1C-SalI

<400> SEQUENCE: 182
tgagcacaca ggtcgacgca gtctgtcgtg acgcagccgc c              41

<210> SEQ ID NO 183
<211> LENGTH: 39
<212> TYPE: DNA
<213> ORGANISM: Artificial sequence
<220> FEATURE:
<223> OTHER INFORMATION: HuVlambda2-SalI

<400> SEQUENCE: 183
tgagcacaca ggtcgacgca rtctgccctg actcagcct                39

<210> SEQ ID NO 184
<211> LENGTH: 41
<212> TYPE: DNA
<213> ORGANISM: Artificial sequence
<220> FEATURE:
<223> OTHER INFORMATION: HuVlambda3A-SalI

<400> SEQUENCE: 184
tgagcacaca ggtcgacgtc ctatgwgctg actcagccac c         41

<210> SEQ ID NO 185
<211> LENGTH: 41
<212> TYPE: DNA
<213> ORGANISM: Artificial sequence
<220> FEATURE:
<223> OTHER INFORMATION: HuVlambda3B-SalI

<400> SEQUENCE: 185
tgagcacaca ggtcgacgtc ttctgagctg actcaggacc c         41

<210> SEQ ID NO 186
<211> LENGTH: 41
<212> TYPE: DNA
<213> ORGANISM: Artificial sequence
<220> FEATURE:
<223> OTHER INFORMATION: HuVlambda4-SalI

<400> SEQUENCE: 186
tgagcacaca ggtcgacgca cgttatactg actcaaccgc c         41

<210> SEQ ID NO 187
<211> LENGTH: 41
<212> TYPE: DNA
<213> ORGANISM: Artificial sequence
<220> FEATURE:
<223> OTHER INFORMATION: HuVlambda5-SalI

<400> SEQUENCE: 187
tgagcacaca ggtcgacgca ggctgtgctg actcagccgt c         41

<210> SEQ ID NO 188
<211> LENGTH: 41
<212> TYPE: DNA
<213> ORGANISM: Artificial sequence
<220> FEATURE:
<223> OTHER INFORMATION: HuVlambda6-SalI

<400> SEQUENCE: 188
tgagcacaca ggtcgacgaa ttttatgctg actcagcccc a         41

<210> SEQ ID NO 189
<211> LENGTH: 41
<212> TYPE: DNA
<213> ORGANISM: Artificial sequence
<220> FEATURE:
<223> OTHER INFORMATION: HuVlambda7/8-SalI

<400> SEQUENCE: 189
tgagcacaca ggtcgacgca grctgtggtg acycaggagc c         41

<210> SEQ ID NO 190
<211> LENGTH: 41
<212> TYPE: DNA
<213> ORGANISM: Artificial sequence
<220> FEATURE:

<223> OTHER INFORMATION: HuVlambda9-SalI

<400> SEQUENCE: 190
tgagcacaca ggtcgacgcw gcctgtgctg actcagccmc c          41

<210> SEQ ID NO 191
<211> LENGTH: 48
<212> TYPE: DNA
<213> ORGANISM: Artificial sequence
<220> FEATURE:
<223> OTHER INFORMATION: HuJlambda1-NotI

<400> SEQUENCE: 191
gagtcattct cgacttgcgg ccgcacctag gacggtgacc ttggtccc          48

<210> SEQ ID NO 192
<211> LENGTH: 48
<212> TYPE: DNA
<213> ORGANISM: Artificial sequence
<220> FEATURE:
<223> OTHER INFORMATION: HuJlambda2/3-NotI

<400> SEQUENCE: 192
gagtcattct cgacttgcgg ccgcacctag gacggtcagc ttggtccc          48

<210> SEQ ID NO 193
<211> LENGTH: 48
<212> TYPE: DNA
<213> ORGANISM: Artificial sequence
<220> FEATURE:
<223> OTHER INFORMATION: HuJlambda4/5-NotI

<400> SEQUENCE: 193
gagtcattct cgacttgcgg ccgcacytaa aacggtgagc tgggtccc          48

<210> SEQ ID NO 194
<211> LENGTH: 23
<212> TYPE: DNA
<213> ORGANISM: Artificial sequence
<220> FEATURE:
<223> OTHER INFORMATION: HuVH1B/7A

<400> SEQUENCE: 194
cagrtgcagc tggtgcartc tgg          23

<210> SEQ ID NO 195
<211> LENGTH: 23
<212> TYPE: DNA
<213> ORGANISM: Artificial sequence
<220> FEATURE:
<223> OTHER INFORMATION: HuVH1C

<400> SEQUENCE: 195
saggtccagc tggtrcagtc tgg          23

<210> SEQ ID NO 196
<211> LENGTH: 23
<212> TYPE: DNA
<213> ORGANISM: Artificial sequence
<220> FEATURE:
<223> OTHER INFORMATION: HuVH2B

<400> SEQUENCE: 196
saggtgcagc tggtggagtc tgg          23

```
<210> SEQ ID NO 197
<211> LENGTH: 23
<212> TYPE: DNA
<213> ORGANISM: Artificial sequence
<220> FEATURE:
<223> OTHER INFORMATION: HuVH3B

<400> SEQUENCE: 197
saggtgcagc tggtggagtc tgg                                              23

<210> SEQ ID NO 198
<211> LENGTH: 23
<212> TYPE: DNA
<213> ORGANISM: Artificial sequence
<220> FEATURE:
<223> OTHER INFORMATION: HuVH3C

<400> SEQUENCE: 198
gaggtgcagc tggtggagwc ygg                                              23

<210> SEQ ID NO 199
<211> LENGTH: 23
<212> TYPE: DNA
<213> ORGANISM: Artificial sequence
<220> FEATURE:
<223> OTHER INFORMATION: HuVH4B

<400> SEQUENCE: 199
caggtgcagc tacagcagtg ggg                                              23

<210> SEQ ID NO 200
<211> LENGTH: 23
<212> TYPE: DNA
<213> ORGANISM: Artificial sequence
<220> FEATURE:
<223> OTHER INFORMATION: HuVH4C

<400> SEQUENCE: 200
cagstgcagc tgcaggagtc sgg                                              23

<210> SEQ ID NO 201
<211> LENGTH: 23
<212> TYPE: DNA
<213> ORGANISM: Artificial sequence
<220> FEATURE:
<223> OTHER INFORMATION: HuVH5B

<400> SEQUENCE: 201
gargtgcagc tggtgcagtc tgg                                              23

<210> SEQ ID NO 202
<211> LENGTH: 23
<212> TYPE: DNA
<213> ORGANISM: Artificial sequence
<220> FEATURE:
<223> OTHER INFORMATION: HuVH6A

<400> SEQUENCE: 202
caggtacagc tgcagcagtc agg                                              23

<210> SEQ ID NO 203
<211> LENGTH: 56
<212> TYPE: DNA
<213> ORGANISM: Artificial sequence
<220> FEATURE:
<223> OTHER INFORMATION: HuVH1B/7A-SfiI
```

<400> SEQUENCE: 203
gtcctcgcaa ctgcggccca gccggccatg gcccagrtgc agctggtgca rtctgg       56

<210> SEQ ID NO 204
<211> LENGTH: 56
<212> TYPE: DNA
<213> ORGANISM: Artificial sequence
<220> FEATURE:
<223> OTHER INFORMATION: HuVH1C-SfiI

<400> SEQUENCE: 204
gtcctcgcaa ctgcggccca gccggccatg gccsaggtcc agctggtrca gtctgg       56

<210> SEQ ID NO 205
<211> LENGTH: 56
<212> TYPE: DNA
<213> ORGANISM: Artificial sequence
<220> FEATURE:
<223> OTHER INFORMATION: HuVH2B-SfiI

<400> SEQUENCE: 205
gtcctcgcaa ctgcggccca gccggccatg gcccagrtca ccttgaagga gtctgg       56

<210> SEQ ID NO 206
<211> LENGTH: 56
<212> TYPE: DNA
<213> ORGANISM: Artificial sequence
<220> FEATURE:
<223> OTHER INFORMATION: HuVH3B-SfiI

<400> SEQUENCE: 206
gtcctcgcaa ctgcggccca gccggccatg gccsaggtgc agctggtgga gtctgg       56

<210> SEQ ID NO 207
<211> LENGTH: 56
<212> TYPE: DNA
<213> ORGANISM: Artificial sequence
<220> FEATURE:
<223> OTHER INFORMATION: HuVH3C-SfiI

<400> SEQUENCE: 207
gtcctcgcaa ctgcggccca gccggccatg gccgaggtgc agctggtgga gwcygg       56

<210> SEQ ID NO 208
<211> LENGTH: 56
<212> TYPE: DNA
<213> ORGANISM: Artificial sequence
<220> FEATURE:
<223> OTHER INFORMATION: HuVH4B-SfiI

<400> SEQUENCE: 208
gtcctcgcaa ctgcggccca gccggccatg gcccaggtgc agctacagca gtgggg       56

<210> SEQ ID NO 209
<211> LENGTH: 56
<212> TYPE: DNA
<213> ORGANISM: Artificial sequence
<220> FEATURE:
<223> OTHER INFORMATION: HuVH4C-SfiI

<400> SEQUENCE: 209
gtcctcgcaa ctgcggccca gccggccatg gcccagstgc agctgcagga gtcsgg       56

<210> SEQ ID NO 210
<211> LENGTH: 56

<212> TYPE: DNA
<213> ORGANISM: Artificial sequence
<220> FEATURE:
<223> OTHER INFORMATION: HuVH5B-SfiI

<400> SEQUENCE: 210
gtcctcgcaa ctgcggccca gccggccatg gccgargtgc agctggtgca gtctgg      56

<210> SEQ ID NO 211
<211> LENGTH: 56
<212> TYPE: DNA
<213> ORGANISM: Artificial sequence
<220> FEATURE:
<223> OTHER INFORMATION: HuVH6A-SfiI

<400> SEQUENCE: 211
gtcctcgcaa ctgcggccca gccggccatg gcccaggtac agctgcagca gtcagg      56

<210> SEQ ID NO 212
<211> LENGTH: 36
<212> TYPE: DNA
<213> ORGANISM: Artificial sequence
<220> FEATURE:
<223> OTHER INFORMATION: HuJH1/2-XhoI

<400> SEQUENCE: 212
gagtcattct cgactcgaga cggtgaccag ggtgcc      36

<210> SEQ ID NO 213
<211> LENGTH: 36
<212> TYPE: DNA
<213> ORGANISM: Artificial sequence
<220> FEATURE:
<223> OTHER INFORMATION: HuJH3-XhoI

<400> SEQUENCE: 213
gagtcattct cgactcgaga cggtgaccat tgtccc      36

<210> SEQ ID NO 214
<211> LENGTH: 36
<212> TYPE: DNA
<213> ORGANISM: Artificial sequence
<220> FEATURE:
<223> OTHER INFORMATION: HuJH4/5-XhoI

<400> SEQUENCE: 214
gagtcattct cgactcgaga cggtgaccag ggttcc      36

<210> SEQ ID NO 215
<211> LENGTH: 36
<212> TYPE: DNA
<213> ORGANISM: Artificial sequence
<220> FEATURE:
<223> OTHER INFORMATION: HuJH6-XhoI

<400> SEQUENCE: 215
gagtcattct cgactcgaga cggtgaccgt ggtccc      36

<210> SEQ ID NO 216
<211> LENGTH: 5855
<212> TYPE: DNA
<213> ORGANISM: Artificial sequence
<220> FEATURE:
<223> OTHER INFORMATION: Vector pCR-IgM

<400> SEQUENCE: 216

```
gttctttcct gcgttatccc ctgattctgt ggataaccgt attaccgcct ttgagtgagc    60
tgataccgct cgccgcagcc gaacgaccga gcgcagcgag tcagtgagcg aggaagcgga   120
agagcgccca atacgcaaac cgcctctccc cgcgcgttgg ccgattcatt aatgcagctg   180
gcacgacagg tttcccgact ggaaagcggg cagtgagcgc aacgcaatta atgtgagtta   240
gctcactcat taggcacccc aggctttaca ctttatgctt ccggctcgta tgttgtgtgg   300
aattgtgagc ggataacaat ttcacacagg aaacagctat gaccatgatt acgccaagct   360
cagaattaac cctcactaaa gggactagtc ctgcaggttt aaacgaattc gcccttcagg   420
gagtgctagc gccccaaccc ttttccccct cgtctcctgt gagaattccc cgtcggatac   480
gagcagcgtg gccgttggct gcctcgcaca ggacttcctt cccgactcca tcactttctc   540
ctggaaatac aagaacaact ctgacatcag cagcacccgg ggcttcccat cagtcctgag   600 aggggggcaag tacgcagcca cctcacaggt gctgctgcct tccaaggacg tcatgcaggg   660
cacagacgaa cacgtggtgt gcaaagtcca gcaccccaac ggcaacaaag aaaagaacgt   720
gcctcttcca ggtgagggcc gggcccagcc accgggacag agagggagcc aaggggggcg   780
ggagtggcgg gcaccgggct gacacgtgtc cctcactgca gtgattgctg agctgcctcc   840
caaagtgagc gtcttcgtcc caccccgcga cggcttcttc ggcaaccccc gcaagtccaa   900
gctcatctgc caggccacgg gtttcagtcc ccggcagatt caggtgtcct ggctgcgcga   960
ggggaagcag gtggggtctg gcgtcaccac ggaccaggtg caggctgagg ccaaagagtc  1020
tgggcccacg acctacaagg tgaccagcac actgaccatc aaagagagcg actggctcag  1080
ccagagcatg ttcacctgcc gcgtggatca caggggcctg accttccagc agaatgcgtc  1140
ctccatgtgt gtccccggtg agtgacctgt cccagggggc agcacccacc gacacacagg  1200
ggtccactcg ggtctggcat tcgccacccc ggatgcagcc atctactccc tgagccttgg  1260
cttcccagag cggccaaggg caggggctcg ggcggcagga cccctgggct cggcagaggc  1320
agttgctact cttgggtgg gaaccatgcc tccgcccaca tccacacctg ccccacctct  1380
gactcccttc tcttgactcc agatcaagac acagccatcc gggtcttcgc catcccccca  1440
tcctttgcca gcatcttcct caccaagtcc accaagttga cctgcctggt cacagacctg  1500
accacctatg acagcgtgac catctcctgg acccgccaga atggcgaagc tgtgaaaacc  1560
cacaccaaca tctccgagag ccacccccaat gccactttca gcgccgtggg tgaggccagc  1620
atctgcgagg atgactggaa ttccggggag aggttcacgt gcaccgtgac ccacacagac  1680
ctgccctcgc cactgaagca gaccatctcc cggcccaagg gtaggcccca ctcttgcccc  1740
tcttcctgca ctcccgggg cctcccttgg cctctggggc atggtggaaa gcacccctca  1800 ctccccgtt gtctgggcaa ctggggaaaa ggggactcaa cccagcccag caggctggtc  1860 ccccactgc ccgcccctca ccaccatctc tgttcacagg ggtggccctg cacaggcccg  1920
atgtctactt gctgccacca gcccgggagc agctgaacct gcgggagtcg gccaccatca  1980
cgtgcctggt gacgggcttc tctcccgcgg acgtcttcgt gcagtggatg cagaggggggc  2040 agccccttgtc cccggagaag tatgtgacca gcgcccccaat gcctgagccc caggcccccag  2100 gccggtactt cgcccacagc atcctgaccg tgtccgaaga ggaatggaac acggggggaga  2160 cctacacctg cgtggtggcc catgaggccc tgcccaacag ggtcaccgag aggaccgtgg  2220
acaagtccac cggtaaaccc accctgtaca acgtgtccct ggtcatgtcc gacacagctg  2280
gcacctgcta ctgatgatct agatctgaaa cacaaagggc gaattcgcgg ccgctaaatt  2340
caattcgccc tatagtgagt cgtattacaa ttcactggcc gtcgttttac aacgtcgtga  2400
```

```
ctgggaaaac cctggcgtta cccaacttaa tcgccttgca gcacatcccc ctttcgccag    2460
ctggcgtaat agcgaagagg cccgcaccga tcgcccttcc caacagttgc gcagcctata    2520
cgtacggcag tttaaggttt acacctataa aagagagagc cgttatcgtc tgtttgtgga    2580
tgtacagagt gatattattg acacgccggg gcgacggatg gtgatccccc tggccagtgc    2640
acgtctgctg tcagataaag tctcccgtga actttacccg gtggtgcata tcggggatga    2700
aagctggcgc atgatgacca ccgatatggc cagtgtgccg gtctccgtta tcggggaaga    2760
agtggctgat ctcagccacc gcgaaaatga catcaaaaac gccattaacc tgatgttctg    2820
gggaatataa atgtcaggca tgagattatc aaaaaggatc ttcacctaga tccttttcac    2880
gtagaaagcc agtccgcaga aacggtgctg accccggatg aatgtcagct actgggctat    2940
ctggacaagg gaaaacgcaa gcgcaaagag aaagcaggta gcttgcagtg gcttacatg    3000 gcgatagcta gactgggcgg ttttatggac agcaagcgaa ccggaattgc cagctggggc    3060
gccctctggt aaggttggga agccctgcaa agtaaactgg atggctttct cgccgccaag    3120
gatctgatgg cgcaggggat caagctctga tcaagagaca ggatgaggat cgtttcgcat    3180
gattgaacaa gatggattgc acgcaggttc tccggccgct tgggtggaga ggctattcgg    3240
ctatgactgg gcacaacaga caatcggctg ctctgatgcc gccgtgttcc ggctgtcagc    3300 gcagggggcgc ccggttcttt ttgtcaagac cgacctgtcc ggtgccctga atgaactgca    3360
agacgaggca gcgcggctat cgtggctggc cacgacgggc gttccttgcg cagctgtgct    3420
cgacgttgtc actgaagcgg gaagggactg gctgctattg ggcgaagtgc cggggcagga    3480
tctcctgtca tctcaccttg ctcctgccga gaaagtatcc atcatggctg atgcaatgcg    3540
gcggctgcat acgcttgatc cggctacctg cccattcgac caccaagcga aacatcgcat    3600
cgagcgagca cgtactcgga tggaagccgg tcttgtcgat caggatgatc tggacgaaga    3660
gcatcagggg ctcgcgccag ccgaactgtt cgccaggctc aaggcgagca tgcccgacgg    3720
cgaggatctc gtcgtgaccc atggcgatgc ctgcttgccg aatatcatgg tggaaaatgg    3780
ccgcttttct ggattcatcg actgtggccg gctgggtgtg gcggaccgct atcaggacat    3840
agcgttggct acccgtgata ttgctgaaga gcttggcggc gaatgggctg accgcttcct    3900
cgtgctttac ggtatcgccg ctcccgattc gcagcgcatc gccttctatc gccttcttga    3960
cgagttcttc tgaattatta acgcttacaa tttcctgatg cggtattttc tccttacgca    4020
tctgtgcggt atttcacacc gcatacaggt ggcactttc ggggaaatgt gcgcggaacc    4080
cctatttgtt tatttttcta aatacattca aatatgtatc cgctcatgag acaataaccc    4140
tgataaatgc ttcaataata ttgaaaaagg aagagtatga gtattcaaca tttccgtgtc    4200
gcccttattc cctttttgc ggcattttgc cttcctgttt ttgctcaccc agaaacgctg    4260
gtgaaagtaa aagatgctga agatcagttg ggtgcacgag tgggttacat cgaactggat    4320
ctcaacagcg gtaagatcct tgagagtttt cgccccgaag aacgttttcc aatgatgagc    4380
acttttaaag ttctgctatg tggcgcggta ttatcccgta ttgacgccgg caagagcaa    4440 ctcggtcgcc gcatacacta ttctcagaat gacttggttg agtactcacc agtcacagaa    4500
aagcatctta cggatggcat gacagtaaga gaattatgca gtgctgccat aaccatgagt    4560
gataacactg cggccaactt acttctgaca acgatcggag gaccgaagga gctaaccgct    4620
tttttgcaca acatggggga tcatgtaact cgccttgatc gttgggaacc ggagctgaat    4680
gaagccatac caaacgacga gcgtgacacc acgatgcctg tagcaatggc aacaacgttg    4740
```

-continued

```
cgcaaactat taactggcga actacttact ctagcttccc ggcaacaatt aatagactgg    4800
atggaggcgg ataaagttgc aggaccactt ctgcgctcgg cccttccggc tggctggttt    4860
attgctgata atctggagc cggtgagcgt gggtctcgcg gtatcattgc agcactgggg     4920
ccagatggta agccctcccg tatcgtagtt atctacacga cggggagtca ggcaactatg    4980
gatgaacgaa atagacagat cgctgagata ggtgcctcac tgattaagca ttggtaactg    5040
tcagaccaag tttactcata tatactttag attgatttaa aacttcattt ttaatttaaa    5100
aggatctagg tgaagatcct ttttgataat ctcatgacca aaatccctta acgtgagttt    5160
tcgttccact gagcgtcaga ccccgtagaa aagatcaaag gatcttcttg agatcctttt    5220
tttctgcgcg taatctgctg cttgcaaaca aaaaaaccac cgctaccagc ggtggtttgt    5280
ttgccggatc aagagctacc aactctttt ccgaaggtaa ctggcttcag cagagcgcag    5340
ataccaaata ctgtccttct agtgtagccg tagttaggcc accacttcaa gaactctgta    5400
gcaccgccta catacctcgc tctgctaatc ctgttaccag tggctgctgc cagtggcgat    5460
aagtcgtgtc ttaccgggtt ggactcaaga cgatagttac cggataaggc gcagcggtcg    5520
ggctgaacgg ggggttcgtg cacacagccc agcttggagc gaacgaccta caccgaactg    5580
agatacctac agcgtgagct atgagaaagc gccacgcttc ccgaagggag aaaggcggac    5640
aggtatccgg taagcggcag ggtcggaaca ggagagcgca cgagggagct tccaggggga    5700
aacgcctggt atctttatag tcctgtcggg tttcgccacc tctgacttga gcgtcgattt    5760
ttgtgatgct cgtcaggggg gcggagccta tggaaaaacg ccagcaacgc ggcctttta    5820 cggttcctgg gctttgctg gccttttgct cacat    5855
```

<210> SEQ ID NO 217
<211> LENGTH: 2257
<212> TYPE: DNA
<213> ORGANISM: Artificial sequence
<220> FEATURE:
<223> OTHER INFORMATION: Heavy chain CRM4374
<220> FEATURE:
<221> NAME/KEY: Intron
<222> LOCATION: (697)..(786)
<220> FEATURE:
<221> NAME/KEY: Intron
<222> LOCATION: (1589)..(1867)
<220> FEATURE:
<221> NAME/KEY: Intron
<222> LOCATION: (1123)..(1366)

<400> SEQUENCE: 217

```
cagatcacct tgaaggagtc tggtcctacg ctggtgaaac ccacacagac cctcacgttg     60
acctgcacct tctctgggtt ctcactcagc actagtggag tgggtgtggg ctggatccgt    120
cagcccccag gaaaggccct ggagtggctt gcagtcattt attggaatga tgataagctc    180
tacaggccat ctctgaagag caggctcacc atcaccaagg acacctccaa aaaccaggtg    240
gtccttacaa tgaccaagat ggaccctgtg acacagcca catattactg tgcacacaga    300
caccgttact atgatattag tggttattac cgtctcttct ctgatgcttt tgatatctgg    360
ggccagggca ccatggtgac cgtgtccagc gctagcgccc aaccctttt ccccctcgtc    420 tcctgtgaga attccccgtc ggatacgagc agcgtggccg ttggctgcct cgcacaggac    480
ttccttcccg actccatcac tttctcctgg aaatacaaga caactctga catcagcagc    540 acccggggct tccatcagt cctgagaggg ggcaagtacg cagccacctc acaggtgctg    600
ctgccttcca aggacgtcat gcagggcaca gacgaacacg tggtgtgcaa agtccagcac    660
```

```
cccaacggca acaaagaaaa gaacgtgcct cttccaggtg agggccgggc ccagccaccg    720
ggacagagag ggagccgaag ggggcgggag tggcgggcac cgggctgaca cgtgtccctc    780
actgcagtga ttgctgagct gcctcccaaa gtgagcgtct tcgtcccacc ccgcgacggc    840
ttcttcggca accccgcaa gtccaagctc atctgccagg ccacgggttt cagtccccgg     900
cagattcagg tgtcctggct gcgcgagggg aagcaggtgg ggtctggcgt caccacggac    960
caggtgcagg ctgaggccaa agagtctggg cccacgacct acaaggtgac cagcacactg    1020
accatcaaag agagcgactg gctcagccag agcatgttca cctgccgcgt ggatcacagg    1080
ggcctgacct tccagcagaa tcgtcctcc atgtgtgtcc ccggtgagtg acctgtcccc    1140
aggggcagca cccaccgaca cacaggggtc cactcgggtc tggcattcgc cacccccggat    1200
gcagccatct actccctgag ccttggcttc cagagcggc caagggcagg ggctcgggcg    1260
gcaggacccc tgggctcggc agaggcagtt gctactcttt gggtgggaac catgcctccg    1320
cccacatcca cacctgcccc acctctgact cccttctctt gactccagat caagacacag    1380
ccatccgggt cttcgccatc ccccatcct ttgccagcat cttcctcacc aagtccacca    1440
agttgacctg cctggtcaca gacctgacca cctatgacag cgtgaccatc tcctggaccc    1500
gccagaatgg cgaagctgtg aaaacccaca ccaacatctc cgagagccac cccaatgcca    1560
ctttcagcgc cgtgggtgag gccagcatct gcgaggatga ctggaattcc ggggagaggt    1620
tcacgtgcac cgtgacccac acagacctgc cctcgccact gaagcagacc atctcccggc    1680
ccaagggtag gccccactct tgcccctctt cctgcactcc ctgggacctc ccttggcctc    1740
tggggcatgg tggaaagcac ccctcactcc cccgttgtct gggcaactgg ggaaaagggg    1800
actcaaccc agcccacagg ctggtccccc cactgccccg ccctcaccac catctctgtt    1860
cacaggggtg gccctgcaca ggcccgatgt ctacttgctg ccaccagccc gggagcagct    1920
gaacctgcgg gagtcggcca ccatcacgtg cctggtgacg ggcttctctc ccgcggacgt    1980
cttcgtgcag tggatgcaga gggggcagcc cttgtccccg gagaagtatg tgaccagcgc    2040
cccaatgcct gagccccagg ccccaggccg gtacttcgcc cacagcatcc tgaccgtgtc    2100
cgaagaggaa tggaacacgg gggagaccta cacctgcgtg gtggcccatg aggccctgcc    2160
caacagggtc accgagagga ccgtggacaa gtccaccggt aaacccaccc tgtacaacgt    2220
gtccctggtc atgtccgaca cagctggcac ctgctac                             2257
```

<210> SEQ ID NO 218
<211> LENGTH: 581
<212> TYPE: PRT
<213> ORGANISM: Artificial sequence
<220> FEATURE:
<223> OTHER INFORMATION: Heavy chain CRM4374

<400> SEQUENCE: 218

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
    50                  55                  60

Leu Lys Ser Arg Leu Thr Ile Thr Lys Asp Thr Ser Lys Asn Gln Val
65                  70                  75                  80
```

-continued

```
Val Leu Thr Met Thr Lys Met Asp Pro Val Asp Thr Ala Thr Tyr Tyr
            85                  90                  95
Cys Ala His Arg His Arg Tyr Tyr Asp Ile Ser Gly Tyr Tyr Arg Leu
            100                 105                 110
Phe Ser Asp Ala Phe Asp Ile Trp Gly Gln Gly Thr Met Val Thr Val
            115                 120                 125
Ser Ser Ala Ser Ala Pro Thr Leu Phe Pro Leu Val Ser Cys Glu Asn
130                 135                 140
Ser Pro Ser Asp Thr Ser Ser Val Ala Val Gly Cys Leu Ala Gln Asp
145                 150                 155                 160
Phe Leu Pro Asp Ser Ile Thr Phe Ser Trp Lys Tyr Lys Asn Asn Ser
                165                 170                 175
Asp Ile Ser Ser Thr Arg Gly Phe Pro Ser Val Leu Arg Gly Gly Lys
                180                 185                 190
Tyr Ala Ala Thr Ser Gln Val Leu Leu Pro Ser Lys Asp Val Met Gln
                195                 200                 205
Gly Thr Asp Glu His Val Val Cys Lys Val Gln His Pro Asn Gly Asn
210                 215                 220
Lys Glu Lys Asn Val Pro Leu Pro Val Ile Ala Glu Leu Pro Pro Lys
225                 230                 235                 240
Val Ser Val Phe Val Pro Pro Arg Asp Gly Phe Phe Gly Asn Pro Arg
                245                 250                 255
Lys Ser Lys Leu Ile Cys Gln Ala Thr Gly Phe Ser Pro Arg Gln Ile
                260                 265                 270
Gln Val Ser Trp Leu Arg Glu Gly Lys Gln Val Gly Ser Gly Val Thr
            275                 280                 285
Thr Asp Gln Val Gln Ala Glu Ala Lys Glu Ser Gly Pro Thr Thr Tyr
290                 295                 300
Lys Val Thr Ser Thr Leu Thr Ile Lys Glu Ser Asp Trp Leu Ser Gln
305                 310                 315                 320
Ser Met Phe Thr Cys Arg Val Asp His Arg Gly Leu Thr Phe Gln Gln
                325                 330                 335
Asn Ala Ser Ser Met Cys Val Pro Asp Gln Asp Thr Ala Ile Arg Val
                340                 345                 350
Phe Ala Ile Pro Pro Ser Phe Ala Ser Ile Phe Leu Thr Lys Ser Thr
            355                 360                 365
Lys Leu Thr Cys Leu Val Thr Asp Leu Thr Thr Tyr Asp Ser Val Thr
370                 375                 380
Ile Ser Trp Thr Arg Gln Asn Gly Glu Ala Val Lys Thr His Thr Asn
385                 390                 395                 400
Ile Ser Glu Ser His Pro Asn Ala Thr Phe Ser Ala Val Gly Glu Ala
                405                 410                 415
Ser Ile Cys Glu Asp Asp Trp Asn Ser Gly Glu Arg Phe Thr Cys Thr
                420                 425                 430
Val Thr His Thr Asp Leu Pro Ser Pro Leu Lys Gln Thr Ile Ser Arg
            435                 440                 445
Pro Lys Gly Val Ala Leu His Arg Pro Asp Val Tyr Leu Leu Pro Pro
450                 455                 460
Ala Arg Glu Gln Leu Asn Leu Arg Glu Ser Ala Thr Ile Thr Cys Leu
465                 470                 475                 480
Val Thr Gly Phe Ser Pro Ala Asp Val Phe Val Gln Trp Met Gln Arg
                485                 490                 495
Gly Gln Pro Leu Ser Pro Glu Lys Tyr Val Thr Ser Ala Pro Met Pro
```

```
              500             505             510
Glu Pro Gln Ala Pro Gly Arg Tyr Phe Ala His Ser Ile Leu Thr Val
            515             520             525

Ser Glu Glu Glu Trp Asn Thr Gly Glu Thr Tyr Thr Cys Val Val Ala
        530             535             540

His Glu Ala Leu Pro Asn Arg Val Thr Glu Arg Thr Val Asp Lys Ser
545             550             555             560

Thr Gly Lys Pro Thr Leu Tyr Asn Val Ser Leu Val Met Ser Asp Thr
                565             570             575

Ala Gly Thr Cys Tyr
            580

<210> SEQ ID NO 219
<211> LENGTH: 8792
<212> TYPE: DNA
<213> ORGANISM: Artificial sequence
<220> FEATURE:
<223> OTHER INFORMATION: Vector pIg-C910-Clambda

<400> SEQUENCE: 219
```

| | | | | | |
|---|---|---|---|---|---|
| tcgacggatc | gggagatctc | ccgatcccct | atggtgcact | ctcagtacaa | tctgctctga | 60 |
| tgccgcatag | ttaagccagt | atctgctccc | tgcttgtgtg | ttggaggtcg | ctgagtagtg | 120 |
| cgcgagcaaa | atttaagcta | caacaaggca | aggcttgacc | gacaattgtt | aattaacatg | 180 |
| aagaatctgc | ttagggttag | gcgttttgcg | ctgcttcgct | aggtggtcaa | tattggccat | 240 |
| tagccatatt | attcattggt | tatatagcat | aaatcaatat | tggctattgg | ccattgcata | 300 |
| cgttgtatcc | atatcataat | atgtacattt | atattggctc | atgtccaaca | ttaccgccat | 360 |
| gttgacattg | attattgact | agttattaat | agtaatcaat | tacggggtca | ttagttcata | 420 |
| gcccatatat | ggagttccgc | gttacataac | ttacggtaaa | tggcccgcct | ggctgaccgc | 480 |
| ccaacgaccc | ccgcccattg | acgtcaataa | tgacgtatgt | tcccatagta | acgccaatag | 540 |
| ggactttcca | ttgacgtcaa | tgggtggagt | atttacggta | aactgcccac | ttggcagtac | 600 |
| atcaagtgta | tcatatgcca | agtacgcccc | ctattgacgt | caatgacggt | aaatggcccg | 660 |
| cctggcatta | tgcccagtac | atgaccttat | gggactttcc | tacttggcag | tacatctacg | 720 |
| tattagtcat | cgctattacc | atggtgatgc | ggttttggca | gtacatcaat | gggcgtggat | 780 |
| agcggtttga | ctcacgggga | tttccaagtc | tccaccccat | tgacgtcaat | gggagtttgt | 840 |
| tttggcacca | aaatcaacgg | gactttccaa | aatgtcgtaa | caactccgcc | ccattgacgc | 900 |
| aaatgggcgg | taggcgtgta | cggtgggagg | tctatataag | cagagctcgt | ttagtgaacc | 960 |
| gtcagatcgc | ctggagacgc | catccacgct | gttttgacct | ccatagaaga | caccgggacc | 1020 |
| gatccagcct | ccgcggccgg | gaacggtgca | ttggaatcga | tgactctctt | aggtagcctt | 1080 |
| gcagaagttg | gtcgtgaggc | actgggcagg | taagtatcaa | ggttacaaga | caggtttaag | 1140 |
| gagatcaata | gaaactgggc | ttgtcgagac | agagaagact | cttgcgtttc | tgataggcac | 1200 |
| ctattggtct | tactgacatc | cactttgcct | ttctctccac | aggtgtccac | tcccagttca | 1260 |
| attacagctc | gccaccatgc | ggttctccgc | tcagctgctg | ggccttctgg | tgctgtggat | 1320 |
| tcccggcgtc | tcgagatcta | tcgatgcatg | ccatggtacc | aagcttgcca | ccatgagcag | 1380 |
| cagctcttgg | ctgctgctga | gcctggtggc | cgtgacagcc | gccagagca | ccatcgagga | 1440 |
| gcaggccaag | accttcctgg | acaagttcaa | ccacgaggcc | gaggacctgt | tctaccagag | 1500 |
| cagcctggcc | agctggaact | acaacaccaa | catcaccgag | gagaacgtgc | agaacatgaa | 1560 |

```
caacgccggc gacaagtgga gcgccttcct gaaggagcag agcacactgg cccagatgta   1620
cccCctgcag gagatccaga acctgaccgt gaagctgcag ctgcaggccc tgcagcagaa   1680
cggcagcagc gtgctgagcg aggacaagag caagcggctg aacaccatcc tgaacaccat   1740
gtccaccatc tacagcaccg gcaaagtgtg caaccccgac aaccccagg agtgcctgct    1800
gctggagccc ggcctgaacg agatcatggc caacagcctg gactacaacg agcggctgtg   1860
ggcctgggag agctggcgga gcgaagtggg caagcagctg cggcccctgt acgaggagta   1920
cgtggtgctg aagaacgaga tggccagggc caaccactac gaggactacg cgactactg    1980
gagaggcgac tacgaagtga acggcgtgga cggctacgac tacagcagag ccagctgat    2040
cgaggacgtg gagcacacct tcgaggagat caagcctctg tacgagcacc tgcacgccta   2100
cgtgcgggcc aagctgatga acgcctaccc cagctacatc agccccatcg ctgcctgcc    2160
cgcccacctg ctgggcgaca tgtggggccg gttctggacc aacctgtaca gcctgaccgt   2220
gcccttcggc cagaagccca acatcgacgt gaccgacgcc atggtggacc aggcctggga   2280
cgcccagcgg atcttcaagg aggccgagaa gttcttcgtg agcgtgggcc tgcccaacat   2340
gacccagggc ttttgggaga acagcatgct gaccgacccc ggcaatgtgc agaaggccgt   2400
gtgccacccc accgcctggg acctgggcaa gggcgacttc cggatcctga tgtgcaccaa   2460
agtgaccatg gacgacttcc tgaccgccca ccacgagatg ggccacatcc agtacgacat   2520
ggcctacgcc gcccagccct cctgctgcg gaacggcgcc aacgagggct tcacgaggc     2580
cgtgggcgag atcatgagcc tgagcgccgc caccccaag cacctgaaga gcatcggcct    2640
gctgagcccc gacttccagg aggacaacga gaccgagatc aacttcctgc tgaagcaggc   2700
cctgaccatc gtgggcaccc tgccCttcac ctacatgctg gagaagtggc ggtggatggt   2760
gtttaagggc gagatcccca aggaccagtg gatgaagaag tggtgggaga tgaagcggga   2820
gatcgtgggc gtggtggagc ccgtgcccca cgacgagacc tactgcgacc ccgccagcct   2880
gttccacgtg agcaacgact actccttcat ccggtactac acccggaccc tgtaccagtt   2940
ccagttccag gaggccctgt gccaggccgc caagcacgag ggcccctgc acaagtgcga    3000
catcagcaac agcaccgagg ccggacagaa actgttcaac atgctgcggc tgggcaagag   3060
cgagccctgg accctggccc tggagaatgt ggtgggcgcc aagaacatga atgtgcgccc   3120
cctgctgaac tacttcgagc ccctgttcac ctggctgaag gaccagaaca gaacagctt    3180
cgtgggctgg agcaccgact ggagccccta cgccgaccag agcatcaaag tgcggatcag   3240
cctgaagagc gccctgggcg acaaggccta cgagtggaac gacaacgaga tgtacctgtt   3300
ccggagcagc gtggcctatg ccatgcggca gtacttcctg aaagtgaaga accagatgat   3360
cctgttcggc gaggaggacg tgagagtggc caacctgaag cccggatca gcttcaactt    3420
cttcgtgacc gccCccaaga acgtgagcga catcatcccc cggaccgaag tggagaaggc   3480
catccggatg agccggagcc ggatcaacga cgccttccgg ctgaacgaca ctccctgga    3540
gttcctgggc atccagccca ccctgggccc tcccaaccag cccCccgtga gcatctggct   3600
gatcgtgttt ggcgtggtga tgggcgtgat cgtggtggga atcgtgatcc tgatcttcac   3660
cggcatccgg gaccggaaga agaagaacaa ggccCggagc ggcgagaacc cctacgccag   3720
catcgatatc agcaagggcg agaacaaccc cggcttccag aacaccgacg acgtgcagac   3780
cagcttctga taatctagaa cgagctcgaa ttcgaagctt ctgcagacgc gtcgacgtca   3840
tatggatccg atatcgccgt ggcggccgca ggccagccca aggccgctcc cagcgtgacc   3900
ctgttccccc cctcctccga ggagctgcag gccaacaagg ccaccctggt gtgcctcatc   3960
```

```
agcgacttct accctggcgc cgtgaccgtg gcctggaagg ccgacagcag ccccgtgaag   4020
gccggcgtgg agaccaccac ccccagcaag cagagcaaca acaagtacgc cgccagcagc   4080
tacctgagcc tcaccccgga gcagtggaag agccaccgga gctacagctg ccaggtgacc   4140
cacgagggca gcaccgtgga agaccgtgg gcccccaccg agtgcagcta atagacttaa   4200
gtttaaaccg ctgatcagcc tcgactgtgc cttctagttg ccagccatct gttgtttgcc   4260
cctcccccgt gccttccttg accctggaag gtgccactcc cactgtcctt tcctaataaa   4320
atgaggaaat tgcatcgcat tgtctgagta ggtgtcattc tattctgggg ggtggggtgg   4380
ggcaggacag caaggggag gattgggaag acaatagcag gcatgctggg gatgcggtgg   4440
gctctatggc ttctgaggcg gaaagaacca gctggggctc tagggggtat ccccacgcgc   4500
cctgtagcgg cgcattaagc gcggcgggtg tggtggttac gcgcagcgtg accgctacac   4560
ttgccagcgc cctagcgccc gctcctttcg ctttcttccc ttcctttctc gccacgttcg   4620
ccggctttcc ccgtcaagct ctaaatcggg ggctcccttt agggttccga tttagtgctt   4680
tacggcacct cgaccccaaa aaacttgatt agggtgatgg ttcacgtagt gggccatcgc   4740
cctgatagac ggttttttcgc cctttgacgt tggagtccac gttctttaat agtggactct   4800
tgttccaaac tggaacaaca ctcaaccta tctcggtcta ttcttttgat ttataaggga   4860
ttttggccat ttcggcctat tggttaaaaa atgagctgat ttaacaaaaa tttaacgcga   4920
attaattctg tggaatgtgt gtcagttagg gtgtggaaag tccccaggct ccccagcagg   4980
cagaagtatg caaagcatgc atctcaatta gtcagcaacc aggtgtggaa agtccccagg   5040
ctccccagca ggcagaagta tgcaaagcat gcatctcaat tagtcagcaa ccatagtccc   5100
gcccctaact ccgcccatcc cgcccctaac tccgcccagt tccgcccatt ctccgcccca   5160
tggctgacta atttttttta tttatgcaga ggccgaggcc gcctctgcct ctgagctatt   5220
ccagaagtag tgaggaggct ttttggagg cctaggcttt tgcaaaaagc tcccgggagc   5280
ttgtatatcc attttcggat ctgatcagca cgtgatgaaa aagcctgaac tcaccgcgac   5340
gtctgtcgag aagtttctga tcgaaaagtt cgacagcgtc tccgacctga tgcagctctc   5400
ggagggcgaa gaatctcgtg ctttcagctt cgatgtagga gggcgtggat atgtcctgcg   5460
ggtaaatagc tgcgccgatg gtttctacaa agatcgttat gtttatcggc actttgcatc   5520
ggccgcgctc ccgattccgg aagtgcttga cattgggaa ttcagcgaga gcctgaccta   5580
ttgcatctcc cgccgtgcac agggtgtcac gttgcaagac ctgcctgaaa ccgaactgcc   5640
cgctgttctg cagccggtcg cggaggccat ggatgcgatc gctgcggccg atcttagcca   5700
gacgagcggg ttcggcccat tcggaccgca aggaatcggt caatacacta catggcgtga   5760
tttcatatgc gcgattgctg atccccatgt gtatcactgg caaactgtga tggacgacac   5820
cgtcagtgcg tccgtcgcgc aggctctcga tgagctgatg ctttgggccg aggactgccc   5880
cgaagtccgg cacctcgtgc acgcggattt cggctccaac aatgtcctga cggacaatgg   5940
ccgcataaca gcggtcattg actggagcga ggcgatgttc ggggattccc aatacgaggt   6000
cgccaacatc ttcttctgga ggccgtggtt ggcttgtatg gagcagcaga cgcgctactt   6060
cgagcggagg catccggagc ttgcaggatc gccgcggctc cgggcgtata tgctccgcat   6120
tggtcttgac caactctatc agagcttggt tgacggcaat ttcgatgatg cagcttgggc   6180
gcagggtcga tgcgacgcaa tcgtccgatc cggagccggg actgtcgggc gtacacaaat   6240
cgcccgcaga agcgcggccg tctggaccga tggctgtgta gaagtactcg ccgatagtgg   6300
```

```
aaaccgacgc cccagcactc gtccgagggc aaaggaatag cacgtgctac gagatttcga   6360
ttccaccgcc gccttctatg aaaggttggg cttcggaatc gttttccggg acgccggctg   6420
gatgatcctc cagcgcgggg atctcatgct ggagttcttc gcccacccca acttgtttat   6480
tgcagcttat aatggttaca ataaagcaa tagcatcaca aatttcacaa ataaagcatt    6540
tttttcactg cattctagtt gtggtttgtc caaactcatc aatgtatctt atcatgtctg   6600
tataccgtcg acctctagct agagcttggc gtaatcatgg tcatagctgt ttcctgtgtg   6660
aaattgttat ccgctcacaa ttccacacaa catacgagcc ggaagcataa agtgtaaagc   6720
ctggggtgcc taatgagtga gctaactcac attaattgcg ttgcgctcac tgcccgcttt   6780
ccagtcggga aacctgtcgt gccagctgca ttaatgaatc ggccaacgcg cggggagagg   6840
cggtttgcgt attgggcgct cttccgcttc ctcgctcact gactcgctgc gctcggtcgt   6900
tcggctgcgg cgagcggtat cagctcactc aaaggcggta atacggttat ccacagaatc   6960
aggggataac gcaggaaaga acatgtgagc aaaaggccag caaaaggcca ggaaccgtaa   7020
aaaggccgcg ttgctggcgt ttttccatag gctccgcccc cctgacgagc atcacaaaaa   7080
tcgacgctca gtcagaggt ggcgaaaccc gacaggacta taaagatacc aggcgtttcc    7140
ccctggaagc tccctcgtgc gctctcctgt tccgaccctg ccgcttaccg gatacctgtc   7200
cgcctttctc ccttcgggaa gcgtggcgct ttctcatagc tcacgctgta ggtatctcag   7260
ttcggtgtag gtcgttcgct ccaagctggg ctgtgtgcac gaaccccccg ttcagcccga   7320
ccgctgcgcc ttatccggta actatcgtct gagtccaac ccgtaagac acgacttatc     7380
gccactggca gcagccactg gtaacaggat tagcagagcg aggtatgtag gcggtgctac   7440
agagttcttg aagtggtggc ctaactacgg ctacactaga agaacagtat ttggtatctg   7500
cgctctgctg aagccagtta ccttcggaaa aagagttggt agctcttgat ccggcaaaca   7560
aaccaccgct ggtagcggtt ttttgtttg caagcagcag attacgcgca gaaaaaaagg    7620
atctcaagaa gatcctttga tcttttctac ggggtctgac gctcagtgga acgaaaactc   7680
acgttaaggg attttggtca tgagattatc aaaaaggatc ttcacctaga tccttttaaa   7740
ttaaaaatga gttttaaat caatctaaag tatatatgag taaacttggt ctgacagtta    7800
ccaatgctta atcagtgagg cacctatctc agcgatctgt ctatttcgtt catccatagt   7860
tgcctgactc cccgtcgtgt agataactac gatacgggag ggcttaccat ctggccccag   7920
tgctgcaatg ataccgcgag acccacgctc accggctcca gatttatcag caataaacca   7980
gccagccgga agggccgagc gcagaagtgg tcctgcaact ttatccgcct ccatccagtc   8040
tattaattgt tgccgggaag ctagagtaag tagttcgcca gttaatagtt tgcgcaacgt   8100
tgttgccatt gctacaggca tcgtggtgtc acgctcgtcg tttggtatgg cttcattcag   8160
ctccggttcc caacgatcaa ggcgagttac atgatccccc atgttgtgca aaaaagcggt   8220
tagctccttc ggtcctccga tcgttgtcag aagtaagttg gccgcagtgt tatcactcat   8280
ggttatggca gcactgcata attctcttac tgtcatgcca tccgtaagat gcttttctgt   8340
gactggtgag tactcaacca agtcattctg agaatagtgt atgcggcgac cgagttgctc   8400
ttgcccggcg tcaatacggg ataataccgc gccacatagc agaactttaa agtgctcat    8460
cattggaaaa cgttcttcgg ggcgaaaact ctcaaggatc ttaccgctgt tgagatccag   8520
ttcgatgtaa cccactcgtg cacccaactg atcttcagca tcttttactt tcaccagcgt   8580
ttctgggtga gcaaaaacag gaaggcaaaa tgccgcaaaa aagggaataa gggcgacacg   8640
gaaatgttga atactcatac tcttcctttt tcaatattat tgaagcattt atcagggtta   8700
```

```
ttgtctcatg agcggataca tatttgaatg tatttagaaa aataaacaaa tagggggttcc     8760 gcgcacattt ccccgaaaag tgccacctga cg                                    8792

<210> SEQ ID NO 220
<211> LENGTH: 663
<212> TYPE: DNA
<213> ORGANISM: Artificial sequence
<220> FEATURE:
<223> OTHER INFORMATION: Light chain of CR5074
<220> FEATURE:
<221> NAME/KEY: CDS
<222> LOCATION: (1)..(663)

<400> SEQUENCE: 220 cag tct gtg ttg acg cag ccg ccc tca gtg tct ggg gcc cca ggg cag       48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg aca ggt       96
Arg Val Thr Ile Ser Cys Thr Gly Ser Ser Ser Asn Ile Gly Thr Gly
            20                  25                  30 tat gat gta cac tgg tac cag cag ctt cca gga aca gcc ccc aaa ctc      144
Tyr Asp Val His Trp Tyr Gln Gln Leu Pro Gly Thr Ala Pro Lys Leu
        35                  40                  45 ctc atc tat gct gac acc aat cgg ccc tca ggg gtc cct gac cga ttc      192
Leu Ile Tyr Ala Asp Thr Asn Arg Pro Ser Gly Val Pro Asp Arg Phe
    50                  55                  60 tct ggc tcc aag tct ggc acc tca gcc tcc ctg gcc atc act ggg gtc      240
Ser Gly Ser Lys Ser Gly Thr Ser Ala Ser Leu Ala Ile Thr Gly Val
65                  70                  75                  80 cag gct gag gat gag gct gat tat tac tgc cag tcc tat gac acc agc      288
Gln Ala Glu Asp Glu Ala Asp Tyr Tyr Cys Gln Ser Tyr Asp Thr Ser
                85                  90                  95 ctg act ggt tgg gtg ttc ggc gga ggg acc aag gtc acc gtc cta ggt      336
Leu Thr Gly Trp Val Phe Gly Gly Gly Thr Lys Val Thr Val Leu Gly
            100                 105                 110 gcg gcc gca ggc cag ccc aag gcc gct ccc agc gtg acc ctg ttc ccc      384
Ala Ala Ala Gly Gln Pro Lys Ala Ala Pro Ser Val Thr Leu Phe Pro
        115                 120                 125 ccc tcc tcc gag gag ctg cag gcc aac aag gcc acc ctg gtg tgc ctc      432
Pro Ser Ser Glu Glu Leu Gln Ala Asn Lys Ala Thr Leu Val Cys Leu
    130                 135                 140 atc agc gac ttc tac cct ggc gcc gtg acc gtg gcc tgg aag gcc gac      480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag      528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag      576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc      624
Gln Trp Lys Ser His Arg Ser Tyr Ser Cys Gln Val Thr His Glu Gly
        195                 200                 205 agc acc gtg gag aag acc gtg gcc ccc acc gag tgc agc                  663
Ser Thr Val Glu Lys Thr Val Ala Pro Thr Glu Cys Ser
    210                 215                 220

<210> SEQ ID NO 221
<211> LENGTH: 221
<212> TYPE: PRT
<213> ORGANISM: Artificial sequence
```

-continued

```
<220> FEATURE:
<223> OTHER INFORMATION: Light chain of CR5074

<400> SEQUENCE: 221

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Thr Gly
            20                  25                  30

Tyr Asp Val His Trp Tyr Gln Gln Leu Pro Gly Thr Ala Pro Lys Leu
        35                  40                  45

Leu Ile Tyr Ala Asp Thr Asn Arg Pro Ser Gly Val Pro Asp Arg Phe
    50                  55                  60

Ser Gly Ser Lys Ser Gly Thr Ser Ala Ser Leu Ala Ile Thr Gly Val
65                  70                  75                  80

Gln Ala Glu Asp Glu Ala Asp Tyr Tyr Cys Gln Ser Tyr Asp Thr Ser
                85                  90                  95

Leu Thr Gly Trp Val Phe Gly Gly Gly Thr Lys Val Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 222
<211> LENGTH: 663
<212> TYPE: DNA
<213> ORGANISM: Artificial sequence
<220> FEATURE:
<223> OTHER INFORMATION: Light chain of CR5080
<220> FEATURE:
<221> NAME/KEY: CDS
<222> LOCATION: (1)..(663)

<400> SEQUENCE: 222 cag tct gtg ctg act cag cca ccc tca gtg tct ggg gcc cca ggg cag      48
Gln Ser Val Leu Thr Gln Pro Pro Ser Val Ser Gly Ala Pro Gly Gln
1               5                   10                  15 agg gtc acc atc tcc tgc act ggg agc agc tcc aac atc ggg gca ggt      96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc     144
Tyr Asp Val His Trp Tyr Gln Gln Leu Pro Gly Thr Ala Pro Lys Leu
        35                  40                  45 ctc atc tat ggt aac agc aat cgg ccc tca ggg gtc cct gac cga ttc     192
Leu Ile Tyr Gly Asn Ser Asn Arg Pro Ser Gly Val Pro Asp Arg Phe
    50                  55                  60 tct ggc tcc aag tct ggc acc tca gcc tcc ctg gcc atc act ggg ctc     240
Ser Gly Ser Lys Ser Gly Thr Ser Ala Ser Leu Ala Ile Thr Gly Leu
65                  70                  75                  80
```

```
cag gct gag gat gag gct gat tat tac tgc cag tcc tat gac agc agc      288
Gln Ala Glu Asp Glu Ala Asp Tyr Tyr Cys Gln Ser Tyr Asp Ser Ser
                85                  90                  95 ctg agt ggt tgg gcg ttc ggc gga ggg acc aag ctg acc gtc cta ggt      336
Leu Ser Gly Trp Ala Phe Gly Gly Gly Thr Lys Leu Thr Val Leu Gly
            100                 105                 110 gcg gcc gca ggc cag ccc aag gcc gct ccc agc gtg acc ctg ttc ccc      384
Ala Ala Ala Gly Gln Pro Lys Ala Ala Pro Ser Val Thr Leu Phe Pro
        115                 120                 125 ccc tcc tcc gag gag ctg cag gcc aac aag gcc acc ctg gtg tgc ctc      432
Pro Ser Ser Glu Glu Leu Gln Ala Asn Lys Ala Thr Leu Val Cys Leu
    130                 135                 140 atc agc gac ttc tac cct ggc gcc gtg acc gtg gcc tgg aag gcc gac      480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag      528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag      576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc      624
Gln Trp Lys Ser His Arg Ser Tyr Ser Cys Gln Val Thr His Glu Gly
        195                 200                 205 agc acc gtg gag aag acc gtg gcc ccc acc gag tgc agc                  663
Ser Thr Val Glu Lys Thr Val Ala Pro Thr Glu Cys Ser
    210                 215                 220

<210> SEQ ID NO 223
<211> LENGTH: 221
<212> TYPE: PRT
<213> ORGANISM: Artificial sequence
<220> FEATURE:
<223> OTHER INFORMATION: Light chain of CR5080

<400> SEQUENCE: 223

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Ala Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175
```

```
Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 224
<211> LENGTH: 663
<212> TYPE: DNA
<213> ORGANISM: Artificial sequence
<220> FEATURE:
<223> OTHER INFORMATION: Light chain of CR5085
<220> FEATURE:
<221> NAME/KEY: CDS
<222> LOCATION: (1)..(663)

<400> SEQUENCE: 224 cag tct gtc gtg acg cag ccg ccc tca gtg tct ggg gcc cca ggg cag         48
Gln Ser Val Val Thr Gln Pro Pro Ser Val Ser Gly Ala Pro Gly Gln
1               5                   10                  15 agg gtc acc atc tcc tgc act ggg agc agc tcc aac atc ggg gca ggt         96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc        144
Tyr Asp Val His Trp Tyr Gln Gln Leu Pro Gly Thr Ala Pro Lys Leu
        35                  40                  45 ctc atc tat ggt aac agc aat cgg ccc tca ggg gtc cct gac cga ttc        192
Leu Ile Tyr Gly Asn Ser Asn Arg Pro Ser Gly Val Pro Asp Arg Phe
    50                  55                  60 tct ggc tcc aag tct ggc acc tca gcc tcc ctg gcc atc act ggg ctc        240
Ser Gly Ser Lys Ser Gly Thr Ser Ala Ser Leu Ala Ile Thr Gly Leu
65                  70                  75                  80 cag gct gag gat gag act gat tat tac tgc cag tcc tat gac agc agc        288
Gln Ala Glu Asp Glu Thr Asp Tyr Tyr Cys Gln Ser Tyr Asp Ser Ser
                85                  90                  95 ctg aat ggt tgg gtg ttc ggc gga ggg acc aag ctg acc gtc cta ggt        336
Leu Asn Gly Trp Val Phe Gly Gly Gly Thr Lys Leu Thr Val Leu Gly
            100                 105                 110 gcg gcc gca ggc cag ccc aag gct gct ccc agc gtg acc ctg ttc ccc        384
Ala Ala Ala Gly Gln Pro Lys Ala Ala Pro Ser Val Thr Leu Phe Pro
        115                 120                 125 ccc tcc tcc gag gag ctg cag gcc aac aag gcc acc ctg gtg tgc ctc        432
Pro Ser Ser Glu Glu Leu Gln Ala Asn Lys Ala Thr Leu Val Cys Leu
    130                 135                 140 atc agc gac ttc tac cct ggc gcc gtg acc gtg gcc tgg aag gcc gac        480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag        528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag        576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc        624
Gln Trp Lys Ser His Arg Ser Tyr Ser Cys Gln Val Thr His Glu Gly
        195                 200                 205 agc acc gtg gag aag acc gtg gcc ccc acc gag tgc agc                    663
Ser Thr Val Glu Lys Thr Val Ala Pro Thr Glu Cys Ser
    210                 215                 220
```

<210> SEQ ID NO 225
<211> LENGTH: 221
<212> TYPE: PRT
<213> ORGANISM: Artificial sequence
<220> FEATURE:
<223> OTHER INFORMATION: Light chain of CR5085

<400> SEQUENCE: 225

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Ser Ser
                85                  90                  95

Leu Asn Gly Trp Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220
```

<210> SEQ ID NO 226
<211> LENGTH: 663
<212> TYPE: DNA
<213> ORGANISM: Artificial sequence
<220> FEATURE:
<223> OTHER INFORMATION: Light chain of CR5088
<220> FEATURE:
<221> NAME/KEY: CDS
<222> LOCATION: (1)..(663)

<400> SEQUENCE: 226

```
cag tct gtc gtg acg cag ccg ccc tca gtg tct ggg gcc cca ggg cag      48
Gln Ser Val Val Thr Gln Pro Pro Ser Val Ser Gly Ala Pro Gly Gln
1               5                   10                  15 agg atc acc atc tcc tgc act ggg agc agc tcc aac atc ggg gca ggt      96
Arg Ile Thr Ile Ser Cys Thr Gly Ser Ser Ser Asn Ile Gly Ala Gly
            20                  25                  30 tat gat gta cac tgg tac cag cag ctt cca gga aca gcc ccc aaa ttc     144
Tyr Asp Val His Trp Tyr Gln Gln Leu Pro Gly Thr Ala Pro Lys Phe
        35                  40                  45 ctc atc tat ggt aac agc aat cgg ccc tca ggg gtc cct gac cga ttc     192
Leu Ile Tyr Gly Asn Ser Asn Arg Pro Ser Gly Val Pro Asp Arg Phe
```

```
                     50                  55                  60
tct ggc tcc aag tct ggc acc tca gcc tcc ctg gcc atc act ggg ctc      240
Ser Gly Ser Lys Ser Gly Thr Ser Ala Ser Leu Ala Ile Thr Gly Leu
 65                  70                  75                  80 cag gct gag gat gag gct gat tat tac tgc cag tcc tat gac agc agc      288
Gln Ala Glu Asp Glu Ala Asp Tyr Tyr Cys Gln Ser Tyr Asp Ser Ser
                 85                  90                  95 ctg agt ggt tgg gtg ttc ggc gga ggg acc aag ctg acc gtc cta ggt      336
Leu Ser Gly Trp Val Phe Gly Gly Gly Thr Lys Leu Thr Val Leu Gly
            100                 105                 110 gcg gcc gca ggc cag ccc aag gcc gct ccc agc gtg acc ctg ttc ccc      384
Ala Ala Ala Gly Gln Pro Lys Ala Ala Pro Ser Val Thr Leu Phe Pro
        115                 120                 125 ccc tcc tcc gag gag ctg cag gcc aac aag gcc acc ctg gtg tgc ctc      432
Pro Ser Ser Glu Glu Leu Gln Ala Asn Lys Ala Thr Leu Val Cys Leu
    130                 135                 140 atc agc gac ttc tac cct ggc gcc gtg acc gtg gcc tgg aag gcc gac      480
Ile Ser Asp Phe Tyr Pro Gly Ala Val Thr Val Ala Trp Lys Ala Asp
145                 150                 155                 160 agc agc ccc gtg aag gcc ggc gtg gag acc acc acc ccc agc aag cag      528
Ser Ser Pro Val Lys Ala Gly Val Glu Thr Thr Thr Pro Ser Lys Gln
                165                 170                 175 agc aac aac aag tac gcc gcc agc agc tac ctg agc ctc acc ccc gag      576
Ser Asn Asn Lys Tyr Ala Ala Ser Ser Tyr Leu Ser Leu Thr Pro Glu
            180                 185                 190 cag tgg aag agc cac cgg agc tac agc tgc cag gtg acc cac gag ggc      624
Gln Trp Lys Ser His Arg Ser Tyr Ser Cys Gln Val Thr His Glu Gly
        195                 200                 205 agc acc gtg gag aag acc gtg gcc ccc acc gag tgc agc                  663
Ser Thr Val Glu Lys Thr Val Ala Pro Thr Glu Cys Ser
    210                 215                 220

<210> SEQ ID NO 227
<211> LENGTH: 221
<212> TYPE: PRT
<213> ORGANISM: Artificial sequence
<220> FEATURE:
<223> OTHER INFORMATION: Light chain of CR5088

<400> SEQUENCE: 227

Gln Ser Val Val Thr Gln Pro Pro Ser Val Ser Gly Ala Pro Gly Gln
 1               5                  10                  15

Arg Ile Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Phe
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
 65                 70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140
```

```
Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 228
<211> LENGTH: 771
<212> TYPE: DNA
<213> ORGANISM: Artificial sequence
<220> FEATURE:
<223> OTHER INFORMATION: SC05-074
<220> FEATURE:
<221> NAME/KEY: CDS
<222> LOCATION: (1)..(771)

<400> SEQUENCE: 228 cag gtc acc ttg aag gag tct ggt cct acg ctg gtg aaa ccc aca cag      48
Gln Val Thr Leu Lys Glu Ser Gly Pro Thr Leu Val Lys Pro Thr Gln
1               5                   10                  15 acc ctc acg ttg acc tgc acc ttc tct ggg ttc tca ctc agc act agt      96
Thr Leu Thr Leu Thr Cys Thr Phe Ser Gly Phe Ser Leu Ser Thr Ser
            20                  25                  30 gga gtg ggt gtg ggc tgg atc cgt cag ccc cca gga aag gcc ctg gag     144
Gly Val Gly Val Gly Trp Ile Arg Gln Pro Pro Gly Lys Ala Leu Glu
        35                  40                  45 tgg ctt gca gtc att tat tgg aat gat gat aag ctc tac agg cca tct     192
Trp Leu Ala Val Ile Tyr Trp Asn Asp Asp Lys Leu Tyr Arg Pro Ser
    50                  55                  60 ctg aag agc agg ctc acc atc acc aag gac acc tcc aaa aac cag gtg     240
Leu Lys Ser Arg Leu Thr Ile Thr Lys Asp Thr Ser Lys Asn Gln Val
65                  70                  75                  80 gtc ctt aca atg acc aag atg gac cct gtg gac aca gcc aca tat tac     288
Val Leu Thr Met Thr Lys Met Asp Pro Val Asp Thr Ala Thr Tyr Tyr
                85                  90                  95 tgt gca cac aga cac cgt tac tat gat att agt ggt tat tac cgt ctc     336
Cys Ala His Arg His Arg Tyr Tyr Asp Ile Ser Gly Tyr Tyr Arg Leu
            100                 105                 110 ttc tct gat gct ttt gat atc tgg ggc caa ggg aca atg gtc acc gtc     384
Phe Ser Asp Ala Phe Asp Ile Trp Gly Gln Gly Thr Met Val Thr Val
        115                 120                 125 tcg agc ggt acg ggc ggt tca ggc gga acc ggc agc ggc act ggc ggg     432
Ser Ser Gly Thr Gly Gly Ser Gly Gly Thr Gly Ser Gly Thr Gly Gly
    130                 135                 140 tcg acg cag tct gtg ttg acg cag ccg ccc tca gtg tct ggg gcc cca     480
Ser Thr Gln Ser Val Leu Thr Gln Pro Pro Ser Val Ser Gly Ala Pro
145                 150                 155                 160 ggg cag agg gtc acc atc tcc tgc act ggg agc agc tcc aac atc ggg     528
Gly Gln Arg Val Thr Ile Ser Cys Thr Gly Ser Ser Ser Asn Ile Gly
                165                 170                 175 aca ggt tat gat gta cac tgg tac cag cag ctt cca gga aca gcc ccc     576
Thr Gly Tyr Asp Val His Trp Tyr Gln Gln Leu Pro Gly Thr Ala Pro
            180                 185                 190 aaa ctc ctc atc tat gct gac acc aat cgg ccc tca ggg gtc cct gac     624
Lys Leu Leu Ile Tyr Ala Asp Thr Asn Arg Pro Ser Gly Val Pro Asp
        195                 200                 205
```

```
cga ttc tct ggc tcc aag tct ggc acc tca gcc tcc ctg gcc atc act    672
Arg Phe Ser Gly Ser Lys Ser Gly Thr Ser Ala Ser Leu Ala Ile Thr
    210                 215                 220 ggg gtc cag gct gag gat gag gct gat tat tac tgc cag tcc tat gac    720
Gly Val Gln Ala Glu Asp Glu Ala Asp Tyr Tyr Cys Gln Ser Tyr Asp
225                 230                 235                 240 acc agc ctg act ggt tgg gtg ttc ggc gga ggg acc aag gtc acc gtc    768
Thr Ser Leu Thr Gly Trp Val Phe Gly Gly Gly Thr Lys Val Thr Val
                245                 250                 255 cta                                                                771
Leu

<210> SEQ ID NO 229
<211> LENGTH: 257
<212> TYPE: PRT
<213> ORGANISM: Artificial sequence
<220> FEATURE:
<223> OTHER INFORMATION: SC05-074

<400> SEQUENCE: 229

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Gln Ser Val Leu Thr Gln Pro Pro Ser Val Ser Gly Ala Pro
145                 150                 155                 160

Gly Gln Arg Val Thr Ile Ser Cys Thr Gly Ser Ser Ser Asn Ile Gly
                165                 170                 175

Thr Gly Tyr Asp Val His Trp Tyr Gln Gln Leu Pro Gly Thr Ala Pro
            180                 185                 190

Lys Leu Leu Ile Tyr Ala Asp Thr Asn Arg Pro Ser Gly Val Pro Asp
        195                 200                 205

Arg Phe Ser Gly Ser Lys Ser Gly Thr Ser Ala Ser Leu Ala Ile Thr
    210                 215                 220

Gly Val Gln Ala Glu Asp Glu Ala Asp Tyr Tyr Cys Gln Ser Tyr Asp
225                 230                 235                 240

Thr Ser Leu Thr Gly Trp Val Phe Gly Gly Gly Thr Lys Val Thr Val
                245                 250                 255

Leu

<210> SEQ ID NO 230
<211> LENGTH: 771
```

<212> TYPE: DNA
<213> ORGANISM: Artificial sequence
<220> FEATURE:
<223> OTHER INFORMATION: SC05-080
<220> FEATURE:
<221> NAME/KEY: CDS
<222> LOCATION: (1)..(771)

<400> SEQUENCE: 230

| | | | | | | | | | | | | | | | | |
|---|---|---|---|---|---|---|---|---|---|---|---|---|---|---|---|---|
| cag | gtc | acc | ttg | aag | gag | tct | ggt | cct | acg | ctg | gtg | aaa | ccc | aca | cag | 48 |
| Gln | Val | Thr | Leu | Lys | Glu | Ser | Gly | Pro | Thr | Leu | Val | Lys | Pro | Thr | Gln | |
| 1 | | | | 5 | | | | | 10 | | | | | 15 | | |
| acc | ctc | acg | ttg | acc | tgc | acc | ttc | tct | ggg | ttc | tca | ctc | agc | act | agt | 96 |
| Thr | Leu | Thr | Leu | Thr | Cys | Thr | Phe | Ser | Gly | Phe | Ser | Leu | Ser | Thr | Ser | |
| | | 20 | | | | | 25 | | | | | 30 | | | | |
| gga | gtg | ggt | gtg | ggc | tgg | atc | cgt | cag | ccc | cca | gga | aag | gcc | ctg | gag | 144 |
| Gly | Val | Gly | Val | Gly | Trp | Ile | Arg | Gln | Pro | Pro | Gly | Lys | Ala | Leu | Glu | |
| | 35 | | | | | 40 | | | | | 45 | | | | | |
| tgg | ctt | gca | gtc | att | tat | tgg | aat | gat | gat | aag | ctc | tac | agg | cca | tct | 192 |
| Trp | Leu | Ala | Val | Ile | Tyr | Trp | Asn | Asp | Asp | Lys | Leu | Tyr | Arg | Pro | Ser | |
| 50 | | | | | 55 | | | | | 60 | | | | | | |
| ctg | aag | agc | agg | ctc | acc | atc | acc | aag | gac | acc | tcc | aaa | aac | cag | gtg | 240 |
| Leu | Lys | Ser | Arg | Leu | Thr | Ile | Thr | Lys | Asp | Thr | Ser | Lys | Asn | Gln | Val | |
| 65 | | | | 70 | | | | | 75 | | | | | 80 | | |
| gtc | ctt | aca | atg | acc | aag | atg | gac | cct | gtg | gac | aca | gcc | aca | tat | tac | 288 |
| Val | Leu | Thr | Met | Thr | Lys | Met | Asp | Pro | Val | Asp | Thr | Ala | Thr | Tyr | Tyr | |
| | | | 85 | | | | | 90 | | | | | 95 | | | |
| tgt | gca | cac | aga | cac | cgt | tac | tat | gat | att | agt | ggt | tat | tac | cgt | ctc | 336 |
| Cys | Ala | His | Arg | His | Arg | Tyr | Tyr | Asp | Ile | Ser | Gly | Tyr | Tyr | Arg | Leu | |
| | | 100 | | | | | 105 | | | | | 110 | | | | |
| ttc | tct | gat | gct | ttt | gat | atc | tgg | ggc | caa | ggg | aca | atg | gtc | acc | gtc | 384 |
| Phe | Ser | Asp | Ala | Phe | Asp | Ile | Trp | Gly | Gln | Gly | Thr | Met | Val | Thr | Val | |
| | 115 | | | | | 120 | | | | | 125 | | | | | |
| tcg | agc | ggt | acg | ggc | ggt | tca | ggc | gga | acc | ggc | agc | ggc | act | ggc | ggg | 432 |
| Ser | Ser | Gly | Thr | Gly | Gly | Ser | Gly | Gly | Thr | Gly | Ser | Gly | Thr | Gly | Gly | |
| 130 | | | | | 135 | | | | | 140 | | | | | | |
| tcg | acg | cag | tct | gtg | ctg | act | cag | cca | ccc | tca | gtg | tct | ggg | gcc | cca | 480 |
| Ser | Thr | Gln | Ser | Val | Leu | Thr | Gln | Pro | Pro | Ser | Val | Ser | Gly | Ala | Pro | |
| 145 | | | | 150 | | | | | 155 | | | | | 160 | | |
| ggg | cag | agg | gtc | acc | atc | tcc | tgc | act | ggg | agc | agc | tcc | aac | atc | ggg | 528 |
| Gly | Gln | Arg | Val | Thr | Ile | Ser | Cys | Thr | Gly | Ser | Ser | Ser | Asn | Ile | Gly | |
| | | | 165 | | | | | 170 | | | | | 175 | | | |
| gca | ggt | tat | gat | gta | cac | tgg | tac | cag | cag | ctt | cca | gga | aca | gcc | ccc | 576 |
| Ala | Gly | Tyr | Asp | Val | His | Trp | Tyr | Gln | Gln | Leu | Pro | Gly | Thr | Ala | Pro | |
| | | 180 | | | | | 185 | | | | | 190 | | | | |
| aaa | ctc | ctc | atc | tat | ggt | aac | agc | aat | cgg | ccc | tca | ggg | gtc | cct | gac | 624 |
| Lys | Leu | Leu | Ile | Tyr | Gly | Asn | Ser | Asn | Arg | Pro | Ser | Gly | Val | Pro | Asp | |
| | 195 | | | | | 200 | | | | | 205 | | | | | |
| cga | ttc | tct | ggc | tcc | aag | tct | ggc | acc | tca | gcc | tcc | ctg | gcc | atc | act | 672 |
| Arg | Phe | Ser | Gly | Ser | Lys | Ser | Gly | Thr | Ser | Ala | Ser | Leu | Ala | Ile | Thr | |
| 210 | | | | | 215 | | | | | 220 | | | | | | |
| ggg | ctc | cag | gct | gag | gat | gag | gct | gat | tat | tac | tgc | cag | tcc | tat | gac | 720 |
| Gly | Leu | Gln | Ala | Glu | Asp | Glu | Ala | Asp | Tyr | Tyr | Cys | Gln | Ser | Tyr | Asp | |
| 225 | | | | 230 | | | | | 235 | | | | | 240 | | |
| agc | agc | ctg | agt | ggt | tgg | gcg | ttc | ggc | gga | ggg | acc | aag | ctg | acc | gtc | 768 |
| Ser | Ser | Leu | Ser | Gly | Trp | Ala | Phe | Gly | Gly | Gly | Thr | Lys | Leu | Thr | Val | |
| | | | 245 | | | | | 250 | | | | | 255 | | | |
| cta | | | | | | | | | | | | | | | | 771 |
| Leu | | | | | | | | | | | | | | | | |

<210> SEQ ID NO 231

<211> LENGTH: 257
<212> TYPE: PRT
<213> ORGANISM: Artificial sequence
<220> FEATURE:
<223> OTHER INFORMATION: SC05-080

<400> SEQUENCE: 231

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Gln Ser Val Leu Thr Gln Pro Pro Ser Val Ser Gly Ala Pro
145                 150                 155                 160

Gly Gln Arg Val Thr Ile Ser Cys Thr Gly Ser Ser Asn Ile Gly
                165                 170                 175

Ala Gly Tyr Asp Val His Trp Tyr Gln Gln Leu Pro Gly Thr Ala Pro
            180                 185                 190

Lys Leu Leu Ile Tyr Gly Asn Ser Asn Arg Pro Ser Gly Val Pro Asp
        195                 200                 205

Arg Phe Ser Gly Ser Lys Ser Gly Thr Ser Ala Ser Leu Ala Ile Thr
    210                 215                 220

Gly Leu Gln Ala Glu Asp Glu Ala Asp Tyr Tyr Cys Gln Ser Tyr Asp
225                 230                 235                 240

Ser Ser Leu Ser Gly Trp Ala Phe Gly Gly Gly Thr Lys Leu Thr Val
                245                 250                 255

Leu
```

<210> SEQ ID NO 232
<211> LENGTH: 771
<212> TYPE: DNA
<213> ORGANISM: Artificial sequence
<220> FEATURE:
<223> OTHER INFORMATION: SC05-085
<220> FEATURE:
<221> NAME/KEY: CDS
<222> LOCATION: (1)..(771)

<400> SEQUENCE: 232

```
cag gtc acc ttg aag gag tct ggt cct acg ctg gtg aaa ccc aca cag     48
Gln Val Thr Leu Lys Glu Ser Gly Pro Thr Leu Val Lys Pro Thr Gln
1               5                   10                  15 acc ctc acg ttg acc tgc acc ttc tct ggg ttc tca ctc agc act agt     96
Thr Leu Thr Leu Thr Cys Thr Phe Ser Gly Phe Ser Leu Ser Thr Ser
            20                  25                  30
```

```
gga gtg ggt gtg ggc tgg atc cgt cag ccc cca gga aag gcc ctg gag        144
Gly Val Gly Val Gly Trp Ile Arg Gln Pro Pro Gly Lys Ala Leu Glu
         35                  40                  45 tgg ctt gca gtc att tat tgg aat gat gat aag ctc tac agg cca tct        192
Trp Leu Ala Val Ile Tyr Trp Asn Asp Asp Lys Leu Tyr Arg Pro Ser
 50                  55                  60 ctg aag agc agg ctc acc atc acc aag gac acc tcc aaa aac cag gtg        240
Leu Lys Ser Arg Leu Thr Ile Thr Lys Asp Thr Ser Lys Asn Gln Val
65                  70                  75                  80 gtc ctt aca atg acc aag atg gac cct gtg gac aca gcc aca tat tac        288
Val Leu Thr Met Thr Lys Met Asp Pro Val Asp Thr Ala Thr Tyr Tyr
                 85                  90                  95 tgt gca cac aga cac cgt tac tat gat att agt ggt tat tac cgt ctc        336
Cys Ala His Arg His Arg Tyr Tyr Asp Ile Ser Gly Tyr Tyr Arg Leu
            100                 105                 110 ttc tct gat gct ttt gat atc tgg ggc caa ggg aca atg gtc acc gtc        384
Phe Ser Asp Ala Phe Asp Ile Trp Gly Gln Gly Thr Met Val Thr Val
        115                 120                 125 tcg agc ggt acg ggc ggt tca ggc gga acc ggc agc ggc act ggc ggg        432
Ser Ser Gly Thr Gly Gly Ser Gly Gly Thr Gly Ser Gly Thr Gly Gly
    130                 135                 140 tcg acg cag tct gtc gtg acg cag ccg ccc tca gtg tct ggg gcc cca        480
Ser Thr Gln Ser Val Val Thr Gln Pro Pro Ser Val Ser Gly Ala Pro
145                 150                 155                 160 ggg cag agg gtc acc atc tcc tgc act ggg agc agc tcc aac atc ggg        528
Gly Gln Arg Val Thr Ile Ser Cys Thr Gly Ser Ser Ser Asn Ile Gly
                165                 170                 175 gca ggt tat gat gta cac tgg tac cag cag ctt cca gga aca gcc ccc        576
Ala Gly Tyr Asp Val His Trp Tyr Gln Gln Leu Pro Gly Thr Ala Pro
            180                 185                 190 aaa ctc ctc atc tat ggt aac agc aat cgg ccc tca ggg gtc cct gac        624
Lys Leu Leu Ile Tyr Gly Asn Ser Asn Arg Pro Ser Gly Val Pro Asp
        195                 200                 205 cga ttc tct ggc tcc aag tct ggc acc tca gcc tcc ctg gcc atc act        672
Arg Phe Ser Gly Ser Lys Ser Gly Thr Ser Ala Ser Leu Ala Ile Thr
    210                 215                 220 ggg ctc cag gct gag gat gag act gat tat tac tgc cag tcc tat gac        720
Gly Leu Gln Ala Glu Asp Glu Thr Asp Tyr Tyr Cys Gln Ser Tyr Asp
225                 230                 235                 240 agc agc ctg aat ggt tgg gtg ttc ggc gga ggg acc aag ctg acc gtc        768
Ser Ser Leu Asn Gly Trp Val Phe Gly Gly Gly Thr Lys Leu Thr Val
                245                 250                 255 cta                                                                    771
Leu

<210> SEQ ID NO 233
<211> LENGTH: 257
<212> TYPE: PRT
<213> ORGANISM: Artificial sequence
<220> FEATURE:
<223> OTHER INFORMATION: SC05-085

<400> SEQUENCE: 233

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
```

```
                    50                  55                  60
Leu Lys Ser Arg Leu Thr Ile Thr Lys Asp Thr Ser Lys Asn Gln Val
 65                  70                  75                  80

Val Leu Thr Met Thr Lys Met Asp Pro Val Asp Thr Ala Thr Tyr Tyr
                 85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
            115                 120                 125

Ser Ser Gly Thr Gly Gly Ser Gly Gly Thr Gly Ser Gly Thr Gly Gly
    130                 135                 140

Ser Thr Gln Ser Val Val Thr Gln Pro Pro Ser Val Ser Gly Ala Pro
145                 150                 155                 160

Gly Gln Arg Val Thr Ile Ser Cys Thr Gly Ser Ser Asn Ile Gly
                165                 170                 175

Ala Gly Tyr Asp Val His Trp Tyr Gln Gln Leu Pro Gly Thr Ala Pro
            180                 185                 190

Lys Leu Leu Ile Tyr Gly Asn Ser Asn Arg Pro Ser Gly Val Pro Asp
            195                 200                 205

Arg Phe Ser Gly Ser Lys Ser Gly Thr Ser Ala Ser Leu Ala Ile Thr
    210                 215                 220

Gly Leu Gln Ala Glu Asp Glu Thr Asp Tyr Tyr Cys Gln Ser Tyr Asp
225                 230                 235                 240

Ser Ser Leu Asn Gly Trp Val Phe Gly Gly Gly Thr Lys Leu Thr Val
                245                 250                 255

Leu

<210> SEQ ID NO 234
<211> LENGTH: 771
<212> TYPE: DNA
<213> ORGANISM: Artificial sequence
<220> FEATURE:
<223> OTHER INFORMATION: SC05-088
<220> FEATURE:
<221> NAME/KEY: CDS
<222> LOCATION: (1)..(771)

<400> SEQUENCE: 234 cag gtc acc ttg aag gag tct ggt cct acg ctg gtg aaa ccc aca cag      48
Gln Val Thr Leu Lys Glu Ser Gly Pro Thr Leu Val Lys Pro Thr Gln
  1               5                  10                  15 acc ctc acg ttg acc tgc acc ttc tct ggg ttc tca ctc agc act agt      96
Thr Leu Thr Leu Thr Cys Thr Phe Ser Gly Phe Ser Leu Ser Thr Ser
             20                  25                  30 gga gtg ggt gtg ggc tgg atc cgt cag ccc cca gga aag gcc ctg gag     144
Gly Val Gly Val Gly Trp Ile Arg Gln Pro Pro Gly Lys Ala Leu Glu
         35                  40                  45 tgg ctt gca gtc att tat tgg aat gat gat aag ctc tac agg cca tct     192
Trp Leu Ala Val Ile Tyr Trp Asn Asp Asp Lys Leu Tyr Arg Pro Ser
     50                  55                  60 ctg aag agc agg ctc acc atc acc aag gac acc tcc aaa aac cag gtg     240
Leu Lys Ser Arg Leu Thr Ile Thr Lys Asp Thr Ser Lys Asn Gln Val
 65                  70                  75                  80 gtc ctt aca atg acc aag atg gac cct gtg gac aca gcc aca tat tac     288
Val Leu Thr Met Thr Lys Met Asp Pro Val Asp Thr Ala Thr Tyr Tyr
                 85                  90                  95 tgt gca cac aga cac cgt tac tat gat att agt ggt tat tac cgt ctc     336
Cys Ala His Arg His Arg Tyr Tyr Asp Ile Ser Gly Tyr Tyr Arg Leu
            100                 105                 110
```

```
ttc tct gat gct ttt gat atc tgg ggc caa ggg aca atg gtc acc gtc      384
Phe Ser Asp Ala Phe Asp Ile Trp Gly Gln Gly Thr Met Val Thr Val
        115                 120                 125 tcg agc ggt acg ggc ggt tca ggc gga acc ggc agc ggc act ggc ggg      432
Ser Ser Gly Thr Gly Gly Ser Gly Gly Thr Gly Ser Gly Thr Gly Gly
    130                 135                 140 tcg acg cag tct gtc gtg acg cag ccg ccc tca gtg tct ggg gcc cca      480
Ser Thr Gln Ser Val Val Thr Gln Pro Pro Ser Val Ser Gly Ala Pro
145                 150                 155                 160 ggg cag agg atc acc atc tcc tgc act ggg agc agc tcc aac atc ggg      528
Gly Gln Arg Ile Thr Ile Ser Cys Thr Gly Ser Ser Ser Asn Ile Gly
                165                 170                 175 gca ggt tat gat gta cac tgg tac cag cag ctt cca gga aca gcc ccc      576
Ala Gly Tyr Asp Val His Trp Tyr Gln Gln Leu Pro Gly Thr Ala Pro
            180                 185                 190 aaa ttc ctc atc tat ggt aac agc aat cgg ccc tca ggg gtc cct gac      624
Lys Phe Leu Ile Tyr Gly Asn Ser Asn Arg Pro Ser Gly Val Pro Asp
        195                 200                 205 cga ttc tct ggc tcc aag tct ggc acc tca gcc tcc ctg gcc atc act      672
Arg Phe Ser Gly Ser Lys Ser Gly Thr Ser Ala Ser Leu Ala Ile Thr
    210                 215                 220 ggg ctc cag gct gag gat gag gct gat tat tac tgc cag tcc tat gac      720
Gly Leu Gln Ala Glu Asp Glu Ala Asp Tyr Tyr Cys Gln Ser Tyr Asp
225                 230                 235                 240 agc agc ctg agt ggt tgg gtg ttc ggc gga ggg acc aag ctg acc gtc      768
Ser Ser Leu Ser Gly Trp Val Phe Gly Gly Gly Thr Lys Leu Thr Val
                245                 250                 255 cta                                                                   771
Leu

<210> SEQ ID NO 235
<211> LENGTH: 257
<212> TYPE: PRT
<213> ORGANISM: Artificial sequence
<220> FEATURE:
<223> OTHER INFORMATION: SC05-088

<400> SEQUENCE: 235

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asn Asp Asp Lys Leu Tyr Arg Pro Ser
    50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg His Arg Tyr Tyr Asp Ile Ser Gly Tyr Tyr Arg Leu
            100                 105                 110

Phe Ser Asp Ala Phe Asp Ile Trp Gly Gln Gly Thr Met Val Thr Val
        115                 120                 125

Ser Ser Gly Thr Gly Gly Ser Gly Gly Thr Gly Ser Gly Thr Gly Gly
    130                 135                 140

Ser Thr Gln Ser Val Val Thr Gln Pro Pro Ser Val Ser Gly Ala Pro
```

-continued

```
                145                 150                 155                 160
Gly Gln Arg Ile Thr Ile Ser Cys Thr Gly Ser Ser Asn Ile Gly
                165                 170                 175

Ala Gly Tyr Asp Val His Trp Tyr Gln Gln Leu Pro Gly Thr Ala Pro
            180                 185                 190

Lys Phe Leu Ile Tyr Gly Asn Ser Asn Arg Pro Ser Gly Val Pro Asp
        195                 200                 205

Arg Phe Ser Gly Ser Lys Ser Gly Thr Ser Ala Ser Leu Ala Ile Thr
    210                 215                 220

Gly Leu Gln Ala Glu Asp Glu Ala Asp Tyr Tyr Cys Gln Ser Tyr Asp
225                 230                 235                 240

Ser Ser Leu Ser Gly Trp Val Phe Gly Gly Gly Thr Lys Leu Thr Val
                245                 250                 255

Leu

<210> SEQ ID NO 236
<211> LENGTH: 14
<212> TYPE: PRT
<213> ORGANISM: Artificial sequence
<220> FEATURE:
<223> OTHER INFORMATION: LCDR1

<400> SEQUENCE: 236

Thr Gly Ser Ser Ser Asn Ile Gly Thr Gly Tyr Asp Val His
1               5                   10

<210> SEQ ID NO 237
<211> LENGTH: 14
<212> TYPE: PRT
<213> ORGANISM: Artificial sequence
<220> FEATURE:
<223> OTHER INFORMATION: LCDR1

<400> SEQUENCE: 237

Thr Gly Ser Ser Ser Asn Ile Gly Ala Gly Tyr Asp Val His
1               5                   10

<210> SEQ ID NO 238
<211> LENGTH: 14
<212> TYPE: PRT
<213> ORGANISM: Artificial sequence
<220> FEATURE:
<223> OTHER INFORMATION: LCDR1

<400> SEQUENCE: 238

Thr Gly Ser Ser Ser Asn Ile Gly Ala Gly Tyr Asp Val His
1               5                   10

<210> SEQ ID NO 239
<211> LENGTH: 14
<212> TYPE: PRT
<213> ORGANISM: Artificial sequence
<220> FEATURE:
<223> OTHER INFORMATION: LCDR1

<400> SEQUENCE: 239

Thr Gly Ser Ser Ser Asn Ile Gly Ala Gly Tyr Asp Val His
1               5                   10

<210> SEQ ID NO 240
<211> LENGTH: 7
<212> TYPE: PRT
<213> ORGANISM: Artificial sequence
```

```
<220> FEATURE:
<223> OTHER INFORMATION: LCDR2

<400> SEQUENCE: 240

Ala Asp Thr Asn Arg Pro Ser
1               5

<210> SEQ ID NO 241
<211> LENGTH: 7
<212> TYPE: PRT
<213> ORGANISM: Artificial sequence
<220> FEATURE:
<223> OTHER INFORMATION: LCDR2

<400> SEQUENCE: 241

Gly Asn Ser Asn Arg Pro Ser
1               5

<210> SEQ ID NO 242
<211> LENGTH: 7
<212> TYPE: PRT
<213> ORGANISM: Artificial sequence
<220> FEATURE:
<223> OTHER INFORMATION: LCDR2

<400> SEQUENCE: 242

Gly Asn Ser Asn Arg Pro Ser
1               5

<210> SEQ ID NO 243
<211> LENGTH: 7
<212> TYPE: PRT
<213> ORGANISM: Artificial sequence
<220> FEATURE:
<223> OTHER INFORMATION: LCDR2

<400> SEQUENCE: 243

Gly Asn Ser Asn Arg Pro Ser
1               5

<210> SEQ ID NO 244
<211> LENGTH: 11
<212> TYPE: PRT
<213> ORGANISM: Artificial sequence
<220> FEATURE:
<223> OTHER INFORMATION: LCDR3

<400> SEQUENCE: 244

Gln Ser Tyr Asp Thr Ser Leu Thr Gly Trp Val
1               5                   10

<210> SEQ ID NO 245
<211> LENGTH: 11
<212> TYPE: PRT
<213> ORGANISM: Artificial sequence
<220> FEATURE:
<223> OTHER INFORMATION: LCDR3

<400> SEQUENCE: 245

Gln Ser Tyr Asp Ser Ser Leu Ser Gly Trp Ala
1               5                   10

<210> SEQ ID NO 246
<211> LENGTH: 11
<212> TYPE: PRT
<213> ORGANISM: Artificial sequence
<220> FEATURE:
```

-continued

```
<223> OTHER INFORMATION: LCDR3

<400> SEQUENCE: 246

Gln Ser Tyr Asp Ser Ser Leu Asn Gly Trp Val
1               5                   10

<210> SEQ ID NO 247
<211> LENGTH: 11
<212> TYPE: PRT
<213> ORGANISM: Artificial sequence
<220> FEATURE:
<223> OTHER INFORMATION: LCDR3

<400> SEQUENCE: 247

Gln Ser Tyr Asp Ser Ser Leu Ser Gly Trp Val
1               5                   10

<210> SEQ ID NO 248
<211> LENGTH: 25
<212> TYPE: DNA
<213> ORGANISM: Artificial sequence
<220> FEATURE:
<223> OTHER INFORMATION: Sense primer WN-313F

<400> SEQUENCE: 248
aacaaacaaa cagcgatgaa acacc                                         25

<210> SEQ ID NO 249
<211> LENGTH: 24
<212> TYPE: DNA
<213> ORGANISM: Artificial sequence
<220> FEATURE:
<223> OTHER INFORMATION: Antisense primer WN-2588R

<400> SEQUENCE: 249
tgtggcgttt cagggtaata cttg                                          24

<210> SEQ ID NO 250
<211> LENGTH: 22
<212> TYPE: DNA
<213> ORGANISM: Artificial sequence
<220> FEATURE:
<223> OTHER INFORMATION: Antisense primer WN1617R

<400> SEQUENCE: 250
ccactcacga tggaccaaga ac                                            22

<210> SEQ ID NO 251
<211> LENGTH: 22
<212> TYPE: DNA
<213> ORGANISM: Artificial sequence
<220> FEATURE:
<223> OTHER INFORMATION: Primer WN-1242F

<400> SEQUENCE: 251
cagacaagga gtggtggaca gg                                            22

<210> SEQ ID NO 252
<211> LENGTH: 20
<212> TYPE: DNA
<213> ORGANISM: Artificial sequence
<220> FEATURE:
<223> OTHER INFORMATION: Primer WN-708F

<400> SEQUENCE: 252
caccaagaca cgccactcaa                                               20
```

<210> SEQ ID NO 253
<211> LENGTH: 21
<212> TYPE: DNA
<213> ORGANISM: Artificial sequence
<220> FEATURE:
<223> OTHER INFORMATION: Primer WN-1026F

<400> SEQUENCE: 253
ggtggatttg gttctcgaag g                                        21

<210> SEQ ID NO 254
<211> LENGTH: 21
<212> TYPE: DNA
<213> ORGANISM: Artificial sequence
<220> FEATURE:
<223> OTHER INFORMATION: Primer WN-1449F

<400> SEQUENCE: 254
cactcaggca gggagattca g                                        21

<210> SEQ ID NO 255
<211> LENGTH: 21
<212> TYPE: DNA
<213> ORGANISM: Artificial sequence
<220> FEATURE:
<223> OTHER INFORMATION: Primer WN-1991F

<400> SEQUENCE: 255
cagtggcttc attgaacgac c                                        21

<210> SEQ ID NO 256
<211> LENGTH: 25
<212> TYPE: DNA
<213> ORGANISM: Artificial sequence
<220> FEATURE:
<223> OTHER INFORMATION: Primer WN-315F

<400> SEQUENCE: 256
caaacaaaca gcgatgaaac acctt                                    25

<210> SEQ ID NO 257
<211> LENGTH: 24
<212> TYPE: DNA
<213> ORGANISM: Artificial sequence
<220> FEATURE:
<223> OTHER INFORMATION: Primer WN-2585R

<400> SEQUENCE: 257
ggcgtttcag ggtaatactt gtac                                     24

<210> SEQ ID NO 258
<211> LENGTH: 21
<212> TYPE: DNA
<213> ORGANISM: Artificial sequence
<220> FEATURE:
<223> OTHER INFORMATION: Primer WN-2086R

<400> SEQUENCE: 258
caatcaggac cttagcgttg g                                        21

<210> SEQ ID NO 259
<211> LENGTH: 19
<212> TYPE: DNA
<213> ORGANISM: Artificial sequence
<220> FEATURE:

<223> OTHER INFORMATION: Primer WN-1560R

<400> SEQUENCE: 259
ggtgtcaatc cctgaccgt                                              19

<210> SEQ ID NO 260
<211> LENGTH: 21
<212> TYPE: DNA
<213> ORGANISM: Artificial sequence
<220> FEATURE:
<223> OTHER INFORMATION: Primer WN-1049R

<400> SEQUENCE: 260
tcgccttcga gaaccaaatc c                                           21

<210> SEQ ID NO 261
<211> LENGTH: 21
<212> TYPE: DNA
<213> ORGANISM: Artificial sequence
<220> FEATURE:
<223> OTHER INFORMATION: Primer WN-741R

<400> SEQUENCE: 261
cctccgactg cgtcttgagt g                                           21

<210> SEQ ID NO 262
<211> LENGTH: 29
<212> TYPE: DNA
<213> ORGANISM: Artificial sequence
<220> FEATURE:
<223> OTHER INFORMATION: Primer K307E forward

<400> SEQUENCE: 262
cggcgtgtgc agcgaggcct tcaagttcc                                   29

<210> SEQ ID NO 263
<211> LENGTH: 29
<212> TYPE: DNA
<213> ORGANISM: Artificial sequence
<220> FEATURE:
<223> OTHER INFORMATION: Primer K307E reverse

<400> SEQUENCE: 263
ggaacttgaa ggcctcgctg cacacgccg                                   29

<210> SEQ ID NO 264
<211> LENGTH: 28
<212> TYPE: DNA
<213> ORGANISM: Artificial sequence
<220> FEATURE:
<223> OTHER INFORMATION: Primer T332K forward

<400> SEQUENCE: 264
gcagtacacc ggcaaggacg gcccctgc                                    28

<210> SEQ ID NO 265
<211> LENGTH: 28
<212> TYPE: DNA
<213> ORGANISM: Artificial sequence
<220> FEATURE:
<223> OTHER INFORMATION: Primer T332K reverse

<400> SEQUENCE: 265
gcaggggccg tccttgccgg tgtactgc                                    28

```
<210> SEQ ID NO 266
<211> LENGTH: 28
<212> TYPE: DNA
<213> ORGANISM: Artificial sequence
<220> FEATURE:
<223> OTHER INFORMATION: Primer A365V forward

<400> SEQUENCE: 266
cttcgtgagc gtggtcaccg ccaacgcc                                        28

<210> SEQ ID NO 267
<211> LENGTH: 28
<212> TYPE: DNA
<213> ORGANISM: Artificial sequence
<220> FEATURE:
<223> OTHER INFORMATION: Primer A365V reverse

<400> SEQUENCE: 267
ggcgttggcg gtgaccacgc tcacgaag                                        28
```

US 7,537,764 B2

BINDING MOLECULES CAPABLE OF NEUTRALIZING WEST NILE VIRUS AND USES THEREOF

CROSS-REFERENCE TO RELATED APPLICATIONS

This application is a continuation in part of the following PCT International Patent Application Nos., each of which designating the United States, PCT/EP2005/052160 filed May 12, 2005, PCT/EP2004/053609 filed Dec. 12, 2004, PCT/EP2005/056926 filed Dec. 19, 2005, PCT/EP2005/054002 filed Aug. 15, 2005, PCT/EP2005/052946 filed Jun. 23, 2005, PCT/EP2005/052648 filed Jun. 8, 2005, the contents of the entirety of each of which are hereby incorporated herein by this reference.

STATEMENT ACCORDING TO 37 C.F.R. §1.52(e)(5)—SEQUENCE LISTING SUBMITTED ON COMPACT DISC

Pursuant to 37 C.F.R. § 1.52(e)(1)(ii), a compact disc containing an electronic version of the Sequence Listing has been submitted concomitant with this application, the contents of which are hereby incorporated by this reference. A second compact disc is submitted and is an identical copy of the first compact disc, the contents of which are hereby incorporated by this reference. The discs are labeled "copy 1" and "copy 2," respectively, and each disc contains one file entitled "2578-7964 Sequence Listing.txt" which is 385 KB and created on Aug. 28, 2006.

TECHNICAL FIELD

The invention relates to biotechnology and medicine. In particular, the invention relates to the diagnosis, prophylaxis and/or treatment of infection by the West Nile virus.

BACKGROUND

West Nile virus ("WNV") is a member of the Flaviviridae family, genus *Flavivirus*. *Flaviviruses* are small spherical enveloped positive-strand RNA viruses. The *Flavivirus* genus comprises more than 60 highly related viruses including several human pathogens such as inter alia yellow fever virus, Japanese encephalitis virus, St. Louis encephalitis virus, Murray Valley encephalitis virus, tick-borne encephalitis virus, and dengue virus.

WNV was initially isolated in 1937 in the West Nile region of Uganda but has now an almost worldwide distribution including parts of Africa, Asia, Australia, Europe and, most recently, North America. WNV was first diagnosed in the New York area in 1999 and has continued to spread rapidly across North America causing infections in persons in over 40 different states reaching as far as California.

WNV is mainly transmitted to man by mosquitoes but occasionally transmission has been linked to blood transfusion and organ transplantation. WNV infections generally have mild symptoms, which generally last three to six days, varying from a fever of sudden onset, headache, tremors, skin rash to swollen lymph glands. However, in 30% of the cases, particularly in elderly and immunocompromised patients, the disease progresses to a more severe state (e.g., encephalitis or aseptic meningitis), which can lead to death. By 2002, human mortality increased to over 150 cases. Besides infecting humans, WNV is also known to infect horses and several bird species and can cause severe illness and death in those species.

The two main strategies for preventing WNV infections are a) controlling the spread of WNV by spraying large areas with insecticides to kill mosquito vectors and b) reducing the contact between humans and mosquitoes by using personal protection such as anti-insect repellents. Unfortunately, these strategies are however highly inefficacious. Furthermore, there are concerns regarding the toxic effects of insecticides. Moreover, spraying requires repeated applications and is considered to be unreliable, as it does not provide complete coverage of mosquito breeding areas or eradication of mosquitoes.

There is no specific treatment of WNV infection. Treatment has only been supportive, since there are no available anti-viral or other drugs with proven efficacy. The most promising potential treatment options currently available for humans include the anti-viral compounds ribavirin and interferon-alpha2b (Anderson and Rahal, 2002), and human anti-WNV immunoglobulins (Ben Nathan et al., 2003). A disadvantage associated with ribavirin and interferon alpha2b are their significant toxicities. A disadvantage of anti-WNV immunoglobulins is that they are not available in sufficient amounts and are too expensive. In addition, the possibility of contamination by known or unknown pathogens is an additional concern associated with anti-WNV immunoglobulins. Furthermore, in PCT International Application WO 02/072036, the contents of which are incorporated by this reference, it has been suggested that the WNV E protein may be used to prepare murine anti-WNV monoclonal antibodies. However, murine antibodies, in naked or immunoconjugated format, are limited for their use in vivo due to problems associated with administration of murine antibodies to humans, such as short serum half life, an inability to trigger certain human effector functions and elicitation of an unwanted dramatic immune response against the murine antibody in a human. Accordingly, an urgent need exists for a medicament suitable for detection, prevention and/or treatment of WNV infections.

SUMMARY OF THE INVENTION

Described are human binding molecules capable of specifically binding to WNV and capable of neutralizing WNV. Also described are nucleic acid molecules encoding at least the binding region of the human binding molecules. Further described is the use of the human binding molecules of the invention in the prophylaxis and/or treatment of a subject having, or at risk of developing, a WNV infection. Besides that, the invention pertains to the use of the human binding molecules of the invention in the diagnosis/detection of WNV.

In one aspect, the invention encompasses binding molecules capable of specifically binding to WNV. Preferably, the binding molecules are human binding molecules. Preferably, the binding molecules of the invention are capable of neutralizing WNV. More preferably, the binding molecules of the invention are capable of binding to and neutralizing both WNV lineage I variants such as inter alia strain 385-99 and WNV lineage II variants such as inter alia strain H-442. In the presently most preferred embodiment, the binding molecules of the invention are capable of neutralizing essentially all WNV variants currently known. In one embodiment, the binding molecules of the invention may even neutralize at least one other *flavivirus* including, but not limited to, yellow fever virus, Japanese encephalitis virus, St. Louis encephalitis virus, Murray Valley encephalitis virus, tick-borne encephalitis virus, and dengue virus. The binding molecules of the invention may be capable of specifically binding to WNV in activated or inactivated/attenuated form. Methods for inactivating/attenuating viruses are well known in the art and include, but are not limited to, heat inactivation, inactivation by UV irradiation, and inactivation by gamma irradiation.

The binding molecules of the invention may also be capable of specifically binding to one or more fragments of WNV such as inter alia a preparation of one or more proteins and/or (poly)peptides derived from WNV or one or more recombinantly produced WNV proteins and/or polypeptides. Alternatively, the fragments have the form of WNV-like particles. Such particles comprise WNV structural proteins including, but not limited to, the WNV envelope (E) protein and/or the WNV membrane (preM/M) protein. For methods of treatment and/or prevention of WNV the binding molecules are preferably capable of specifically binding to surface accessible proteins of WNV including the E protein and preM/M protein. For diagnostical purposes the binding molecules may also be capable of specifically binding to proteins not present on the surface of WNV including the WNV capsid (C) protein and/or the WNV non-structural (NS) proteins NS1, NS2A, NS2B, NS3, NS4A, NS4B, and NS5. The nucleotide and/or amino acid sequence of proteins of various strains of WNV can be found in the GenBank-database, EMBL-database and/or other databases. The complete or partial genomes of a number of WNV isolates from outbreaks in for instance the United States have been sequenced. The complete sequence of WNV isolated from a dead Chilean flamingo (WN-NY99, strain 382-99) at the Bronx Zoo can be found in the GenBank database under accession number AF196835 (see Lanciotti et al., 1999). The genome of a WNV isolate from human victims of the 1999 New York outbreak (WNV-NY1999) was sequenced and can be found in the GenBank database under accession number AF202541 (see Jia et al., 1999). Partial sequences of isolates from two species of mosquito, a crow and a hawk from Connecticut can be found in the GenBank database under accession numbers AF206517-AF206520, respectively (see Anderson et al., 1999). It is well within the reach of the skilled person to find further sequences of WNV isolates and proteins in databases.

Preferably, the fragment at least comprises an antigenic determinant recognized by the binding molecules of the invention. An "antigenic determinant" as used herein is a moiety, such as a WNV (poly)peptide, protein, glycoprotein, analog or fragment thereof, that is capable of binding to a binding molecule of the invention with sufficiently high affinity to form a detectable antigen-binding molecule complex.

In one embodiment, the binding molecules of the invention are capable of specifically binding to the WNV E protein. The human binding molecules of the invention may be capable of binding to domain I, II and/or III of the E protein. The binding molecules of the invention can be intact immunoglobulin molecules such as polyclonal or monoclonal antibodies or the binding molecules can be antigen-binding fragments including, but not limited to, Fab, F(ab'), F(ab')$_2$, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to the WNV or a fragment thereof. In a preferred embodiment, the human binding molecules having WNV neutralizing activity are administered in IgG1 format.

The binding molecules of the invention can be used in non-isolated or isolated form. Furthermore, the binding molecules of the invention can be used alone or in a mixture comprising at least one binding molecule (or variant or fragment thereof) of the invention. In other words, the binding molecules can be used in combination for example as a pharmaceutical composition comprising two or more binding molecules of the invention, variants or fragments thereof. For example, binding molecules having different, but complementary activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. The mixture may further comprise at least one other therapeutic agent. Preferably, the therapeutic agent is useful in the prophylaxis and/or treatment of a condition resulting from WNV.

Typically, binding molecules according to the invention can bind to their binding partners, i.e., WNV or fragments thereof, with an affinity constant ($K_d$-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ M, even more preferably lower than $1.0*10^{-11}$ M, and in particular lower than $1.0*10^{-12}$ M. The affinity constants can vary for antibody isotypes. For example, affinity binding for an IgM isotype refers to a binding affinity of at least about $1.0*10^{-7}$ M. Affinity constants can for instance be measured using surface plasmon resonance, i.e., an optical phenomenon that allows for the analysis of real-time biospecific interactions by detection of alterations in protein concentrations within a biosensor matrix, for example using the BIACORE system (Pharmacia Biosensor AB, Uppsala, Sweden).

The binding molecules according to the invention may bind to WNV or a fragment thereof in soluble form such as for instance in a sample or may bind to WNV or a fragment thereof bound or attached to a carrier or substrate for example microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to WNV in purified/isolated or non-purified/non-isolated form.

The binding molecules described herein are capable of neutralizing WNV infectivity. This may be achieved by preventing the attachment of WNV to possible receptors on susceptible host cells or inhibition of the fusion of WNV and cell membranes. Neutralization can, for instance, be measured as described herein. Alternative neutralization assays are described in for instance Gollins and Porterfield (1986).

Furthermore, the neutralizing binding molecules of the invention may abolish replication of WNV, be complement fixing human binding molecules capable of assisting in the lysis of WNV, and/or might act as opsonins and augment phagocytosis of WNV either by promoting its uptake via Fc or C3b receptors or by agglutinating WNV to make it more easily phagocytosed.

In a preferred embodiment, the binding molecules described herein comprise at least a CDR3 region, preferably a heavy chain CDR3 region, comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Particularly preferred is a binding molecule according to the invention comprising at least a CDR3 region, preferably a heavy chain CDR3 region, comprising the amino acid sequence of SEQ ID NO:10. More preferably, the binding molecule according to the invention comprises at least a heavy chain CDR1 and CDR2 region comprising the amino acid sequence of SEQ ID NOS:30 and 40, respectively. In one embodiment, the binding molecules of the invention may comprise two, three, four, five or even all six CDR regions of the binding molecules of the invention. The heavy chain CDR1 region, heavy chain CDR2 region, light chain CDR1 region, light chain CDR2 region and light chain CDR3 region of each binding molecule of the invention are shown in Table 9. CDR regions are according to Kabat et al. (1991) as described in Sequences of Proteins of Immunological Interest. In a specific embodiment, the binding molecule comprising at least a CDR3 region, preferably a heavy chain CDR3 region, comprising the amino acid sequence of SEQ ID NO:10 comprises a heavy chain CDR1 and heavy chain CDR2 region comprising the amino acid sequence of SEQ ID NOS:30 and 40, respectively, and a light chain CDR1 region comprising the amino acid sequence selected from the group consisting of SEQ ID NOS:236-239, a light chain CDR2 region comprising the amino acid sequence selected from the group consisting of SEQ ID NOS:240-243 and/or a light chain CDR3 region comprising the amino acid sequence selected from the group consisting of SEQ ID NOS:244-247.

In yet another embodiment, the binding molecules according to the invention comprise a heavy chain comprising the variable heavy chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80. In a further embodiment, the binding molecules according to the invention comprise a light chain comprising the variable light chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:229, SEQ ID NO:231, SEQ ID NO:233, and SEQ ID NO:235. Table 8 and 18 specify, next to the heavy chain CDR3 region, the heavy and light chain variable regions of the binding molecule of the invention.

In a further embodiment, the binding molecules of the invention comprise a heavy chain comprising the variable heavy chain of the amino acid sequence selected from the group consisting of SEQ ID NOS:113, 115, 117, 119, 121, 123, 125, 127, 129, and 131. In another embodiment, the binding molecules of the invention comprise a light chain comprising the variable light chain of the amino acid sequence selected from the group consisting of SEQ ID NOS: 133, 135, 137, 139, 141, 143, 145, 147, 149, 151, 221, 223, 225, and 227.

In yet a further embodiment, the binding molecules of the invention comprise a heavy chain comprising the amino acid sequence selected from the group consisting of SEQ ID NOS: 113, 115, 117, 119, 121, 123, 125, 127, 129, and 131, and/or comprise a light chain comprising the amino acid sequence selected from the group consisting of SEQ ID NOS:133, 135, 137, 139, 141, 143, 145, 147, 149, 151, 221, 223, 225, and 227.

In another aspect, the invention includes functional variants of the binding molecules as defined herein. Molecules are considered to be functional variants of a binding molecule according to the invention, if the variants are capable of competing for specifically binding to WNV or a fragment thereof with the parent human binding molecules. In other words, when the functional variants are still capable of binding to WNV or a fragment thereof. Furthermore, molecules are considered to be functional variants of a binding molecule according to the invention, if they have WNV neutralizing activity. Functional variants include, but are not limited to, derivatives that are substantially similar in primary structural sequence, but which contain e.g., in vitro or in vivo modifications, chemical and/or biochemical, that are not found in the parent binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Alternatively, functional variants can be binding molecules as defined in the invention comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxyl termini. Functional variants according to the invention may have the same or different, either higher or lower, binding affinities compared to the parental binding molecule but are still capable of binding to WNV or a fragment thereof. For instance, functional variants according to the invention may have increased or decreased binding affinities for WNV or a fragment thereof compared to the parent binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the invention have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence homology with the parent human binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parent binding molecules or parts thereof by general molecular biology methods known in the art including, but not limited to, error-prone PCR, oligonucleotide-directed mutagenesis, site-directed mutagenesis and heavy or light chain shuffling. Preferably, the functional variants of the invention have WNV neutralizing activity. This neutralizing activity may either be identical, or be higher or lower compared to the parent binding molecules. Furthermore, the functional variants having neutralizing activity may inhibit or down regulate WNV replication, are complement fixing binding molecules capable of assisting in the lysis of WNV and/or act as opsonins and augment phagocytosis of WNV either by promoting its uptake via Fc or C3b receptors or by agglutinating WNV to make it more easily phagocytosed. Henceforth, when the term (human) binding molecule is used, this also encompasses functional variants of the (human) binding molecule.

In yet a further aspect, the invention includes immunoconjugates, molecules comprising at least one binding molecule as defined herein and further comprising at least one tag, such as, inter alia, a detectable moiety/agent. Also contemplated in the invention are mixtures of immunoconjugates according to the invention or mixtures of at least one immunoconjugates according to the invention and another molecule, such as a therapeutic agent or another binding molecule or immunoconjugate. In a further embodiment, the immunoconjugates of the invention may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates of the invention may be therapeutic agents, but preferably they are detectable moieties/agents. The tags may also be toxins, such as botulinum toxin or functional parts thereof. Immunoconjugates comprising a detectable agent can be used diagnostically to, for example, assess if a subject has been infected with WNV or monitor the development or progression of a WNV infection as part of a clinical testing procedure to for example determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. Suitable labels for the detection/analysis/diagnosis techniques and/or methods known in the art are well within the reach of the skilled artisan.

Furthermore, the human binding molecules or immunoconjugates of the invention can also be attached to solid supports, which are particularly useful for in vitro immunoassays or purification of WNV or a fragment thereof. Such solid supports might be porous or nonporous, planar or non-planar. The binding molecules of the invention can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect the binding molecules of the invention may be conjugated/attached to one or more antigens. Preferably, these antigens are antigens which are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules of the invention will bind to WNV and the antigens attached to the binding molecules will initiate a powerful T-cell attack on the conjugate, which will eventually lead to the destruction of the WNV.

Next to producing immunoconjugates chemically by conjugating, directly or indirectly, via for instance a linker, the immunoconjugates can be produced as fusion proteins comprising the binding molecules of the invention and a suitable tag. Fusion proteins can be produced by methods known in the art such as for example recombinantly by constructing nucleic acid molecules comprising nucleotide sequences encoding the binding molecules in frame with nucleotide sequences encoding the suitable tag(s) and then expressing the nucleic acid molecules.

It is another aspect, the invention provides a nucleic acid molecule encoding at least a binding molecule or immunoconjugate of the invention. Such nucleic acid molecules can be used as intermediates for cloning purposes for example in the process of affinity maturation as described above. In a preferred embodiment, the nucleic acid molecules are isolated or purified.

One of skill in the art appreciate that functional variants of these nucleic acid molecules are also intended to be a part of the invention. Functional variants are nucleic acid sequences that can be directly translated, using the standard genetic code, to provide an amino acid sequence identical to that translated from the parent nucleic acid molecules.

Preferably, the nucleic acid molecules encode binding molecules comprising a CDR3 region, preferably a heavy chain CDR3 region, comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. In a further embodiment the nucleic acid molecules encode binding molecules comprising two, three, four, five or even all six CDR regions of the binding molecules of the invention.

In another embodiment, the nucleic acid molecules encode binding molecules comprising a heavy chain comprising the variable heavy chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80. In another embodiment the nucleic acid molecules encode binding molecules comprising a light chain comprising the variable light chain of the amino acid sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:229, SEQ ID NO:231, SEQ ID NO:233, and SEQ ID NO:235.

In a further embodiment, the nucleic acid molecules encode binding molecules comprising a heavy chain comprising the variable heavy chain of the amino acid sequence selected from the group consisting of SEQ ID NOS:113, 115, 117, 119, 121, 123, 125, 127, 129, and 131. In another embodiment, the nucleic acid molecules encode binding molecules comprising a light chain comprising the variable light chain of the amino acid sequence selected from the group consisting of SEQ ID NOS:133, 135, 137, 139, 141, 143, 145, 147, 149, 151, 221, 223, 225, and 227.

In yet a further embodiment, the nucleic acid molecules encode binding molecules comprising a heavy chain comprising the amino acid sequence selected from the group consisting of SEQ ID NOS:113, 115, 117, 119, 121, 123, 125, 127, 129, and 131, and/or comprising a light chain comprising the amino acid sequence selected from the group consisting of SEQ ID NOS:133, 135, 137, 139, 141, 143, 145, 147, 149, 151, 221, 223, 225, and 227.

It is another aspect of the invention to provide vectors, i.e., nucleic acid constructs, comprising one or more nucleic acid molecules according to the invention. Vectors can be derived from plasmids such as, inter alia, F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses. Vectors can be used for cloning and/or for expression of the binding molecules of the invention and might even be used for gene therapy purposes. Vectors comprising one or more nucleic acid molecules according to the invention operably linked to one or more expression-regulating nucleic acid molecules are also covered by the invention. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the invention. Preferably, the hosts are host cells. Host cells include, but are not limited to, cells of mammalian, plant, insect, fungal or bacterial origin. Bacterial cells include, but are not limited to, cells from Gram positive bacteria such as several species of the genera *Bacillus, Streptomyces* and *Staphylococcus* or cells of Gram negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells or Bowes melanoma cells are preferred in the invention. Mammalian cells provide expressed proteins with posttranslational modifications that are most similar to natural molecules of mammalian origin. Since the invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in PCT International Publication WO 00/63403 the disclosure of which is incorporated herein by reference in its entirety.

A method of producing a binding molecule or an immunoconjugate according to the invention is an additional part of the invention. The method comprises the steps of a) culturing a host according to the invention under conditions conducive to the expression of the binding molecule, or immunoconjugate, and b) optionally, recovering the expressed binding molecule or immunoconjugate. The expressed binding molecules or immunoconjugates can be recovered from the cell free extract, but preferably they are recovered from the culture medium. The above method of producing can also be used to make functional variants of the binding molecules and immunoconjugates of the invention. Methods to recover proteins, such as binding molecules, from cell free extracts or culture medium are well known to the man skilled in the art. Binding molecules or immunoconjugates as obtainable by the above-described method are also a part of the invention.

Alternatively, next to the expression in hosts, such as host cells, the binding molecules and immunoconjugates of the invention can be produced synthetically by conventional peptide synthesizers or in cell-free translation systems using RNA nucleic acid derived from DNA molecules according to the invention. Binding molecules and immunoconjugates as obtainable by the above described synthetic production methods or cell-free translation systems are also a part of the invention.

In yet another embodiment, binding molecules of the invention can also be produced in transgenic, non-human, mammals such as inter alia rabbits, goats or cows, and secreted into for instance the milk thereof.

In yet another embodiment, binding molecules according to the invention, preferably human binding molecules specifically binding to WNV or a fragment thereof, may be generated by transgenic non-human mammals, such as for instance transgenic mice or rabbits, that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of WNV or a fragment thereof. Protocols for immunizing non-human mammals are well established in the art. See *Using Antibodies: A Laboratory Manual*, edited by: E. Harlow, D. Lane (1998), Cold Spring Harbor Laboratory, Cold Spring Harbor, N.Y., and *Current Protocols in Immunology*, edited by: J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B cells or plasma cells derived from the transgenic animals. In yet another embodiment, the human binding molecules are produced by hybridomas, which are prepared by fusion of B cells obtained from the above-described transgenic non-human mammals to immortalized cells. B cells, plasma cells and hybridomas as obtainable from the above described transgenic non-human mammals and human binding molecules as obtainable from the above described transgenic non-human mammals, B cells, plasma cells and hybridomas are also a part of the invention.

In a further aspect, the invention provides a method of identifying binding molecules according to the invention, such as human binding molecules for example monoclonal antibodies or fragments thereof, specifically binding to WNV or nucleic acid molecules encoding such binding molecules and comprises the steps of a) contacting a collection of binding molecules on the surface of replicable genetic packages with WNV or a fragment thereof under conditions conducive to binding, b) selecting at least once for a replicable genetic package binding to the WNV or the fragment thereof, and c) separating and recovering the replicable genetic package binding to the WNV or the fragment thereof from replicable genetic packages that do not bind.

A replicable genetic package as used herein can be prokaryotic or eukaryotic and includes cells, spores, yeasts, bacteria, viruses, (bacterio)phage, ribosomes and polysomes. A preferred replicable genetic package is a phage. The binding molecules, such as for instance single chain Fvs, are displayed on the replicable genetic package, they are attached to a group or molecule located at an exterior surface of the replicable genetic package. The replicable genetic package is a screenable unit comprising a binding molecule to be screened linked to a nucleic acid molecule encoding the binding molecule. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of binding molecules is formed by introducing nucleic acid molecules encoding exogenous binding molecules to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages.

In one embodiment, the selection step in the method according to the invention is performed in the presence of WNV that is inactivated. The inactivation of the WNV may be performed by viral inactivation methods well known to the skilled artisan such as inter alia pasteurization (wet heat), e.g., heat treatment while still in aqueous solution, at 60° C. for ten hours; dry heat treatment, e.g., heat treatment in the lyophilized state, at 80° C. for 72 hours; vapor heat treatment at 60° C. for ten hours and then 80° C. for one hour; treatment with low pH, e.g., pH 4 for six hours to 21 days; treatment with organic solvent/detergent, i.e., addition of organic solvents and detergents (Triton X-100 or Tween-80) to the virus; treatment by means of cold ethanol fractionation; column chromatography; nanofiltration; UV/light irradiation; gamma-irradiation; and addition of iodine. Preferably, the inactivation is performed by gamma- or UV-irradiation. Methods to test if a virus is still infective or partly or completely inactivated are well known to the person skilled in the art. The WNV used in the above method may be non-isolated for example present in serum and/or blood of an infected individual. The WNV used may also be isolated either before or after inactivation. Purification may be performed by means of well-known purification methods suitable for viruses such as for instance centrifugation through a glycerol cushion.

Alternatively, the selection step may be performed in the presence of a fragment of WNV such as recombinant WNV proteins or WNV-like particles expressing one or more WNV proteins such as WNV E and M protein. In yet another embodiment, the selection step may be performed in the presence of one or more proteins or (poly)peptides derived from WNV, fusion proteins comprising these proteins or (poly)peptides, and the like. Preferred WNV proteins are WNV proteins present on the surface of WNV such as the E and M protein. Extracellularly exposed parts of these proteins can also be used as selection material. The inactivated WNV or fragment thereof may be immobilized to a suitable material before use. In a specific embodiment the selection can be performed on different materials derived from WNV. For instance, the first selection round can be performed on inactivated WNV, while the second and third selection round can be performed on recombinant WNV E protein and WNV-like particles, respectively. Of course, other combinations are also suitable. Different WNV materials can also be used during one selection/panning step.

In yet a further aspect, the invention provides a method of obtaining a binding molecule specifically binding to WNV or a nucleic acid molecule encoding such a binding molecule specifically binding to a WNV, wherein the method comprises the steps of a) performing the above described method of identifying binding molecules, and b) isolating from the recovered replicable genetic package the binding molecule and/or the nucleic acid molecule encoding the binding molecule. The collection of binding molecules on the surface of replicable genetic packages can be a collection of scFvs or Fabs. Once a new scFv or Fab has been established or identified with the above mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see Huls et al., 1999; Boel et al., 2000).

As mentioned before, the preferred replicable genetic package is a phage. Phage display methods for identifying and obtaining (human) binding molecules for example monoclonal antibodies, are by now well-established methods known by the person skilled in the art. They are for example described in U.S. Pat. No. 5,696,108; Burton and Barbas, 1994; de Kruif et al., 1995b; and *Phage Display: A Laboratory Manual*, edited by: C. F. Barbas, D. R. Burton, J. K. Scott and G. J. Silverman (2001), Cold Spring Harbor Laboratory Press, Cold Spring Harbor, N.Y. All these references are herewith incorporated herein in their entirety. For the construction of phage display libraries, collections of human monoclonal antibody heavy and light chain variable region genes are expressed on the surface of bacteriophage, preferably filamentous bacteriophage, particles, in for example single-chain Fv (scFv) or in Fab format (see de Kruif et al., 1995b). Large libraries of antibody fragment-expressing phages typically contain more than $1.0*10^9$ antibody specificities and may be assembled from the immunoglobulin V regions expressed in the B-lymphocytes of immunized- or non-immunized individuals. In a specific embodiment of the invention the phage library of binding molecules, preferably scFv phage library, is prepared from RNA isolated from cells obtained from a subject that has been vaccinated or exposed to a WNV. RNA can be isolated from inter alia bone marrow or peripheral blood, preferably peripheral blood lymphocytes. The subject can be an animal vaccinated or exposed to WNV, but is preferably a human subject which has been vaccinated or has been exposed to WNV. Preferably, the human subject has recovered from WNV.

Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity for example CDR regions. WNV specific phage antibodies can be selected from the library by for instance immobilizing target antigens such as antigens from WNV on a solid phase and subsequently exposing the target antigens to a phage library to allow binding of phages expressing antibody fragments specific for the solid phase-bound antigen(s). Non-bound phages are removed by washing and bound phages eluted from the solid phase for infection of *E. coli* bacteria and subsequent propagation. Multiple rounds of selection and propagation are usually required to sufficiently enrich for phages binding specifically to the target antigen(s). If desired, before exposing the phage library to target antigens the phage library can first be subtracted by exposing the phage library to non-target antigens bound to a solid phase. Phages may also be selected for binding to complex antigens such as complex mixtures of WNV proteins or (poly)peptides, host cells expressing one or more proteins or (poly)peptides of WNV, WNV-like particles comprising WNV proteins, or whole inactivated WNV. Antigen specific phage antibodies can be selected from the library by incubating a solid phase with bound thereon inactivated WNV with the phage antibody library to let for example the scFv or Fab part of the phage bind to the WNV. After incubation and several washes to remove unbound and loosely attached phages, the phages that have bound with their scFv or Fab part to the WNV are eluted and used to infect *E. coli* to allow amplification of the new specificity. Generally, one or more selection rounds are required to separate the phages of interest from the large excess of non-binding phages. Alternatively, known proteins or (poly)peptides of WNV can be expressed in host cells and these cells can be used for selection of phage antibodies specific for the proteins or (poly) peptides. A phage display method using these host cells can be extended and improved by subtracting non-relevant binders during screening by addition of an excess of host cells comprising no target molecules or non-target molecules that are similar, but not identical, to the target, and thereby strongly enhance the chance of finding relevant binding molecules. Of course, the subtraction may also be performed before or after the screening with WNV or antigens thereof. The process is referred to as the Mabstract® process (Mabstract® is a registered trademark of Crucell Holland B.V., see also U.S. Pat. No. 6,265,150 which is incorporated herein by reference).

In yet another aspect, the invention provides a method of obtaining a binding molecule potentially having neutralizing activity against WNV, wherein the method comprises the steps of a) performing the method of obtaining a binding molecule specifically binding to WNV or a nucleic acid molecule encoding such a binding molecule specifically binding to a WNV as described above, and b) verifying if the binding molecule isolated has neutralizing activity against the WNV. Assays for verifying if a binding molecule has neutralizing activity are well known in the art (see, for instance, Beasley and Barrett, 2002).

In a further aspect, the invention pertains to a binding molecule having neutralizing activity against WNV and being obtainable by the methods as described above. A pharmaceutical composition comprising the binding molecule, the pharmaceutical composition further comprising at least one pharmaceutically acceptable excipient is also an aspect of the invention. Pharmaceutically acceptable excipients are well known to the skilled person. The pharmaceutical composition according to the invention may further comprise at least one other therapeutic agent. Suitable agents are also well known to the skilled artisan.

In yet a further aspect, the invention provides compositions comprising at least one binding molecule, at least one functional variant thereof, at least one immunoconjugate according to the invention or a combination thereof. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules of the invention may be coated in or on a material to protect them from the action of acids or other natural or non-natural conditions that may inactivate the binding molecules.

In yet a further aspect, the invention provides compositions comprising at least one nucleic acid molecule as defined in the invention. The compositions may comprise aqueous solutions such as aqueous solutions containing salts (e.g., NaCl or salts as described above), detergents (e.g., SDS) and/or other suitable components.

In another aspect, the invention is concerned with a composition comprising at least two binding molecules, preferably human binding molecules, having WNV neutralizing activity. The binding molecules should be capable of reacting with different, non-competing epitopes of WNV. Preferably, the epitopes are located on the WNV E protein. In one embodiment the first WNV neutralizing binding molecule is capable of reacting with an epitope located in domain II of the WNV E protein and the second WNV neutralizing binding molecule is capable of reacting with an epitope located in domain III of the WNV E protein.

In one embodiment, the compositions comprising two or more binding molecules having WNV neutralizing activity exhibit synergistic WNV neutralizing activity. In other words, the compositions comprise at least two binding molecules having WNV neutralizing activity, characterized in that the binding molecules act synergistically in neutralizing WNV. As used herein, the term "synergistic" means that the combined effect of the binding molecules when used in combination is greater than their additive effects when used individually. In one embodiment none of the binding molecules present in the synergistic WNV neutralizing activity exhibiting compositions may have WNV neutralizing activity when used as an individual binding molecule. Alternatively, one binding molecule of the at least two binding molecules in the compositions exhibiting synergistic WNV neutralizing activity may have WNV neutralizing activity when used individually. In a preferred embodiment both of the at least two binding molecules have WNV neutralizing activity when used individually. In one embodiment, one of the at least two binding molecules in the synergistic WNV neutralizing activity exhibiting compositions may bind to a WNV and the other binding molecule may bind to a cell associated receptor of the WNV. Alternatively, both binding molecules may bind to either the WNV or cell associated receptor. In one embodiment the binding molecules acting synergistically in neutralizing WNV may also be capable of neutralizing other *flaviviruses* synergistically. The at least two synergistically acting anti-WNV binding molecules may bind to the E protein of WNV. They may bind to different domains, such as one binding to domain II and one binding to domain III of the E protein of WNV. Alternatively, the antibodies may bind to the same domain. A way of calculating synergy is by means of the combination index. The concept of the combination index (CI) has been described by Chou and Talalay, 1984. In an alternative embodiment, the compositions comprise two or more binding molecules having different modes of action for example a first binding molecule may have WNV neutralizing activity, while the second binding molecule may be non-neutralizing, and have complement fixing activity.

Furthermore, the invention pertains to pharmaceutical compositions comprising at least one binding molecule (or functional fragment or variant thereof), at least one immunoconjugate according to the invention, at least one composition according to the invention, or combinations thereof. The pharmaceutical composition of the invention further comprises at least one pharmaceutically acceptable excipient.

A pharmaceutical composition according to the invention can further comprise at least one other therapeutic, prophylactic and/or diagnostic agent. Preferably, the pharmaceutical composition comprises at least one other prophylactic and/or therapeutic agent. Preferably, the further therapeutic and/or prophylactic agents are agents capable of preventing and/or treating an infection and/or a condition resulting from WNV. Therapeutic and/or prophylactic agents include, but are not limited to, anti-viral agents. Such agents can be binding molecules, small molecules, organic or inorganic compounds, enzymes, polynucleotide sequences, etc. Other agents that are currently used to treat patients infected with WNV are interferon-alpha and ribavirin. These can be used in combination with the binding molecules of the invention. Agents capable of preventing and/or treating an infection with WNV and/or a condition resulting from WNV that are in the experimental phase might also be used as other therapeutic and/or prophylactic agents useful in the invention.

The binding molecules or pharmaceutical compositions of the invention can be tested in suitable animal model systems prior to use in humans. Such animal model systems include, but are not limited to, a murine model, a hamster model, and geese model system.

Typically, pharmaceutical compositions must be sterile and stable under the conditions of manufacture and storage. The binding molecules, immunoconjugates, nucleic acid molecules or compositions of the invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, nucleic acid molecules or compositions of the invention can be in solution and the appropriate pharmaceutically acceptable excipient can be added and/or mixed before or at the time of delivery to provide a unit dosage injectable form. Preferably, the pharmaceutically acceptable excipient used in the invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the binding molecules of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is intravenous.

Oral dosage forms can be formulated inter alia as tablets, troches, lozenges, aqueous or oily suspensions, dispersable powders or granules, emulsions, hard capsules, soft gelatin capsules, syrups or elixirs, pills, dragees, liquids, gels, or slurries. These formulations can contain pharmaceutically excipients including, but not limited to, inert diluents, granulating and disintegrating agents, binding agents, lubricating agents, preservatives, coloring, flavoring or sweetening agents, vegetable or mineral oils, wetting agents, and thickening agents.

Pharmaceutical compositions of the invention can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anesthetic agents, preservatives, buffers, viscosity or solubility increasing agents, water-soluble antioxidants, oil-soluble antioxidants, and metal chelating agents.

In a further aspect, the binding molecules (functional fragments and variants thereof), immunoconjugates, compositions, or pharmaceutical compositions of the invention can be used as a medicament. So, a method of treatment and/or prevention of a WNV infection using the binding molecules, immunoconjugates, compositions, or pharmaceutical compositions of the invention is another part of the invention. The above-mentioned molecules can inter alia be used in the diagnosis, prophylaxis, treatment, or combination thereof, of one or more conditions resulting from WNV. They are suitable for treatment of yet untreated patients suffering from a condition resulting from WNV and patients who have been or are treated from a condition resulting from WNV. They protect against further infection by WNV for approximately one month and/or will retard the onset or progress of the symptoms associated with WNV. They may also be used in post-exposure prophylaxis, when there is a chance of infection but symptoms are absent. They may also be used as prophylaxis in the transplant of infected organs or in other patient populations at high risk of exposure and progression to disease due to inter alia age or immune status. It is known that WNV causes neuroinvasive disease in humans in <1% of infections with a case-fatality ratio of ±9%. However, ±60% of the survivors have not regained their normal neurological functions after 12 months and many of the 13% of neuroinvasive cases which develop an acute flaccid paralysis (AFP) syndrome do not recover. Persistence of WNV has been described in different vertebrate hosts including in the brain of monkeys. Currently there is no specific therapy for WNV encephalitis.

The above-mentioned molecules or compositions may be employed in conjunction with other molecules useful in diagnosis, prophylaxis and/or treatment. They can be used in vitro, ex vivo or in vivo. For instance, the binding molecules, immunoconjugates or pharmaceutical compositions of the invention can be co-administered with a vaccine against WNV. Alternatively, the vaccine may also be administered before or after administration of the molecules of the invention. Instead of a vaccine, interferon-alpha and/or ribavirin can also be employed in conjunction with the binding molecules of the invention.

The molecules are typically formulated in the compositions and pharmaceutical compositions of the invention in a therapeutically or diagnostically effective amount. Alternatively, they may be formulated and administered separately. For instance the other molecules such as interferon-alpha or ribavirin may be applied systemically, while the binding molecules of the invention may be applied intrathecally or intraventricularly.

Dosage regimens can be adjusted to provide the optimum desired response (e.g., a therapeutic response). A suitable dosage range may for instance be 0.1-100 mg/kg body weight, preferably 0.5-15 mg/kg body weight. Furthermore, for example, a single bolus may be administered, several divided doses may be administered over time or the dose may be proportionally reduced or increased as indicated by the exigencies of the therapeutic situation. The molecules and compositions according to the invention are preferably sterile. Methods to render these molecules and compositions sterile are well known in the art. The other molecules useful in diagnosis, prophylaxis and/or treatment can be administered in a similar dosage regimen as proposed for the binding molecules of the invention. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions of the invention. The exact dosing regimen is usually sorted out during clinical trials in human patients.

Human binding molecules and pharmaceutical compositions comprising the human binding molecules are particularly useful, and often preferred, when to be administered to human beings as in vivo therapeutic agents, since recipient immune response to the administered antibody will often be substantially less than that occasioned by administration of a monoclonal murine, chimeric or humanized binding molecule.

In another aspect, the invention concerns the use of the (human) binding molecules (functional fragments and variants thereof), immunoconjugates, nucleic acid molecules, compositions or pharmaceutical compositions according to the invention in the preparation of a medicament for the diagnosis, prophylaxis, treatment, or combination thereof, of a condition resulting from WNV.

Next to that, kits comprising at least one binding molecule (functional fragments and variants thereof), at least one immunoconjugate, at least one nucleic acid molecule, at least one composition, at least one pharmaceutical composition, at least one vector, at least one host according to the invention or a combination thereof are also a part of the invention. Optionally, the above-described components of the kits of the invention are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about for example the indications, usage, dosage, manufacture, administration, contraindications and/or warnings concerning the use of such therapeutic, prophylactic or diagnostic products.

The invention further pertains to a method of detecting WNV in a sample, wherein the method comprises the steps of a) contacting a sample with a diagnostically effective amount of a binding molecule (functional fragments and variants thereof) or an immunoconjugate according to the invention, and b) determining whether the binding molecule or immunoconjugate specifically binds to a molecule of the sample. The sample may be a biological sample including, but not limited to blood, serum, urine, tissue or other biological material from (potentially) infected subjects, or a non-biological sample such as water, drink, etc. The (potentially) infected subjects may be human subjects, but also animals that are suspected as carriers of WNV might be tested for the presence of WNV using the human binding molecules or immunoconjugates of the invention. The sample may first be manipulated to make it more suitable for the method of detection. Manipulation means inter alia treating the sample suspected to contain and/or containing WNV in such a way that the WNV will disintegrate into antigenic components such as proteins, (poly)peptides or other antigenic fragments. Preferably, the human binding molecules or immunoconjugates of the invention are contacted with the sample under conditions which allow the formation of an immunological complex between the human binding molecules and WNV or antigenic components thereof that may be present in the sample. The formation of an immunological complex, if any, indicating the presence of WNV in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates of the invention are conveniently bonded to the inside surface of microtiter wells. The binding molecules or immunoconjugates of the invention may be directly bonded to the microtiter well. However, maximum binding of the binding molecules or immunoconjugates of the invention to the wells might be accomplished by pre-treating the wells with polylysine prior to the addition of the binding molecules or immunoconjugates of the invention. Furthermore, the binding molecules or immunoconjugates of the invention may be covalently attached by known means to the wells. Generally, the binding molecules or immunoconjugates are used between 0.01 to 100 μg/ml for coating, although higher as well as lower amounts may also be used. Samples are then added to the wells coated with the binding molecules or immunoconjugates of the invention.

Furthermore, binding molecules of the invention can be used to identify epitopes of WNV. The epitopes can be linear, but also structural and/or conformational. In one embodiment, binding of binding molecules of the invention to a series of overlapping peptides, such as 15-mer peptides, of a protein from WNV can be analyzed by means of PEPSCAN analysis (see inter alia WO 84/03564, WO 93/09872, Slootstra et al., 1996). The binding of the molecules to each peptide can be tested in a PEPSCAN-based enzyme-linked immunoassay (ELISA). In another embodiment, a random peptide library comprising peptides from WNV can be screened for peptides capable of binding to the binding molecules of the invention. In the above assays the use of neutralizing binding molecules may identify one or more neutralizing epitopes. The peptides/epitopes found can be used as vaccines and for the diagnosis of WNV. In yet a further embodiment, the binding of (neutralizing) binding molecules of the invention to domains of a surface protein of WNV, such as the E or preM/M protein, may be analyzed. Alternatively, the human binding molecules of the invention may identify one or more epitopes of another protein of WNV.

In a further aspect, the invention provides a method of screening a binding molecule (or a functional fragment or variant thereof) for specific binding to the same epitope of WNV as the epitope bound by a human binding molecule of the invention, wherein the method comprises the steps of a) contacting a binding molecule to be screened, a binding molecule of the invention and a WNV or fragment thereof, b) measure if the binding molecule to be screened is capable of competing for specifically binding to the WNV or fragment thereof with the binding molecule of the invention. In a further step it may be determined, if the screened binding molecules that are capable of competing for specifically binding to WNV or fragment thereof have neutralizing activity. A binding molecule that is capable of competing for specifically binding to WNV or a fragment thereof with the binding molecule of the invention is another part of the invention. In the above-described screening method, "specifically binding to the same epitope" also contemplates specific binding to substantially or essentially the same epitope as the epitope bound by the a binding molecule of the invention. The capacity to block, or compete with, the binding of the binding molecules of the invention to WNV typically indicates that a binding molecule to be screened binds to an epitope or binding site on WNV that structurally overlaps with the binding site on WNV that is immunospecifically recognized by the binding molecules of the invention. Alternatively, this can indicate that a binding molecule to be screened binds to an epitope or binding site which is sufficiently proximal to the binding site immunospecifically recognized by the binding molecules of the invention to sterically or otherwise inhibit binding of the binding molecules of the invention to WNV.

In general, competitive inhibition is measured by means of an assay, wherein an antigen composition, i.e., a composition comprising WNV or fragments thereof, is admixed with reference binding molecules, i.e., the binding molecules of the invention, and binding molecules to be screened. Usually, the binding molecules to be screened are present in excess. Protocols based upon ELISAs and Western blotting are suitable for use in such simple competition studies. In certain embodiments, one may pre-mix the reference binding molecules with varying amounts of the binding molecules to be screened (e.g., 1:10, 1:20, 1:30, 1:40, 1:50, 1:60, 1:70, 1:80, 1:90 or 1:100) for a period of time prior to applying to the antigen composition. In other embodiments, the reference binding molecules and varying amounts of binding molecules to be screened can simply be admixed during exposure to the antigen composition. In yet another embodiment, the reference binding molecules or binding molecules to be screened are contacted before the binding molecules to be screened or reference binding molecules, respectively, are contacted with the WNV or fragment thereof. In any event, by using species or isotype secondary antibodies one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such asfor example biotin, an enzymatic, a radioactive or other label to enable subsequent identification. In these cases, one would pre-mix or incubate the labeled reference binding molecules with the binding molecules to be screened at various ratios (e.g., 1:10, 1:20, 1:30, 1:40, 1:50, 1:60, 1:70, 1:80, 1:90 or 1:100) and (optionally after a suitable period of time) then assay the reactivity of the labeled reference binding molecules and compare this with a control value in which no potentially competing binding molecule was included in the incubation. The assay may again be any one of a range of immunological assays based upon antibody hybridization, and the reference binding molecules would be detected by means of detecting their label for example using streptavidin in the case of biotinylated reference binding molecules or by using a chromogenic substrate in connection with an enzymatic label (such as 3,3'5,5'-tetramethylbenzidine (TMB) substrate with peroxidase enzyme) or by simply detecting a radioactive label. A binding molecule to be screened that binds to the same epitope as the reference binding molecule will be able to effectively compete for binding and thus will significantly reduce reference binding molecule binding, as evidenced by a reduction in bound label. The reactivity of the (labeled) reference binding molecule in the absence of a completely irrelevant binding molecule would be the control high value. The control low value would be obtained by incubating the labeled reference binding molecule with unlabelled reference binding molecules of exactly the same type, when competition would occur and reduce binding of the labeled reference binding molecule. In a test assay, a significant reduction in labeled reference binding molecule reactivity in the presence of a binding molecule to be screened is indicative of a binding molecule that recognizes the same epitope, i.e., one that "cross-reacts" with the labeled reference binding molecule.

Binding molecules identified by these competition assays ("competitive binding molecules" or "cross-reactive binding molecules") include, but are not limited to, antibodies, antibody fragments and other binding agents that bind to an epitope or binding site bound by the reference binding molecule, i.e., a binding molecule of the invention, as well as antibodies, antibody fragments and other binding agents that bind to an epitope or binding site sufficiently proximal to an epitope bound by the reference binding molecule for competitive binding between the binding molecules to be screened and the reference binding molecule to occur. Preferably, competitive binding molecules of the invention will, when present in excess, inhibit specific binding of a reference binding molecule to a selected target species by at least 10%, preferably by at least 25%, more preferably by at least 50%, and most preferably by at least 75%-90% or even greater. The identification of one or more competitive binding molecules that bind to about, substantially, essentially or at the same epitope as the binding molecules of the invention is a straightforward technical matter. As the identification of competitive binding molecules is determined in comparison to a reference binding molecule, a binding molecule of the invention, it will be understood that actually determining the epitope to which the reference binding molecule and the competitive binding molecule bind is not in any way required in order to identify a competitive binding molecule that binds to the same or substantially the same epitope as the reference binding molecule.

In another aspect, the invention pertains to a method of identifying a binding molecule specifically binding to a virus or a nucleic acid molecule encoding a binding molecule specifically binding to a virus, wherein the method comprises the steps of a) contacting a collection of binding molecules on the surface of replicable genetic packages with a virus-like particle comprising at least one protein of the virus under conditions conducive to binding, b) selecting at least once for a replicable genetic package binding to the virus-like particle, and c) separating and recovering the replicable genetic package binding to the virus-like particle from replicable genetic packages that do not bind.

In another aspect, the invention provides a method of obtaining a binding molecule specifically binding to a virus or a nucleic acid molecule encoding a binding molecule specifically binding to a virus, wherein the method comprises the steps of a) performing the method of identifying a binding molecule specifically binding to a virus or a nucleic acid molecule encoding a binding molecule specifically binding to a virus as described above, and b) isolating from the recovered replicable genetic package the binding molecule and/or the nucleic acid molecule encoding the binding molecule.

In yet another aspect, the invention provides a method of obtaining a binding molecule potentially having neutralizing activity against the virus, wherein the method comprises the steps of performing the method of obtaining a binding molecule specifically binding to a virus or a nucleic acid molecule encoding a binding molecule specifically binding to a virus as described above, and b) verifying if the binding molecule isolated has neutralizing activity against the virus. Further details and specific embodiments of methods of identifying and obtaining binding molecules have been described above.

Preferably, the binding molecule is a human binding molecule as herein defined.

As used herein, "virus-like particle" refers to a virus particle that assembles into intact enveloped viral structures. A virus-like particle does however not contain genetic information sufficient to replicate. Virus-like particles have essentially a similar physical appearance as the wild-type virus, i.e., they are morphologically and antigenically essentially similar to authentic virions. The virus-like particles as used herein may comprise wild-type viral amino acid sequences. The virus-like particles may also include functional copies of certain genes. Furthermore, the virus-like particles may also include foreign nucleic acid. The virus-like particles can be naturally or non-naturally occurring viral particles. They may lack functional copies of certain genes of the wild-type virus, and this may result in the virus-like particle being incapable of some function which is characteristic of the wild-type virus, such as replication and/or cell-cell movement. The missing functional copies of the genes can be provided by the genome of a host cell or on a plasmid present in the host cell, thereby restoring the function of the wild-type virus to the virus-like particle when in the host cell. Preferably, virus-like particles display the same cellular tropism as the wild-type virus. The virus-like particle may be non-infectious, but is preferably infectious. The term "infectious" as used herein means the capacity of the virus-like particle to complete the initial steps of viral cycle that lead to cell entry. In one embodiment, the virus-like particle self assembles. In another embodiment, the above methods are performed using pseudoviruses instead of virus-like particles. Pseudoviruses and their production are well known to the skilled person. Preferably, the pseudoviruses as used herein comprise a heterologous viral envelope protein, such as a WNV E and/or M protein, on their surface.

Virus-like particles can be produced in suitable host cells such as inter alia mammalian cells as described above. They can be produced intracellularly and/or extracellularly and can be harvested, isolated and/or purified as intact virus-like particles by means known to the skilled person such as inter alia affinity chromatography, gel filtration chromatography, ion exchange chromatography, and/or density gradient sedimentation. The protein comprised in and/or on the virus-like particle can be a viral structural protein. Preferably, the protein is a protein present on the surface of the virus such as a viral envelope protein. The protein may be wild-type, modified, chimeric, or a part thereof. A virus-like particle as herein described is also part of the invention. Preferably, the virus-like particle is produced extracellularly when the WNV E and preM/M protein is expressed in host cells, preferably human host cells.

Preferably, the virus is a member of the Flaviviridae family, preferably the genus *Flavivirus* including, but not limited to, Dengue virus, Japanese Encephalitis virus, Kunjin virus, Murray Valley Encephalitis virus, St. Louis Encephalitis virus, Tick-borne Encephalitis virus, Yellow Fever virus and West Nile virus. Other viruses belonging to the genus *Flavivirus* can inter alia be found in Kuno et al. (1998), which is incorporated by reference herein. In a preferred embodiment, the virus is WNV.

In one embodiment, the virus-like particle comprises WNV E protein. In another embodiment, the virus-like particle further comprises WNV M protein. By an "WNV E and M protein" is meant an envelope and membrane protein, respectively, from any WNV strain. Preferably, the WNV E and M protein are derived from a same WNV strain. In one embodiment the WNV E and M protein have the amino acid sequences as herein described.

The replicable genetic package suitable for the above methods of the invention is selected from the group consisting of a phage particle, a bacterium, a yeast, a fungus, a spore of a microorganism and a ribosome.

In one embodiment, the above methods of the invention the collection of binding molecules on the surface of replicable genetic packages is a scFv phage display library.

DETAILED DESCRIPTION OF THE INVENTION

Definitions

Figure 1:
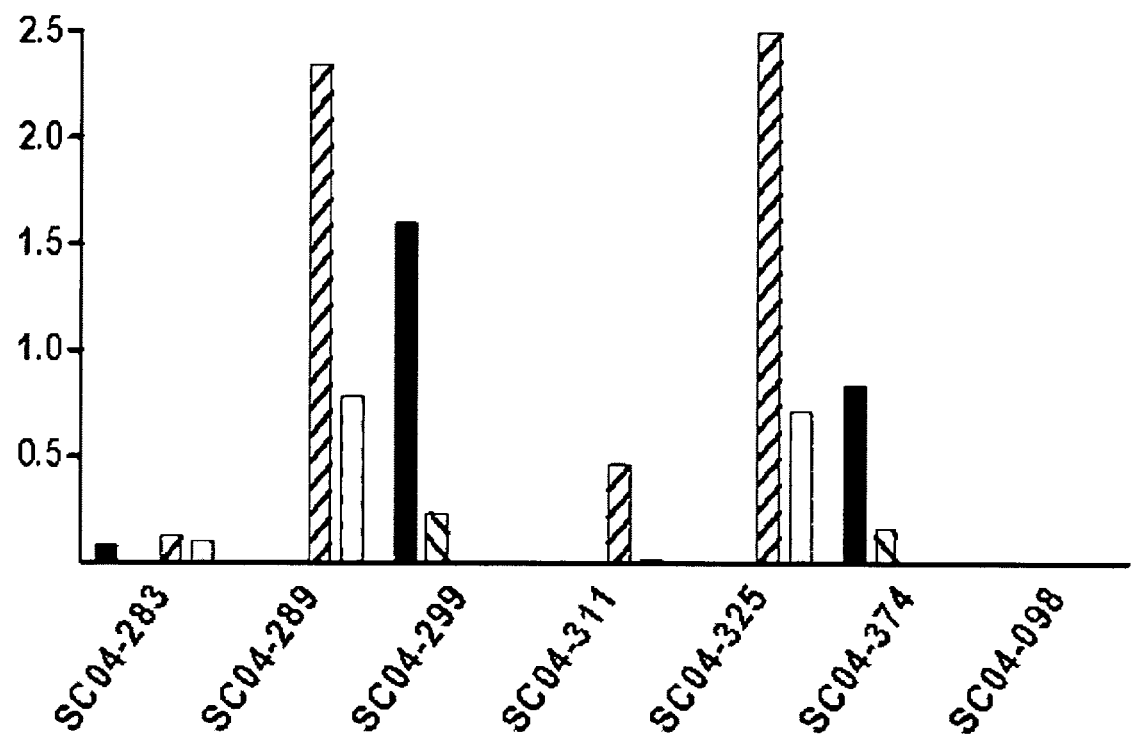
FIG. 1 shows the domain mapping of anti WNV-E protein binding scFvs. On the X-axis the tested scFvs are shown and on the Y-axis the OD 492 nm value is given. The filled bars show competition ELISA of the scFvs with the murine anti-WNV monoclonal antibody 6B6C-1, the striped (upwards from left to right) bars show competition ELISA of the scFvs with the murine anti-WNV monoclonal antibody 7H2, the striped (upwards from right to left) bars show competition ELISA of the scFvs with the anti-WNV monoclonal antibody 4G2, and the open bars show competition ELISA of the scFvs with the anti-WNV monoclonal antibody 3A3.

Amino acid sequence. The term "amino acid sequence" as used herein refers to naturally occurring or synthetic molecules and to a peptide, oligopeptide, polypeptide or protein sequence.

Binding molecule. As used herein the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin for example WNV. Regardless of structure, the antigen-binding fragment binds with the same antigen that is recognized by the intact immunoglobulin. An antigen-binding fragment can comprise a peptide or polypeptide comprising an amino acid sequence of at least two contiguous amino acid residues, at least five contiguous amino acid residues, at least ten contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least 200 contiguous amino acid residues, or at least contiguous 250 amino acid residues of the amino acid sequence of the binding molecule.

The term "binding molecule," as used herein includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes)for example IgA1, IgA2, IgG1, IgG2, IgG3 and IgG4.

Antigen-binding fragments include, inter alia, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by: E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in vivo.

Biological sample. As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

Complementarity determining regions (CDR). The term "complementarity determining regions" as used herein means sequences within the variable regions of binding molecules, such as immunoglobulins, that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured for example by solubilization in SDS. Epitopes may also consist of posttranslational modifications of proteins.

Deletion. The term "deletion," as used herein, denotes a change in either amino acid or nucleotide sequence in which one or more amino acid or nucleotide residues, respectively, are absent as compared to the parent, often the naturally occurring, molecule.

Expression-regulating nucleic acid sequence. The term "expression-regulating nucleic acid sequence" as used herein refers to polynucleotide sequences necessary for and/or affecting the expression of an operably linked coding sequence in a particular host organism. The expression-regulating nucleic acid sequences, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

Functional variant. The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner for example WNV, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). It will be clear to the skilled artisan that other classifications of amino acid residue families than the one used above can also be employed. Furthermore, a variant may have non-conservative amino acid substitutions for example replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host. The term "host," as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human. The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences or based on variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by for instance random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

Insertion. The term "insertion," also known as the term "addition," denotes a change in an amino acid or nucleotide sequence resulting in the addition of one or more amino acid or nucleotide residues, respectively, as compared to the parent sequence.

Isolated. The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. The term "isolated" when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than WNV. Furthermore, the term "isolated" refers to nucleic acid molecules that are substantially separated from other cellular components that naturally accompany the native nucleic acid molecule in its natural host for example ribosomes, polymerases, or genomic sequences with which it is naturally associated. Moreover, "isolated" nucleic acid molecules, such as cDNA molecules, can be substantially free of other cellular material, or culture medium when produced by recombinant techniques, or substantially free of chemical precursors or other chemicals when chemically synthesized.

Monoclonal antibody. The term "monoclonal antibody" as used herein refers to a preparation of antibody molecules of single molecular composition. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant.

Naturally occurring. The term "naturally occurring" as used herein as applied to an object refers to the fact that an object can be found in nature. For example, a polypeptide or polynucleotide sequence that is present in an organism that can be isolated from a source in nature and which has not been intentionally modified by man in the laboratory is naturally occurring.

Nucleic acid molecule. The term "nucleic acid molecule" as used in the invention refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful for example for anti-sense therapy, hybridization probes and PCR primers.

Operably linked. The term "operably linked" refers to two or more nucleic acid sequence elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

Pharmaceutically acceptable excipient. By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed, and is compatible with other ingredients of the formulation comprising the drug, agent or binding molecule.

Specifically Binding. The term "specifically binding," as used herein, in reference to the interaction of a binding molecule for example an antibody, and its binding partner for example an antigen, means that the interaction is dependent upon the presence of a particular structure for example an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by for example radioimmunoassays (RIA), enzyme-linked immunosorbent assays (ELISA), BIACORE, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

Substitutions. A "substitution," as used herein, denotes the replacement of one or more amino acids or nucleotides by different amino acids or nucleotides, respectively.

Therapeutically effective amount. The term "therapeutically effective amount" refers to an amount of the binding molecule as defined herein that is effective for preventing, ameliorating and/or treating a condition resulting from infection with WNV.

Treatment. The term "treatment" refers to therapeutic treatment as well as prophylactic or preventative measures to cure or halt or at least retard disease progress. Those in need of treatment include those already inflicted with a condition resulting from infection with WNV as well as those in which infection with WNV is to be prevented. Subjects partially or totally recovered form infection with WNV might also be in need of treatment. Prevention encompasses inhibiting or reducing the spread of WNV or inhibiting or reducing the onset, development or progression of one or more of the symptoms associated with infection with WNV.

Vector. The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

EXAMPLES

To illustrate the invention, the following examples are provided. The examples are not intended to limit the scope of the invention in any way.

Example 1

Construction of a scFv Phage Display Library Using RNA Extracted from Peripheral Blood of WNV Convalescent Donors From three convalescent WNV patients samples of blood were taken one, two and three months after infection. Peripheral blood leukocytes were isolated by centrifugation and the blood serum was saved and frozen at −80° C. All donors at all time points had high titers of neutralizing antibodies to WNV as determined using a virus neutralization assay. Total RNA was prepared from the cells using organic phase separation and subsequent ethanol precipitation. The obtained RNA was dissolved in RNAse free water and the concentration was determined by OD 260 nm measurement. Thereafter, the RNA was diluted to a concentration of 100 ng/µl. Next, 1 µg of RNA was converted into cDNA as follows: To 10 µl total RNA, 13 µl DEPC-treated ultrapure water and 1 µl random hexamers (500 ng/µl) were added and the obtained mixture was heated at 65° C. for five minutes and quickly cooled on wet-ice. Then, 8 µl 5× First-Strand buffer, 2 µl dNTP (10 mM each), 2 µl DTT (0.1 M), 2 µl Rnase-inhibitor (40 U/µl) and 2 µl Superscript™III MMLV reverse transcriptase (200 U/µl) were added to the mixture, incubated at room temperature for five minutes and incubated for one hour at 50° C. The reaction was terminated by heat inactivation, i.e., by incubating the mixture for 15 minutes at 75° C.

The obtained cDNA products were diluted to a final volume of 200 µl with DEPC-treated ultrapure water. The OD 260 nm of a 50 times diluted solution (in 10 mM Tris buffer) of the dilution of the obtained cDNA products gave a value of 0.1.

For each donor, 5 to 10 µl of the diluted cDNA products were used as template for PCR amplification of the immunoglobulin gamma heavy chain family and kappa or lambda light chain sequences using specific oligonucleotide primers (see Tables 1-6). PCR reaction mixtures contained, besides the diluted cDNA products, 25 µmol sense primer and 25 µmol anti-sense primer in a final volume of 50 µl of 20 mM Tris-HCl (pH 8.4), 50 mM KCl, 2.5 mM $MgCl_2$, 250 µM dNTPs and 1.25 units Taq polymerase. In a heated-lid thermal cycler having a temperature of 96° C., the mixtures obtained were quickly melted for two minutes, followed by 30 cycles of: 30 seconds at 96° C., 30 seconds at 60° C. and 60 seconds at 72° C.

In a first round amplification, each of seventeen light chain variable region sense primers (eleven for the lambda light chain (see Table 1) and six for the kappa light chain (see Table 2) were combined with an anti-sense primer recognizing the C-kappa called HuCk 5'-ACACTCTCCCCTGTTGAAGCT CTT-3' (see SEQ ID NO:81) or C-lambda constant region HuCλ2 5'-TGAACATTCTGTAGGGGCCACTG-3' (see SEQ ID NO:82) and HuCλ7 5'-AGAGCATTCTG-CAGGGGCCACTG-3' (see SEQ ID NO:83) (the $HuC\lambda_2$ and HuCλ7 anti-sense primers were mixed to equimolarity before use), yielding four times 17 products of about 600 base pairs. These products were purified on a 2% agarose gel and isolated from the gel using Qiagen gel-extraction columns. ¹⁄₁₀ of each of the isolated products was used in an identical PCR reaction as described above using the same seventeen sense primers, whereby each lambda light chain sense primer was combined with one of the three Jlambda-region specific anti-sense primers and each kappa light chain sense primer was combined with one of the five Jkappa-region specific anti-sense primers. The primers used in the second amplification were extended with restriction sites (see Table 3) to enable directed cloning in the phage display vector PDV-C06 (see SEQ ID NO:84). This resulted in four times 63 products of approximately 350 base pairs that were pooled to a total of ten fractions. This number of fractions was chosen to maintain the natural distribution of the different light chain families within the library and not to over or under represent certain families. The number of alleles within a family was used to determine the percentage of representation within a library (see Table 4). In the next step, 2.5 µg of pooled fraction and 100 µg PDV-C06 vector were digested with SalI and NotI and purified from gel. Thereafter, a ligation was performed overnight at 16° C. as follows. To 500 ng PDV-C06 vector 70 ng pooled fraction was added in a total volume of 50 µl ligation mix containing 50 mM Tris-HCl (pH 7.5), 10 mM MgCl$_2$, 10 mM DTT, 1 mM ATP, 25 µg/ml BSA and 2.5 µl T4 DNA Ligase (400 U/µl). This procedure was followed for each pooled fraction. The ligation mixes were purified by phenol/chloroform, followed by a chloroform extraction and ethanol precipitation, methods well known to the skilled artisan. The DNA obtained was dissolved in 50 µl ultrapure water and per ligation mix two times 2.5 µl aliquots were electroporated into 40 µl of TG1 competent E. coli bacteria according to the manufacturer's protocol (Stratagene). Transformants were grown overnight at 37° C. in a total of 30 dishes (three dishes per pooled fraction; dimension of dish: 240 mm×240 mm) containing 2TY agar supplemented with 50 µg/ml ampicillin and 4.5% glucose. A (sub)library of variable light chain regions was obtained by scraping the transformants from the agar plates. This (sub)library was directly used for plasmid DNA preparation using a Qiagen™ QIAFilter MAXI prep kit.

For each donor the heavy chain immunoglobulin sequences were amplified from the same cDNA preparations in a similar two round PCR procedure and identical reaction parameters as described above for the light chain regions with the proviso that the primers depicted in Tables 5 and 6 were used. The first amplification was performed using a set of nine sense directed primers (see Table 5; covering all families of heavy chain variable regions) each combined with an IgG specific constant region anti-sense primer called HuCIgG 5'-GTC CAC CTT GGT GTT GCT GGG CTT-3' (SEQ ID NO:85) yielding four times nine products of about 650 base pairs. These products were purified on a 2% agarose gel and isolated from the gel using Qiagen gel-extraction columns. ⅒ of each of the isolated products was used in an identical PCR reaction as described above using the same nine sense primers, whereby each heavy chain sense primer was combined with one of the four JH-region specific anti-sense primers. The primers used in the second round were extended with restriction sites (see Table 6) to enable directed cloning in the light chain (sub)library vector. This resulted per donor in 36 products of approximately 350 base pairs. These products were pooled for each donor per used (VH) sense primer into nine fractions. The products obtained were purified using Qiagen PCR purification columns. Next, the fractions were digested with SfiI and XhoI and ligated in the light chain (sub)library vector, which was cut with the same restriction enzymes, using the same ligation procedure and volumes as described above for the light chain (sub)library. Alternatively, the fractions were digested with NcoI and XhoI and ligated in the light chain vector, which was cut with the same restriction enzymes, using the same ligation procedure and volumes as described above for the light chain (sub)library. Ligation purification and subsequent transformation of the resulting definitive library was also performed as described above for the light chain (sub)library and at this point the ligation mixes of each donor were combined per VH pool. The transformants were grown in 27 dishes (three dishes per pooled fraction; dimension of dish: 240 mm×240 mm) containing 2TY agar supplemented with 50 µg/ml ampicillin and 4.5% glucose. All bacteria were harvested in 2TY culture medium containing 50 µg/ml ampicillin and 4.5% glucose, mixed with glycerol to 15% (v/v) and frozen in 1.5 ml aliquots at −80° C. Rescue and selection of each library were performed as described below.

Example 2

Selection of Phages Carrying Single Chain Fv Fragments Specifically Recognizing WNV Envelope (E) Protein Antibody fragments were selected using antibody phage display libraries, general phage display technology and MAbstract® technology, essentially as described in U.S. Pat. No. 6,265,150 and in WO 98/15833 (both of which are incorporated by reference herein). The antibody phage libraries used were two different semi-synthetic scFv phage libraries (JK1994 and WT2000) and the immune library prepared as described in Example 1. The first semi-synthetic scFv phage library (JK1994) has been described in de Kruif et al., 1995b, the second one (WT2000) was build essentially as described in de Kruif et al., 1995b. Briefly, the library has a semi-synthetic format whereby variation was incorporated in the heavy and light chain V genes using degenerated oligonucleotides that incorporate variation within CDR regions. Only VH3 heavy chain genes were used, in combination with kappa and lambda light chain genes. CDR1 and CDR3 of the heavy chain and CDR3 of the light chain were recreated synthetically in a PCR-based approach similar as described in de Kruif et al., 1995b. The thus created V region genes were cloned sequentially in scFv format in a phagemid vector and amplified to generate a phage library as described before. Furthermore, the methods and helper phages as described in PCT International publication WO 02/103012 (incorporated by reference herein) were used in the invention. For identifying phage antibodies recognizing WNV E protein, phage selection experiments were performed using whole WNV (called strain USA99b or strain 385-99) inactivated by gamma irradiation (50 Gy for one hour), recombinantly expressed WNV E protein (strain 382-99), and/or WNV-like particles expressing WNV E protein (strain 382-99) on their surface.

The recombinantly expressed E protein was produced as follows. The nucleotide sequence coding for the preM/M protein and the full length E protein of WNV strain 382-99 (see SEQ ID NO:86 for the amino acid sequence of a fusion protein comprising both WNV polypeptides) was synthesized. Amino acids 1-93 of SEQ ID NO:86 constitute the WNV preM protein, amino acids 94-168 of SEQ ID NO:86 constitute the WNV M protein, amino acids 169-669 of SEQ ID NO:86 constitute the WNV E protein (the soluble WNV E protein (ectodomain) constitutes amino acids 169-574 of SEQ ID NO:86, while the WNV E protein stem and transmembrane region constitutes amino acids 575-669 of SEQ ID NO:86) The synthesized nucleotide sequence was cloned into the plasmid pAdapt and the plasmid obtained was called pAdapt.WNV.prM-E (FL).

To produce a soluble secreted form of the E protein a construct was made lacking the transmembrane spanning regions present in the final 95 amino acids at the carboxyl terminal of the full length E protein (truncated form). For that purpose the full length construct pAdapt.WNV.prM-E (FL) was PCR amplified with the primers CMV-Spe (SEQ ID NO:87) and WNV-E-95 REV (SEQ ID NO:88) and the fragment obtained was cloned into the plasmid pAdapt.myc.his to create the plasmid called pAdapt.WNV-95. Next, the region coding for the preM protein, the truncated E protein, the Myc tag and His tag were PCR amplified with the primers clefsmaquwnv (SEQ ID NO:89) and reverse WNVmychis (SEQ ID NO:90) and cloned into the vector pSyn-C03 containing the HAVT20 leader peptide using the restriction sites EcoRI and SpeI. The expression construct obtained, pSyn-C03-WNV-E-95, was transfected into 90% confluent HEK293T cells using lipofectamine according to the manufacturers instructions. The cells were cultured for five days in serum-free ultra CHO medium, then the medium was harvested and purified by passage over HisTrap chelating columns (Amersham Bioscience) pre-charged with nickel ions. The truncated E protein was eluted with 5 ml of 250 mM imidazole and further purified by passage over a G-75 gel filtration column equilibrated with phosphate buffered saline (PBS). Fractions obtained were analyzed by SDS-PAGE analysis and Western blotting using the WNV-E protein specific murine antibody 7H2 (Biorelience, see Beasley and Barrett 2002). Three 5 ml fractions containing a single band of ~45 kDa that was immunoreactive with antibody 7H2 were aliquoted and stored at −20° C. until further use. The protein concentration was determined by OD 280 nm.

WNV-like particles were produced as follows. The construct pSyn-C03-WNV-E-95 described above and pcDNA3.1 (Invitrogen) were digested with the restriction endonucleases MunI and XbaI and the construct pAdapt.WNV.prM-E (FL) described above was digested with the restriction endonucleases ClaI and XbaI. The resulting fragments were combined in a three-point ligation to produce the construct pSyn-H-preM/E FL. This construct contained the full length E protein and expressed the two structural WNV proteins, protein M and E, required for assembly of an enveloped virion. The construct was transfected into 70% confluent HEK293T cells using lipofectamine according to the manufacturer's instructions. The cells were cultured for three days in serum-free ultra CHO medium, then the medium was harvested, layered on to a 30% glycerol solution at a 2:1 ratio and pelleted by centrifugation for two hours at 120,000*g at 4° C. The WNV-like particles were resuspended in PBS, aliquoted and stored at −80° C. Aliquots were analyzed by SDS-PAGE analysis and Western blotting using the WNV-E protein specific murine antibody 7H2 (Biorelience).

Before inactivation, whole WNV was purified by pelleting through a 30% glycerol solution as described above for WNV-like particles. The purified WNV was resuspended in 10 mM Tris/HCl pH 7.4 containing 10 mM EDTA and 200 mM NaCl, the obtained preparation was kept on dry ice during inactivation, tested for infectivity and stored at −80° C. in small aliquots. Aliquots were analyzed by SDS-PAGE analysis and Western blotting using the WNV-E protein specific murine antibody 7H2 (Biorelience).

Whole inactivated WNV, WNV-like particles or recombinantly expressed soluble E protein were diluted in PBS. 2-3 ml of the preparation was added to MaxiSorp™ Nunc-Immuno Tubes (Nunc) and incubated overnight at 4° C. on a rotating wheel. An aliquot of a phage library (500 µl, approximately $10^{13}$ cfu, amplified using CT helper phage (see WO 02/103012)) was blocked in blocking buffer (2% Protifar in PBS) for one to two hours at room temperature. The blocked phage library was added to the immunotubes, incubated for two hours at room temperature, and washed with wash buffer (0.1% v/v Tween-20 in PBS) to remove unbound phages. Bound phages were eluted from the antigen by incubation with 1 ml of 50 mM Glycine-HCl pH 2.2 for 10 minutes at room temperature. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for ten minutes at 3200*g at room temperature and the bacterial pellet was resuspended in 0.5 ml 2-trypton yeast extract (2TY) medium. The obtained bacterial suspension was divided over two 2TY agar plates supplemented with tetracyclin, ampicillin and glucose. After overnight incubation of the plates at 37° C., the colonies were scraped from the plates and used to prepare an enriched phage library, essentially as described by De Kruif et al. (1995a) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection.

Typically, two rounds of selections were performed before isolation of individual phage antibodies. After the second round of selection, individual *E. coli* colonies were used to prepare monoclonal phage antibodies. Essentially, individual colonies were grown to log-phase in 96-well plate format and infected with CT helper phages after which phage antibody production was allowed to proceed overnight. The produced phage antibodies were PEG/NaCl-precipitated and filter-sterilized and tested in ELISA for binding to WNV-like particles purified as described supra.

Example 3

Validation of the WNV Specific Single-Chain Phage Antibodies

Selected single-chain phage antibodies that were obtained in the screens described above were validated in ELISA for specificity, i.e., binding to WNV E protein, whole inactivated WNV and WNV-like particles, all purified as described supra. Additionally, the single-chain phage antibodies were also tested for binding to 5% FBS. For this purpose, whole inactivated WNV, the WNV E protein, WNV-like particles or 5% FBS preparation was coated to Maxisorp ELISA plates. In addition, whole inactivated rabies virus was coated onto the plates as a control. After coating, the plates were blocked in PBS containing 1% Protifar for one hour at room temperature. The selected single-chain phage antibodies were incubated for 15 minutes in an equal volume of PBS containing 1% Protifar to obtain blocked phage antibodies. The plates were emptied, and the blocked single-chain phage antibodies were added to the wells. Incubation was allowed to proceed for one hour, the plates were washed in PBS containing 0.1% v/v Tween-20 and bound phage antibodies were detected (using OD 492 nm measurement) using an anti-M13 antibody conjugated to peroxidase. As a control, the procedure was performed simultaneously without single-chain phage antibody, with a negative control single-chain phage antibody directed against rabies virus glycoprotein (antibody called SC02-447), with a negative control single-chain phage antibody directed against SARS-CoV (antibody called SC03-014) and a positive control single-chain phage antibody directed against rabies virus. As shown in Table 7, the selected phage antibodies called SC04-271, SC04-274, SC04-283, SC04-289, SC04-299, SC04-311, SC04-325, SC04-353, SC04-361 and SC04-374 displayed significant binding to immobilized whole inactivated WNV (see Table 7) and WNV-like particles (data not shown). In addition, for SC04-325, SC04-353, SC04-361 and SC04-374 no binding to rabies virus was observed. When the ELISA was performed with recombinantly expressed purified soluble WNV E protein prepared as described supra all single-chain phage antibodies bound with the exception of SC04-283, SC04-299, SC04-353 and SC04-361, suggesting they either bind to a region not present in the truncated soluble E protein, bind to an unrelated protein on the virion surface, do not bind to the monomeric form of the E protein or do not bind because of the phage antibody format.

Example 4

Characterization of the WNV Specific scFvs

From the selected specific single-chain phage antibody (scFv) clones plasmid DNA was obtained and nucleotide sequences were determined according to standard techniques. The nucleotide sequences of the scFvs (including restriction sites for cloning) called SC04-271, SC04-274, SC04-283, SC04-289, SC04-299, SC04-311, SC04-325, SC04-353, SC04-361 and SC04-374 are shown in SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, and SEQ ID NO:79, respectively. The amino acid sequences of the scFvs called SC04-271, SC04-274, SC04-283, SC04-289, SC04-299, SC04-311, SC04-325, SC04-353, SC04-361 and SC04-374 are shown in SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80, respectively.

The VH and VL gene identity (see I. M. Tomlinson, S. C. Williams, O. Ignatovitch, S. J. Corbett, G. Winter, V-BASE Sequence Directory, Cambridge United Kingdom: MRC Centre for Protein Engineering (1997)) and heavy chain CDR3 sequences of the scFvs specifically binding WNV are depicted in Table 8. Table 9 shows the other CDR regions of the WNV specific scFvs.

Example 5

Construction of Fully Human Immunoglobulin Molecules (Human Monoclonal Anti-WNV Antibodies) from the Selected Anti-WNV Single Chain Fvs Heavy and light chain variable regions of the scFvs called SC04-271, SC04-274, SC04-283, SC04-299, SC04-311, SC04-325, and SC04-374 were PCR-amplified using oligonucleotides to append restriction sites and/or sequences for expression in the IgG expression vectors pSyn-C18-HCγ1 (see SEQ ID NO:91) pSyn-C05-Cκ (see SEQ ID NO:92) and pSyn-C04-Cλ (see SEQ ID NO:93). The heavy chain variable regions of the scFvs called SC04-271, SC04-274, SC04-283, SC04-299, SC04-311, SC04-325, and SC04-374 were cloned into the vector pSyn-C18-HCγ1; the light chain variable regions of the scFv called SC04-274, SC04-283 and SC04-325 were cloned into the vector pSyn-C05-Cκ; the light chain variable regions of the scFvs called SC04-271, SC04-299, SC04-311, and SC04-374 were cloned into the vector pSyn-C04-Cλ. The VL kappa genes were first amplified using the following oligonucleotide sets; SC04-274, 5K-G (SEQ ID NO:94) and sy3K-F (SEQ ID NO:95); SC04-283, 5K-B (SEQ ID NO:96) and sy3K-F (SEQ ID NO:95); SC04-325, 5K-J (SEQ ID NO:97) and sy3K-F (SEQ ID NO:95) and the PCR products cloned into vector pSyn-C05-Cκ. The VL lambda genes were first amplified using the following oligonucleotides sets; SC04-271, 5L-B (SEQ ID NO:98) and sy3L-E (SEQ ID NO:99); SC04-299, 5L-G (SEQ ID NO:100) and sy3L-Cmod (SEQ ID NO:101); SC04-311, 5L-C (SEQ ID NO:102) and sy3L-Cmod (SEQ ID NO:101); SC04-374, 5L-C (SEQ ID NO:102) and sy3L-Cmod (SEQ ID NO:101) and the PCR products cloned into vector pSyn-C04-Cλ. Nucleotide sequences for all constructs were verified according to standard techniques known to the skilled artisan. VH genes were first amplified using the following oligonucleotide sets: SC04-271, 5H-H (SEQ ID NO:103) and sy3H-A (SEQ ID NO:104); SC04-274, 5H-H (SEQ ID NO:103) and sy3H-C (SEQ ID NO:105); SC04-283, 5H-H (SEQ ID NO:103) and sy3H-A (SEQ ID NO:104); SC04-299, 5H-C (SEQ ID NO:106) and sy3H-C (SEQ ID NO:105); SC04-311, 5H-C (SEQ ID NO:106) and sy3H-A (SEQ ID NO:104); SC04-325, 5H-A (SEQ ID NO:107) and sy3H-A (SEQ ID NO:104); SC04-374; First 5H-N (SEQ ID NO:108) and sy3H-D (SEQ ID NO:109). Thereafter, the PCR products were cloned into vector pSyn-C18-HCγ1 and nucleotide sequences were verified according to standard techniques known to the skilled person in the art.

Heavy and light chain variable regions of the scFvs called SC04-289, SC04-353, and SC04-361 were cloned directly by restriction digest for expression in the IgG expression vectors pIg-C911-HCgamma1 (see SEQ ID NO:110) and pIg-C909-Ckappa (see SEQ ID NO:111). The heavy chain variable regions of the scFvs called SC04-289, SC04-353, and SC04-361 were cloned into the vector pIg-C911-HCgamma1 by restriction digest using the enzymes SfiI and XhoI and the light chain variable region of the scFv called SC04-289, SC04-353, and SC04-361 were cloned into the vector pIg-C909-Ckappa by restriction digest using the enzymes SalI and NotI. Thereafter, the nucleotide sequences were verified according to standard techniques known to the person skilled in the art.

The resulting expression constructs pgG104-271C18, pgG104-274C18, pgG104-283C18, pgG104-289C911, pgG104-299C18, pgG104-311C18, pgG104-325C18, pgG104-353C911, pgG104-361C911, and pgG104-374C18 encoding the anti-WNV human IgG1 heavy chains and pgG104-271C04, pgG104-274C05, pgG104-283C05, pgG104-289C909, pgG104-299C04, pgG104-311C04, pgG104-325C05, pgG104-353C909, pgG104-361C909, and pgG104-374C04 encoding the anti-WNV human IgG1 light chains were transiently expressed in combination in 293T cells and supernatants containing human IgG1 antibodies were obtained. The nucleotide sequences of the heavy chains of the antibodies called CR4271, CR4274, CR4283, CR4289, CR4299, CR4311, CR4325, CR4353, CR4361, and CR4374 are shown in SEQ ID NOS:112, 114, 116, 118, 120, 122, 124, 126, 128, and 130, respectively. The amino acid sequences of the heavy chains of the antibodies called CR4271, CR4274, CR4283, CR4289, CR4299, CR4311, CR4325, CR4353, CR4361, and CR4374 are shown in SEQ ID NOS:113, 115, 117, 119, 121, 123, 125, 127, 129, and 131, respectively.

The nucleotide sequences of the light chain of antibodies CR4271, CR4274, CR4283, CR4289, CR4299, CR4311, CR4325, CR4353, CR4361, and CR4374 are shown in SEQ ID NOS:132, 134, 136, 138, 140, 142, 144, 146, 148, and 150, respectively. The amino acid sequences of the light chain of antibodies CR4271, CR4274, CR4283, CR4289, CR4299, CR4311, CR4325, CR4353, CR4361, and CR4374 are shown in SEQ ID NOS:133, 135, 137, 139, 141, 143, 145, 147, 149, and 151, respectively. A person skilled in the art can determine the variable regions of the heavy and light chains of the above antibodies by following Kabat et al. (1991), as described in Sequences of Proteins of Immunological Interest. The human anti-WNV IgG1 antibodies were validated for their ability to bind to irradiated WNV in ELISA essentially as described for scFvs (see Table 10). Three dilutions of the respective antibodies in blocking buffer were tested. The positive control was the murine anti-WNV antibody 7H2 and the negative control was an anti-rabies virus antibody.

Alternatively, batches of greater than 1 mg of each antibody were produced and purified using standard procedures. The antibodies were then titrated on a fixed concentration of irradiated West Nile virus and tested in ELISA as described above. The results are shown in Table 11. As a negative control an anti-rabies virus antibody was used. All antibodies showed binding to the virus in a dose dependent manner.

Figure 5:
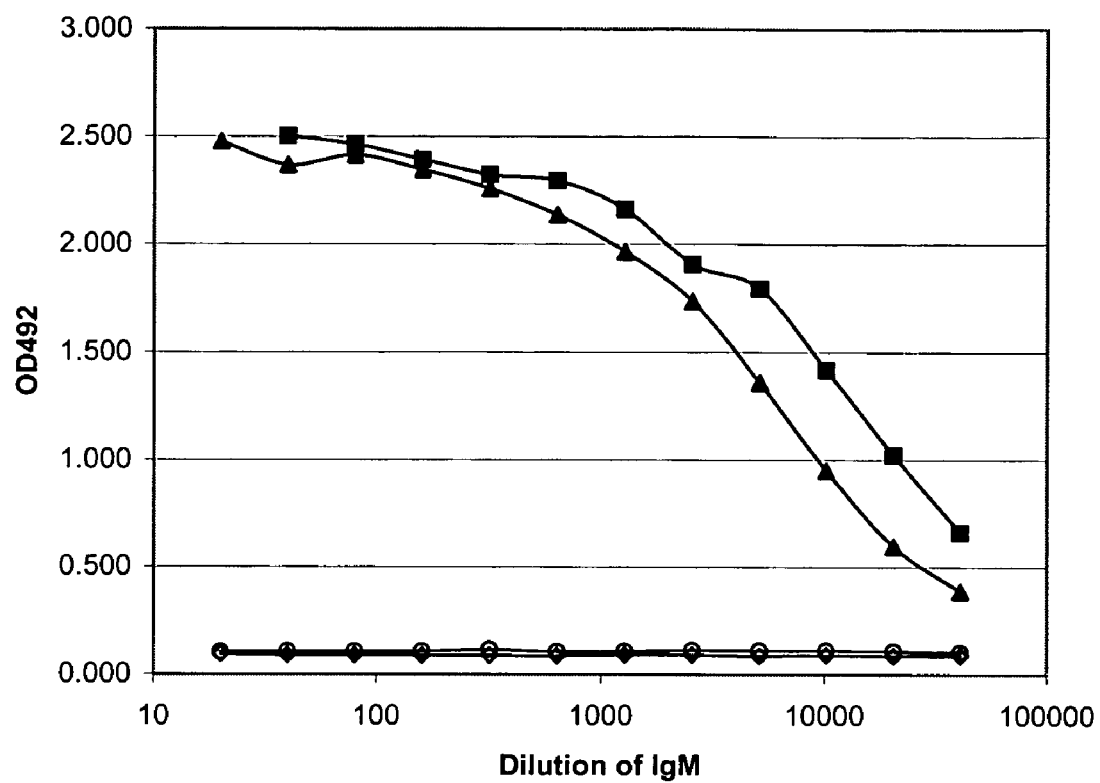
FIG. 5. Binding curve of IgM form of CR4374 (CRM4374) to virus-like particles (VLPs). Two different purification runs are shown (▲ and ■, IgM; ○ and ◇, control).

Furthermore, CR4374 was converted into a fully human IgM format by removing the gamma Fc region from construct pgG104-374C18 by restriction digestion with the endonucleases NheI and XbaI. The vector pCR-IgM (SEQ ID NO:216) containing a mu Fc region was digested with the same restriction enzymes and the obtained mu Fc region was ligated into vector pgG104-374C18 and fused in frame with the variable heavy chain gene derived from SC04-374 to make vector pgM104-374C899. This construct was transiently expressed in combination together with the light chain construct pgG104-374C04 (see above) in 293T cells and supernatants containing human IgM antibodies were obtained. The nucleotide sequence of vector pgM104-374C899 is shown in SEQ ID NO:217. The amino acid sequence of the heavy chain the antibody called CRM4374 is shown in SEQ ID NO:218. The IgM antibody was purified from the supernatant by adding ammonium sulphate to a final concentration of 2.4 M and incubating the mixture overnight on ice, while stirring. The precipitated IgM was recovered by centrifugation at 10,395×g for 30 minutes. The pellet was resuspended in PBS and further purified by gel filtration. A HiLoad 26/60 Superdex 200 prep grade column (GE Healthcare) equilibrated with PBS was loaded with the resuspended IgM and fractions were collected from the column, while being flushed under a constant flow rate with PBS. The first major elution peak, which contained the purified IgM, was collected. Binding activity of the antibody was confirmed by titration on West Nile virus-like particles (VLPs) (see FIG. 5).

Example 6

In Vitro Neutralization of WNV by WNV Specific scFvs and IgGs (Virus Neutralization Assay)

In order to determine whether the selected scFvs are capable of blocking WNV infection, in vitro virus neutralization assays (VNA) are performed. The VNA are performed on Vero cells (ATCC CCL 81). The WNV strain 385-99 which is used in the assay is diluted to a titer of $4 \times 10^3 TCID_{50}$/ml (50% tissue culture infective dose per ml), with the titer calculated according to the method of Spearman and Kaerber. The scFv preparations are serially two-fold-diluted in PBS starting from 1:2 (1:2-1:1024). 25 µl of the respective scFv dilution is mixed with 25 µl of virus suspension (100 $TCID_{50}$/25 µl) and incubated for one hour at 37° C. The suspension is then pipetted twice in triplicate into 96-well plates. Next, 50 µl of a freshly trypsinized and homogenous suspension of Vero cells (1:3 split of the confluent cell monolayer of a T75-flask) resuspended in DMEM with 10% v/v fetal calf serum and antibiotics is added. The inoculated cells are cultured for three to four days at 37° C. and observed daily for the development of cytopathic effect (CPE). CPE is compared to the positive control (WNV inoculated cells) and negative controls (mock-inoculated cells or cells incubated with scFV only). The complete absence of CPE in an individual cell culture is defined as protection (=100% titer reduction). The serum dilution giving protection in 50% percent of wells (i.e., three out of six wells) is defined as the 50% neutralizing antibody titer. The murine neutralizing antibody 7H2 (Biorelience) is used as a positive control in the assay. A 50% neutralization titer of $\leq 1:4$ (meaning the antibody is diluted 4 times or more) is regarded as specific evidence of neutralizing activity of the scFv against WNV.

Alternatively, in vitro virus neutralization assays (VNA) were performed in order to determine whether the anti-WNV IgGs were capable of blocking WNV infection. The VNA were performed essentially as described for scFvs, with the proviso that the serum dilution giving protection in 66% percent of wells (i.e., two out of three wells) was defined as the 66% neutralizing antibody titer and a 66% neutralization titer of $\leq 1:2$ was regarded as specific evidence of neutralizing activity of the IgG against WNV.

Supernatants containing the human anti-WNV antibodies called CR4271, CR4274, CR4283, CR4289, CR4299, CR4311, CR4325, CR4353, CR4361, and CR374 were expressed as described in Example 5 and subjected to the above-described VNA. All antibodies had a neutralizing titer $\leq 1:2$. The potency of the antibodies (in µg/ml) is given in Table 12. The neutralizing antibodies recognized WNV E protein by Western Blot analysis or immunoprecipitation of an inactivated WNV preparation (data not shown).

Example 7

WNV E Protein Competition ELISA with scFvs

To identify antibodies that bind to non-overlapping, non-competing epitopes, a WNV E protein competition ELISA is performed. Nunc-Immuno™ Maxisorp F96 plates (Nunc) are coated overnight at 4° C. with a 1:100 dilution of purified WNV E protein (100 µg/ml) in PBS (50 µl). Uncoated protein is washed away before the wells are blocked with 100 µl PBS containing 1% Protifar for one hour at room temperature. Subsequently, the blocking solution is discarded and 50 µl of the non-purified anti-WNV scFvs in PBS containing 1% Protifar (2× diluted) is added. Wells are washed five times with 100 µl of PBS containing 0.05% Tween-20. Then, 50 µl biotinylated anti-WNV competitor murine monoclonal IgGs, 7H2 or 6B6C-1, is added to each well, incubated for five minutes at room temperature, and the wells washed five times with 100 µl of PBS containing 0.05% Tween-20. To detect the binding of 7H2 or 6B6C-1, 50 µl of a 1:2000 dilution of streptavidin-HRP antibody (Becton Dickinson) is added to the wells and incubated for one hour at room temperature. Wells are washed again as above and the ELISA is further developed by addition of 100 µl of OPD reagent (Sigma). The reaction is stopped by adding 50 µl 1 M $H_2SO_4$ before measuring the OD at 492 nm.

Alternatively, to investigate if antibodies are capable of binding to non-overlapping, non-competing epitopes, the following competition ELISA was performed. Nunc-Immuno™ Maxisorp F96 plates (Nunc) were coated overnight at 4° C. with a 1:1000 dilution with either of the murine anti-WNV monoclonal IgGs 7H2 (see Beasley and Barrett 2002) or 6B6C-1 (see Roehrig et al. 1983, Blitvich et al. 2003, and Roehrig et al. 2001). Uncoated antibody was washed away before the wells were blocked with 100 µl PBS containing 1% Protifar for one hour at room temperature. Subsequently, the blocking solution was discarded and 100 µl of purified recombinant WNV-E protein in PBS containing 1% Protifar (2× diluted) was added and incubated for one hour at room temperature. Wells were washed three times with 100 µl of PBS containing 0.05% Tween-20. Then, 100 µl of anti-WNV scFvs were added to the wells and incubated for one hour at room temperature. The wells were then washed five times with 100 µl of PBS containing 0.05% Tween-20. To detect the binding of scFV, 100 µl of a 1:4000 dilution of anti-VSV-HRP antibody (Boehringer Mannheim) was added to the wells and incubated for one hour at room temperature. Wells were washed again as above and the ELISA was further developed by addition of 100 µl of OPD reagent (Sigma). The reaction was stopped by adding 50 µl 1 M $H_2SO_4$ before measuring the OD at 492 nm. The results of the assay are shown in FIG. 1 for the scFv SC04-283, SC04-289, SC04-299, SC04-311, SC04-325, and SC04-374. When recombinant WNV-E protein was captured with the antibody 7H2, whose binding epitope has been mapped to domain III, the scFv SC04-299 and SC04-374 were blocked from binding, whereas SC04-289, SC04-311, and SC04-325 were able to bind. In contrast, when the antibody 6B6C-1, whose binding epitope has been mapped to domain II, was used for capture, SC04-299 and SC04-374 were able to bind recombinant WNV-E protein, but SC04-289, SC04-311, and SC04-325 were blocked from binding. These data indicate that both SC04-299 and SC04-374 bind to an epitope in domain III of the WNV-E protein and SC04-289, SC04-311, and SC04-325 bind to an epitope in domain II of the WNV-E protein. SC04-283 was not blocked by either antibody, suggesting that it might recognize an epitope away from the binding regions of 7H2 and 6B6C-1. Similar results as above were observed for the monoclonal antibodies called 4G2 and 3A3 which recognize an epitope on domain II and III, respectively. It has been suggested that domain III is the putative receptor binding site responsible for cellular attachment, while it has been suggested that domain II of the WNV-E protein contains the fusion peptide necessary for viral entry into the cytoplasm of the infected cell. The scFvs SC04-271 and SC04-274 did not bind to recombinant WNV-E protein either directly coated or coated by means of any of the two murine antibodies (data not shown). The negative control SC04-098 also did not bind to recombinant WNV-E protein coated by means of any of the two murine antibodies.

Example 8

In Vivo Protection by Anti-WNV Monoclonal Antibodies from Lethal WNV Infection in a Murine Challenge Model A murine challenge model was adapted from the literature (see Ben-Nathan et al. 2003; Beasley et al. 2002; Wang et al. 2001). In Ben-Nathan et al. (2003) four-week old BALB/c mice were used and the animals were inoculated intraperitoneally (i.p.) with 20-times the viral dose resulting in 50% survival ($LD_{50}$) of WNV strain ISR52 ($LD_{50}$ was equivalent to 5 pfu). Under this dosing mice succumbed to infection six to seven days after inoculation and reached 100% mortality after eleven days. In another study, the WNV strain USA99 (used in the experiments described here) was shown to have an $LD_{50}$ of 0.5 pfu. This is ten-fold lower than the $LD_{50}$ of ISR52, which may indicate a higher degree of neuroinvasiveness for this viral strain or differences associated with the mouse strain used (see Beasley et al. 2002).

To determine the i.p., $LD_{50}$ of USA99 in four-week BALB/c mice, animals (five per group) were injected with USA99 at $TCID_{50}$ (tissue culture infectious dose) of 100, 30, 10, 3, 1, 0.3, 0.1, 0.03 the 50% in two separate experiments. The $LD_{50}$ calculated from the first experiment was 5.75 $TCID_{50}$ and from the second experiment 13.25 $TCID_{50}$. For the calculation of the viral dose in further experiments the average of the two experiments, i.e., 9.5 $TCID_{50}$, was calculated by probit regression analysis.

The protective capacity of the in vitro neutralizing antibodies CR4271, CR4274, CR4283, CR4289, CR4299, CR4311, CR4325, CR4353, CR4361, and CR4374 was tested in the in vivo model. Purified antibodies were injected i.p. into four-week BALB/c mice (five animals per group) at a concentration of 15 mg/kg. After 24 hours, the WNV strain USA99 was injected i.p. at a dose of 20-times the $LD_{50}$ calculated. The animals were observed for signs of disease over 21 days and sacrificed when symptoms of encephalitis were evident. In the model unprotected animals generally succumbed to infection between day 8 and day 10.

Table 13 shows that one antibodies, CR4374, is 100% protective in vivo and an additional antibody CR4353 is 75% protective at the dose of 15 mg/kg. The positive control antibody 7H2 (an anti-WNv murine monoclonal) was fully protective and the negative control antibody (binding an irrelevant antigen) showed no protection in the experiment.

To establish a dose protection relationship, the protective antibodies CR4353 and CR4374 were titrated in the mouse model using doses of 10, 3, 1, 0.3, 0.1, 0.03, 0.01, 0.003 and 0.001 mg/kg. A negative control antibody binding an irrelevant antigen was included as a control at a dose 10 mg/kg.

Figure 2:
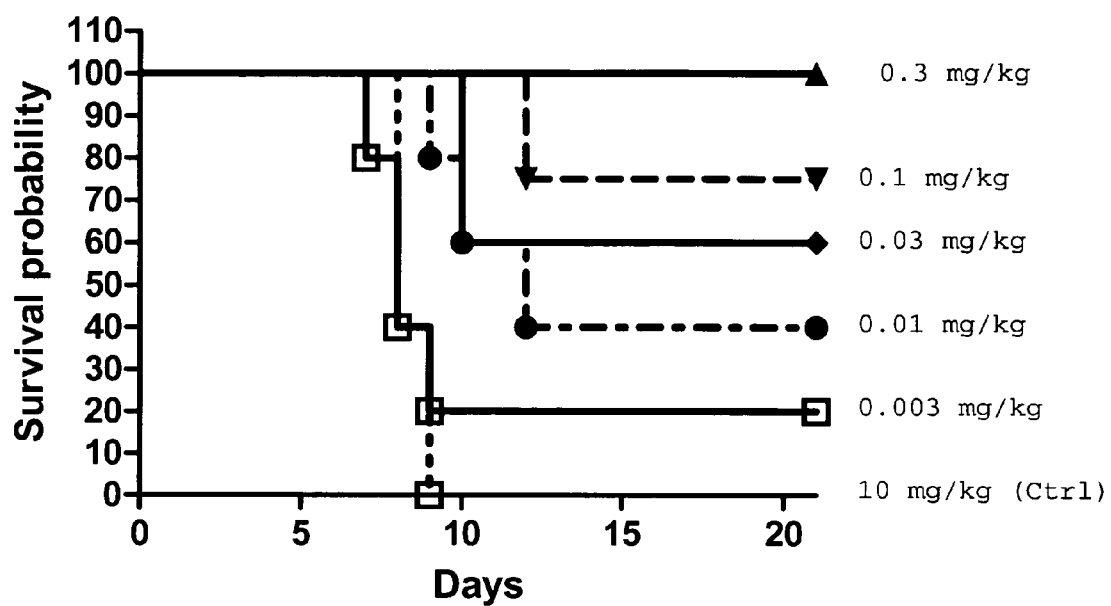
FIG. 2 shows the titration of anti-WNV monoclonal antibody CR4374 in a murine WNV challenge model. From top to bottom titration of anti-WNV monoclonal antibody CR4374 using doses of 0.3, 0.1, 0.03, 0.01, and 0.003 mg/kg and titration with a control antibody at a concentration of 10 mg/kg are shown. On the X-axis days are shown and on the Y-axis the survival probability (%) is represented.

As shown in FIG. 2, the antibody CR4374 is 100% protective at a dose of 0.3 mg/kg. The doses 10, 3 and 1 mg/kg were also 100% protective (data not shown). FIG. 2 also shows that there is a direct correlation between dose and protective capacity. The 50% protective dose calculated by probit regression analysis is 0.013 mg/kg.

Figure 3:
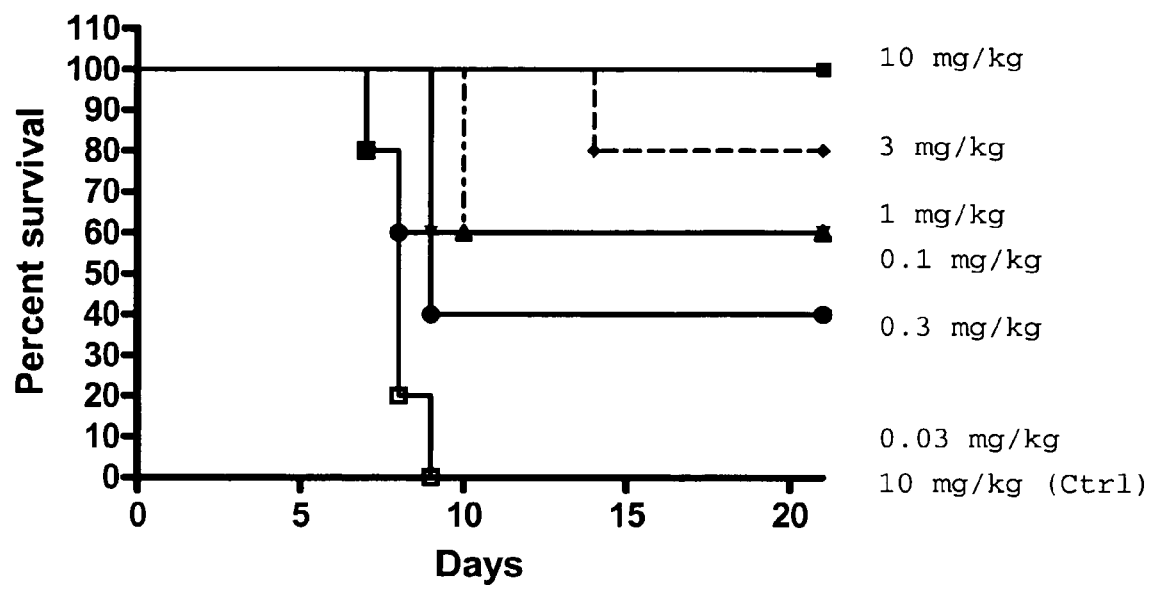
FIG. 3 shows the titration of anti-WNV monoclonal antibody CR4353 in a murine WNV challenge model. From top to bottom titration of anti-WNV monoclonal antibody CR4353 using doses of 10, 3, 1, 0.1, 0.3, and 0.03 mg/kg and titration with a control antibody at a concentration of 10 mg/kg are shown. On the X-axis days are shown and on the Y-axis the survival probability is represented.

FIG. 3 shows that the antibody CR4353 is 100% protective at a dose of 10 mg/kg. Moreover, FIG. 3 shows that there is a direct correlation between dose and protective capacity. The 50% protective dose calculated by probit regression analysis is 0.357 mg/kg.

The titration data of the antibodies were compared by probit regression analysis. Values for the Pearson Goodness-of-Fit test (Chi Square=10.38, DF=30, p=1.00) demonstrated that the model was valid and the results of the Parallelism Test (Chi Square=3.47, DF=3, p=0.324) meant that the curves could be reliably compared. The values for the 50% protective dose and 95% protective dose are summarized in Table 14.

Example 9

Affinity Analysis Using Biacore

Affinity studies were performed using surface plasmon resonance analysis with a BIAcore3000™ analytical system at 25° C., using HBS-EP (Biacore AB, Sweden) as running buffer at a flow rate of 30 µl/minute. IgG CR4283 was immobilized on a research grade CM5 four-flow channel (Fc) sensor chip (Biacore AB, Sweden) using amine coupling. A constant amount of inactivated and purified West Nile Virus was then captured on the chip via the immobilized CR4283, followed by injection of a varying amount of the antibody of interest to analyze the binding interaction between this antibody and the captured virus. Regeneration using 15, 20, 30 or 40 mM NaOH was performed at the end of each measurement to remove bound antibody as well as captured virus, while leaving the immobilized CR4283 on the chip.

Figure 4:
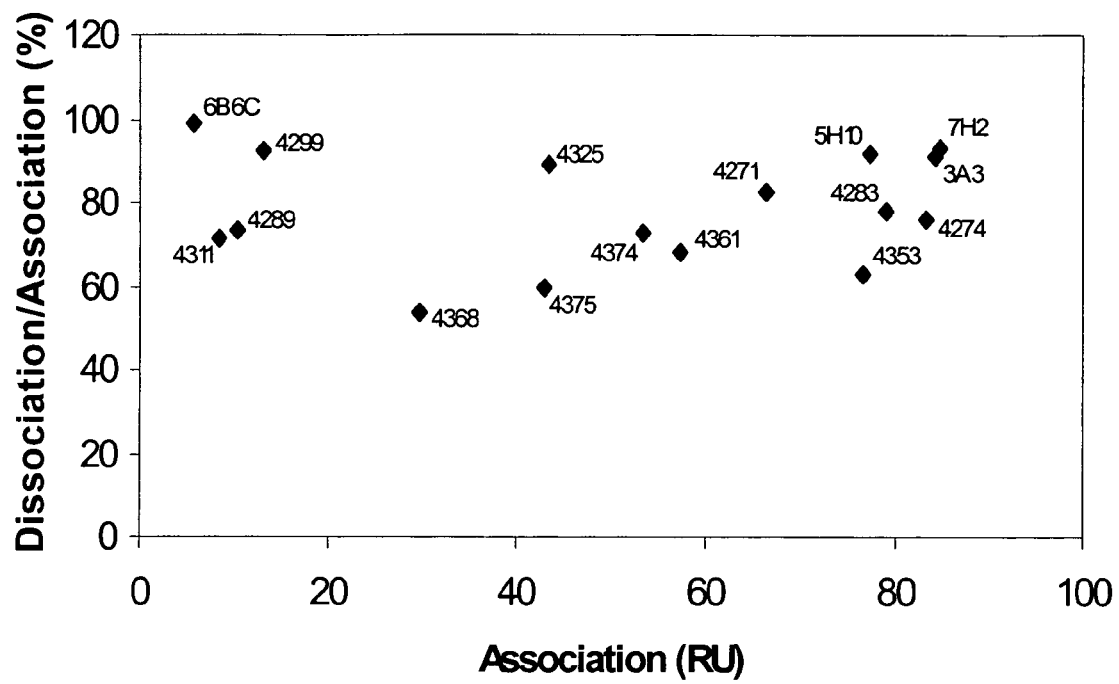
FIG. 4. Affinity ranking of antibodies using surface plasmon resonance. Antibodies with a relatively high affinity for West Nile Virus are located in the upper right corner of this plot, indicating good association and slow dissociation. The average of two measurements is shown for each antibody.

For affinity ranking studies, 60 µl of purified West Nile virus was injected, followed by injection of 40 µl 1000 nM antibody. Then, running buffer was applied for 770 seconds, followed by regeneration of the CM5 chip with 5 µl 30 or 40 mM NaOH. The resonance signals expressed as resonance units (RU) were recorded as a function of time for each antibody. The response after the association phase was determined, as well as the response after 370 seconds of dissociation. The dissociation response expressed as percentage of the association response was then plotted against the association response (see FIG. 4). Antibodies CR4368 and CR4375 have the same heavy chain CDR3 as CR4374, but differ in other parts of the sequences. Mouse monoclonal antibodies 7H2, 3A3, 5H10 (all from BioReliance) and 6B6C-1 (Chemicon) were included for comparison. Antibodies with a relatively high affinity are located in the upper right corner of the plot, indicating good association combined with slow dissociation.

Affinity constants were determined for CR4283, CR4353, CR4374 and mouse antibody 7H2. After capture of 22, 23 or 60 µl West Nile virus, 40 µl of antibody was injected, followed by a dissociation phase of 770 seconds, and regeneration using 5 µl 15, 20 or 30 mM NaOH. Twelve concentrations in two-fold dilutions from 1000 nM down to 0.39 nM were measured for each antibody. The resulting data were fitted using a bivalent analyte model and the dissociation constant KD was calculated. Average KD values from duplicate experiments were 0.8±0.6 nM for CR4283, 6.5±0.4 nM for CR4353, 56±4 nM for CR4374 and 0.32±0.06 nM for 7H2.

Example 10

In Vitro Neutralization Potency by Plaque Reduction Neutralization Test (PRNT)

To further investigate the neutralizing activity of the anti-WNV antibodies of the invention a PRNT was developed. Briefly, Vero-E6 cells were trypsinized and counted. $2.5 \times 10^5$ cells were added to each well of a twelve-well plate and incubated overnight at 37° C. in a humidified $CO_2$ incubator. Serial dilutions (ten-fold) of a titrated stock of West Nile virus USA99b were made in complete medium. Equal volume (250 µl) mixtures of virus (100 pfu) and serial dilutions of purified IgG1 antibodies were incubated in duplicate at 37° C. for one hour. Dilutions of both virus and antibodies were done in DMEM medium. The mixture was then added (400 µl) to the twelve-well plates containing Vero cell monolayers after careful aspiration of the overnight medium. After the plates had been incubated at 37° C. for one hour, an 1.5 ml overlay of CMC carboxymethyl-cellulose medium with 10% FBS (v/v) (CMC:complete medium) was added per well and the plates placed in a humidified $CO_2$ incubator for three days at 37° C. One day before staining the CMC:complete medium was removed from the wells and replaced with a mixture of CMC:PBS (1:1; v/v) containing 8.25 mg/ml of neutral red (2 ml neutral red at 3.3 g/l in 80 ml CMC:PBS). Plates were incubated one day further at 37° C. in a humidified $CO_2$ incubator, after which the number of visible plaques was quantified.

To analyze the antibody potency data from the PRNT a binary regression model known as probit analysis was used. Probit analysis is valid, if it can be assumed that the probability of neutralizing WNV in vitro follows a normal distribution with regard to the amount of antibodies used. The assumption of normality most likely holds on a logarithmic scale, hence the neutralization of virus was modeled as a function of the logarithm of the amount of antibodies administered. Antibodies were compared directly in the regression model, with significance level alpha set at 0.05. Antibody concentrations yielding 50% and 90% neutralization were estimated from the model, together with 95% confidence intervals. A summary of the final analysis of the panel is given in Table 15. Taking the PRNT50 and PRNT90 values into account, CR4374 is the most potent neutralizing antibody. CR4353 has a lower PRNT50 value, but its PRNT90 value is high due to the fact that it retains neutralizing activity at very low concentrations, but is not able to completely neutralize the virus even at very high concentrations. The above may be related to differences in the mechanisms of action of both antibodies. As shown above however, CR4374 is more protective than CR4353 in the murine challenge model. For CR4271, CR4274 and CR4283 no value could be given for PRNT50, because of low potency and for CR4368 and CR4361 no value could be given for PRNT90, because of the high degree of uncertainty again due to low potency. By converting CR4374 into IgM format (CRM4374) the in vitro potency was increased dramatically (see Tables 15 and 18).

Example 11

Measurement of the Breadth of Neutralizing Activity Against Different West Nile Virus and *Flavivirus* Strains by Plaque Reduction Neutralization Test (PRNT)

Figure 6:
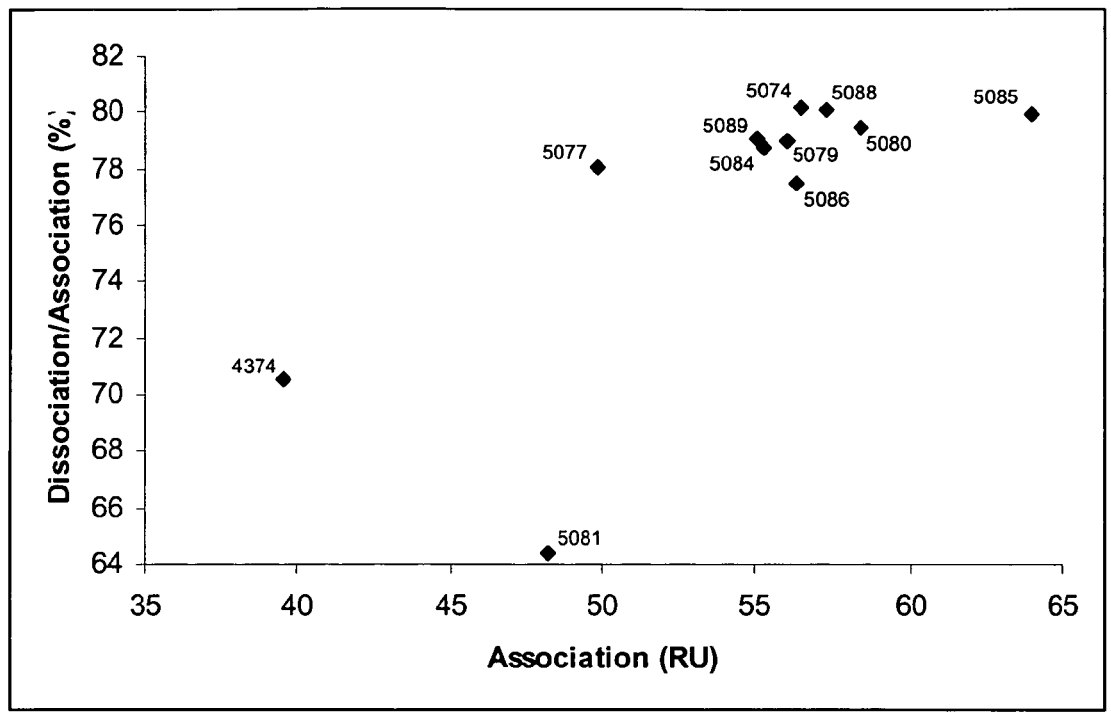
FIG. 6. Affinity ranking of affinity matured CR4374 variants using surface plasmon resonance. Antibodies with a relatively high affinity for West Nile Virus are located in the upper right corner of this plot, indicating good association and slow dissociation. The average of two measurements is shown for each antibody.

Using the assay described above, the anti-WNV IgG1 antibody CR4374, that was protective in the murine challenge model, was tested for its neutralizing potency against different strains of West Nile virus (see Table 16 for the description of the WNV strains tested) and other *flaviviruses* including yellow fever virus, Japanese encephalitis virus, St. Louis encephalitis virus and dengue virus 2 and 4. CR4374 had no significant neutralizing activity against any of the other *flaviviruses* (data not shown). CR4374 neutralized however all of the lineage I and lineage II WNV strains tested with equal potency with the exception of TUN97 which was even neutralized significantly better than USA99b, the original strain used for selection (see Table 17).

Example 12

Affinity Maturation of CR4374 and Affinity and Neutralizing Potency Analysis Using Biacore and Plaque Reduction Neutralization Test, Respectively Affinity maturation of CR4374 was performed as follows. The variable heavy chain region of SC04-374 was cloned into the (sub)library of variable light chain regions according to the same method as described in Example 1 for cloning of the heavy chain repertoire into the (sub)library. Phage display selections using the constructed library were performed essentially as described in Example 2, followed by screening and analysis of selected clones essentially as described in Examples 3 and 4. The nucleotide and amino acid sequences of the selected scFvs SC05-074, SC05-080, SC05-085 and SC05-088 as well as the amino acid sequences of their CDR regions are shown in Tables 18 and 19, respectively. Fully human immunoglobulin molecules of isolated clones were generated essentially as described in Example 5, using vector pIg-C910-Clambda (SEQ ID NO:219) instead of pIg-C909-Ckappa for cloning of the light chains. The nucleotide sequences of the light chains of the affinity matured immunoglobulins called CR5074, CR5080, CR5085 and CR5088 are shown in SEQ ID NO:220, SEQ ID NO:222, SEQ ID NO:224, and SEQ ID NO:226. The amino acid sequences of the light chains of the affinity matured immunoglobulins called CR5074, CR5080, CR5085 and CR5088 are shown in SEQ ID NO:221, SEQ ID NO:223, SEQ ID NO:225, and SEQ ID NO:227. A person skilled in the art can determine the variable region of the light chains of the above antibodies by following Kabat et al. (1991) as described in *Sequences of Proteins of Immunological Interest*. Affinity ranking studies with these affinity matured immunoglobulins were performed using surface plasmon resonance analysis essentially as described in Example 9. The dissociation response expressed as percentage of the association response was plotted against the association response (see FIG. 6). As shown in FIG. 6, the affinity of all but one mutated antibody (CR5081) had clearly improved. Affinity constants for the mutated immunoglobulins CR5074, CR5080, CR5085 and CR5088 were also determined essentially as described in Example 9. Average KD values from duplicate experiments were 3.9±0.5 nM for CR5074, 2.7±0.1 nM for CR5080, 3.7±0.7 nM for CR5085, and 1.7±0.1 nM for CR5088. These KD values are all an order of magnitude higher compared to CR4374.

In addition to the affinity, the neutralizing potency of the mutated immunoglobulins against West Nile virus strain USA99b was measured by PRNT. From Table 20 can be deducted that the PRNT50 and PRNT90 values of all affinity matured immunoglobulins are an order of magnitude higher compared to CR4374. This is in agreement with the affinity data.

Example 13

Systemic and Intrathecal/Intraventricular Therapy of WNV Encephalitis in a Hamster Model with Anti-WNV Monoclonal Antibodies or Combinations Thereof with or without Interferon-Alpha It is investigated by means of a hamster model of WNV encephalitis, if the administration of the anti-WNV monoclonal antibodies of the invention in combination with interferon-alpha has a beneficial effect on the course of established human WNV encephalitis through reduction of viral load in the cerebrospinal fluid and brain, reduction of neuronal death, reduction of mortality, reduction of neurological signs and symptoms and/or prevention of persistent infection. To model the intrathecal administration of the antibodies, which is the preferred route used in humans, the antibodies of the invention are installed intraventricularily in the animals, because it is technically easier to perform. It has been shown that hamsters can be infected with WNV and that this species is well suited to evaluate the effects of therapeutic strategies because of the balanced mortality after WNV infection (Morrey et al., 2004a). The animals develop an encephalitis with neurological symptoms and approximately 50% do not survive the infection, if left untreated. Outbread Syrian golden hamsters (female, seven to eleven weeks) are used for the experiments and challenged s.c. with $10^4$ $TCID_{50}$ of the NY99 strain of WNV. For establishment of the model and evaluation of the efficacy of peripheral vs. intraventricular administration of the human monoclonal antibodies of the invention and interferon-alpha, animals are given the antibodies with or without interferon-alpha (Infergen™, Intermune, Inc., Brisbane, Calif., USA): (a) prophylactically intraperitoneally (i.p.) 24 hours pre-challenge, (b) as post-exposure prophylaxis/early systemical therapy i.p. at day 1, 2, 3, etc., post infection until first encephalitic symptoms appear (usually at day 6), and (c) as early intraventricular (i.v.) therapy at onset of encephalitic symptoms. The experimental details of the above treatments are:

(a) prophylactic passive immunization: antibodies are administered at a dose range of 30, 100, 300, 1000, and 3000 μg/kg 24 hours pre-challenge. The endpoint is mortality. Preferably, the mortality is reduced by at least 90%.

(b) post-exposure prophylaxis (PEP)/early therapy of infection: antibodies are administered at a dose range of 1×, 10×, and 100× the minimal prophylactic dose leading to a 90% reduction of mortality at day 1 post infection, day 2 post infection, day 3 post infection, etc., until the first day of encephalitic symptoms. The endpoint is mortality. Preferably, the mortality is reduced by at least 50%.

(c) Early therapy of established encephalitis: antibodies are administered systemically at a dose of 10× the minimal systemical therapeutic dose for 50% mortality reduction at the latest time point of early therapy of infection. Furthermore, antibodies are administered intraventricularly at a dose of 1× and 10× the minimal systemical therapeutic dose for 50% mortality reduction at the latest time point of early therapy of infection. The antibodies are administered the first day of severe neurological symptoms (normally day 6). The endpoints are (a) mortality, (b) viral load in cerebrospinal fluid (CSF), (c) neurological symptoms and behavioral changes, and (d) persistent infection, as measured by immunostaining and RT/PCR. Preferably, the mortality is reduced by at least 50%, the viral load in the CSF is reduced by at least 99%, the neurological and behavioral sequelae in treated animals is significantly reduced and no persistent infection does occur. The above treatments are performed without interferon-alpha and with interferon-alpha at concentrations of 0.5 and 5 μg/kg. For the intraventricular administration of the antibodies a procedure for stereotactically guided injections into the brain ventricles using a Hamilton syringe is developed. Recently, a stereotactic atlas has been published that helps to identify the appropriate coordinates (Morin & Wood, 2001). Furthermore, a technique is developed that allows to take samples of cerebrospinal fluid via a guiding cannula that has been implanted into the lateral ventricle.

Neuropathological changes due to the infection are evaluated in surviving and non-surviving animals of the treatment and control group at different time points. Viral antigen will be detected in different regions of the brain known to be preferentially infected by WNV (e.g., cerebellum, brain stem, deep gray nuclei), using immunohistochemistry and quantitative RT/PCR. Because the virus targets Purkinje cells in the cerebellum which leads to neurological deficits, a range of neurological tests are established for assessing the behavioral effects of WNV infection. A strong predictor of mortality in hamster is the ramp-climbing test (see Morrey et al. 2004b). Other tests are used to follow the dynamics of these behavioral disturbances, and to assess the long-term effects of treatments. These techniques have been established for studying the effects of the occlusion of the middle cerebral artery (MCA-O; e.g., van der Staay et al., 1996a,b), and to assess the behavioral effects of hemorrhage (subdural hematoma) in rodents (e.g., Eijkenboom et al., 2000). One of the tests expected to be sensitive to virus-induced infections is the analysis of walking patterns (see Leyssen et al., 2003). Because hippocampal and cortical areas may be affected through apoptotic processes, the long term cognitive performance of untreated survivors, treated animals and uninfected control animals is also investigated. Furthermore, the cone-field spatial discrimination task, in which an animal must learn to collect food from four out of 16 alternative locations, is used for testing spatial cognition. Sample size considerations for endpoint mortality based on $\chi 2$ testing are shown in Table 21.

Sample size considerations for other tests are shown in Tables 22 and 23. Differences among treatment groups in weight, ramp climbing and viral titers in cerebrospinal fluid are analyzed using the t-test. Survival data are analyzed using the Wilcoxon test.

Example 14

In Vivo Protection by Affinity Maturated Anti-WNV Monoclonal Antibody CR5080 from Lethal WNV Infection in a Murine Challenge Model The murine challenge model was essentially as described above (see Example 8) except animals were inoculated intraperitoneally (i.p.) with 100-times the viral dose resulting in 50% survival ($LD_{50}$) of WNV strain USA99. To establish the dose protection relationship of CR5080 it was titrated along with the parent antibody CR4374 in the mouse model using doses of 1, 0.3, 0.1, 0.03, 0.01, 0.003 and 0.001 mg/kg. A negative control antibody binding an irrelevant antigen was included as a control at a dose 1 mg/kg.

Figure 7:
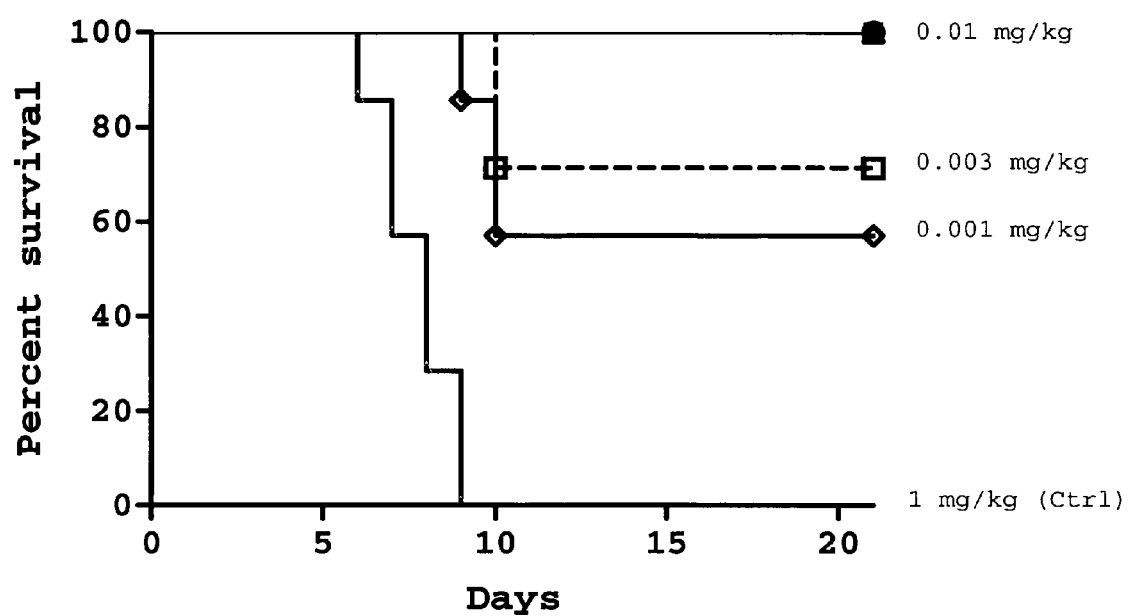
FIG. 7 shows the titration of anti-WNV monoclonal antibody CR5080 in a murine WNV challenge model. From top to bottom titration of anti-WNV monoclonal antibody CR5080 using doses of 0.01, 0.003, and 0.001 mg/kg and titration with a control antibody at a concentration of 1 mg/kg are shown. On the X-axis days are shown and on the Y-axis the survival probability (%) is represented.

As shown in FIG. 7, the antibody CR5080 is 100% protective at a dose of 0.01 mg/kg. The doses 1, 0.3, 0.1 and 0.03 mg/kg were also 100% protective (data not shown). FIG. 7 also shows that there is a direct correlation between dose and protective capacity. The parental antibody CR4374 that was included in this study was found to be fully protective at a dose of 0.1 mg/kg (data not shown). The 50% protective dose calculated by probit regression analysis for CR5080 is 0.00075 mg/kg compared to 0.011 mg/kg for CR4374. Thus, in both the in vitro neutralization assay and in vivo protection model the affinity maturated variant CR5080 is an order of magnitude more potent than its parent antibody CR4374. The consistency of the model is demonstrated by the fact that the 50% protective dose for CR4374 in this experiment (0.011 mg/kg) is similar to that calculated in Example 8 (0.013 mg/kg).

Example 15

Epitope Fine Mapping of the Antibodies CR4374 and CR5080

To map the location of the binding epitope of CR4374 and CR5080 more precisely within domain III of the WNV E protein, neutralization escape variants were generated. WNV strain USA99 (100 PFU) in MM (maintenance medium; DMEM, 5% FCS with antibiotic) was mixed one to one with CR4374 to a final concentration equal to the PRNT95 (1 µg/ml) and incubated for one hour at 37° C. The mixture was added to Vero-E6 cells grown to sub-confluency in GM (growth medium; 10% FCS in DMEM with 1% penicillin/streptomycin) in six-well flat bottom plates at 37° C./10% $CO_2$ in a humidified chamber. After a further hour of incubation the inoculum was aspirated and replaced with GM containing the antibody CR4374 at the selecting concentration of PRNT95 (1 µg/ml). Three days post infection potential escape variants were passaged. Supernatant (50 µl) was removed from each well and incubated with 1 ml of MM containing 1 µg/ml of CR4374 for one hour at 37° C./10% $CO_2$. The mixture was then inoculated onto cells (six-well plate) for one hour, removed and replaced with fresh GM containing 1 µg/ml of CR4374 and incubated further. The virus preparation was passaged a total of three times. To generate plaques for purification, supernatant (50 µl) was mixed with 1 ml of MM, placed on Vero-E6 cells and kept at 37° C./10% $CO_2$ for one hour. The inoculum was replaced with 3 ml of 1.8% agarose/2x growth medium and incubated for 2 days at 37° C./10% $CO_2$. Then, an overlay of 1% agarose/neutral red 0.025% was added for visualization of the plaques. The above attempt failed to generate any escape mutants and therefore the procedure was repeated, but this time with a lower concentration of CR4374 (0.75 µg/ml). However, this attempt also failed. The third experiment was done with 0.5 µg/ml of CR4374 and resulted in a small number of plaques that could be picked. Six of these were individually mixed with 1 ml MM each and used to infect fresh Vero-E6 cells on a six-well plate. After three days, supernatant was harvested from each well and checked for infection by indirect immunofluorescence. Each virus was further amplified in 75 $cm^2$ flasks containing confluent Vero-E6 cells for three to four days. After harvest, the supernatant was aliquoted and kept at –70° C. until further use. The escape viruses were titrated and the neutralizing potency of CR4374 at PRNT95 (i.e., 1 µg/ml) against 100 PFU of each virus was determined as described in Example 10. The experiment was done in duplicate and as shown in Table 24, five out of six of the escape viruses met the predefined cut off of less than or equal to 20% neutralization by CR4374, although none of them were completely resistant to neutralization. This was consistent with the difficulty in generating the escape viruses and may indicate that mutation of the binding epitope of CR4374 is inherently difficult for the virus. Next, viral RNA was extracted using organic phase separation and subsequent ethanol precipitation. The obtained RNA was dissolved in RNAse free water and the concentration was determined by OD260 nm measurement. cDNA was prepared as described in Example 1 and amplified with the sense primer WN-313F (SEQ ID NO:248) and the antisense primers WN-2588R (SEQ ID NO:249) and WN1617R (SEQ ID NO:250). The products were cloned into a standard vector and the nucleotide sequences of the prM and envelope protein were determined according to standard techniques known to the skilled person in the art using the overlapping primer set WN-1242F (SEQ ID NO:251), WN-708F (SEQ ID NO:252), WN-1026F (SEQ ID NO:253), WN-1449F (SEQ ID NO:254), WN-1991F (SEQ ID NO:255), WN-315F (SEQ ID NO:256), WN-2585R (SEQ ID NO:257), WN-2086R (SEQ ID NO:258), WN-1560R (SEQ ID NO:259), WN-1049R (SEQ ID NO:260), WN-741R (SEQ ID NO:261). Comparison of the escape viruses' sequences compared to USA99 revealed that the five escape viruses each contained a non-silent substitution of cytosine to uracil at position 1601 of the prM/E nucleotide sequence. This resulted in a substitution at position E365 of alanine to valine in the amino acid sequence. This residue is exposed as part of a peptide loop on the lateral face of domain III and would therefore be accessible for antibody binding. Moreover, this loop is one of four exposed peptide loops on domain III that make up a region predicted to harbor the cell attachment site of the virus. Thus, antibody binding in this region may neutralize the virus by blocking virus attachment to the cell surface.

Figure 8:
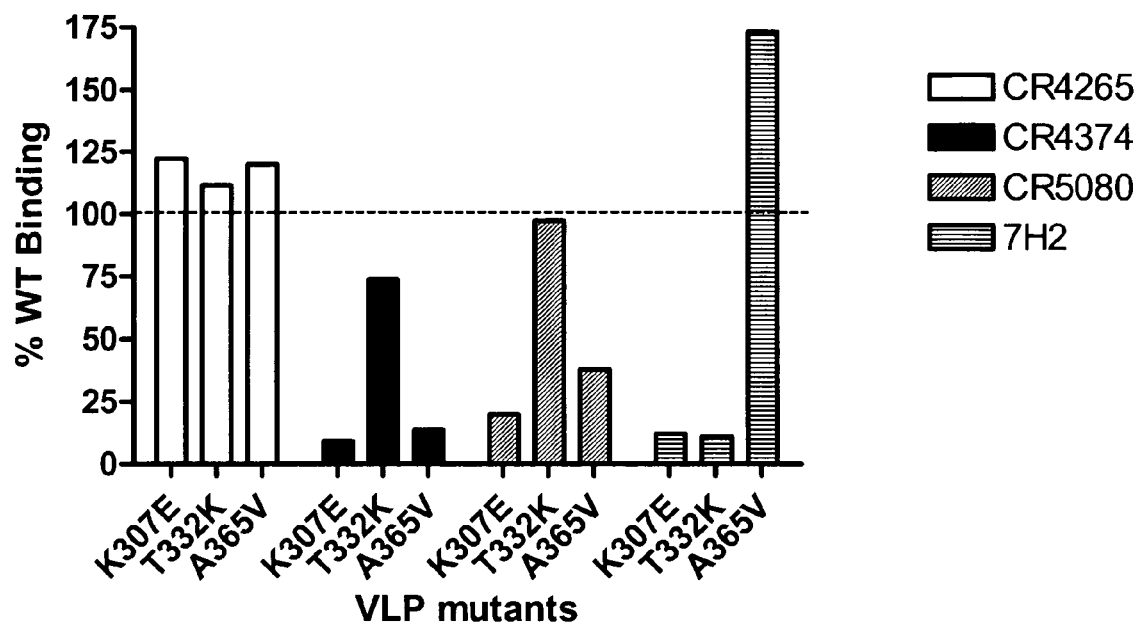
FIG. 8 shows four antibodies, CR4265 (white bars, bars 1-3 counting from the left side), CR4374 (black bars, bars 4-6 counting from the left side), CR5080 (bars having diagonal lines, bars 7-9 counting from the left side) and 7H2 (bars having horizontal lines, bars 10-12 counting from the left side) that were titrated for binding to wild-type and mutant VLPs by ELISA. Binding activity was normalized to wild-type binding levels (% WT binding).

To confirm that CR5080 as well as CR4374 binds in this region of the envelope protein and to determine the contribution of adjacent peptide loops of domain III in the binding epitope, various VLP mutants were constructed and produced. More specifically a VLP with the mutation identified in the CR4374 escape viruses (A365V) was generated along with two other mutants with the substitutions K307E and T332K. Both of these residues appear on adjacent solvent exposed peptide loops of domain III and their mutation has been reported to abrogate the neutralizing activity of potent domain III binding monoclonal antibodies (see Beasly et al. (2002); Oliphant, et al. (2005)). Mutations were introduced into the VLP construct (described in Example 2) using a QuickChange II kit (Stratagene) in combination with the primers K307E forward (SEQ ID NO:262), K307E reverse (SEQ ID NO:263), T332K forward (SEQ ID NO:264), T332K reverse (SEQ ID NO:265), A365V forward (SEQ ID NO:266) and A365V reverse (SEQ ID NO:267) according to the manufacturer's instructions. After PCR the resulting fragment was cloned back into the original expression vector using the restriction sites BamHI and PmeI. The constructs were verified by sequencing and the mutant and wild-type VLPs were produced and purified as described in Example 2. Four antibodies were titrated for binding to the wild-type and mutant VLP by ELISA as described in Example 3 and binding activity normalized to wild-type (WT) binding levels. As shown in FIG. 8, antibody CR4265, included as a positive control as its binding site is outside domain III, bound equally well to all mutants. As expected from the escape viruses' data binding of CR4374 to the mutant A365V was reduced dramatically compared to wild-type. The mutation K307E also blocked CR4374 binding, but about 75% binding was still retained with mutation T332K. The same pattern of binding was observed with CR5080, however, the relative intensity of binding was higher probably due to its higher binding affinity. Binding to A365V was about 37% of binding to wild-type, suggesting that it might retain significant neutralizing activity against viruses with this mutation. The potent murine monoclonal 7H2, like CR4374 and CR5080, did not bind to the mutant K307E but remarkably bound almost two-fold better to mutant A365V than to wild-type. The reason for this difference is unknown. Most significantly, however was the lack of binding of 7H2 to the mutant T332K, which confirms previous reports (see Beasly et al. (2002)). In comparison, CR5080 bound this mutant equally well as wild-type and CR4374 still bound about 75% compared to wild-type. Thus, based on this data CR4374 (and also CR5080) and 7H2 are likely to bind overlapping but different epitopes. Consequently, CR4374 and CR5080 can be used to neutralize virus strains (e.g., lineage II WNV strain H-442) that are not neutralized by 7H2, as they comprise the mutation T332K (see Beasly et al. (2002)). In a prophylactic setting the combination of 7H2 or a similar antibody and CR4374 (or CR5080) might dramatically increase the odds of a

TABLE 1

Human lambda chain variable region primers (sense).

| Primer name | Primer nucleotide sequence | SEQ ID NO: |
|---|---|---|
| HuVλ1A | 5'-CAGTCTGTGCTGACT CAGCCACC-3' | SEQ ID NO:152 |
| HuVλ1B | 5'-CAGTCTGTGYTGACG CAGCCGCC-3' | SEQ ID NO:153 |
| HuVλ1C | 5'-CAGTCTGTCGTGACG CAGCCGCC-3' | SEQ ID NO:154 |
| HuVλ2 | 5'-CARTCTGCCCTGACT CAGCCT-3' | SEQ ID NO:155 |
| HuVλ3A | 5'-TCCTATGWGCTGACT CAGCCACC-3' | SEQ ID NO:156 |
| HuVλ3B | 5'-TCTTCTGAGCTGACT CAGGACCC-3' | SEQ ID NO:157 |
| HuVλ4 | 5'-CACGTTATACTGACT CAACCGCC-3' | SEQ ID NO:158 |

TABLE 1-continued

Human lambda chain variable region primers (sense).

| Primer name | Primer nucleotide sequence | SEQ ID NO: |
|---|---|---|
| HuVλ5 | 5'-CAGGCTGTGCTGACT CAGCCGTC-3' | SEQ ID NO:159 |
| HuVλ6 | 5'-AATTTTATGCTGACT CAGCCCCA-3' | SEQ ID NO:160 |
| HuVλ7/8 | 5'-CAGRCTGTGGTGACY CAGGAGCC-3' | SEQ ID NO:161 |
| HuVλ9 | 5'-CWGCCTGTGCTGACT CAGCCMCC-3' | SEQ ID NO:162 |

TABLE 2

Human kappa chain variable region primers (sense).

| Primer name | Primer nucleotide sequence | SEQ ID NO: |
|---|---|---|
| HuVκ1B | 5'-GACATCCAGWTGACCC AGTCTCC-3' | SEQ ID NO:163 |
| HuVκ2 | 5'-GATGTTGTGATGACT CAGTCTCC-3' | SEQ ID NO:164 |
| HuVκ3 | 5'-GAAATTGTGWTGACR CAGTCTCC-3' | SEQ ID NO:165 |
| HUVκ4 | 5'-GATATTGTGATGACC CACACTCC-3' | SEQ ID NO:166 |
| HuVκ5 | 5'-GAAACGACACTCACG CAGTCTCC-3' | SEQ ID NO:167 |
| HuVκ6 | 5'-GAAATTGTGCTGACTC AGTCTCC-3' | SEQ ID NO:168 |

TABLE 3

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO: |
|---|---|---|
| HuVκ1B-SalI | 5'-TGAGCACACAGGTCGACG GACATCCAGWTGACCCAGTCT CC-3' | SEQ ID NO:169 |
| HuVκ2-SalI | 5'-TGAGCACACAGGTCGACG GATGTTGTGATGACTCAGTCT CC-3' | SEQ ID NO:170 |
| HuVκ3B-SalI | 5'-TGAGCACACAGGTCGACG GAAATTGTGWTGACRCAGTCT CC-3' | SEQ ID NO:171 |
| HuVκ4B-SalI | 5'-TGAGCACACAGGTCGACG GATATTGTGATGACCCACACT CC-3' | SEQ ID NO:172 |
| HuVκ5-SalI | 5'-TGAGCACACAGGTCGACG GAAACGACACTCACGCAGTCT CC-3' | SEQ ID NO:173 |

TABLE 3-continued

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO: |
| --- | --- | --- |
| HuVκ6-SalI | 5'-TGAGCACACAGGTCGACG GAAATTGTGCTGACTCAGTCT CC-3' | SEQ ID NO:174 |
| HuJκ1-NotI | 5'-GAGTCATTCTCGACTTGC GGCCGCACGTTTGATTTCCAC CTTGGTCCC-3' | SEQ ID NO:175 |
| HuJκ2-NotI | 5'-GAGTCATTCTCGACTTGC GGCCGCACGTTTGATCTCCAG CTTGGTCCC-3' | SEQ ID NO:176 |
| HuJκ3-NotI | 5'-GAGTCATTCTCGACTTGC GGCCGCACGTTTGATATCCAC TTTGGTCCC-3' | SEQ ID NO:177 |
| HuJκ4-NotI | 5'-GAGTCATTCTCGACTTGC GGCCGCACGTTTGATCTCCAC CTTGGTCCC-3' | SEQ ID NO:178 |
| HuJκ5-NotI | 5'-GAGTCATTCTCGACTTGC GGCCGCACGTTTAATCTCCAG TCGTGTCCC-3' | SEQ ID NO:179 |
| HuVλ1A-SalI | 5'-TGAGCACACAGGTCGACG CAGTCTGTGCTGACTCAGCCA CC-3' | SEQ ID NO:180 |
| HuVλ1B-SalI | 5'-TGAGCACACAGGTCGACG CAGTCTGTGYTGACGCAGCCG CC-3' | SEQ ID NO:181 |
| HuVλ1C-SalI | 5'-TGAGCACACAGGTCGACG CAGTCTGTCGTGACGCAGCCG CC-3' | SEQ ID NO:182 |
| HuVλ2-SalI | 5'-TGAGCACACAGGTCGACG CARTCTGCCCTGACTCAGC CT-3' | SEQ ID NO:183 |
| HuVλ3A-SalI | 5'-TGAGCACACAGGTCGACG TCCTATGWGCTGACTCAGCCA CC-3' | SEQ ID NO:184 |
| HuVλ3B-SalI | 5'-TGAGCACACAGGTCGACG TCTTCTGAGCTGACTCAGGAC CC-3' | SEQ ID NO:185 |
| HuVλ4-SalI | 5'-TGAGCACACAGGTCGACG CACGTTATACTGACTCAACCG CC-3' | SEQ ID NO:186 |
| HuVλ5-SalI | 5'-TGAGCACACAGGTCGACG CAGGCTGTGCTGACTCAGCCG TC-3' | SEQ ID NO:187 |
| HuVλ6-SalI | 5'-TGAGCACACAGGTCGACG AATTTTATGCTGACTCAGCCC CA-3' | SEQ ID NO:188 |
| HuVλ7/8-SalI | 5'-TGAGCACACAGGTCGACG CAGRCTGTGGTGACYCAGGAG CC-3' | SEQ ID NO:189 |
| HuVλ9-SalI | 5'-TGAGCACACAGGTCGACG CWGCCTGTGCTGACTCAGCCM CC-3' | SEQ ID NO:190 |
| HuJλ1-NotI | 5'-GAGTCATTCTCGACTTGC GGCCGCACCTAGGACGGTGAC CTTGGTCCC-3' | SEQ ID NO:191 |
| HuJλ2/3-NotI | 5'-GAGTCATTCTCGACTTGC GGCCGCACCTAGGACGGTCAG CTTGGTCCC-3' | SEQ ID NO:192 |
| HuJλ4/5-NotI | 5'-GAGTCATTCTCGACTTGC GGCCGCACYTAAAACGGTGAG CTGGGTCCC-3' | SEQ ID NO:193 |

TABLE 4

Distribution of the different light chain products over the ten fractions.

| Light chain products | Number of alleles | Fraction number | alleles/fraction |
| --- | --- | --- | --- |
| Vk1B/Jk1-5 | 19 | 1 and 2 | 9.5 |
| Vk2/Jk1-5 | 9 | 3 | 9 |
| Vk3B/Jk1-5 | 7 | 4 | 7 |
| Vk4B/Jk1-5 | 1 | 5 | 5 |
| Vk5/Jk1-5 | 1 | | |
| Vk6/Jk1-5 | 3 | | |
| Vλ1A/Jl1-3 | 5 | 6 | 5 |
| Vλ1B/Jl1-3 | | | |
| Vλ1C/Jl1-3 | | | |
| Vλ2/Jl1-3 | 5 | 7 | 5 |
| Vλ3A/Jl1-3 | 9 | 8 | 9 |
| Vλ3B/Jl1-3 | | | |
| Vλ4/Jl1-3 | 3 | 9 | 5 |
| Vλ5/Jl1-3 | 1 | | |
| Vλ6/Jl1-3 | 1 | | |
| Vλ7/8/Jl1-3 | 3 | 10 | 6 |
| Vλ9/Jl1-3 | 3 | | |

TABLE 5

Human IgG heavy chain variable region primers (sense).

| Primer name | Primer nucleotide sequence | SEQ ID NO: |
| --- | --- | --- |
| HuVH1B/7A | 5'-CAGRTGCAGCTGGTG CARTCTGG-3' | SEQ ID NO:194 |
| HuVH1C | 5'-SAGGTCCAGCTGGTR CAGTCTGG-3' | SEQ ID NO:195 |
| HuVH2B | 5'-SAGGTGCAGCTGGTG GAGTCTGG-3' | SEQ ID NO:196 |
| HuVH3B | 5'-SAGGTGCAGCTGGTG GAGTCTGG-3' | SEQ ID NO:197 |

TABLE 5-continued

Human IgG heavy chain variable region primers (sense).

| Primer name | Primer nucleotide sequence | SEQ ID NO: |
|---|---|---|
| HuVH3C | 5'-GAGGTGCAGCTGGTGGAGWCYGG-3' | SEQ ID NO:198 |
| HuVH4B | 5'-CAGGTGCAGCTACAGCAGTGGGG-3' | SEQ ID NO:199 |
| HuVH4C | 5'-CAGSTGCAGCTGCAGGAGTCSGG-3' | SEQ ID NO:200 |
| HuVH5B | 5'-GARGTGCAGCTGGTGCAGTCTGG-3' | SEQ ID NO:201 |
| HuVH6A | 5'-CAGGTACAGCTGCAGCAGTCAGG-3' | SEQ ID NO:202 |

TABLE 6

Human IgG heavy chain variable region primers extended with SfiI/NcoI restriction sites (sense) and human IgG heavy chain J-region primers extended with XhoI/BstEII restriction sites (anti-sense).

| Primer name | Primer nucleotide sequence | SEQ ID NO: |
|---|---|---|
| HuVH1B/7A-SfiI | 5'-GTCCTCGCAACTGCGGCCCAGCCGGCCATGGCCCAGRTGCAGCTGGTGCARTCTGG-3' | SEQ ID NO:203 |
| HuVH1C-SfiI | 5'-GTCCTCGCAACTGCGGCCCAGCCGGCCATGGCCSAGGTCCAGCTGGTRCAGTCTGG-3' | SEQ ID NO:204 |
| HuVH2B-SfiI | 5'-GTCCTCGCAACTGCGGCCCAGCCGGCCATGGCCCAGRTCACCTTGAAGGAGTCTGG-3' | SEQ ID NO:205 |
| HuVH3B-SfiI | 5'-GTCCTCGCAACTGCGGCCCAGCCGGCCATGGCCSAGGTGCAGCTGGTGGAGTCTGG-3' | SEQ ID NO:206 |
| HuVH3C-SfiI | 5'-GTCCTCGCAACTGCGGCCCAGCCGGCCATGGCCGAGGTGCAGCTGGTGGAGWCYGG-3' | SEQ ID NO:207 |
| HuVH4B-SfiI | 5'-GTCCTCGCAACTGCGGCCCAGCCGGCCATGGCCCAGGTGCAGCTACAGCAGTGGGG-3' | SEQ ID NO:208 |
| HuVH4C-SfiI | 5'-GTCCTCGCAACTGCGGCCCAGCCGGCCATGGCCCAGSTGCAGCTGCAGGAGTCSGG-3' | SEQ ID NO:209 |
| HuVH5B-SfiI | 5'-GTCCTCGCAACTGCGGCCCAGCCGGCCATGGCCGARGTGCAGCTGGTGCAGTCTGG-3' | SEQ ID NO:210 |
| HuVH6A-SfiI | 5'-GTCCTCGCAACTGCGGCCCAGCCGGCCATGGCCCAGGTACAGCTGCAGCAGTCAGG-3' | SEQ ID NO:211 |
| HuJH1/2-XhoI | 5'-GAGTCATTCTCGACTCGAGACGGTGACCAGGGTGCC-3' | SEQ ID NO:212 |
| HuJH3-XhoI | 5'-GAGTCATTCTCGACTCGAGACGGTGACCATTGTCCC-3' | SEQ ID NO:213 |
| HuJH4/5-XhoI | 5'-GAGTCATTCTCGACTCGAGACGGTGACCAGGGTTCC-3' | SEQ ID NO:214 |
| HuJH6-XhoI | 5'-GAGTCATTCTCGACTCGAGACGGTGACCGTGGTCCC-3' | SEQ ID NO:215 |

TABLE 7

Binding of single-chain (scFv) phage antibodies to West Nile virus (WNV), recombinant WNV E protein, FBS, and rabies virus as measured by ELISA at 492 nm).

| Name phage antibody | WN virus | WNV E protein | FBS (5%) | Rabies virus |
|---|---|---|---|---|
| SC04-271 | 0.984 | 0.608 | ND | ND |
| SC04-274 | 0.961 | 0.496 | ND | ND |
| SC04-283 | 1.205 |

TABLE 8-continued

Data of the WNV specific single-chain Fvs.

| Name scFv | SEQ ID NO of nucl. sequence | SEQ ID NO of amino acid sequence* | HCDR3 (SEQ ID NO:) | VH-locus | VL-locus |
|---|---|---|---|---|---|
| SC04-283 | 65 | 66 (Vh 1-130; Vl 147-253) | LTFRRGYSGSDSF LPPGDFDY (SEQ ID NO:3) | 5-51 (DP-73) | Vk I (L12) |
| SC04-289 | 67 | 68 (Vh 1-125; Vl 142-250) | DVVGVGASDYYY YMDV (SEQ ID NO:4) | 5-51 (DP-73) | Vk III (L2 - DPK21) |
| SC04-299 | 69 | 70 (Vh 1-124; Vl 141-250) | ESGGPIWYKYYG VDV (SEQ ID NO:5) | 3-30 (DP-49) | Vl 1 (1a - Vl-11) |
| SC04-311 | 71 | 72 (Vh 1-119; Vl 136-245) | GYNSGHYFDY (SEQ ID NO:6) | 3-30 (DP-49) | Vl 1 (1b- Vl-19) |
| SC04-325 | 73 | 74 (Vh 1-117; Vl 134-246) | GGMATTPGLDY (SEQ ID NO:7) | 1-69 (DP-10) | Vk IV (B3- DPK24) |
| SC04-353 | 75 | 76 (Vh 1-127; Vl 144-250) | DFWSGYSMVDSY YYYMDV (SEQ ID NO:8) | 3-30 (DP-49) | Vk III (A27 - DPK22) |
| SC04-361 | 77 | 78 (Vh 1-130; Vl 147-259) | LRGPYYDFWNGY RETHDAFNV (SEQ ID NO:9) | 5-51 (DP-73) | Vk IV (B3 - DPK24) |
| SC04-374 | 79 | 80 (Vh 1-130; Vl 147-257) | HRYYDISGYYRLF SDAFDI (SEQ ID NO: 10) | 2-05 | Vl 1 (1e- Vl-13) |

*between brackets the amino acids making up the heavy chain variable region (VH) and the light chain variable region (VL) is shown

TABLE 9

Data of the CDR regions of the WNV specific single-chain Fvs.

| Name scFv | HCDR1 (SEQ ID NO:) | HCDR2 (SEQ ID NO:) | LCDR1 (SEQ ID NO:) | LCDR2 (SEQ ID NO:) | LCDR3 (SEQ ID NO:) |
|---|---|---|---|---|---|
| SC04-271 | 21 | 31 | 41 | 51 | 11 |
| SC04-274 | 22 | 32 | 42 | 52 | 12 |
| SC04-283 | 23 | 33 | 43 | 53 | 13 |
| SC04-289 | 24 | 34 | 44 | 54 | 14 |
| SC04-299 | 25 | 35 | 45 | 55 | 15 |
| SC04-311 | 26 | 36 | 46 | 56 | 16 |
| SC04-325 | 27 | 37 | 47 | 57 | 17 |
| SC04-353 | 28 | 38 | 48 | 58 | 18 |
| SC04-361 | 29 | 39 | 49 | 59 | 19 |
| SC04-374 | 30 | 40 | 50 | 60 | 20 |

TABLE 10

Binding of IgG1 antibodies to WNV as measured by ELISA (OD 492 nm).

| Antibody | WN virus (dilution) | | |
|---|---|---|---|
| | 1:5* | 1:25 | 1:125 |
| CR4271 | 1.785 | 1.853 | 1.818 |
| CR4274 | 2.308 | 2.351 | 2.164 |
| CR4299 | 1.477 | 1.337 | 0.929 |
| CR4311 | 1.047 | 0.817 | 0.754 |
| CR4374 | 2.321 | 2.272 | 2.121 |
| pos ctrl | 2.092 | 2.122 | 2.135 |
| neg ctrl | 0.062 | 0.056 | 0.046 |

*dilution of the antibody

TABLE 11

Binding of IgG1 antibodies to WNV as measured by ELISA (OD 492 nm).

Antibody Concentration (µg/ml)

| Ab | 20.000 | 10.000 | 5.000 | 2.500 | 1.250 | 0.630 | 0.310 | 0.160 | 0.078 | 0.039 | 0.000 |
|---|---|---|---|---|---|---|---|---|---|---|---|
| CR4271 | 1.554 | 1.632 | 1.585 | 1.488 | 1.560 | 1.580 | 1.449 | 1.414 | 1.199 | 0.761 | 0.003 |
| CR4274 | 1.698 | 1.645 | 1.538 | 1.492 | 1.538 | 1.519 | 1.378 | 1.146 | 0.841 | 0.448 | 0.003 |
| CR4283 | 1.678 | 1.645 | 1.761 | 1.621 | 1.633 | 1.618 | 1.542 | 1.564 | 1.351 | 1.019 | 0.003 |
| CR4289 | ND | 0.752 | 0.586 | 0.492 | 0.415 | 0.351 | 0.313 | 0.250 | 0.209 | 0.147 | 0.003 |
| CR4299 | 1.193 | 1.125 | 1.073 | 1.031 | 0.977 | 0.891 | 0.756 | 0.610 | 0.446 | 0.227 | 0.003 |
| CR4311 | 0.852 | 0.773 | 0.627 | 0.527 | 0.444 | 0.352 | 0.236 | 0.174 | 0.105 | 0.044 | 0.003 |
| CR4325 | 1.545 | 1.656 | 1.444 | 1.245 | 1.048 | 0.845 | 0.597 | 0.421 | 0.269 | 0.132 | 0.003 |
| CR4353 | ND | 1.567 | 1.554 | 1.432 | 1.418 | 1.330 | 1.169 | 1.069 | 0.734 | 0.595 | 0.003 |
| CR4374 | 1.687 | 1.723 | 1.645 | 1.577 | 1.499 | 1.451 | 1.242 | 0.997 | 0.729 | 0.458 | 0.003 |
| Neg. control | 0.051 | ND | ND | ND | ND | ND | ND | ND | ND | ND | ND |

TABLE 12

Potency of the anti-WNV antibodies in the 66% neutralizing antibody titer assay.

| Antibody name | µg/ml |
|---|---|
| CR4271 | 13.50 |
| CR4274 | 11.00 |
| CR4283 | 23.44 |
| CR4289 | 10.13 |
| CR4299 | 3.00 |
| CR4311 | 20.00 |
| CR4325 | 5.25 |
| CR4353 | 2.11 |
| CR4361 | 2.50 |
| CR4374 | 0.34 |

TABLE 13

Protection from lethal WNV challenge in mice by anti-WNV monoclonal antibodies.

| Antibody (15 mg/kg) | Surviving animals |
|---|---|
| CR4271 | 3/5 |
| CR4274 | 0/5 |
| CR4283 | 1/5 |
| CR4289 | 1/5 |
| CR4299 | 0/5 |
| CR4311 | 1/5 |
| CR4325 | 1/5 |
| CR4353 | 3/4* |
| CR4361 | 1/5 |
| CR4374 | 5/5 |
| 7H2 | 5/5 |
| Negative Control IgG1 | 0/5 |

*Four instead of five mice tested due to injection error as measured by IgG1 levels in serum of mouse taken 24 hours after antibody injection.

TABLE 14

Probit analysis of the protective activity of human anti-WNV IgG1 in a murine lethal challenge model

| Antibody | 50% protection (µg/kg) | 95% protection (µg/kg) |
|---|---|---|
| CR4374 | 12.9 | 270 |
| CR4353 | 357 | 7475 |

TABLE 15

Neutralizing potency against West Nile virus strain USA99b as measured by PRNT.

| Antibody | PRNT50 (95% CI) (µg/ml) | PRNT90 (95% CI) (µg/ml) |
|---|---|---|
| CR4271 | >100 | NA |
| CR4274 | >100 | NA |
| CR4283 | >100 | NA |
| CR4289 | 2.62 (1.16-6.10) | 37.4 (13.7-241) |
| CR4299 | 0.78 (0.28-1.82) | 10.3 (3.92-67.7) |
| CR4311 | 2.91 (2.26-3.74) | 39.6 (27.3-62.3) |
| CR4325 | 1.45 (0.66-3.05) | 15.8 (6.58-75.6) |
| CR4353 | 0.026 (0.012-0.045) | 36.4 (19.1-82.6) |
| CR4361 | 2.03 (0.90-4.34) | >100 |
| CR4368 | 2.05 (1.07-3.76) | >100 |
| CR4374 | 0.18 (0.17-0.20) | 0.95 (0.82-1.12) |
| CRM4374 | <0.1 | <0.1 |
| CR4375 | 0.17 (0.12-0.23) | 2.29 (1.59-3.67) |
| 7H2 | 0.0030 (0.0020-0.0040) | 0.026 (0.020-0.037) |
| 6B6C-1 | 0.70 (0.37-1.55) | 6.32 (2.42-106) |
| 5H10 | 0.016 (0.009-0.024) | 0.096 (0.074-0.140) |
| 3A3 | 0.0062 (0.0044-0.0079) | 0.042 (0.031-0.067) |

TABLE 16

Description of WNV strains used.

| Name | Strain | Origin | Year | Source | Lineage | CHOb* |
|---|---|---|---|---|---|---|
| USA99b | 385-99 | United States | 1999 | Bird | I | + |
| FRA00 | PaAn001 | France | 2000 | Horse | I | + |
| TUN97 | paH001 | Tunisia | 1997 | Human | I | + |
| SEN90 | ArD-76104 | Senegal | 1990 | Mosquito | II | − |

TABLE 16-continued

Description of WNV strains used.

| Name | Strain | Origin | Year | Source | Lineage | CHOb* |
|---|---|---|---|---|---|---|
| CAR82 | ArB3573/82 | Central African Republic | 1982 | Tick | II | + |
| MAD78 | DakAnMg798 | Madagascar | 1978 | Bird | II | − |

*CHOb means glycosylation

TABLE 17

Neutralizing potency of CR4374 against lineage I and II strains of WNV.

| Virus | PRNT50 (95% CI) | PRNT90 (95% CI) |
|---|---|---|
| USA99b | 0.17 (0.11-0.25) | 0.82 (0.50-1.77) |
| TUN97 | 0.03 (0.02-0.04) | 0.22 (0.15-0.39) |
| FRA00 | 0.11 (0.08-0.15) | 1.36 (0.09-2.33) |
| SEN90 | 0.29 (0.11-0.67) | 3.92 (1.49-25.37) |
| MAD78 | 0.12 (0.09-0.16) | 4.12 (2.78-6.68) |
| CAR82 | 0.14 (0.08-0.22) | 2.90 (1.52-7.49) |

TABLE 18

Data of the affinity matured immunoglobulins.

| Name scFv | SEQ ID NO of nucl. sequence | SEQ ID NO of amino acid sequence* | VH-locus | VL-locus |
|---|---|---|---|---|
| SC05-074 | 228 | 229 (Vh 1-130; Vl 147-257) | 2-05 | Vl 1 (1e - V1-13) |
| SC05-080 | 230 | 231 (Vh 1-130; Vl 147-257) | 2-05 | Vl 1 (1e - V1-13) |
| SC05-085 | 232 | 233 (Vh 1-130; Vl 147-257) | 2-05 | Vl 1 (1e - V1-13) |
| SC05-088 | 234 | 235 (Vh 1-130; Vl 147-257) | 2-05 | Vl 1 (1e - V1-13) |

*between brackets the amino acids making up the heavy chain variable region (VH) and the light chain variable region (VL) is shown

TABLE 19

Data of the CDR regions of the affinity matured immunoglobulins.

| Name scFv | HCDR1 (SEQ ID NO:) | HCDR2 (SEQ ID NO:) | HCDR3 (SEQ ID NO:) | LCDR1 (SEQ ID NO:) | LCDR2 (SEQ ID NO:) | LCDR3 (SEQ ID NO:) |
|---|---|---|---|---|---|---|
| SC05-074 | 30 | 40 | 10 | 236 | 240 | 244 |
| SC05-080 | 30 | 40 | 10 | 237 | 241 | 245 |
| SC05-085 | 30 | 40 | 10 | 238 | 242 | 246 |
| SC05-088 | 30 | 40 | 10 | 239 | 243 | 247 |

TABLE 20

Neutralizing potency of affinity matured and IgM variants of CR4374 against WNV USA99b.

| Virus | PRNT50 (95% CI) (µg/ml) | PRNT90 (95% CI) (µg/ml) |
|---|---|---|
| CR5074 | 0.013 (0.009-0.020) | 0.067 (0.044-0.106) |
| CR5080 | 0.016 (0.010-0.023) | 0.080 (0.052-0.128) |
| CR5085 | 0.015 (0.010-0.023) | 0.077 (0.050-0.121) |
| CR5088 | 0.017 (0.011-0.026) | 0.087 (0.057-0.139) |
| CRM4374 | 0.011 (0.007-0.017) | 0.057 (0.037-0.091) |

TABLE 21

Number of animals that are required in each group to demonstrate the indicated difference in survival.

| Mortality in experimental group | Mortality in control group | |
|---|---|---|
| | 50% | 90% |
| 0% | 15 | 6 |
| 5% | 19 | 7 |
| 10% | 25 | 8 |
| 15% | 33 | 9 |
| 20% | — | 10 |

TABLE 22

Sample size considerations for the distance hamsters climbed in ten seconds.

| Number of animals | Difference in mean climbing distance between control and experimental groups |
|---|---|
| 6 | 72 cm |
| 10 | 53 cm |
| 15 | 42 cm |
| 19 | 37 cm |

Calculation based on SD of 40 cm

TABLE 23

Sample size considerations for Difference in mean weight change.

| Number of animals | Difference in mean weight change between control and experimental groups |
|---|---|
| 6 | 5.4% |
| 10 | 4.0% |
| 15 | 3.2% |
| 19 | 2.8% |

Calculation based on SD of 3%

TABLE 24

| Percentage neutralization of escape viruses by CR374 (1 μg/ml) | | | | | | |
|---|---|---|---|---|---|---|
| | Virus 1 | Virus 2 | Virus 3 | Virus 4 | Virus 5 | Virus 6 |
| Exp. 1 | 29.1 | 22.7 | 12.0 | 16.6 | 25.4 | 20.0 |
| Exp. 2 | 22.3 | 8.2 | 16.7 | 18.5 | 15.4 | 12.2 |
| Average | 26 | 15 | 14 | 18 | 20 | 16 |

REFERENCES

Anderson J. F., T. G. Andreadis, C. R. Vossbrinck, S. Tirrell, E. M. Wakem, R. A. French, A. E. Garmendia and H. J. Van Kruiningen (1999), Isolation of West Nile virus from mosquitoes, crows, and a Cooper's hawk in Connecticut. *Science* 286:2331-2333.

Anderson J. F. and J. J. Rahal (2002), Efficacy of interferon alpha-2b and ribavirin against WNV in vitro. *Emerg. Infect. Dis.* 8:107-108.

Beasley D. W. and A. D. Barrett (2002), Identification of neutralizing epitopes within structural domain III of the West Nile virus envelope protein. *J. Virol.* 76:13097-13100.

Beasley D. W., L. Li, M. T. Suderman and A. D. Barrett (2002), Mouse neuroinvasive phenotype of West Nile virus strains varies depending upon virus genotype. *Virology* 296:17-23.

Ben-Nathan D., S. Lustig, G. Tam, S. Robinzon, S. Segal and B. Rager-Zisman (2003), Prophylactic and therapeutic efficacy of human intravenous immunoglobulin in treating WNV infection in mice. *J. Infect. Dis.* 188:5-12.

Blitvich B. J., N. L. Marlenee, R. A. Hall, C. H. Calisher, R. A. Bowen, J. T. Roehrig, N. Komar, S. A. Langevin and B. J. Beaty (2003), Epitope-blocking enzyme-linked immunosorbent assays for the detection of serum antibodies to West Nile virus in multiple avian species. *J. Clin. Microbiol.* 41:1041-1047.

Boel E., S. Verlaan, M. J. Poppelier, N. A. Westerdaal, J. A. Van Strijp and T. Logtenberg (2000), Functional human monoclonal antibodies of all isotypes constructed from phage display library-derived single-chain Fv antibody fragments. *J. Immunol. Methods* 239:153-166.

Burton D. R. and C. F. Barbas (1994), Human antibodies from combinatorial libraries. *Adv. Immunol.* 57:191-280.

Chou T. C. and P. Talalay (1984), Quantitative analysis of dose-effect relationships: the combined effects of multiple drugs or enzyme inhibitors. *Adv. Enzyme Regul.* 22:27-55.

De Kruif J., L. Terstappen, E. Boel and T. Logtenberg (1995a), Rapid selection of cell subpopulation-specific human monoclonal antibodies from a synthetic phage antibody library. *Proc. Natl. Acad. Sci. USA* 92:3938.

De Kruif J., E. Boel and T. Logtenberg (1995b), Selection and application of human single-chain Fv antibody fragments from a semi-synthetic phage antibody display library with designed CDR3 regions. *J. Mol. Biol.* 248:97-105.

Eijkenboom M., I. Gerlach, R. Jork, D. Lowe and F. J. van der Staay (2000), Effects of subdural haematoma on sensorimotor functioning and spatial learning in rats. *Neuropharmacology* 39:817-834.

Gollins S. W. and J. S. Porterfield (1986), A new mechanism for the neutralization of enveloped viruses by antiviral antibody. *Nature* 321:244-246.

Huls G., I. J. Heijnen, E. Cuomo, J. van der Linden, E. Boel, J. van de Winkel and T. Logtenberg (1999), Antitumor immune effector mechanisms recruited by phage display-derived fully human IgG1 and IgA1 monoclonal antibodies. *Cancer Res.* 59:5778-5784.

Jia X. Y., T. Briese, I. Jordan, A. Rambaut, H. C. Chi, J. S. Mackenzie, R. A. Hall, J. Scherret and W. I. Lipkin (1999), Genetic analysis of West Nile New York 1999 encephalitis virus. *The Lancet* 354:1971-1972.

Kuno G., G. J. Chang, K. R. Tsuchiya, N. Karabatsos and C. B. Cropp (1998), Phylogeny of the genus *Flavivirus*. *J. Virol.* 72:73-83.

Lanciotti R. S., J. T. Roehrig, V. Deubel, J. Smith, M. Parker, K. Steele, B. Crise, K. E. Volpe, M. B. Crabtree, J. H. Scherret, R. A. Hall, J. S. MacKenzie, C. B. Cropp, B. Panigrahy, E. Ostlund, B. Schmitt, M. Malkinson, C. Banet, J. Weissman, N. Komar, H. M. Savage, W. Stone, T. McNamara and D. J. Gubler (1999), Origin of the West Nile virus responsible for an outbreak of encephalitis in the northeastern United States. *Science* 286:2333-2337.

Leyssen P., R. Croes, P. Rau, S. Heiland, E. Verbeken, R. Sciot, J. Paeshuyse, N. Charlier, E. De Clercq, U. Meyding-Lamadé and J. Neyts (2003), Acute encephalitis, a polyomyelitis-like syndrome and neurological sequelae in a hamster model for *flavivirus* infections. *Brain Pathology* 13:279-290.

Morin L. P. and R. I. Wood (2001), A Stereotaxic Atlas of the Golden Hamster Brain. New York, Elsevier.

Morrey J. D., W. D. Craig, J. G. Julander, L. M. Blatt, D. F. Smee and R. W. Sidwell (2004a), Effect of interferon-alpha and interferon-inducers on West Nile virus in mouse and hamster animal models. *Aniviral Chemistry and Chemotherapy* 15:101-109.

Morrey J. D., C. W. Day, J. G. Julander, A. L. Olsen, R. W. Sidewell, C. D. Cheney and L. M. Blatt (2004b), Modeling hamsters for evaluating West Nile virus therapies. *Antiviral Research* 63:41-50.

Oliphant T., M. Engle, G. E. Nybakken, C. Doane, S. Johnson, L. Huang, S. Gorlatov, E. Mehlhop, A. Marri, K. M. Chung, G. D. Ebel, L. D. Kramer, D. H. Fremont and M. S. Diamond (2005), Development of a humanized monoclonal antibody with therapeutic potential against West Nile virus. *Nat. Med.* 11:522-530.

Roehrig J. T., J. H. Mathews and D. W. Trent (1983), Identification of epitopes on the E glycoprotein of Saint Louis encephalitis virus using monoclonal antibodies. *J. Virol.* 128:118-126.

Roehrig J. T., L. A. Staudinger, A. R. Hunt, J. H. Mathews and C. D. Blair (2001), Antibody prophylaxis and therapy for *flavivirus* encephalitis infections. *Ann. NY Acad. Sci.* 951:286-297.

Slootstra J. W., W. C. Puijk, G. J. Ligtvoet, J. P. Langeveld, R. H. Meloen (1996), Structural aspects of antibody-antigen interaction revealed through small random peptide libraries. *Mol. Divers.* 1:87-96.

van der Staay F. J., K.-H. Augstein and E. Horvath (1996a), Sensorimotor impairments in rats with cerebral infarction, induced by unilateral occlusion of the left middle cerebral artery: strain differences and effects of the occlusion site. *Brain Research* 735:271-284.

van der Staay F. J., K.-H. Augstein and E. Horvath (1996b), Sensorimotor impairments in Wistar Kyoto rats with cerebral infarction, induced by unilateral occlusion of the middle cerebral artery: recovery of function. *Brain Research* 715:180-188.

Wang T., J. F. Anderson, L. A. Magnarelli, S. J. Wong, R. A. Koski and E. Fikrig (2001), Immunization of mice against West Nile virus with recombinant envelope protein. *J. Immunol.* 167:5273-5277.

What is claimed is:

1. A binding molecule capable of specifically binding to an E protein of a lineage I or II West Nile virus ("WNV") and having WNV neutralizing activity, wherein the binding molecule comprises a heavy chain comprising the variable heavy chain of amino acid sequence of SEQ ID NO: 131.

2. The binding molecule of claim 1, wherein the binding molecule is human.

3. A functional variant of a binding molecule capable of specifically binding to an E protein of a lineage I or II West Nile virus ("WNV"), having WNV neutralizing activity, and comprising at least a heavy chain comprising the variable heavy chain of the amino acid sequence SEQ ID NO: 131, wherein the functional variant has WNV neutralizing activity and is able to compete for specific binding to the E protein of WNV.

4. An immunoconjugate comprising:
a binding molecule comprising least a heavy chain comprising the variable heavy chain of the amino acid sequence SEQ ID NO: 131 or a functional variant of the binding molecule, wherein the functional variant is able to compete with the binding molecule for specific binding to an E protein of a lineage I or II West Nile Virus ("WNV"), and further has WNV neutralizing activity, and
at least one tag associated therewith.

5. A process for producing the binding molecule of claim 1, the process comprising:
culturing a host cell comprising a vector that comprises a nucleic acid molecule encoding the variable heavy chain of amino acid sequence SEQ ID NO: 131 under conditions conducive to the expression of the binding molecule.

6. The process of claim 5 further comprising:
recovering the expressed binding molecule.

7. A molecule capable of specifically binding an E protein of a lineage I or II West Nile virus ("WNV") and having WNV neutralizing activity, produced by a process comprising:
culturing a host cell under conditions conducive to expression of the molecule, wherein the host cell includes at least one vector, the vector comprising a nucleic acid encoding the molecule;
wherein the molecule comprises at least a heavy chain comprising the variable heavy chain of the amino acid sequence SEQ ID NO: 131;
wherein the molecule binds to an E protein of a lineage I or II West Nile Virus ("WNV"), and further has WNV neutralizing activity.

8. A composition comprising:
at least two binding molecules having West Nile Virus ("WNV") neutralizing activity, wherein the binding molecules are able to react with different, non-competing epitopes of WNV and wherein one of the at least two binding molecules is the binding molecule of claim 1.

9. The composition of claim 8, wherein the non-competing epitopes are located on the WNV E protein.

10. The composition of claim 9, wherein the first WNV neutralizing binding molecule is able to react with an epitope located in domain II of the WNV E protein and the second WNV neutralizing binding molecule is able to react with an epitope located in domain III of the WNV E protein.

11. The composition of claim 8, wherein the binding molecules are human binding molecules.

12. A composition comprising:
the binding molecule of claim 1; and
at least one pharmaceutically acceptable excipient.

13. The composition of claim 12 further comprising at least one other therapeutic agent.

14. The composition of claim 12 further comprising interferon-alpha.

15. A kit comprising the binding molecule of claim 1.

* * * * *